(12) United States Patent
Wu et al.

(10) Patent No.: US 10,787,435 B2
(45) Date of Patent: Sep. 29, 2020

(54) ASK1 INHIBITOR AND PREPARATION METHOD AND USE THEREOF

(71) Applicant: FUJIAN COSUNTER PHARMACEUTICAL CO., LTD., Fujian (CN)

(72) Inventors: Chengde Wu, Shanghai (CN); Tao Yu, Shanghai (CN); Ning Li, Shanghai (CN); Shuhui Chen, Shanghai (CN)

(73) Assignee: Fuijan Cosunter Pharmaceutical Co. Ltd., Fuijan (CN)

( * ) Notice: Subject to any disclaimer, the term of this patent is extended or adjusted under 35 U.S.C. 154(b) by 0 days.

(21) Appl. No.: 16/479,752

(22) PCT Filed: Jan. 22, 2018

(86) PCT No.: PCT/CN2018/073638
§ 371 (c)(1),
(2) Date: Jul. 22, 2019

(87) PCT Pub. No.: WO2018/133865
PCT Pub. Date: Jul. 26, 2018

(65) Prior Publication Data
US 2019/0375728 A1 Dec. 12, 2019

(30) Foreign Application Priority Data
Jan. 22, 2017 (CN) .......................... 2017 1 0054208

(51) Int. Cl.
| | |
|---|---|
| A61K 31/517 | (2006.01) |
| A61K 31/4709 | (2006.01) |
| C07D 401/14 | (2006.01) |
| C07D 407/14 | (2006.01) |
| C07D 409/14 | (2006.01) |
| C07D 413/14 | (2006.01) |
| C07D 417/14 | (2006.01) |
| C07D 471/04 | (2006.01) |
| C07D 487/04 | (2006.01) |

(52) U.S. Cl.
CPC ......... *C07D 401/14* (2013.01); *C07D 407/14* (2013.01); *C07D 409/14* (2013.01); *C07D 413/14* (2013.01); *C07D 417/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 6,998,408 B2 | 2/2006 | Pinto |
| 8,946,260 B2 | 2/2015 | Bock et al. |
| 10,278,973 B2 | 5/2019 | Wu et al. |

FOREIGN PATENT DOCUMENTS

| | | |
|---|---|---|
| CA | 2850700 A1 | 6/2013 |
| CN | 103108871 A | 5/2013 |
| CN | 104080771 A | 10/2014 |
| CN | 104918936 A | 9/2015 |
| CN | 109071498 A | 12/2018 |
| CN | 109265443 A | 1/2019 |
| CN | 109456308 A | 3/2019 |
| CN | 109956928 A | 7/2019 |
| WO | 2004037176 A2 | 5/2004 |
| WO | 2016184312 A1 | 11/2016 |

OTHER PUBLICATIONS

International Search Report, dated Apr. 18, 2018, issued in corresponding International Application No. PCT/CN2018/073638.
Official Action, dated Aug. 7, 2019, issued in corresponding CN Application No. 20188001395.3.
Pang Y. et al., "Design, Synthesis and Biological Activity Study of New Acridine Ketone ASK1 Inhibitors."J. Med. Chem. 2017, 60, 17, 7300-7314.

*Primary Examiner* — Samantha L Shterengarts
(74) *Attorney, Agent, or Firm* — Kathleen D. Rigaut; Howson & Howson, LLP

(57) ABSTRACT

The present disclosure relates to a compound as shown in formula (II), a tautomer or a pharmaceutically acceptable salt thereof, and disclosed is the use thereof in preparing a drug for treating an ASK1-associated disease.

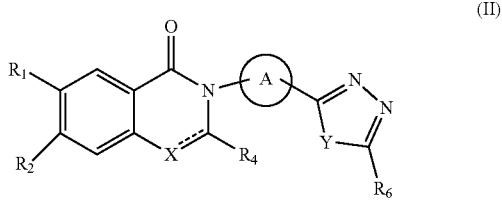

(II)

27 Claims, No Drawings

ASK1 INHIBITOR AND PREPARATION METHOD AND USE THEREOF

CROSS-REFERENCE TO RELATED APPLICATIONS

The present application is a § 371 of International Application No. PCT/CN2018/073638, filed Jan. 22, 2018, which claims priority to Chinese Patent Application No. CN 201710054208.5 filed on Jan. 22, 2017. The entire disclosure of each of the aforesaid applications is incorporated by reference in the present application.

TECHNICAL FIELD

The present disclosure relates to a compound as shown in formula (II), a tautomer thereof or a pharmaceutically acceptable salt thereof, and to use thereof in the preparation of a medicament for the treatment of an ASK1-related disease.

BACKGROUND

Apoptosis signal-regulating kinase 1 (ASK1) is one of the members of the mitogen-activated protein kinase (MAP3K) family. ASK1 can be activated by a series of stimuli such as oxidative stress, reactive oxygen species (ROS), LPS, TNF-a, FasL, endoplasmic reticulum stress, and increased intracellular calcium concentration. ASK1 responds to these series of stimuli by activating JNK (c-Jun N-terminal kinase) and p38 mitogen-activated protein kinases, and induces a variety of apoptosis through signals involving the mitochondrial cell death pathway. Activation and signaling of ASK1 play an important role in many diseases, including neurodegenerative diseases, cardiovascular diseases, inflammatory diseases, autoimmune diseases, and metabolic disorders. Therefore, when a patient suffers from a neurodegenerative disease, a cardiovascular disease, an inflammation, an autoimmune disease, and a metabolic disease, the use of an ASK1 inhibitor as a therapeutic drug can improve the life of the patient.

SUMMARY

The present disclosure provides a compound as shown in formula (II):

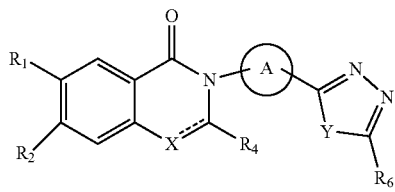

wherein

⚹ is selected from a single bond or a double bond;
X is selected from the group consisting of $C(R_3)$, $CH(R_3)$, N and $N(R_3)$;
Y is selected from the group consisting of $N(R_5)$ and O;
ring A is selected from the group consisting of phenyl and 5- to 6-membered heteroaryl;
$R_1$ is selected from 5- to 10-membered heteroaryl optionally substituted with one, two or three R group(s);

$R_2$ is selected from the group consisting of H, F, Cl, Br, I, OH, and $NH_2$, or selected from the group consisting of $C_{1-6}$ alkyl, $C_{1-3}$ heteroalkyl, 5- to 6-membered heterocycloalkyl, phenyl and 5- to 6-membered heteroaryl, each optionally substituted with one, two or three R group(s);

$R_3$ is selected from the group consisting of H, F, Cl, Br, I, OH, and $NH_2$;

$R_4$ is selected from H, or selected from the group consisting of $C_{1-3}$ alkyl and $C_{1-3}$ alkoxy;

$R_5$ is selected from H, or selected from the group consisting of $C_{1-8}$ alkyl, $C_{3-7}$ cycloalkyl and 3- to 6-membered heterocycloalkyl, each optionally substituted with one, two or three R group(s);

$R_6$ is selected from H, or selected from $C_{1-6}$ alkyl;

or $R_5$ and $R_6$ are joined together to form a 5- to 6-membered ring;

R is selected from the group consisting of H, F, Cl, Br, I, OH, $NH_2$, and $NH_2$—(C=O)—, or selected from the group consisting of $C_{1-3}$ alkyl, $C_{1-3}$ alkoxy, $C_{1-3}$ alkyl-NH—(C=O)—, $C_{1-3}$ alkyl-S(=O)$_2$—, $C_{3-6}$ cycloalkyl, 3- to 6-membered heterocycloalkyl and phenyl;

the "hetero" in the 5- to 10-membered heteroaryl, $C_{1-3}$ heteroalkyl, 5- to 6-membered heterocycloalkyl, 5- to 6-membered heteroaryl, 3- to 6-membered heterocycloalkyl is respectively and independently selected from the group consisting of —NH—, N, —O—, —S—, —S(=O)$_2$— and —NH—C(=O)—;

in any of the above cases, the number of heteroatoms or heteroatomic groups is independently selected from 1, 2 or 3;

and a pharmaceutically acceptable salt and a tautomer thereof.

In some embodiments of the present disclosure, the R as described above is selected from the group consisting of H, F, Cl, Br, I, OH, $NH_2$, Me, Et,

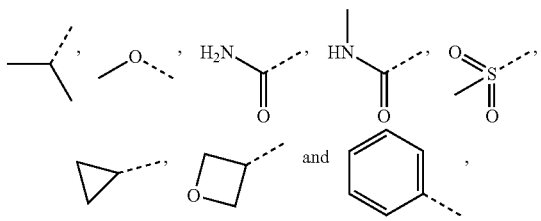

and other variables are as defined in the present disclosure.

In some embodiments of the present disclosure, the $R_1$ as described above is selected from the group consisting of imidazolyl, 4,5,6,7-tetrahydro-1H-benzo[d]imidazolyl and pyridyl, each optionally substituted with one, two or three R group(s), and other variables are as defined in the present disclosure.

In some embodiments of the present disclosure, the $R_1$ as described above is selected from the group consisting of

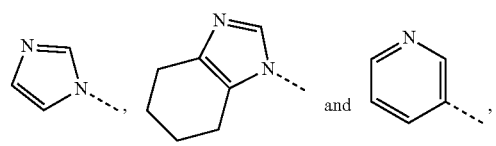

each optionally substituted with one, two or three R group(s), and other variables are as defined in the present disclosure.

In some embodiments of the present disclosure, the $R_1$ as described above is selected from the group consisting of

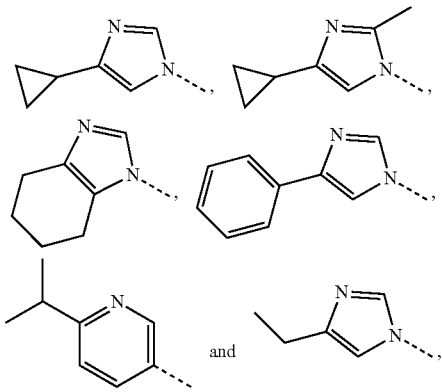

and and other variables are as defined in the present disclosure.

In some embodiments of the present disclosure, the $R_2$ as described above is selected from the group consisting of H, F, Cl, Br, I, OH, and $NH_2$, or selected from the group consisting of $C_{1-3}$ alkyl, $C_{1-3}$ alkylamino, $C_{1-3}$ alkoxy, morpholinyl, phenyl, pyridyl and thienyl, each optionally substituted with one, two or three R group(s), and other variables are as defined in the present disclosure.

In some embodiments of the present disclosure, the $R_2$ as described above is selected from the group consisting of H, F, Cl, Br, I, OH, and $NH_2$, or selected from the group consisting of Me, Et,

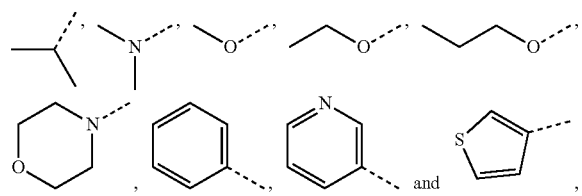

each optionally substituted with one, two or three R group(s), and other variables are as defined in the present disclosure.

In some embodiments of the present disclosure, the $R_2$ as described above is selected from the group consisting of H, F, Cl, Br, I, OH, $NH_2$, Me, Et,

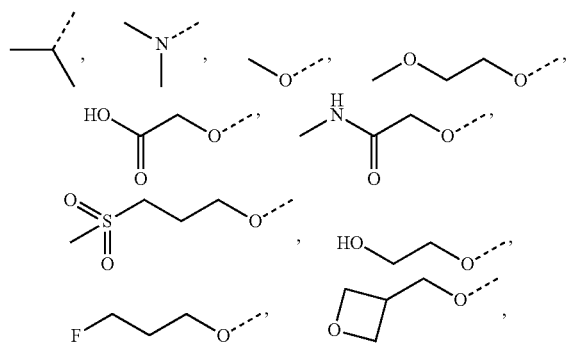

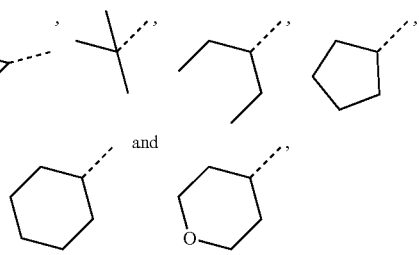

and other variables are as defined in the present disclosure.

In some embodiments of the present disclosure, the $R_4$ as described above is selected from the group consisting of H, Me, Et and

and other variables are as defined in the present disclosure.

In some embodiments of the present disclosure, the $R_5$ as described above is selected from H, or selected from the group consisting of $C_{1-6}$ alkyl, $C_{3-6}$ cycloalkyl and 5- to 6-membered heterocycloalkyl, each optionally substituted with one, two or three R group(s), and other variables are as defined in the present disclosure.

In some embodiments of the present disclosure, the $R_5$ as described above is selected from H, or selected from the group consisting of Me, Et, each optionally substituted with one, two or three R group(s), and other variables are as defined in the present disclosure.

In some embodiments of the present disclosure, the $R_5$ as described above is selected from the group consisting of H, Me, Et,

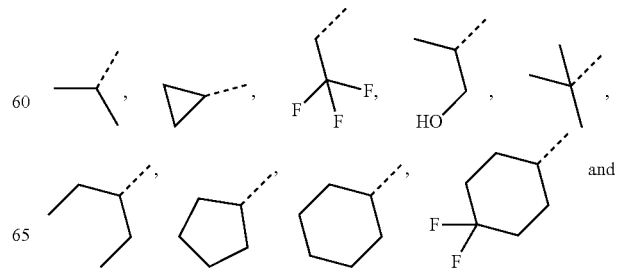

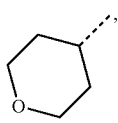

and other variables are as defined in the present disclosure.

In some embodiments of the present disclosure, the $R_6$ as described above is selected from H, or selected from $C_{1-3}$ alkyl, and other variables are as defined in the present disclosure.

In some embodiments of the present disclosure, the $R_6$ as described above is selected from the group consisting of H, Me and Et, and other variables are as defined in the present disclosure.

In some embodiments of the present disclosure, the ring A as described above is selected from the group consisting of phenyl, pyridyl, thienyl and thiazolyl, and other variables are as defined in the present disclosure.

In some embodiments of the present disclosure, the ring A as described above is selected from the group consisting of

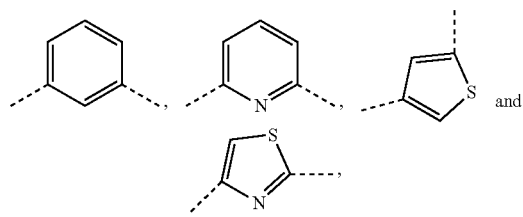

and other variables are as defined in the present disclosure.

In some embodiments of the present disclosure, the structural unit

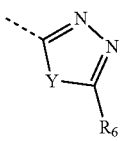

as described above is selected from the group consisting of

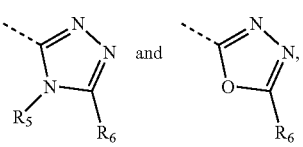

and other variables are as defined in the present disclosure.

In some embodiments of the present disclosure, when the $R_5$ and $R_6$ as described above are joined together to form a 5- to 6-membered ring, the structural unit

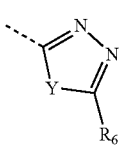

is selected from the group consisting of

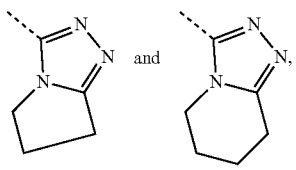

and other variables are as defined in the present disclosure.

In some embodiments of the present disclosure, the structural unit

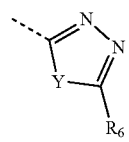

as described above is selected from the group consisting of

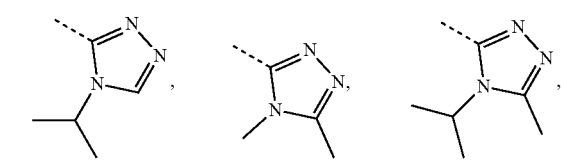

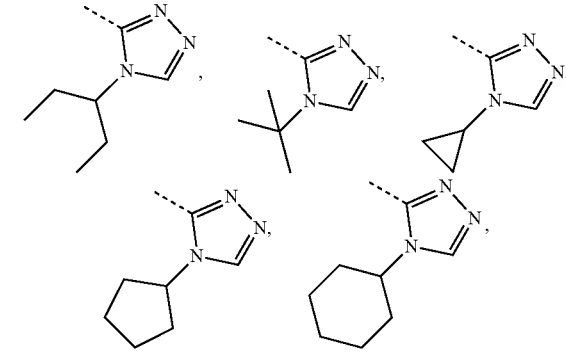

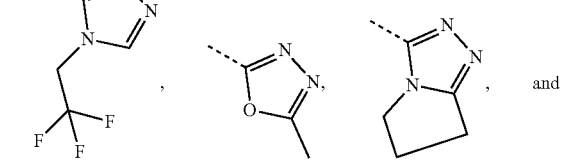

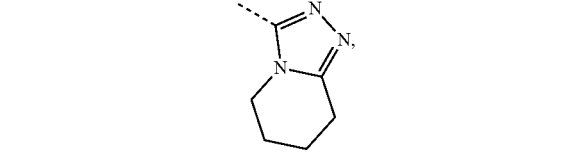

and other variables are as defined in the present disclosure.

In some embodiments of the present disclosure, the structural unit

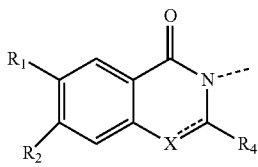

as described above is selected from the group consisting of

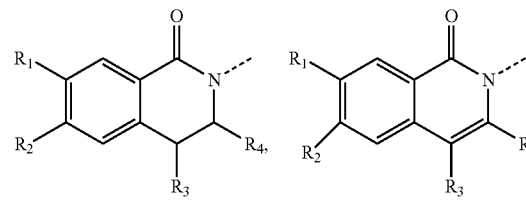

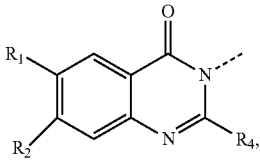

and other variables are as defined in the present disclosure.

The present disclosure also includes some embodiments where the variables as described above are arbitrarily combined.

In some embodiments of the present disclosure, the compound as described above is selected from the group consisting of (2)

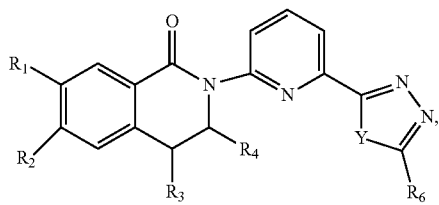

(3)

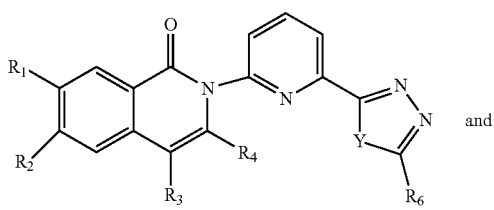

and (4)

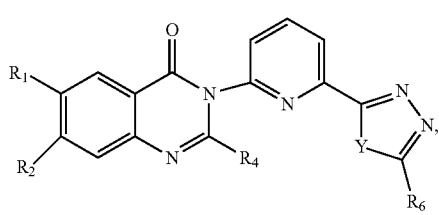

wherein Y, $R_1$, $R_2$, $R_3$, $R_4$, and $R_6$ are as defined in the present disclosure, and a pharmaceutically acceptable salt thereof.

In some embodiments of the present disclosure, the compound as described above is selected from the group consisting of (5)

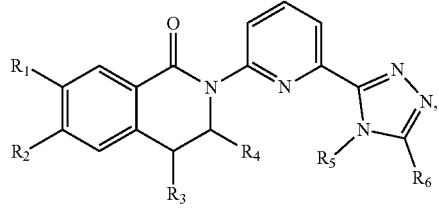

(6)

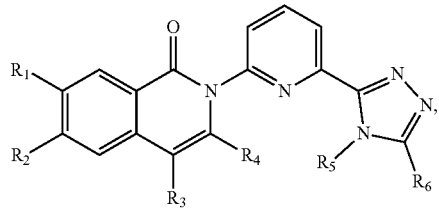

(7)

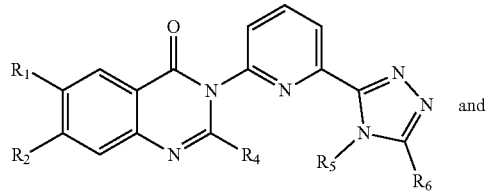

and (8)

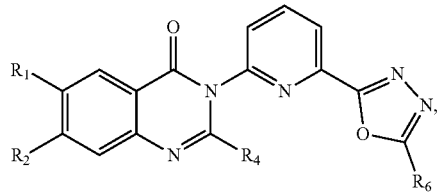

wherein $R_1$, $R_2$, $R_3$, $R_4$, $R_5$, and $R_6$ are as defined in the present disclosure, and a pharmaceutically acceptable salt thereof.

In some embodiments of the present disclosure, the compound as described above is selected from the group consisting of (9)

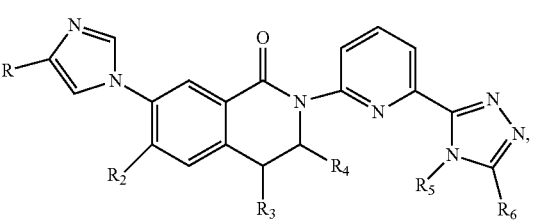

-continued (10)

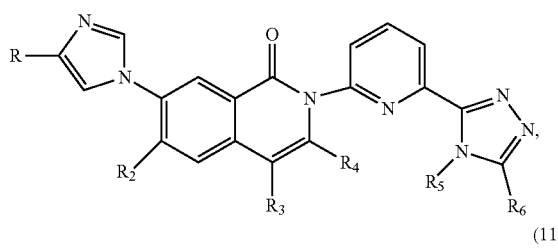

(11)

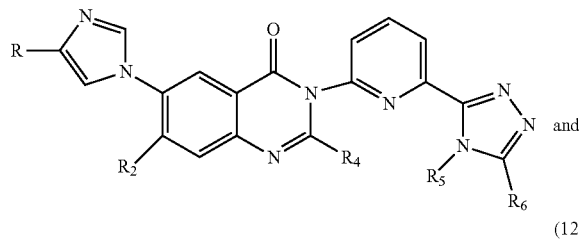
and (12)

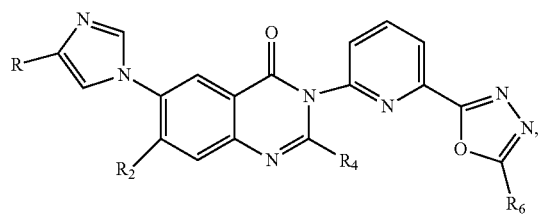

wherein $R_1$, $R_2$, $R_3$, $R_4$, $R_5$, and $R_6$ are as defined in the present disclosure, and a pharmaceutically acceptable salt thereof.

The present disclosure also provides a compound as shown in formula (I):

(1)

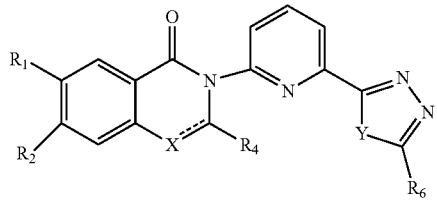

wherein

⚌ is selected from a single bond or a double bond;
X is selected from the group consisting of $C(R_3)$, $CH(R_3)$, N and $N(R_3)$;
Y is selected from the group consisting of $N(R_5)$ and O;
$R_1$ is selected from 5- to 10-membered heteroaryl optionally substituted with one, two or three R group(s);
$R_2$ is selected from H, or selected from $C_{1-3}$ alkyl;
$R_3$ is selected from the group consisting of H, F, Cl, Br, I, OH, and $NH_2$;
$R_4$ is selected from H, or selected from $C_{1-3}$ alkyl;
$R_5$ is selected from H, or selected from the group consisting of $C_{1-3}$ alkyl and $C_{3-6}$ cycloalkyl, each optionally substituted with one, two or three R group(s);
$R_6$ is selected from H, or selected from $C_{1-6}$ alkyl;
or $R_5$ and $R_6$ are joined together to form a 5- to 6-membered ring;
R is selected from the group consisting of H, F, and Cl, or selected from the group consisting of $C_{1-3}$ alkyl and $C_{3-6}$ cycloalkyl;

the "hetero" in the 5- to 10-membered heteroaryl is respectively and independently selected from the group consisting of —NH—, N, and —O—;

in any of the above cases, the number of heteroatoms or heteroatomic groups is independently selected from 1, 2 or 3;

and a pharmaceutically acceptable salt and a tautomer thereof.

In some embodiments of the present disclosure, the R as described above is selected from the group consisting of H, F, Cl, Me, and

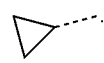

In some embodiments of the present disclosure, the $R_1$ as described above is selected from the group consisting of imidazolyl and 4,5,6,7-tetrahydro-1H-benzo[d]imidazolyl, each optionally substituted with one, two or three R group(s).

In some embodiments of the present disclosure, the $R_1$ as described above is selected from the group consisting of

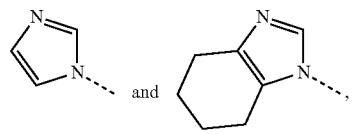

each optionally substituted with one, two or three R group(s).

In some embodiments of the present disclosure, the $R_1$ as described above is selected from the group consisting of

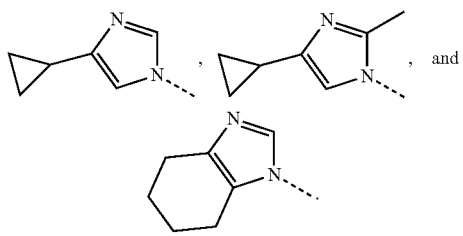

In some embodiments of the present disclosure, the $R_2$ as described above is selected from the group consisting of H, Me, and Et.

In some embodiments of the present disclosure, the $R_4$ as described above is selected from the group consisting of H, Me, and Et.

In some embodiments of the present disclosure, the $R_5$ as described above is selected from H, or selected from the group consisting of $C_{1-3}$ alkyl and $C_{3-6}$ cycloalkyl, each optionally substituted with one, two or three R group(s).

In some embodiments of the present disclosure, the $R_5$ as described above is selected from the group consisting of H, Me, Et,

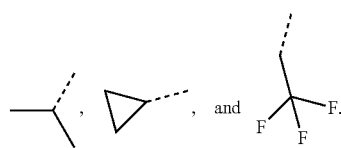

In some embodiments of the present disclosure, the $R_6$ as described above is selected from H, or selected from $C_{1-3}$ alkyl.

In some embodiments of the present disclosure, the $R_6$ as described above is selected from the group consisting of H, Me, and Et.

In some embodiments of the present disclosure, the structural unit

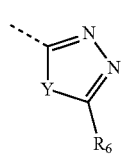

as described above is selected from the group consisting of

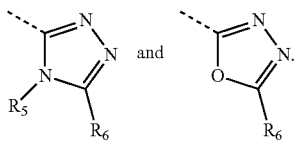

In some embodiments of the present disclosure, when the $R_5$ and $R_6$ as described above are joined together to form a 5- to 6-membered ring, the structural unit

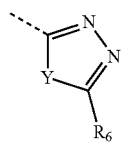

is selected from the group consisting of

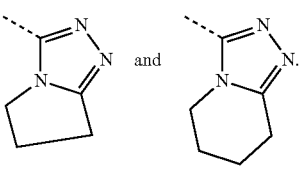

In some embodiments of the present disclosure, the structural unit

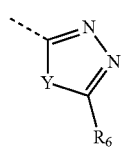

as described above is selected from the group consisting of

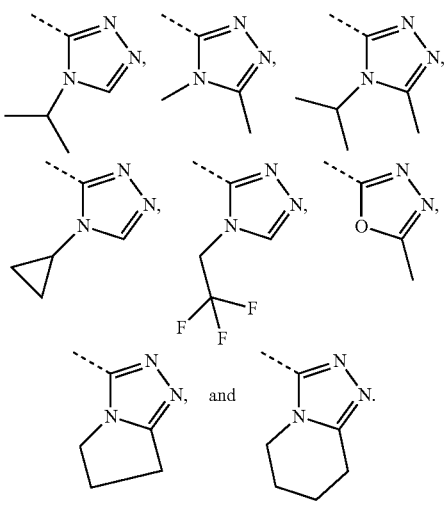

In some embodiments of the present disclosure, in the compound as described above and a pharmaceutically acceptable salt thereof, the structural unit

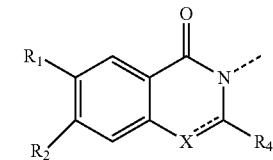

is selected from the group consisting of

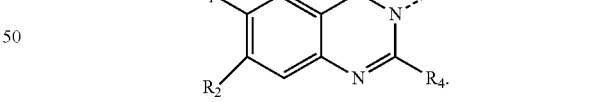

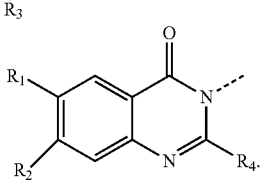

In some embodiments of the present disclosure, the R as described above is selected from the group consisting of H, F, Cl, Me, and

In some embodiments of the present disclosure, the $R_1$ as described above is selected from the group consisting of imidazolyl and 4,5,6,7-tetrahydro-1H-benzo[d]imidazolyl, each optionally substituted with one, two or three R group(s), and other variables are as defined above.

In some embodiments of the present disclosure, the $R_1$ as described above is selected from the group consisting of

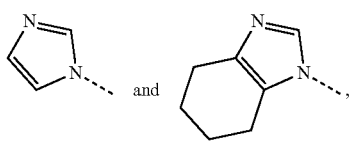

each optionally substituted with one, two or three R group(s), and other variables are as defined above.

In some embodiments of the present disclosure, the $R_1$ as described above is selected from the group consisting of

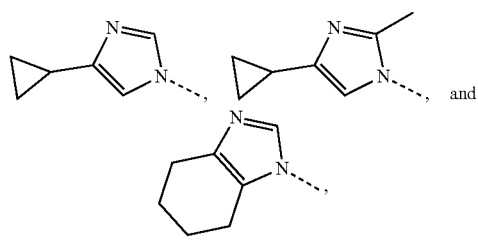

and other variables are as defined above.

In some embodiments of the present disclosure, the $R_2$ as described above is selected from the group consisting of H, Me, and Et, and other variables are as defined above.

In some embodiments of the present disclosure, the $R_4$ as described above is selected from the group consisting of H, Me, and Et, and other variables are as defined above.

In some embodiments of the present disclosure, the $R_5$ as described above is selected from H, or selected from the group consisting of $C_{1-3}$ alkyl and 3-6 cycloalkyl, each optionally substituted with one, two or three R group(s), and other variables are as defined above.

In some embodiments of the present disclosure, the $R_5$ as described above is selected from the group consisting of H, Me, Et,

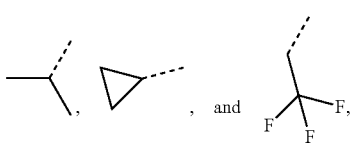

and other variables are as defined above.

In some embodiments of the present disclosure, the $R_6$ as described above is selected from H, or selected from $C_{1-3}$ alkyl, and other variables are as defined above.

In some embodiments of the present disclosure, the $R_6$ as described above is selected from the group consisting of H, Me, and Et, and other variables are as defined above.

In some embodiments of the present disclosure, the structural unit

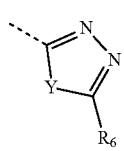

as described above is selected from the group consisting of

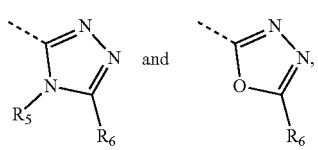

and other variables are as defined above.

In some embodiments of the present disclosure, when the $R_5$ and $R_6$ as described above are joined together to form a 5- to 6-membered ring, the structural unit

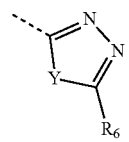

is selected from the group consisting of

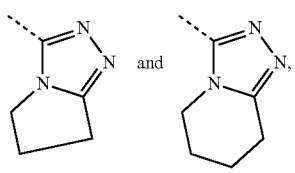

and other variables are as defined above.

In some embodiments of the present disclosure, the structural unit

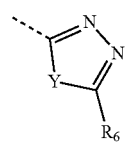

as described above is selected from the group consisting of

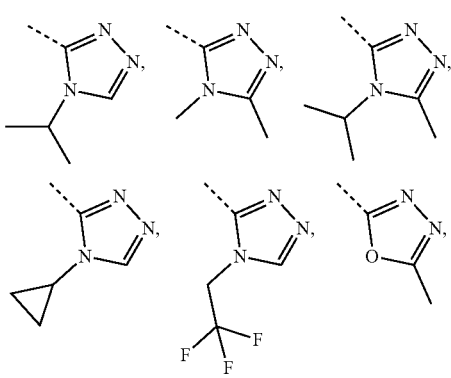

-continued

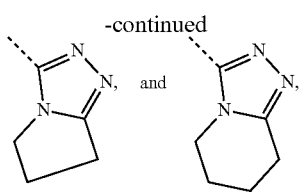 and and other variables are as defined above.

In some embodiments of the present disclosure, in the compound as described above and a pharmaceutically acceptable salt thereof, the structural unit

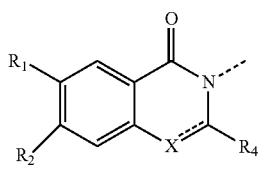

is selected from the group consisting of

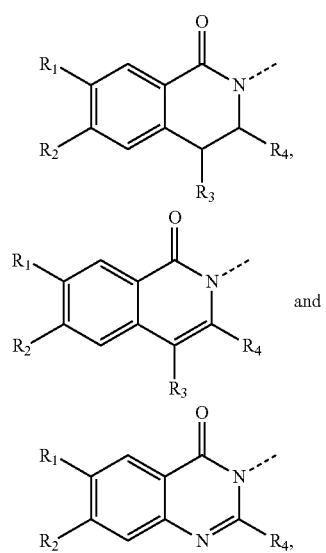

and other variables are as defined above.

The present disclosure also includes some embodiments where the variables as described above are arbitrarily combined.

In some embodiments of the present disclosure, the compound as described above is selected from the group consisting of

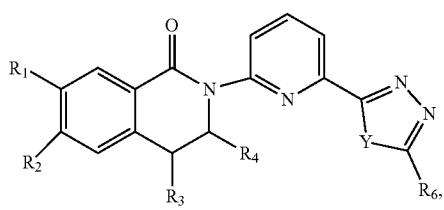

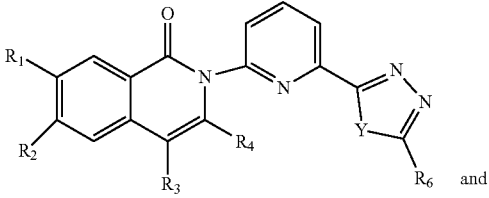

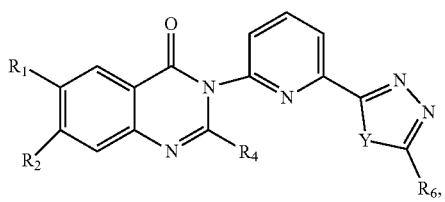

wherein Y, $R_1$, $R_2$, $R_3$, $R_4$, and $R_6$ are as defined above, and a pharmaceutically acceptable salt thereof.

In some embodiments of the present disclosure, the compound as described above is selected from the group consisting of

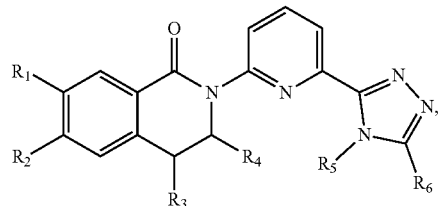

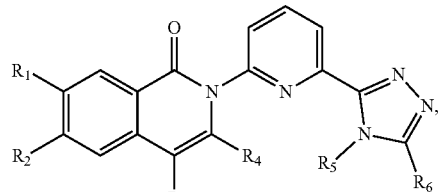

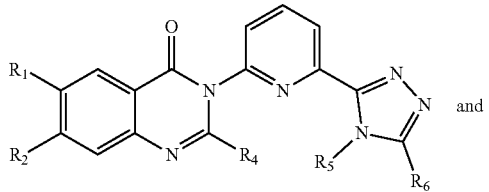

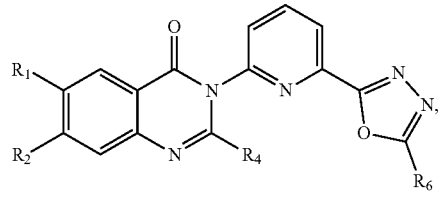

wherein $R_1$, $R_2$, $R_3$, $R_4$, $R_5$, and $R_6$ are as defined above, and a pharmaceutically acceptable salt thereof.

The present disclosure also provides compounds of the following formulas:

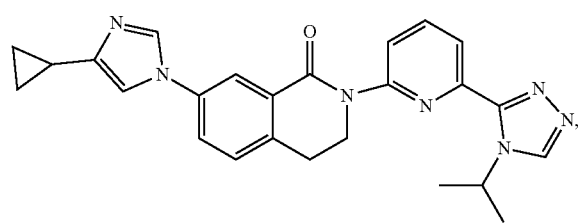
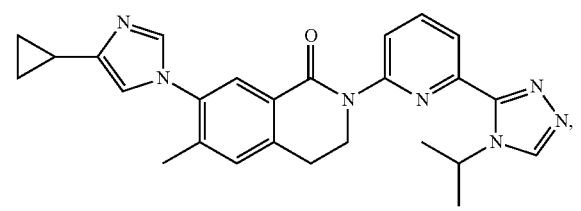
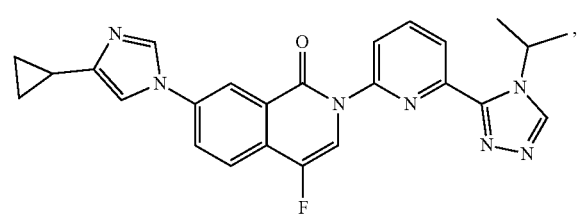
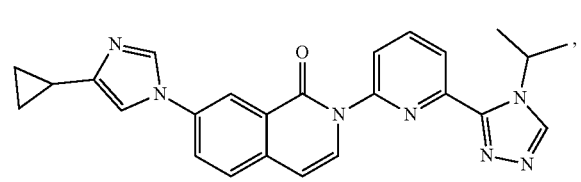
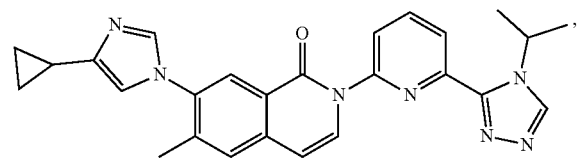
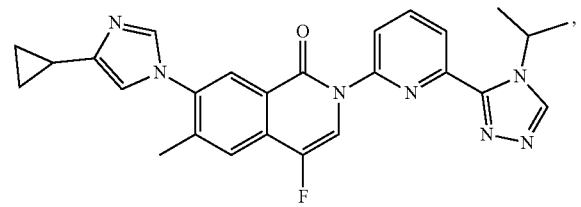
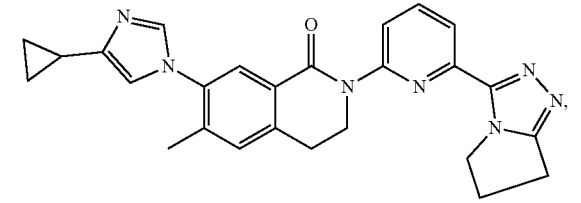
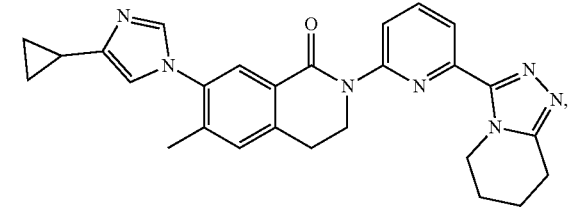
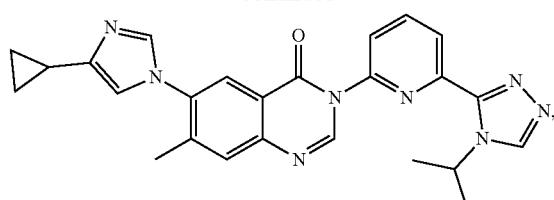
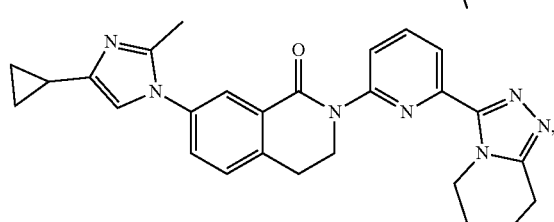
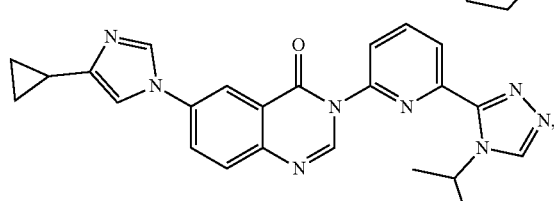
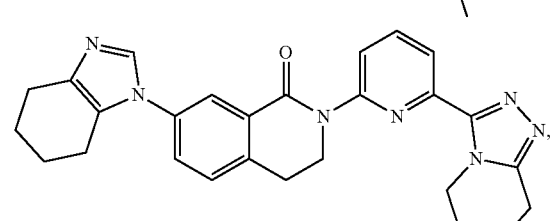
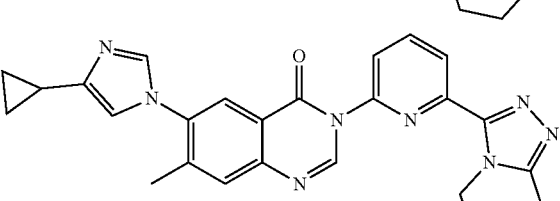
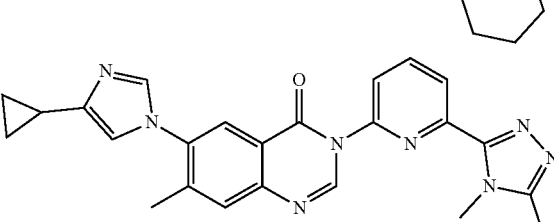
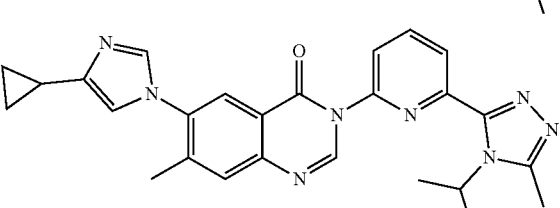
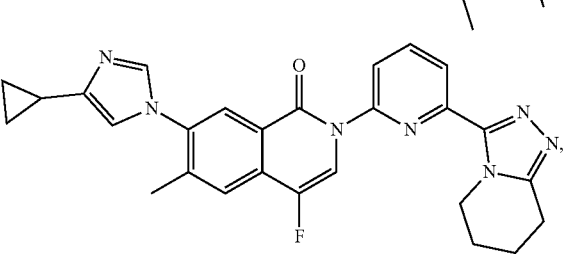

19
-continued
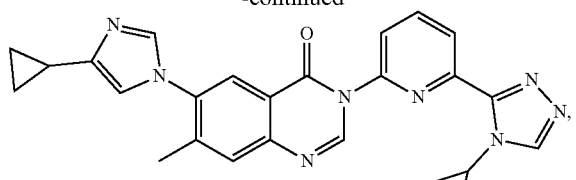
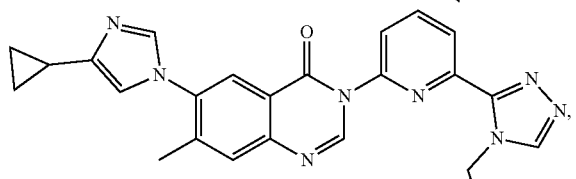
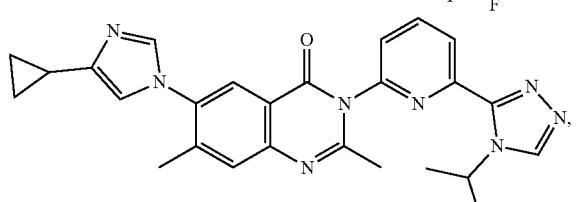
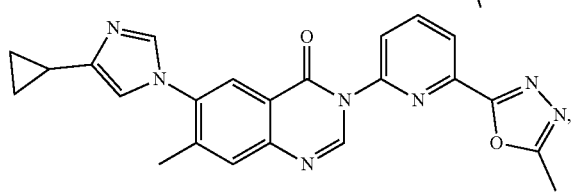
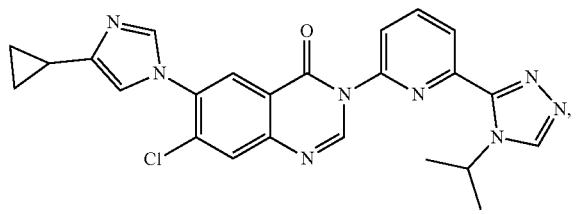
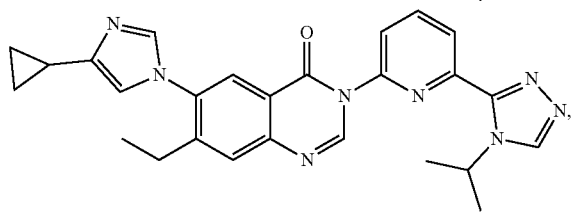
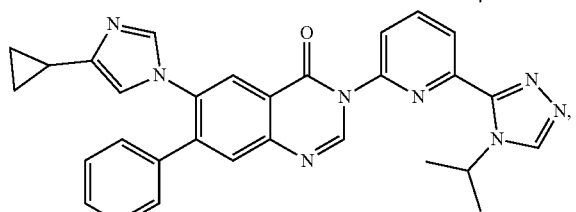
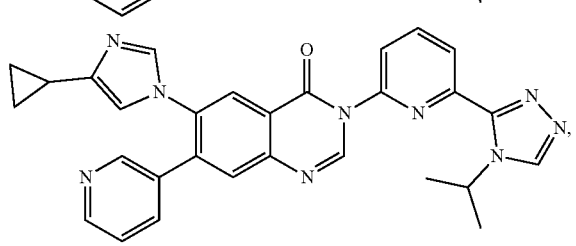
20
-continued
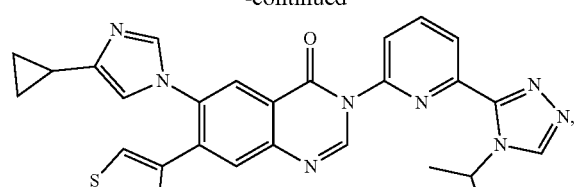
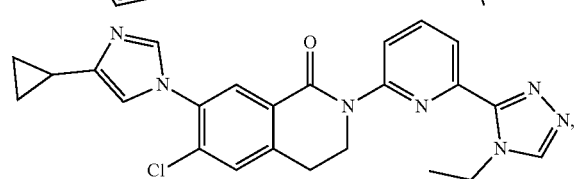
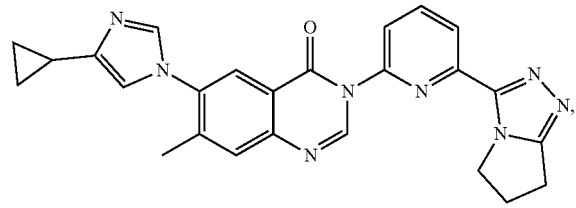
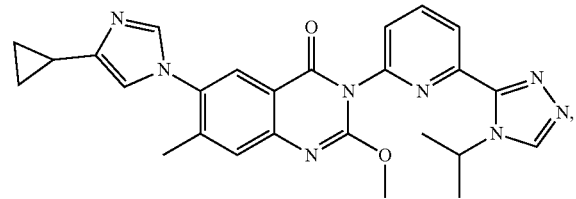
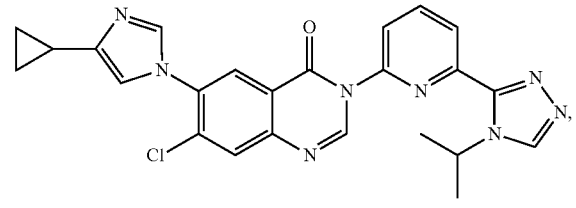
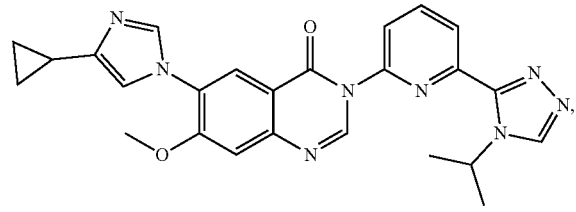
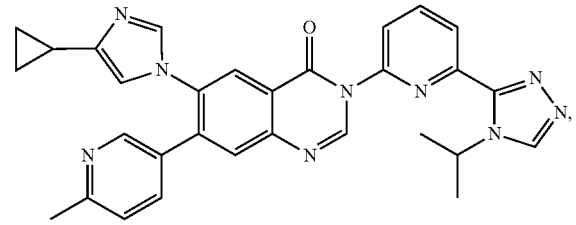
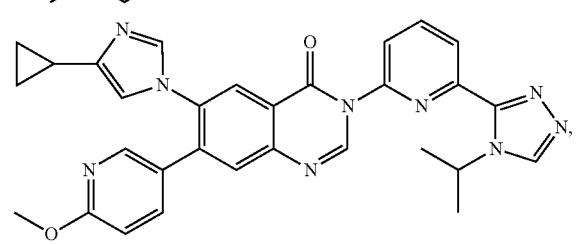

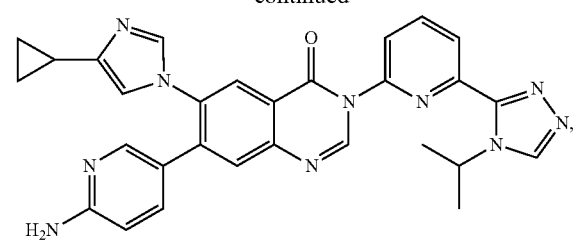
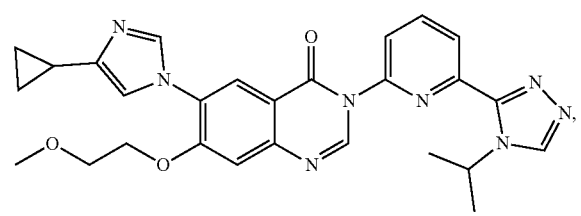
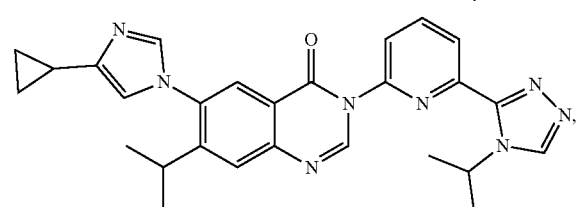
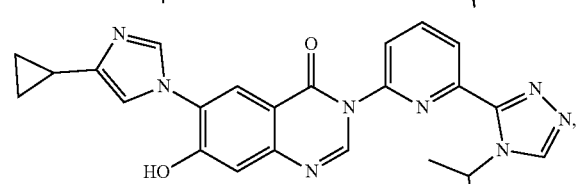
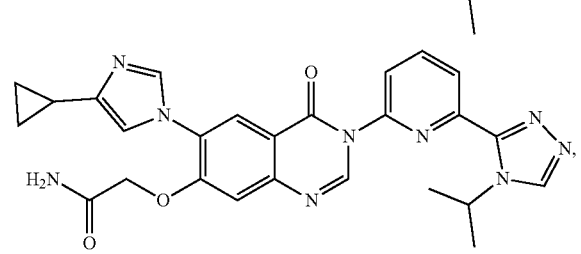
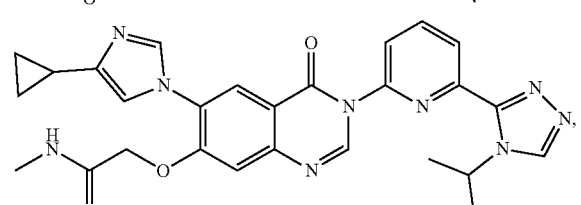
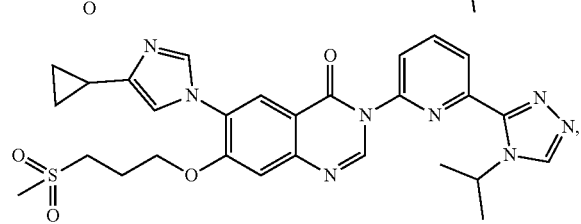
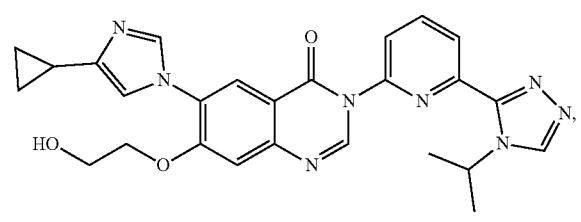
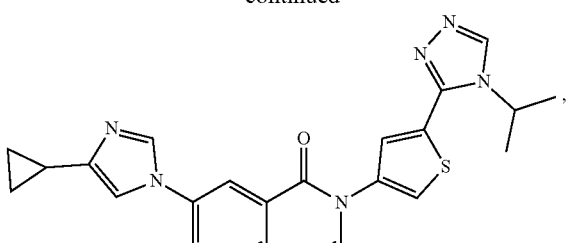
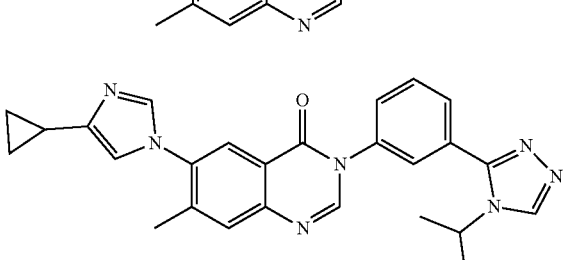
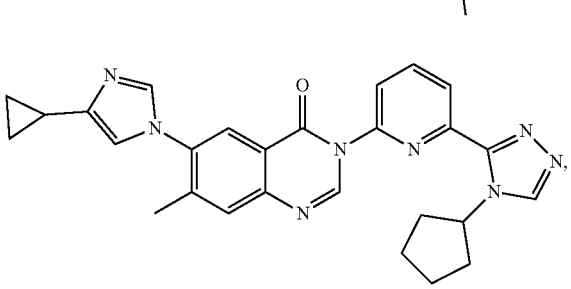
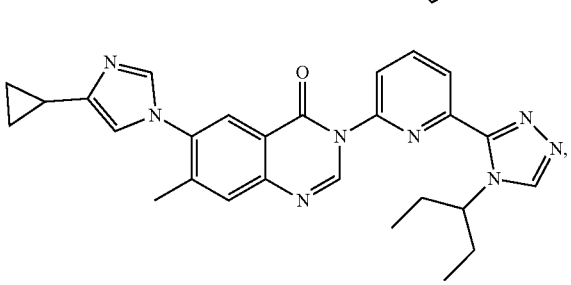
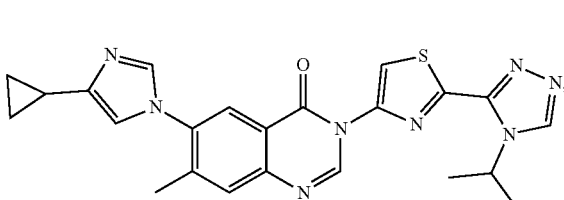
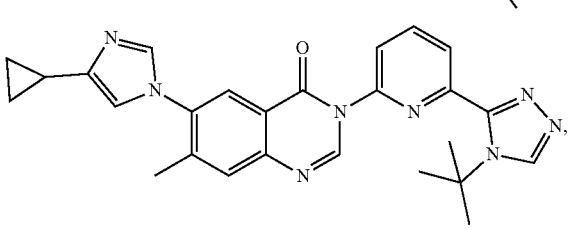
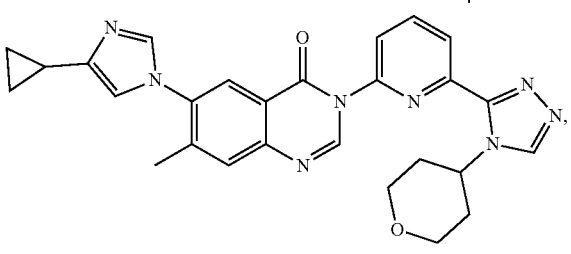

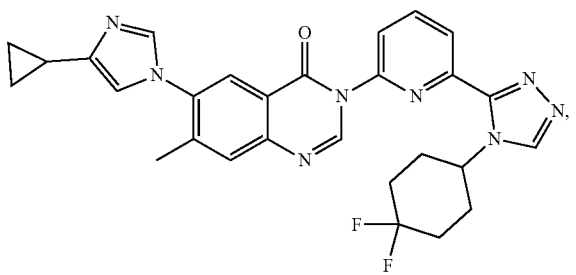

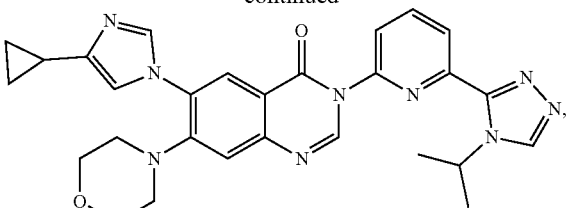

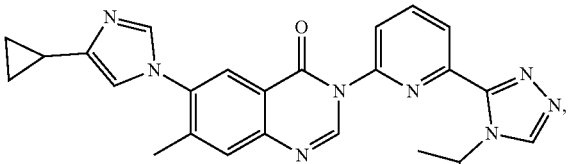

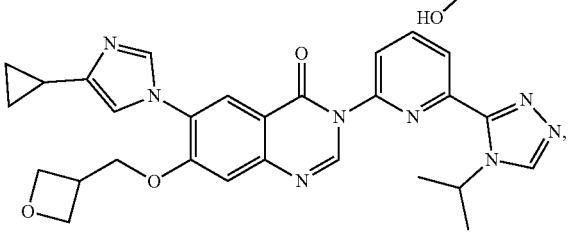

and a pharmaceutically acceptable salt thereof.

The present disclosure also provides a pharmaceutical composition comprising a therapeutically effective amount of the compound as described above, or a pharmaceutically acceptable salt thereof, as an active ingredient, and a pharmaceutically acceptable carrier.

The present disclosure also provides use of the compound as described above, or a pharmaceutically acceptable salt thereof, in the preparation of a medicament for the treatment of an ASK1-related disorder.

The present disclosure also provides use of the composition as described above in the preparation of a medicament for the treatment of an ASK1-related disorder.

Technical Effect

The compound of the present disclosure, as a novel ASK1 inhibitor, has a significant inhibitory effect on ASK1. In addition, the compound of the present disclosure has a good drug-forming property because of its good solubility, good permeability, strong targetability and stable metabolism.

Definition and Terms

Unless otherwise indicated, the following terms and phrases as used herein shall be understood to have the following meanings. A specific term or phrase, in the absence of a specific definition, shall be understood according to its common meaning instead of being considered as uncertain or unclear. The trade name, when referred to herein, is intended to refer to its corresponding commodity or active ingredient(s). The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "a pharmaceutically acceptable salt" refers to a salt of the compound of the present disclosure which is prepared from the compound of the present disclosure comprising a particular substituent and a relatively nontoxic acid or base. When the compound of the present disclosure contains a relatively acidic functional group, a base addition salt can be obtained by contacting the neutral form of such compound with a sufficient amount of a base, either in a neat solution or in a suitable inert solvent. Examples of pharmaceutically acceptable base addition salts include sodium, potassium, calcium, ammonium, organic ammonia or magnesium salt or the like. When the compound of the present disclosure contains a relatively basic functional group, an acid addition salt can be obtained by contacting the neutral form of such compound with a sufficient amount of an acid, either in a neat solution or in a suitable inert solvent. Examples of pharmaceutically acceptable acid addition salts include salts of inorganic acid including hydrochloric, hydrobromic, nitric, carbonic, bicarbonate, phosphoric, monohydrogenphosphoric, dihydrogenphosphoric, sulfuric, monohydrogensulfuric, hydriodic, and phosphorous acid and the like, as well as salts of organic acid including acetic, propionic, isobutyric, maleic, malonic, benzoic, succinic, suberic, fumaric, lactic, mandelic, phthalic, benzenesulfonic, p-tolylsulfonic, citric, tartaric, and methanesulfonic acid, and the like. Also included are salts of amino acid such as arginate and the like, and salts of organic acid like glucuronic acid and the like (see Berge et al., "Pharmaceutical Salts", Journal of Pharmaceutical Science 66: 1-19 (1977)). Certain specific compounds of the present disclosure contain both basic and acidic functional groups that allow the compounds to be converted into either base or acid addition salts.

Preferably, the neutral form of the compound may be regenerated by contacting the salt with a base or acid and then isolating the parent compound in a conventional manner. The parent form of the compound differs from the various salt forms in certain physical properties, such as solubility in a polar solvent.

The "pharmaceutically acceptable salt" as used herein belongs to derivatives of the compound of the present disclosure wherein the parent compound is modified by making a salt with an acid or a base. Examples of a pharmaceutically acceptable salt include, but not limited to, inorganic or organic acid salt of a basic group such as amine, alkali or organic salt of an acidic group such as carboxyl, and the like. The pharmaceutically acceptable salt includes the conventional non-toxic salt or the quaternary ammonium salt of the parent compound, for example, salts derived from non-toxic inorganic or organic acids. The conventional non-toxic salt includes, but not limited to, those derived from inorganic and organic acids selected from the group consisting of 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, hydrobromic, hydrochloric, hydroiodic, hydroxy, hydroxynaphthoic, isethionic, lactic, lactobionic, lauryl sulfonic, maleic, malic, mandelic, methane sulfonic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic acid.

The pharmaceutically acceptable salt of the present disclosure can be synthesized from the parent compound that contains a basic or acidic moiety by a conventional chemical method. Generally, such salt can be prepared by reacting the free acid or base form of such compound with a stoichiometric amount of an appropriate base or acid in water or in an organic solvent, or in a mixture of the two. Generally, nonaqueous media such as ether, ethyl acetate, ethanol, isopropanol, or acetonitrile are preferred.

In addition to salt forms, the compound provided herein also exists in the form of prodrug. Prodrugs of the compounds described herein are those compounds that readily undergo chemical changes under physiological conditions to convert to the compounds of the present disclosure. Additionally, prodrugs can be converted to the compounds of the present disclosure by chemical or biochemical methods in an in vivo environment.

Certain compounds of the present disclosure can exist in unsolvated forms as well as solvated forms, including hydrated forms. In general, the solvated forms are equivalent to unsolvated forms and are intended to be encompassed within the scope of the present disclosure.

Certain compounds of the present disclosure can possess asymmetric carbon atoms (optical centers) or double bonds. The racemates, diastereomers, geometric isomers, regioisomers and individual isomers are all encompassed within the scope of the present disclosure.

Unless otherwise indicated, wedge-shaped and dashed bonds ( ) are used to represent the absolute configuration of a stereocenter, a wavy line  is used to represent a wedge-shaped bond or a dashed bond ( or ), and  are used to represent the relative configuration of a stereocenter. If the compounds described herein contain olefinic double-bonds or other geometric asymmetry centers, unless otherwise indicated, E and Z geometrical isomers are included. Similarly, all tautomeric forms are encompassed within the scope of the present disclosure.

Compounds of the present disclosure may exist in particular geometric or stereoisomeric forms. The present inventor contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as mixtures enriched in isomers or diastereomers. All such mixtures are intended to be included within the scope of the present disclosure. Additional asymmetric carbon atoms may be present in a substituent such as an alkyl group. All such isomers, as well as mixtures thereof, are intended to be included within the scope of the present disclosure.

The optically active (R)- and (S)-isomers as well as the D and L isomers can be prepared by chiral synthesis or with chiral reagents or by other conventional techniques. If an enantiomer of a compound of the present disclosure is desired, it may be prepared by asymmetric synthesis, or by derivation with a chiral auxiliary, where the resulting diastereomeric mixture is separated and the auxiliary group is cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers by conventional methods well known in the art, and subsequent recovery of the pure enantiomers. In addition, the separation of enantiomers and diastereomers is generally accomplished by using chromatography which utilizes a chiral stationary phase, optionally in combination with chemical derivatization (e.g., formation of a carbamate from an amine).

The compound of the present disclosure may contain an unnatural proportion of atomic isotope at one or more of the atoms that constitute such compound. For example, the compound may be labeled with a radioactive isotope, such as tritium ($^3$H), iodine-125 ($^{125}$I) or carbon-14 ($^{14}$C). All isotopic variations of the compound of the present disclosure, whether radioactive or not, are intended to be encompassed within the scope of the present disclosure.

"Optional" or "optionally" means that the subsequently described event or circumstance can or cannot occur, and that the description includes instances where the event or circumstance occurs and instances where it does not.

The term "substituted" refers to one or more hydrogen atom(s) in a specific atom substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of available in chemistry.

When any variable (e.g. R) occurs more than one time in the constituent or formula of a compound, its definition at each occurrence is independent. Thus, for example, if a group is substituted by 0-2R substituents, then said group may optionally be substituted with up to two R substituents and each R substituents is selected independently. In addition, combinations of substituents and/or variables are permissible only if such combinations result in stable compounds.

When the number of the connection group is 0, such as —(CRR)$_0$—, it indicates that the connection group is a single bond.

When one of the variables is selected from a single bond, it indicates that the two groups which it is attached to are directly connected. For example, when the L in A-L-Z represents a single bond, it indicates that the structure actually is A-Z.

When a substituent is a gap, it means that this substituent is absence. For example, when the X in A-X is a gap, it indicates that the structure actually is A. If a substituent can be attached to more than one atom on a ring, it indicates that this substituent may be bonded to any atom on the ring. For example, the structural unit

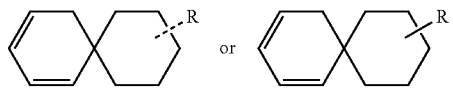

indicates that the substituent R may be substituted at any position on the cyclohexyl or cyclohexadiene. When a substituent is listed without indicating the atom via which such substituent is attached to the substituted group, such substituent may be bonded via any atom thereof. For example, pyridyl may be attached, as a substituent, to the substituted group via any carbon atom on the pyridine ring. When a substituent is listed without indicating in which direction it is attached, such substituent may be attached in any direction. For example, when the linking group L in

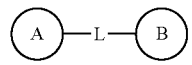

is -M-W-, rings A and B may be linked by -M-W- to either form

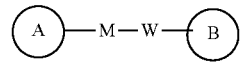

in the direction same as the reading order from left to right, or form

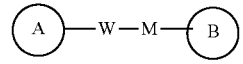

in the direction opposite to the reading order from left to right. Combinations of the linking groups, substituents and/or variables thereof are permissible only if such combinations result in stable compounds.

Unless otherwise specified, the term "hetero" refers to a heteroatom or a heteroatomic group (i.e. a atomic group containing a heteroatom), which includes atoms except carbon (C) and hydrogen (H) and atomic groups containing these heteroatoms, such as including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. The number of atoms in the ring is usually defined as the member of the ring. For example, a "5- to 7-membered ring" is a ring looped with 5 to 7 atoms. Unless otherwise specified, the ring optionally contains 1 to 3 heteroatoms. Therefore, a "5- to 7-membered ring" includes, for example, phenyl pyridine and piperidinyl. On the other hand, the term "5- to 7-membered heterocycloalkyl ring" includes pyridyl and piperidinyl, but does not include phenyl. The term "ring" also includes a ring system containing at least one ring, wherein each ring is of the above definition independently.

Unless otherwise specified, the term "heterocycle" or "heterocyclyl" refers to a stable monocyclic, bicyclic or tricyclic ring containing a heteroatom or a heteroatomic group, which may be saturated, partially unsaturated or unsaturated (aromatic), and which contains carbon atoms and 1, 2, 3 or 4 ring heteroatom(s) selected independently from the group consisting of N, O and S, and wherein any of the above-defined heterocycles can be fused to a benzene ring to form a bicyclic ring. The nitrogen and sulfur atoms can be optionally oxidized (i.e., NO and S(O)p, wherein p is 1 or 2). The nitrogen atom can be substituted or unsubstituted (i.e. N or NR, wherein R is H or any other substituent that has been defined herein). The heterocycle may be attached to the pendant group at any heteroatom or carbon atom to form a stable structure. The heterocycle described herein may be substituted on carbon or a nitrogen atom if the resulting compound is stable. The nitrogen atom in the heterocycle is optionally quaternized. As a preferred embodiment, when the total number of S and O atoms contained in a heterocycle exceeds 1, these heteroatoms are not adjacent to each other. As another preferred embodiment, the total number of S and O atoms in a heterocycle is no more than 1. As used herein, the term "aromatic heterocyclic group" or "heteroaryl" refers to a stable 5-, 6-, 7-membered monocycle or bicycle, or 7-, 8-, 9- or 10-membered bicyclic heteroaromatic ring, which contains carbon atoms and 1, 2, 3 or 4 heteroatom(s) in the ring selected independently from the group consisting of N, O and S. The nitrogen atom can be substituted or unsubstituted (i.e. N or NR, wherein R is H or any other substituent that has been defined herein). The nitrogen and sulfur atoms may optionally be oxidized (i.e., NO and S(O)p, wherein p is 1 or 2). It is worth noted that the total number of S and O atoms in the heteroaromatic ring is no more than 1. Bridged rings are also included in the definition of a heterocycle. When one or more atom(s) (i.e. C, O, N, or S) are connected to two nonadjacent carbon atoms or nitrogen atoms, a bridged ring is formed. A preferred bridged ring includes, but not limited to, one carbon atom, two carbon atoms, one nitrogen atom, two nitrogen atoms and one carbon-nitrogen group. It is worth noted that a bridge always converts a monocyclic ring into a tricyclic ring. In a bridged ring, the substituent in the ring may also locate on the bridge.

Examples of heterocyclic compound include, but not limited to, acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thiophenoxazolyl, thiophenothiazolyl, thiophenoimidazolyl, thienyl, triazinyl, 1,2,3-triazolyl, 1,2,4-triazolyl, 1,2,5-triazolyl, 1,3,4-triazolyl and xanthenyl. Fused ring and spiro ring compounds are also included.

Unless otherwise specified, the term "hydrocarbyl" or its specific concept (such as alkyl, alkenyl, alkynyl, aryl, etc.), as used by itself or as a part of another substituent refers to a linear, branched or cyclic hydrocarbon atomic group, or a combination thereof, which may be fully saturated (such as alkyl), mono- or polyunsaturated (such as alkenyl, alkynyl, or aryl), may be mono- or polysubstituted, may be mono- (such as methyl), di- (such as methylene) or multivalent (such as methine), and may include di- or multivalent atomic groups, having a designated number of carbon atoms (for example, $C_1$-$C_{12}$ means 1 to 12 carbons, and $C_{1-12}$ is selected from the group consisting of $C_1$, $C_2$, $C_3$, $C_4$, $C_5$, $C_6$, $C_7$, $C_8$, $C_9$, $C_{19}$, $C_{11}$ and $C_{12}$; and $C_{3-12}$ is selected from the group consisting of $C_3$, $C_4$, $C_5$, $C_6$, $C_7$, $C_8$, $C_9$, $C_{10}$, $C_{11}$ and $C_{12}$). "Hydrocarbyl" includes, but not limited to, aliphatic hydrocarbyl including linear and cyclic aliphatic hydrocarbyls, and specifically including but not limited to alkyl, alkenyl and alkynyl, as well as aromatic hydrocarbyl including but not limited to 6- to 12-membered aromatic hydrocarbyls, such as benzene and naphthalene. In some embodiments, the term "hydrocarbyl" refers to linear or branched atomic groups, or a combination thereof, which may be fully saturated, mono- or polyunsaturated and may include di- and multivalent atomic groups. Non-limiting examples of saturated hydrocarbon atomic groups include, but not limited to, methyl, ethyl, n-propyl, isopropyl, n-butyl, tertiary butyl, isobutyl, sec-butyl, cyclohexyl, (cyclohexyl)methyl, cyclopropyl methyl, and the homologues or isomers of n-amyl, n-hexyl, n-heptyl, n-octyl and other atomic groups. An unsaturated hydrocarbyl includes one or more double bond(s) or triple bond(s) and examples thereof include, but not limited to, ethenyl, 2-propenyl, butenyl, crotyl, 2-isopentenyl, 2-(butadienyl), 2,4-pentadienyl, 3-(1,4-pentadienyl), acetenyl, 1- and 3-propinyl, 3-butynyl, and more advanced homologues and isomers.

Unless otherwise specified, the term "heterohydrocarbonyl" or its specific concepts (such as heteroalkyl, heteroalkenyl, heteroalkynyl, heteroaryl, etc.), as used by itself or combined with another term, refers to a stable linear, branched or cyclic hydrocarbon atomic group, or a combination thereof, which consists of a certain number of carbon atoms and at least one heteroatom. In some embodiments, the term "heteroalkyl", as used by itself or combined with another term, refers to a stable linear, branched hydrocarbon atomic group, or a combination thereof, which consists of a certain number of carbon atoms and at least one heteroatom. In a typical embodiment, the heteroatom is selected from the group consisting of B, O, N and S, wherein the nitrogen and sulfur atoms are optionally oxidized, and the nitrogen atom is optionally quaternized. The heteroatom or heteroatomic group may be located in any internal position of the heterohydrocarbonyl, including the position where hydrocarbonyl is attached to the remainder of the molecule. However, the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms are adjacent, such as —$CH_2$—NH—$OCH_3$.

Unless otherwise indicated, the term "cyclohydrocarbyl", "heterocyclic hydrocarbyl" or its specific concepts (such as aryl, heteroaryl, cycloalkyl, heterocycloalkyl, cycloalkenyl, heterocycloalkenyl, cycloalkynyl, heterocycloalkynyl and the like), as used by itself or combined with other terms, refers to a cyclized "hydrocarbyl" or "heterohydrocarbyl", respectively. In addition, in terms of heterohydrocarbyl or heterocyclohydrocarbyl, such as heteroalkyl or heterocycloalkyl, the heteroatom may occupy the position at which the heterocycle is attached to the remainder of the molecule. Examples of cyclohydrocarbyl include, but not limited to, cyclopentyl, cyclohexyl, 1-cyclohexenyl, 3-cyclohexenyl, cycloheptyl, etc. Non-limiting examples of heterocyclic groups include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuran-indol-3-yl, thiophane-2-yl, thiophane-3-yl, 1-piperazinyl and 2-piperazinyl.

Unless otherwise indicated, the term "alkyl" refers to a linear or branched saturated hydrocarbyl, which may be mono-substituted (such as —CH$_2$F) or poly-substituted (such as —CF$_3$), and may be monovalent (such as methyl), divalent (such as methylene) or multivalent (such as methenyl). Examples of alkyl include methyl (Me), ethyl (Et), propyl (such as n-propyl and isopropyl), butyl (such as n-butyl, isobutyl, s-butyl, t-butyl), amyl (such as n-amyl, isoamyl, neo-amyl), etc.

Unless otherwise indicated, "alkenyl" refers to an alkyl group that comprises one or more carbon-carbon double bond(s) at any site of a chain, which may be mono- or polysubstituted, and may be mono-, di- or multivalent. Examples of alkenyl include ethenyl, propenyl, butenyl, pentenyl, hexenyl, butadienyl, pentadienyl, hexadienyl, etc.

Unless otherwise indicated, "alkynyl" refers to an alkyl group that comprises one or more carbon-carbon triple bonds at any site of a chain, which may be mono- or polysubstituted, and may be mono-, di- or multivalent. Examples of alkynyl include acetenyl, propinyl, butynyl, pentynyl, etc.

Unless otherwise indicated, cycloalkyl include any stable cyclic or polycyclic hydrocarbyl where all carbon atoms are saturated, which may be mono- or polysubstituted, and may be mono-, di- or multivalent. Examples of such cycloalkyl include, but not limited to, cyclopropyl, norborneol alkyl, [2.2.2] biocyclooctane, [4.4.0] biocyclodecane, etc.

Unless otherwise indicated, cycloalkenyl includes any stable cyclic or polycyclic hydrocarbyl comprising one or more unsaturated carbon-carbon double bonds at any site of the ring, which may be mono- or polysubstituted, and may be mono-, di- or multivalent. Examples of such cycloalkenyl include, but not limited to, cyclopentenyl, cyclohexenyl, etc.

Unless otherwise indicated, cycloalkynyl includes any stable cyclic or polycyclic hydrocarbyl comprising one or more carbon-carbon triple bond(s) at any site of the ring, which may be mono- or polysubstituted, and mono-, di- or multivalent.

Unless otherwise indicated, the term "halogen", as used by itself or as a part of another substituent group, refers to a fluorine, chlorine, bromine or iodine atom. In addition, the term "halogenated alkyl" is intended to include monohalogenated alkyl and polyhalogenated alkyl. For example, the term "halogenated (C$_1$-C$_4$) alkyl" is intended to include, but not limited to, trifluoromethyl, 2,2,2-trifluoroethyl, 4-chlorobutyl and 3-brominepropyl, etc. Unless otherwise indicated, examples of halogenated alkyl include, but not limited to, trifluoromethyl, trichloromethyl, pentafluoroethyl and pentachloroethyl.

The "alkyloxy" represents an alkyl group as described above having the indicated number of carbon atoms attached through an oxygen bridge. C$_{1-6}$ alkoxy includes alkoxy groups of C$_1$, C$_2$, C$_3$, C$_4$, C$_5$ and C$_6$. Examples of alkoxy include, but not limited to, methoxy, ethoxy, n-propoxy, i-propoxy, n-butoxy, s-butoxy, t-butoxy, n-pentoxy, and s-pentoxy.

Unless otherwise specified, the term "aryl" refers to a polyunsaturated aromatic hydrocarbon substituent, which may be mono- or multisubstituted, may be mono-, bi or multivalent, and may be mono- or polycyclic (such as 1 to 3 rings, wherein at least one ring is aromatic) which are fused together or connected by a covalent linkage. The term "heteroaryl" refers to an aryl (or ring) containing 1 to 4 heteroatoms. In an exemplary embodiment, the heteroatom is selected from the group consisting of B, N, O, and S, wherein the nitrogen and sulfur atoms are optionally oxidized, and the nitrogen atom is optionally quaternized. The heteroaryl group may be attached to the rest part of the molecule via a heteroatom. Non-limiting examples of an aryl or a heteroaryl include phenyl, naphthyl, biphenyl, pyrrolyl, pyrazolyl, imidazolyl, pyrazinyl, oxazolyl, phenyloxazolyl, isoxazolyl, thiazolyl, furanyl, thienyl, pyridyl, pyrimidinyl, benzothiazolyl, purinyl, benzoimidazolyl, indolyl, isoquinolyl, quinoxalyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

Unless otherwise specified, the aryl, when used in combination with other terms (e.g. aryloxy, arylthio, aralkyl), includes the aryl and heteroaryl ring as defined above. Therefore, the term "aralkyl" is intended to include those atomic groups where an aryl group is attached to an alkyl group (e.g. benzyl, phenyl ethyl, pyridyl methyl and the like), including those alkyls where a carbon atom(s) (such as methylene) has been replaced by, such as, an oxygen atom, such as phenoxy methyl, 2-pyridyloxymethyl-3-(1-naphthoxy) propyl, etc.

The term "leaving group" refers to a functional group or atom which can be displaced by another functional group or atom in a substitution reaction, such as a nucleophilic substitution reaction. For example, representative leaving groups include trifluoromethanesulfonate; chloro, bromo and iodo groups; and sulfonic ester groups, such as mesylate, tosylate, brosylate, nosylate and the like; acyloxy groups, such as acetoxy, trifluoroacetoxy and the like.

The term "protecting group" includes, but not limited to, "amino-protecting group", "hydroxyl-protecting group", or "mercapto-protecting group". The term "amino-protecting group" refers to a protecting group suitable for preventing undesired reactions at an amino group. Representative amino-protecting groups include, but not limited to, formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS) and the like. The term "hydroxyl-protecting group" refers to a protecting group suitable for preventing undesired reactions at a hydroxyl group. Representative hydroxyl-protecting groups include, but not limited to, alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and the like.

The compound of the present disclosure can be prepared through many synthetic methods well-known to the person skilled in the art, including the specific embodiments listed below, its combination with other chemical synthetic methods and the equivalent alternative methods well-known to the person skilled in the art. The preferred embodiments include, but not limited to, the embodiments of the present disclosure.

The solvents used in the present disclosure are available commercially. The present disclosure adopts the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents 3-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, which is an amine-protecting group; BOC represents tert-butoxycarbonyl, which is an amine-protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluene sulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; DMP represents Dimethyl o-phthalate; Xantphos represents 4,5-bisdiphenylphosphino-9,9-dimethylxanthene; Pd$_2$(dba)$_3$ represents tris(dibenzylideneacetone)dipalladium; XantPhos represents 4,5-bisdiphenylphosphino-9,9-dimethylxanthene; EGTA represents ethylene glycol-bis(2-aminoethylether)-N,N,N',N'-tetraacetic acid; DIEA represents N,N-diisopropylethylamine; Xantphos represents 4,5-bisdiphenylphosphino-9,9-dimethylxanthene; AIBN represents azodiisobutyronitrile; Pd$_2$(dba)$_3$ represents tris(dibenzylideneacetone)dipalladium; Pd(dppf)Cl$_2$ represents [1,1'-bis(diphenylphosphino)ferrocene]palladium dichloride; BnBr represents benzyl bromide; DMAP represents 4-dimethylaminopyridine; and EGTA represents ethylene glycol-bis(2-aminoethylether)-N,N,N',N'-tetraacetic acid.

Compounds are named manually or by software ChemDraw®, and commercially available compounds are named in accordance with suppliers' catalogue.

DETAILED DESCRIPTION

Although the present disclosure is described in detail below by reference to the examples, it should be understood that the present disclosure is not limited thereto. While the present disclosure has been described in detail herein and specific embodiments of the present disclosure have been disclosed herein, it will be apparent to those skilled in the art that various changes and modifications may be made to the specific embodiments of the present disclosure without departing from the spirit and scope of the present disclosure.

Fragment WXBB-1

Synthetic Route:

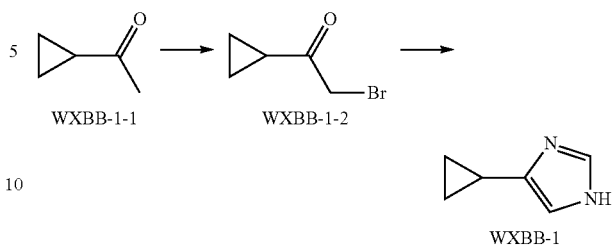

Step 1: Synthesis of Compound WXBB-1-2

Compound WXBB-1-1 (50.00 g, 594.39 mmol, 58.82 mL, 1.00 eq) was dissolved in methanol (500.00 mL), and liquid bromine (94.99 g, 594.39 mmol, 30.64 mL, 1.00 eq) was added dropwise at 0° C. The mixture was warmed to 20° C. and reacted for 2 hours. After the reaction was completed, the reaction solution was added with water (500 mL), and extracted with methyl t-butyl ether (500 mL*3). The organic phases were combined, washed successively with saturated sodium bicarbonate (200 mL) and saturated brine (200 mL), dried over anhydrous sodium sulfate, and filtered. The filtrate was dried on a rotary evaporator under reduced pressure to obtain compound WXBB-1-2 (200.00 g, crude) as a colorless oil, $^1$H NMR (400 MHz, CHLOROFORM-d) δ ppm 3.96-4.10 (m, 2H) 2.17-2.23 (m, 1H) 1.09-1.17 (m, 2H) 0.95-1.05 (m, 2H).

Step 2: Synthesis of Compound WXBB-1

Compound WXBB-1-2 (96.89 g, 594.38 mmol, 1.00 eq) and formamidine acetate (309.40 g, 2.97 mol, 5.00 eq) were dissolved in 2-methoxyethanol (1.00 L). The mixture was reacted at 135° C. for 16 hours under a nitrogen atmosphere. After the reaction was completed, the reaction solution was concentrated to remove 2-methoxyethanol. The reaction solution was added with water (1000 mL), adjusted to pH=2~3 with concentrated hydrochloric acid (50 mL) and washed with dichloromethane (1000 mL*3). The aqueous layer was adjusted to pH=9~10 by adding sodium carbonate, and extracted with dichloromethane (1000 mL*8). The organic phases were combined, dried over anhydrous sodium sulfate, and filtered, and the filtrate was concentrated. Compound WXBB-1 (50.00 g, 462.36 mmol, 77.79% yield) was obtained as a brown oil, $^1$H NMR (400 MHz, CHLOROFORM-d) δ=7.67-7.43 (m, 1H), 6.75 (s, 1H), 1.90-1.73 (m, 1H), 0.85 (q, J=5.9 Hz, 2H), 0.74-0.55 (m, 2H).

Fragment WXBB-2

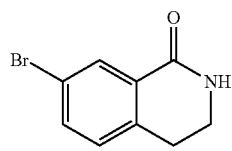 [SMILES: O=C1NCCc2ccc(Br)cc21]

Synthetic Route:

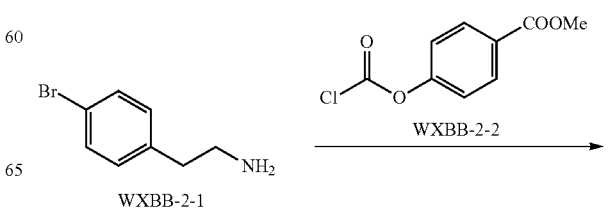

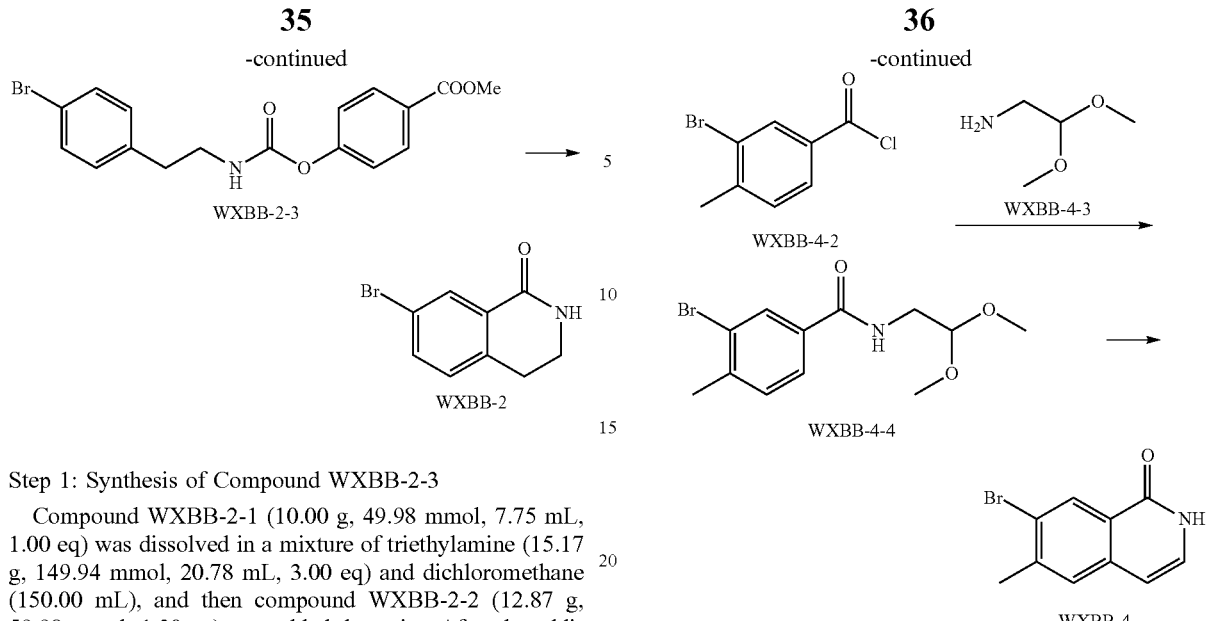

Step 1: Synthesis of Compound WXBB-2-3

Compound WXBB-2-1 (10.00 g, 49.98 mmol, 7.75 mL, 1.00 eq) was dissolved in a mixture of triethylamine (15.17 g, 149.94 mmol, 20.78 mL, 3.00 eq) and dichloromethane (150.00 mL), and then compound WXBB-2-2 (12.87 g, 59.98 mmol, 1.20 eq) was added dropwise. After the addition, the mixture was placed at 0° C. and reacted for 2 hours. After the reaction was completed, the reaction solution was concentrated, and the mixture was added with water (300 mL) and then extracted with dichloromethane (300 mL*3). The organic phases were combined and concentrated. Crude product WXBB-2-3 (15.80 g, crude) was obtained as a white solid, MS m/z: 382 [M+H]+.

Step 2: Synthesis of Compound WXBB-2

Compound WXBB-2-3 (13.80 g, 36.49 mmol, 1.00 eq) was dissolved in dichloromethane (400.00 mL), and then trifluoromethanesulfonic acid (54.76 g, 364.90 mmol, 32.21 mL, 10.00 eq) was added. After the addition, the mixture was first reacted at 0° C. for 2 hours, and then reacted at 20° C. for 16 hours. After the reaction was completed, the reaction solution was neutralized with sodium hydroxide (100 mL, 0.5N), then diluted with water (200 mL) and extracted with dichloromethane (200 mL*2). The organic phase was dried over anhydrous magnesium sulfate, filtered and concentrated. Compound WXBB-2 (11.20 g, crude) was obtained as a purple solid. MS m/z: 226 [M+H]+.

Fragment WXBB-4

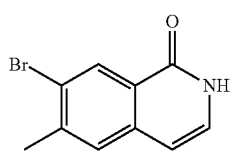

Synthetic Route:

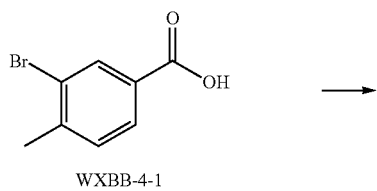

Step 1: Synthesis of Compound WXBB-4-2

Compound WXBB-4-1 (15.00 g, 69.75 mmol, 1.00 mL, 1.00 eq) was dissolved in thionyl chloride (248.96 g, 2.09 mol, 151.81 mL, 30.00 eq). The mixture was reacted at 90° C. for 2 hours under a nitrogen atmosphere. The reaction solution was concentrated to obtain compound WXBB-4-2 (17.00 g, crude) as a brown oil.

Step 2: Synthesis of Compound WXBB-4-4

Compound WXBB-4-3 (7.34 g, 69.77 mmol, 7.57 mL, 1.00 eq) and triethylamine (21.18 g, 209.31 mmol, 29.01 mL, 3.00 eq) were dissolved in dichloromethane (180 mL). Then compound WXBB-4-2 (16.29 g, 69.77 mmol, 1.00 eq) was dissolved in dichloromethane (20 mL) and added dropwise to the reaction solution at 0° C. under a nitrogen atmosphere, followed by reaction at 20° C. for 16 hours. After the reaction was completed, the reaction solution was added with water (300 mL), and extracted with dichloromethane (300 mL). The organic phases were combined, washed successively with water (300 mL) and saturated brine (300 mL), dried over anhydrous sodium sulfate, filtered and concentrated. Compound WXBB-4-4 (21.00 g, 69.50 mmol, 99.61% yield) was obtained as brown oil. $^1$H NMR (400 MHz, CHLOROFORM-d) ppm 2.365 (s, 3H) 3.303-3.366 (d, 6H) 3.510-3.537 (m, 2H) 4.398-4.424 (m, 1H) 6.222 (s, 1H) 7.194-7.207 (d, 1H) 7.522-7.542 (d, 1H) 7.877 (s, 1H).

Step 3: Synthesis of Compound WXBB-4

Compound WXBB-4-4 (21.00 g, 69.50 mmol, 1.00 eq) was dissolved in concentrated sulfuric acid (100.00 mL, purity: 98%) and the mixture was reacted at 100° C. for 16 hours. After the reaction was completed, the reaction solution was cooled to room temperature and added slowly into water (500 mL), filtered, and the filter cake was collected and dried. Compound WXBB-4 (15.00 g, crude) was obtained as a red solid, $^1$H NMR (400 MHz, DMSO-d6) δ ppm 2.431 (s, 3H) 2.488 (s, 2H) 6.463-6.481 (d, 1H) 6.697-6.716 (d, 1H) 7.176-7.194 (d, 1H) 7.287-7.305 (d, 1H) 7.425-7.445 (d, 1H) 7.615 (s, 1H) 8.075-8.095 (d, 1H) 8.249 (s, 1H) 8.296 (s, 1H) 11.308-11.424 (d, 2H). MS m/z: 238.0 [M+H]+.

Fragment WXBB-5

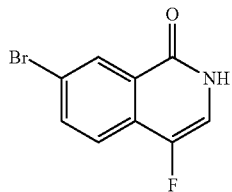 [SMILES: O=c1[nH]cc(F)c2ccc(Br)cc12]

Synthetic Route:

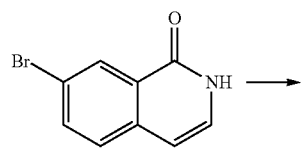

WXBB-5-1

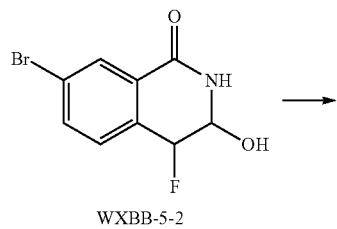

WXBB-5-2

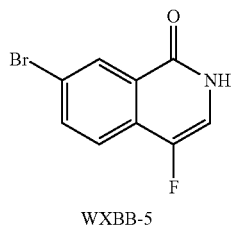

WXBB-5

Step 1: Synthesis of Compound WXBB-5-2

Compound WXBB-5-1 (5.00 g, 22.32 mmol, 1.00 eq) and 1-chloromethyl-4-fluoro-1,4-diazoniabicyclo[2.2.2]octane bis(tetrafluoroborate) (8.70 g, 24.55 mmol, 1.10 eq) were dissolved in acetonitrile (200.00 mL) and water (3.00 mL). The mixture was reacted at 20° C. for 96 hours. The reaction solution was added with water (300 mL), and extracted with dichloromethane (DCM) (300 mL). The organic phases were combined, washed with saturated brine (30 mL), dried over anhydrous sodium sulfate, and filtered. The filtrate was dried on a rotary evaporator under reduced pressure. The obtained crude product was slurried with ethyl acetate (20 mL) at 15° C. for 0.5 hour, filtered and the filter cake was dried. Compound WXBB-5-2 (3.00 g, 11.54 mmol, 51.68% yield) was obtained as a yellow solid, $^1$H NMR (400 MHz, DMSO-d6) δ ppm 3.11 (d, J=6.78 Hz, 1H) 3.36 (br. s., 1H) 5.07 (d, J=4.27 Hz, 1H) 5.75-5.98 (m, 1H) 7.44 (d, J=8.03 Hz, 1H) 7.79-8.04 (m, 3H) 8.87 (br. s., 1H).

Step 2: Synthesis of Compound WXBB-5

Compound WXBB-5-2 (3.00 g, 11.54 mmol, 1.00 eq) and methanesulfonic acid (7.76 g, 80.75 mmol, 5.75 mL, 7.00 eq) were dissolved in dichloromethane (50.00 mL). The mixture was reacted at 20° C. for 16 hours. After the reaction was completed, the reaction solution was added with dichloromethane (15 mL), washed successively with water (20 mL) and saturated brine (20 mL), dried over anhydrous sodium sulfate, and filtered. The filtrate was dried on a rotary evaporator under reduced pressure. The obtained crude product was slurried with ethyl acetate (10 mL) at 15° C. for 0.5 hour, filtered and the filter cake was dried. Compound WXBB-5 (2.50 g, 10.33 mmol, 89.50% yield) was obtained as a red solid, $^1$H NMR (400 MHz, DMSO-d6) ppm 7.46 (d, J=5.77 Hz, 1H) 7.71 (d, J=8.53 Hz, 1H) 8.01 (dd, J=8.53, 1.76 Hz, 1H) 8.30 (s, 1H) 11.37 (br. s., 1H).

Fragment WXBB-6

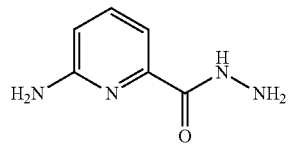 [SMILES: NNC(=O)c1cccc(N)n1]

Synthetic Route:

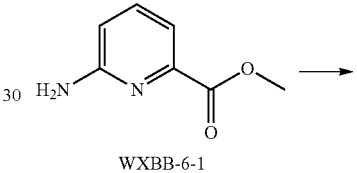

WXBB-6-1

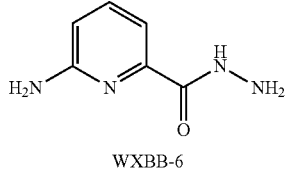

WXBB-6

Step 1: Synthesis of Compound WXBB-6

Compound WXBB-6-1 (20.00 g, 131.45 mmol, 1.00 eq) was dissolved in methanol (200.00 mL) to give a light yellow solution, and then hydrazine hydrate (19.74 g, 394.35 mmol, 19.17 mL, 3.00 eq) was added slowly. The reaction system was stirred at 75° C. for 1.5 hours. After the reaction was completed, the reaction solution was cooled to room temperature and filtered. The filter cake was washed with ethyl acetate (50 mL*2), and dried on a rotary evaporator under reduced pressure. Compound WXBB-6 (20.00 g, 131.45 mmol, 100.00% yield) was obtained as a white solid, $^1$H NMR (400 MHz, DMSO-d6) δ ppm 4.48 (br s, 2H) 6.09 (s, 2H) 6.60 (d, J=8.28 Hz, 1H) 7.11 (d, J=7.03 Hz, 1H) 7.51 (t, J=7.78 Hz, 1H) 9.19 (br s, 1H).

Fragment WXBB-7

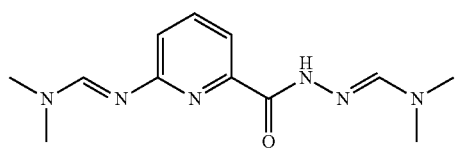

Synthetic Route:

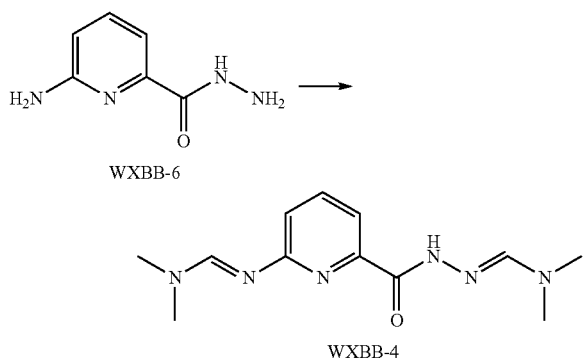

Step 1: Synthesis of Compound WXBB-7

WXBB-6 (49.00 g, 322.05 mmol, 1.00 eq) was added to dimethylformamide dimethyl acetal (500.00 mL). The system was refluxed with stirring at 110° C. for 18 hours. After the reaction was completed, the reaction solution was dried on a rotary evaporator under reduced pressure to obtain a crude product. To the crude product was added ethyl acetate (500 mL), stirred for 20 min at room temperature and filtered. The filter cake was dried to give product. WXBB-7 (65.00 g, 247.80 mmol, 76.94% yield) was obtained as a yellow solid, $^1$H NMR (400 MHz, CHLOROFORM-d) δ ppm 2.95 (s, 6H) 3.11 (d, J=6.27 Hz, 6H) 7.03 (dd, J=7.91, 0.88 Hz, 1H) 7.67 (t, J=7.78 Hz, 1H) 7.78 (dd, J=7.40, 0.88 Hz, 1H) 8.15 (s, 1H) 8.34 (s, 1H) 9.95 (s, 1H).

Fragment WXBB-8

Synthetic Route:

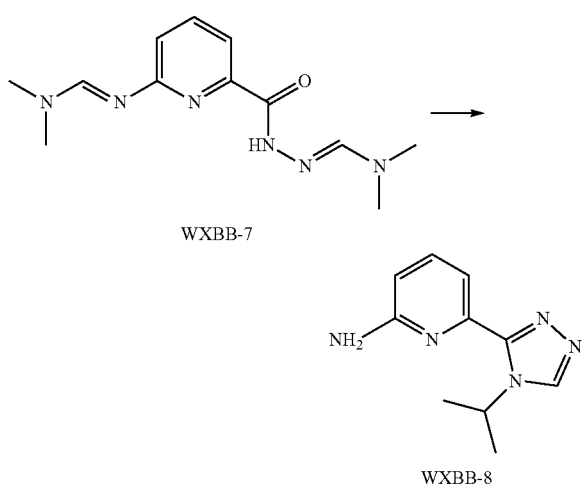

Step 1: Synthesis of Compound WXBB-8

WXBB-7 (65.00 g, 247.80 mmol, 1.00 eq) was dissolved in a mixture of acetonitrile (400.00 mL) and acetic acid (100.00 mL), and isopropyl amine (73.24 g, 1.24 mol, 106.14 mL, 5.00 eq) was added. The system was stirred at 80° C. for 20 hours. After the reaction was completed, the reaction solution was allowed to stand, and filtered. The filtrate was dried on a rotary evaporator under reduced pressure, added with water (200 mL), adjusted to pH 9-10 with sodium hydroxide (200 mL, 1N), and extracted with ethyl acetate (500 mL*6). The organic phases were combined, and evaporated on a rotary evaporator under reduced pressure until a large amount of yellow solid precipitated out, allowed to stand and filtered. The filter cake was washed with cold ethyl acetate (50 mL) and dried to obtain product WXBB-8 (21.00 g, 101.30 mmol, 40.88% yield, 98.043% purity) as a light yellow crystal, $^1$H NMR (400 MHz, CHLOROFORM-d) δ ppm 1.53 (d, J=6.78 Hz, 6H) 4.50 (br s, 2H) 5.62 (spt, J=6.78 Hz, 1H) 6.57 (dd, J=7.40, 1.63 Hz, 1H) 7.51-7.65 (m, 2H) 8.32 (s, 1H).

Fragment WXBB-9

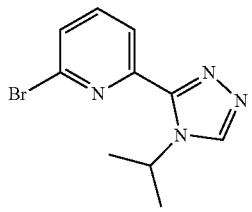

Synthetic Route:

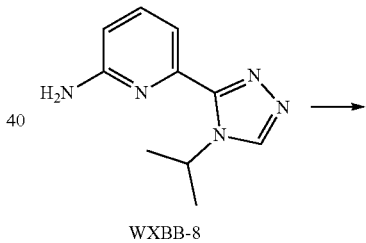

Step 1: Synthesis of Compound WXBB-9

Compound WXBB-8 (10.00 g, 48.71 mmol, 98.99% purity, 1.00 eq) was dissolved in hydrogen bromide (92.90 g, 539.71 mmol, 62.35 mL, 47% purity, 11.08 eq), and then liquid bromine (46.62 g, 291.77 mmol, 15.04 mL, 5.99 eq) was added dropwise slowly at 0° C. Then sodium nitrite (18.72 g, 271.31 mmol, 14.74 mL, 5.57 eq) was dissolved in water (12.60 mL), and then added to the mixture. The system was gradually warmed to 25° C. and stirred for 16 hours. After the reaction was completed, the reaction solution was poured into water (300 mL), adjusted to pH 7-8 with sodium hydroxide and extracted with dichloromethane (300 mL*2).

The organic phases were combined, washed successively with water (300 mL) and saturated brine (300 mL), dried over anhydrous magnesium sulfate, and filtered. The filtrate was dried on a rotary evaporator under reduced pressure to obtain a crude product. The crude product was purified by a column. Compound WXBB-9 (6.00 g, 20.40 mmol, 41.88% yield, 90.81% purity) was obtained as a yellow oil. $^1$H NMR (400 MHz, CHLOROFORM-d) δ=8.370 (s, 1H), 8.306-8.287 (d, 1H), 7.718-7.679 (m, 1H), 7.545-7.509 (t, 1H), 5.634-5.550 (m, 1H), 1.577-1.561 (d, 6H). MS m/z: 268.8 [M+H]+.

Fragment WXBB-10

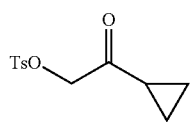 [SMILES: Cc1ccc(S(=O)(=O)OCC(=O)C2CC2)cc1]

Synthetic Route:

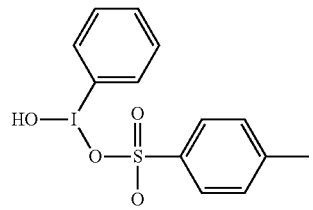

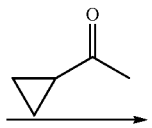

WXBB-10-1

WXBB-10

Step 1: Synthesis of Compound WXBB-10

Compound WXBB-10-1 (200 g, 509.93 mmol, 1.00 eq) was dissolved in acetonitrile (1500 mL), and then cyclopropyl methyl ketone (42.89 g, 509.93 mmol, 50.46 mL, 1.00 eq) was added. The reaction system was stirred at 75° C. for 3 hours. The reaction solution was cooled to room temperature, combined, evaporated by rotary evaporation to remove the solvent, added with water (100 mL), and extracted with dichloromethane (100 mL*3). The organic phase was washed with saturated sodium chloride (100 mL), dried over Na$_2$SO$_4$, and filtered. The filtrate was dried on a rotary evaporator under reduced pressure. The obtained product was slurried with n-hexane (800 mL) at 25° C. for 2 hours, filtered, and the filter cake was dried to give compound WXBB-10. $^1$H NMR (400 MHz, DMSO-d6) ppm 0.82-0.87 (m, 2H) 0.91-0.96 (m, 2H) 2.02-2.10 (m, 1H) 2.43 (s, 3H) 4.99 (s, 2H) 7.48 (s, 1H) 7.50 (s, 1H) 7.81 (s, 1H) 7.83 (s, 1H).

Fragment WXBB-11

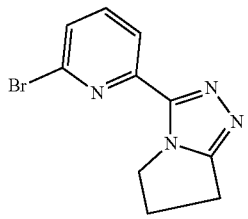

Synthetic Route:

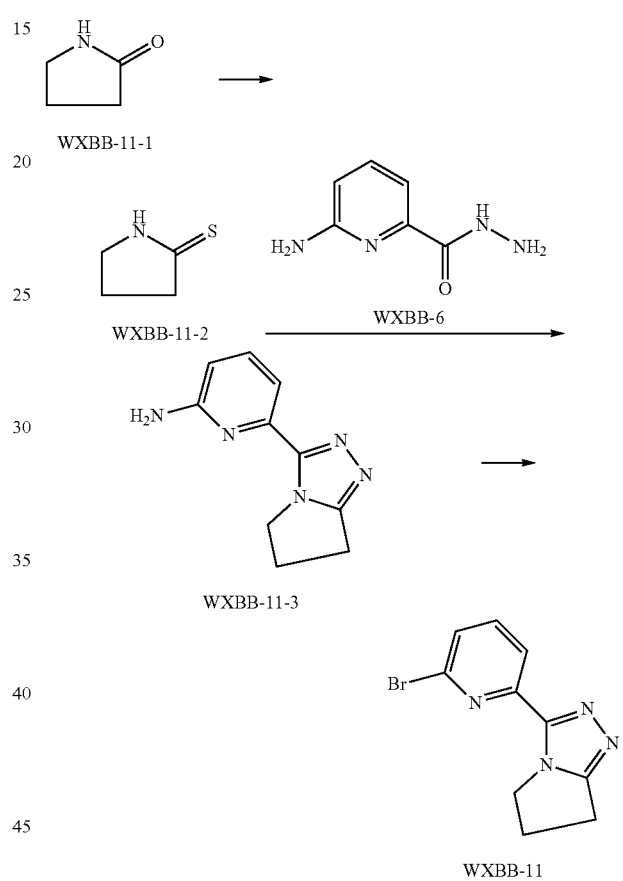

Step 1: Synthesis of Compound WXBB-11-2

Phosphorus pentasulfide (52.24 g, 235.02 mmol, 24.99 mL, 2.00 eq) was dissolved in tetrahydrofuran (300.00 mL), and sodium carbonate (12.45 g, 117.51 mmol, 1.00 eq) was slowly added. The system was stirred at 20° C. for 1 hour. Compound WXBB-11-1 was added to the system. The system was warmed to 60° C. and stirred for 48 hours. The reaction solution was cooled to room temperature and filtered. The filtrate was dried on a rotary evaporator under reduced pressure to obtain a crude product. The crude product was purified by a column (0~60% EA/PE). Compound WXBB-11-2 (6.20 g, 61.28 mmol, 52.15% yield) was obtained as a white solid, $^1$H NMR (400 MHz, CHLOROFORM-d) δ ppm 2.166-2.249 (m, 2H) 2.896-2.936 (m, 2H) 3.664-3.699 (m, 2H) 8.676 (s, 1H).

Step 2: Synthesis of Compound WXBB-11-3

Compound WXBB-11-2 (10.47 g, 68.80 mmol, 1.20 eq) and compound WXBB-6 (400.00 mg, 3.95 mmol, 1.00 eq) were dissolved in cyclohexanol (10.00 mL). The system was stirred at 170° C. for 6 hours under the protection of nitrogen atmosphere. The reaction solution was cooled to room temperature, diluted with water (50 mL), and extracted with ethyl acetate (50 mL*3). The organic phases were combined, washed successively with water (100 mL) and saturated brine (100 mL), dried over anhydrous magnesium sulfate, and filtered. The filtrate was concentrated under reduced pressure to obtain a crude product. The crude product was purified by a column (0~10% MeOH/DCM). Compound WXBB-11-3 (600.00 mg, 2.89 mmol, 73.10% yield, 96.84% purity) was obtained as a yellow solid, $^1$H NMR (400 MHz, DMSO-d6) δ ppm 2.65 (quin, J=7.34 Hz, 2H) 2.80-2.87 (m, 2H) 4.26-4.34 (m, 2H) 6.59 (dd, J=8.28, 0.75 Hz, 1H) 7.09 (dd, J=7.28, 0.75 Hz, 1H) 7.20 (dd, J=7.28, 0.75 Hz, 1H) 7.48 (q, J=8.03 Hz, 2H). MS m/z: 202.0 [M+H]+.

Step 3: Synthesis of Compound WXBB-11

Compound WXBB-11-3 (600.00 mg, 2.98 mmol, 1.00 eq) was dissolved in hydrogen bromide (5.64 g, 32.78 mmol, 3.79 mL, 47% purity, 11.00 eq), and then liquid bromine (2.86 g, 17.88 mmol, 922.58 μL, 6.00 eq) was added dropwise at 0° C. Sodium nitrite (1.23 g, 17.88 mmol, 971.43 μL, 6.00 eq) was dissolved in water (1.00 mL) and added to the reaction system. The system was gradually warmed to 25° C. and stirred for 16 hours. The reaction solution was poured into water (50 mL), adjusted to pH 8 with sodium hydroxide (2N, 20 mL) and extracted with dichloromethane (50 mL*2). The organic phase was washed successively with water (100 mL) and saturated brine (100 mL), dried over anhydrous magnesium sulfate, and filtered. The filtrate was dried on a rotary evaporator under reduced pressure to obtain a crude product. The crude product was purified by a column. Product compound WXBB-11 (200.00 mg, 575.84 μmol, 19.32% yield, 76.33% purity) was obtained as a yellow solid, $^1$H NMR (400 MHz, CHLOROFORM-d) δ ppm 2.80-2.87 (m, 2H) 3.02-3.09 (m, 2H) 4.42-4.49 (m, 2H) 7.47-7.52 (m, 1H) 7.67 (t, J=7.78 Hz, 1H) 8.22-8.27 (m, 1H). MS m/z: 67.0 [M+H]+.

Fragment WXBB-12

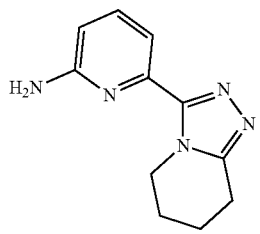 [SMILES: Nc1cccc(-c2nnc3n2CCCC3)n1]

Synthetic Route:

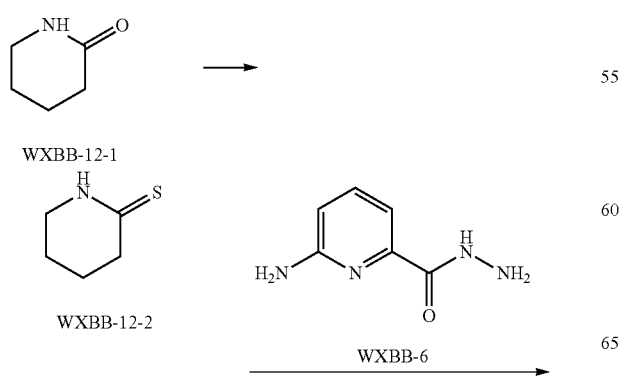

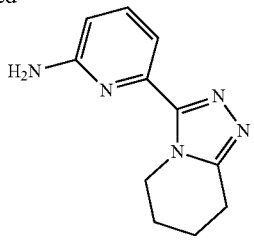

WXBB-12

Step 1: Synthesis of Compound WXBB-12-2

Phosphorus pentasulfide (56.06 g, 252.19 mmol, 26.82 mL, 1.00 eq) was added to acetonitrile (500.00 mL) to form a suspension, and then triethylamine (25.52 g, 252.19 mmol, 34.96 mL, 1.00 eq) was slowly added. The system was stirred at room temperature for 1 hour, and WXBB-12-1 (25.00 g, 252.19 mmol, 1.00 eq) was added. The system was stirred at 60° C. for 19 hours. The reaction solution was poured into sodium hypochlorite (200 mL), concentrated under reduced pressure to remove acetonitrile and extracted with dichloromethane (200 mL*3). The organic phases were combined, washed successively with water (400 mL) and saturated brine (400 mL), dried over anhydrous magnesium sulfate, and filtered. The filtrate was dried on a rotary evaporator under reduced pressure to obtain a crude product. The crude product was purified by a column (0~10% MeOH/DCM). Compound WXBB-12-2 (10.00 g, 86.81 mmol, 34.42% yield) was obtained as a yellow solid, $^1$H NMR (400 MHz, DMSO-d6) δ ppm 1.53-1.71 (m, 4H) 2.57-2.67 (m, 2H) 3.13 (br s, 1H) 3.18 (td, J=5.77, 2.51 Hz, 1H).

Step 2: Synthesis of Compound WXBB-12

Compound WXBB-12-2 (6.00 g, 52.08 mmol, 1.00 eq) and compound WXBB-6 (8.72 g, 57.29 mmol, 1.10 eq) were dissolved in cyclohexanol (100.00 mL). The system was stirred at 170° C. for 6 hours under the protection of nitrogen atmosphere. The reaction solution was cooled to room temperature, diluted with water (200 mL), adjusted to pH 5 with hydrochloric acid (2N, 100 mL) and extracted with ethyl acetate (200 mL). The aqueous phase was adjusted to pH 9 with sodium hydroxide (2N, 100 mL) and extracted with ethyl acetate (200 mL*2). The organic phase was washed successively with water (200 mL) and saturated brine (200 mL), dried over anhydrous magnesium sulfate, and filtered. The filtrate was concentrated under reduced pressure to obtain a crude product. The crude product was purified by a column (0~10% DCM/MeOH). Compound WXBB-12 (5.00 g, 17.50 mmol, 33.60% yield, 75.32% purity) was obtained as a brown solid. MS m/z: 216.0 [M+H]+.

Fragment WXBB-13

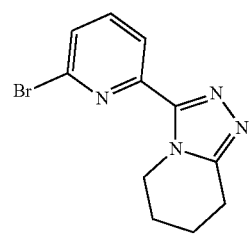

Synthetic Route:

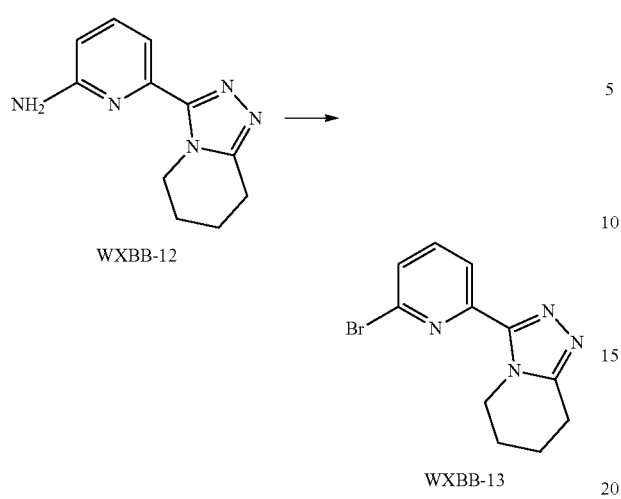

Step 1: Synthesis of Compound WXBB-13

Compound WXBB-12 (4.00 g, 14.00 mmol, 1.00 eq) (purity 75.32%) was dissolved in hydrogen bromide (26.50 g, 153.96 mmol, 17.79 mL, 47% purity, 11.00 eq), and then liquid bromine (13.42 g, 83.98 mmol, 4.33 mL, 6.00 eq) was added dropwise at 0° C. Sodium nitrite (5.79 g, 83.98 mmol, 4.56 mL, 6.00 eq) was dissolved in water (8.00 mL) and added to the system. The system was gradually warmed to 25° C. and stirred for 16 hours. The reaction solution was poured into water (100 mL), adjusted to pH 8 with sodium hydroxide (2N, 100 mL) and extracted with dichloromethane (100 mL*2). The organic phase was washed successively with water (100 mL) and saturated brine (100 mL), dried over anhydrous magnesium sulfate, and filtered. The filtrate was dried on a rotary evaporator under reduced pressure to obtain a crude product. The crude product was purified by a column (0~10% MeOH/DCM). Compound WXBB-13 (2.50 g, 8.96 mmol, 64.00% yield) was obtained as a brown solid, $^1$H NMR (400 MHz, METHANOL-d4) δ ppm 1.98-2.05 (m, 1H) 1.98-2.04 (m, 1H) 2.10 (br d, J=4.77 Hz, 2H) 3.07 (br t, J=6.27 Hz, 2H) 4.50-4.59 (m, 2H) 7.71 (d, J=8.03 Hz, 1H) 7.87 (t, J=7.78 Hz, 1H) 8.15 (d, J=7.78 Hz, 1H).

Fragment WXBB-14

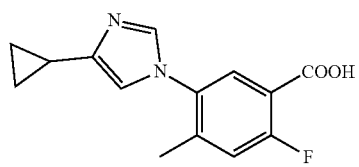 [SMILES: Cc1cc(F)c(C(=O)O)cc1-n1cnc(C2CC2)c1]

Synthetic Route:

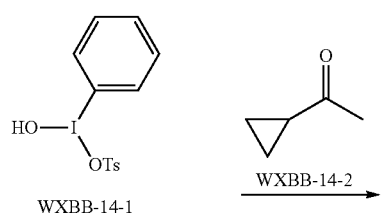

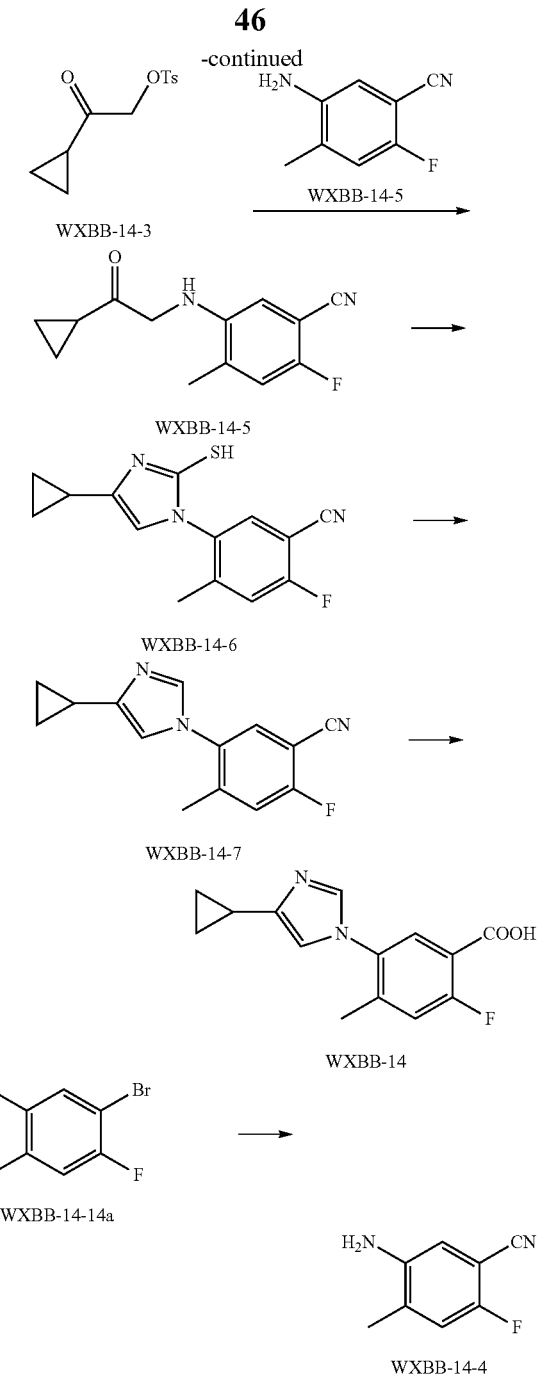

Step 1: Synthesis of Compound WXBB-14-3

WXBB-14-1 (50.00 g, 127.48 mmol, 1.00 eq) was dissolved in acetonitrile (500.00 mL), then WXBB-14-2 (12.87 g, 152.98 mmol, 15.14 mL, 1.20 eq) was added, and the mixture was reacted at 70° C. for 2 hours under the protection of nitrogen atmosphere. After the reaction was completed, the reaction solution was cooled to room temperature, dried on a rotary evaporator with a water pump at 40° C., then dissolved with dichloromethane (150 mL), and washed with water (75 mL*2). The organic phase was then concentrated to about 90 mL remaining, then n-hexane (75 mL*3) (to remove residual dichloromethane) was added to the organic phase to afford a white solid. The white solid was filtered, and the filter cake was washed with 180 mL of n-hexane and dried on a rotary evaporator. WXBB-14-3

(27.00 g, 106.17 mmol, 83.29% yield) was obtained as a white solid. $^1$H NMR (400 MHz, DMSO-$d_6$) δ ppm 0.79-0.86 (m, 2H) 0.88-0.97 (m, 2H) 1.99-2.10 (m, 1H) 2.42 (s, 3H) 4.98 (s, 2H) 7.49 (d, J=8.16 Hz, 2H) 7.82 (d, J=8.28 Hz, 2H), m/z=255.1 (M+1) Step 2: Synthesis of Compound WXBB-14-4

WXBB-14-4a (20.00 g, 98.02 mmol, 1.00 eq) was dissolved in N-methylpyrrolidone (100.00 mL), then cuprous cyanide (17.56 g, 196.04 mmol, 42.83 mL, 2.00 eq) was added, and then reacted at 180° C. for 3 hours. The reaction solution was cooled to room temperature, added with water (300 mL) and aqueous ammonia (300 mL), stirred at room temperature for 30 min, and extracted with ethyl acetate (200 mL*3). The organic phase was washed with saturated brine (200 mL) and water (200 mL), dried over anhydrous sodium sulfate, and subjected to suction filtration and rotary evaporation to obtain a crude product which was a brown-black solid. The crude product was separated by silica gel column chromatography (PE:EA=20:1-3:1) to obtain WXBB-14-4 (12.00 g, 79.92 mmol, 81.53% yield) as a yellow solid. $^1$H NMR (400 MHz, CHLOROFORM-d) δ ppm 2.21 (s, 3H) 3.68 (br s, 2H) 6.80 (d, J=5.40 Hz, 1H) 6.91 (d, J=9.29 Hz, 1H).
Step 3. Synthesis of Compound WXBB-14-5

WXBB-14-3 (6.00 g, 39.96 mmol, 1.00 eq) and WXBB-14-4 were added into a single-neck bottle, then diisopropylethylamine (10.85 g, 83.92 mmol, 14.66 mL, 2.10 eq) was added, and reacted at 100° C. for 18 hours under the protection of nitrogen atmosphere. After the reaction was completed, the reaction solution was cooled to room temperature, added with 50 mL of water and then it was layered. The organic phase was washed successively with 50 mL of ammonium chloride solution (27%), 50 mL of sodium bicarbonate solution (9%) and 45 mL of saturated brine, dried over anhydrous sodium sulfate, and then dried on a rotary evaporator with a water pump at 45° C. until ~30 mL toluene was remained 60 mL of n-hexane was added to the organic phase. A solid precipitated out and was filtered. The filter cake was washed with 60 mL of isopropanol (placed in an ice bath for 10 min), and the filter cake (a white solid) was dried on a rotary evaporator with a water pump at 40° C. The crude product was purified by chromatography column (SiO$_2$, 100-200 mesh, PE:EA=10:1-3:1) to obtain WXBB-14-5 (1.80 g, 7.75 mmol, 19.39% yield) as a yellow solid. $^1$H NMR (400 MHz, DMSO-$d_6$) δ ppm 0.81-0.86 (m, 2H) 0.87-0.90 (m, 2H) 2.42 (s, 3H) 4.98 (s, 2H) 5.20-5.28 (m, 1H) 5.23 (s, 1H) 6.67 (d, J=5.52 Hz, 2H) 6.87 (d, J=5.77 Hz, 1H).
Step 4. Synthesis of Compound WXBB-14-6

WXBB-14-5 (1.25 g, 5.38 mmol, 1.00 eq) was placed in a 100 mL single-neck bottle containing acetic acid (20.00 mL), then a solid potassium thiocyanate (1.05 g, 10.76 mmol, 1.05 mL, 2.00 eq) was added to the reaction solution, followed by purging with nitrogen three times, and the mixture was reacted at 110° C. for 5 hours under the protection of nitrogen atmosphere. After the reaction was completed, the reaction solution was cooled to room temperature, dried on a rotary evaporator with an oil pump at 60° C., and then dissolved with dichloromethane (10 mL). The organic phase was washed with water (5 mL*2) and the aqueous phase was extracted with dichloromethane (10 mL*2). The organic phases were combined, dried over anhydrous sodium sulfate, and dried to give a brown solid. The solid was dissolved in 5 mL of ethyl acetate, 15 mL of n-hexane was added and then the solution was layered. A magnet was added into the upper dark-brown layer and stirred, and no solid precipitated. The mixture was dried on a ratory evaporator to give a brown oil. The crude product was purified by chromatography column (SiO2, 100-200 mesh, PE:EA=10:1-3:1) to obtain WXBB-14-6 (390.00 mg, 756.23 μmol, 14.06% yield, 53% purity) as a yellow solid. m/z=274.0 (M+1).
Step 5. Synthesis of Compound WXBB-14-7

Acetic acid (8.00 mL), water (1.60 mL) and hydrogen peroxide (487.96 mg, 4.30 mmol, 413.53 μL, 30% purity, 3.01 eq) were added into a 100 mL pre-dried three-neck bottle. The mixture was heated to 45° C. (internal temperature) under the protection of nitrogen atmosphere. WXBB-14-6 (390.00 mg, 1.43 mmol, 1.00 eq) was added as a solid (the internal temperature was kept below 55° C.). The reaction solution was reacted at 45° C. for 30 min After the reaction was completed, the reaction solution was cooled to room temperature, added with 4 mL of 20% sodium sulfite solution, stirred at room temperature for 0.5 hour, and dried on a rotary evaporator with an oil pump to give a white solid. 4 mL of water was added to the white solid, and the pH was adjusted to 10 with 4N aqueous ammonia. The aqueous phase was extracted with dichloromethane (6 mL*3). The organic phase was dried over anhydrous sodium sulfate and then dried on a rotary evaporator to give WXBB-14-7 (200.00 mg, 828.98 μmol, 57.97% yield) as a yellow solid. m/z=242.2 (M+1).
Step 6. Synthesis of Compound WXBB-14

WXBB-14-7 (200.00 mg, 828.98 μmol, 1.00 eq) and hydrochloric acid (6.00 mL, 38% purity) were added into a 100 mL dried single-neck bottle. The reaction solution was reacted at 100° C. for 18 hours. After the reaction was completed, the reaction solution was cooled to room temperature and dried on a rotary evaporator. Then toluene (5 mL*2) was added to the obtained WXBB-14 (200.00 mg, 768.46 μmol, 92.70% yield) which was a brown solid. m/z=261.1 (M+1).
Fragment WXBB-15

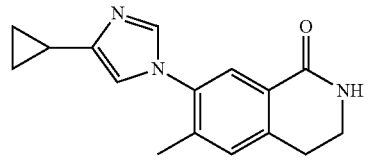 [SMILES: Cc1cc2c(cc1-n1cnc(C3CC3)c1)C(=O)NCC2]

Synthetic Route:

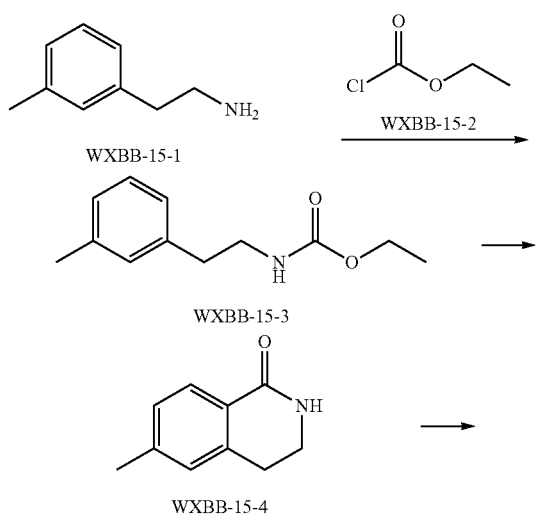

49

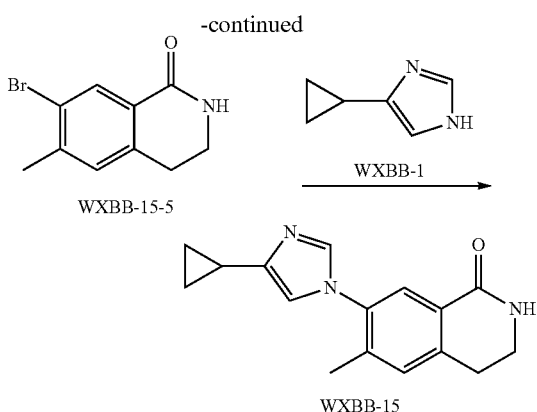

Step 1: Synthesis of Compound WXBB-15-3

Compound WXBB-15-1 (2.00 g, 14.79 mmol, 1.00 eq) and sodium carbonate (3.14 g, 29.58 mmol, 2.00 eq) were dissolved in trichloromethane (20.00 mL), and compound WXBB-15-2 (8.03 g, 73.95 mmol, 7.04 mL, 5.00 eq) was added dropwise. The mixture was reacted at 0° C. for 3 hours. After the reaction was completed, the reaction solution was poured slowly into an ice-water mixture (50 mL), then subjected to rotary evaporation under reduced pressure to remove chloroform, followed by extraction with dichloromethane (50 mL*3). The organic phases were combined, washed with saturated brine, dried over anhydrous sodium sulfate (25 g), and filtered. The filtrate was dried on a rotary evaporator under reduced pressure. The crude product was purified by a column. Compound WXBB-15-3 (1.80 g, 8.33 mmol, 56.32% yield, 95.91% purity) was obtained as a light yellow oil. MS m/z: 208.0 [M+H]+.

Step 2: Synthesis of Compound WXBB-15-4

Compound WXBB-15-3 (1.80 g, 8.68 mmol, 1.00 eq) was dissolved in polyphosphoric acid (8.00 mL). The mixture was reacted at 120° C. for 4 hours. After the reaction was completed, the reaction solution was cooled to room temperature, added with water (35 mL), adjusted to pH=8 with saturated potassium carbonate (50 mL), and extracted with dichloromethane (30 mL*3). The organic phases were combined, dried over anhydrous sodium sulfate (35 g), and filtered. The filtrate was dried on a rotary evaporator under reduced pressure to obtain a crude product. The crude product was purified by a column. Compound WXBB-15-4 (730.00 mg, 4.53 mmol, 52.19% yield) was obtained as a white solid, $^1$H NMR (400 MHz, CHLOROFORM-d) δ ppm 7.96 (d, J=7.8 Hz, 1H), 7.16 (d, J=8.0 Hz, 1H), 6.97-7.06 (m, 1H), 6.31 (br. s., 1H), 3.47-3.58 (m, 2H), 2.91-3.00 (m, 2H), 2.32-2.43 (m, 3H).

Step 3: Synthesis of Compound WXBB-15-5

Compound WXBB-15-4 (730.00 mg, 4.53 mmol, 1.00 eq) was dissolved in concentrated sulfuric acid (3.00 mL), and NBS (805.99 mg, 4.53 mmol, 1.00 eq) was added. The mixture was reacted at 60° C. for 3 hours. After the reaction was completed, the reaction solution was cooled to room temperature, added slowly to an ice-water mixture (15 mL), adjusted to pH=8 with saturated potassium carbonate (50 mL), and extracted with dichloromethane (30 mL*3). The organic phases were combined, dried over anhydrous sodium sulfate (25 g), and filtered. The filtrate was dried on a rotary evaporator under reduced pressure to obtain a crude product. The crude product was purified by a column. Compound WXBB-15-5 (400.00 mg, 1.67 mmol, 36.87% yield) was obtained as a white solid, $^1$H NMR (400 MHz, DMSO-d6) δ ppm 8.01 (br. s., 1H), 7.92 (s, 1H), 7.32 (s, 1H), 3.34-3.39 (m, 2H), 2.84 (t, J=6.5 Hz, 2H), 2.37 (s, 3H). MS m/z: 239.8 [M+H]+.

Step 4: Synthesis of Compound WXBB-15

Compound WXBB-15-5 (135.12 mg, 1.25 mmol, 1.50 eq), compound WXBB-1 (200.00 mg, 832.99 μmol, 1.00 eq), cuprous iodide (79.32 mg, 416.49 μmol, 0.50 eq), potassium carbonate (143.91 mg, 1.04 mmol, 1.25 eq) and 8-hydroxyquinoline (60.46 mg, 416.49 μmol, 71.97 μL, 0.50 eq) were dissolved in dimethyl sulfoxide (2.00 mL), followed by purging with nitrogen three times, and then the mixture was reacted at 130° C. for 16 hours under a nitrogen atmosphere. After the reaction was completed, the reaction solution was cooled to room temperature, added with dichloromethane (15 mL), and then washed with water (20 mL*3). The organic phase was dried over anhydrous sodium sulfate and filtered. The filtrate was dried on a rotary evaporator under reduced pressure. The crude product was separated and purified by a prep-TLC (EA) plate. Compound WXBB-15 (85.00 mg, 317.96 μmol, 38.17% yield, 100% purity) was obtained as a light yellow solid, MS m/z: 267.9 [M+H]+.

Fragment WXBB-16

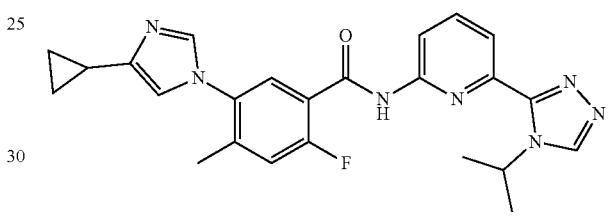

Synthetic Route:

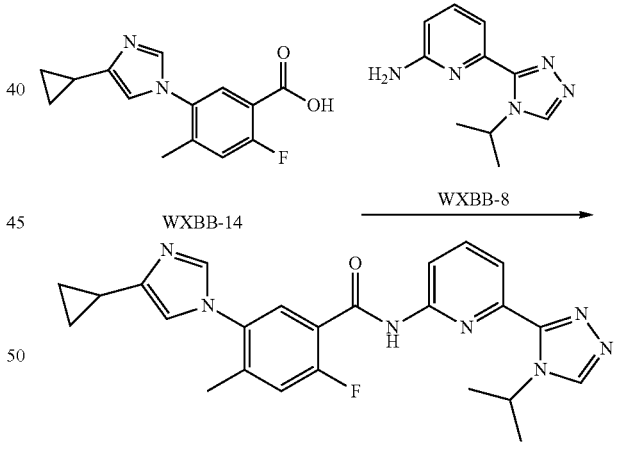

Step 1. Synthesis of Compound WXBB-16

WXBB-14 (1.99 g, 4.39 mmol, 1.00 eq, HCl) (purity 65.50%) was dissolved in anhydrous dichloromethane (25 mL) to form a suspension, and anhydrous N,N-dimethylformamide (20.00 mg, 273.64 μmol, 21.05 μL, 0.06 eq) was added. The system was stirred at 25° C. for 1 hour under N2 condition. The reaction solution was then evaporated on a rotary evaporator to become thick, added with anhydrous dichloromethane (25 mL), evaporated on a rotary evaporator to become thick, repeated three times, then added with anhydrous dichloromethane (25 mL), and added successively with WXBB-8 (1.00 g, 4.92 mmol, 1.12 eq) and diisopropylethylamine (1.14 g, 8.83 mmol, 1.54 mL, 2.01 eq). The system was stirred at 25° C. for 1 hour. The reaction solution was poured into water (100 mL) and extracted with dichloromethane (100 mL*2). The organic phase was dried over anhydrous sodium sulfate and filtered. The filtrate was dried on a rotary evaporator under reduced pressure to obtain a crude product. The crude product was separated and purified with prep-HPLC: Waters Xbridge 150*25 mm 5 μm; mobile phase: [water (10 mM NH$_4$HCO$_3$)-ACN]; B %: 22%-52%, 10 min. WXBB-16 (300.00 mg, 673.42 μmol, 15.33% yield, 100% purity) was obtained as a white solid, $^1$H NMR (400 MHz, CHLOROFORM-d) δ ppm 0.81-0.87 (m, 2H) 0.87-0.95 (m, 2H) 1.62 (s, 6H) 1.86-1.97 (m, 1H) 2.30 (s, 3H) 5.50 (quin, J=6.71 Hz, 1H) 6.81 (d, J=1.25 Hz, 1H) 7.21 (d, J=12.55 Hz, 1H) 7.46 (d, J=1.25 Hz, 1H) 7.91-7.97 (m, 1H) 8.09 (dd, J=7.65, 2.13 Hz, 2H) 8.38 (s, 1H) 8.41 (d, J=7.78 Hz, 1H) 9.07 (br d, J=15.81 Hz, 1H).

Fragment: WXBB-17

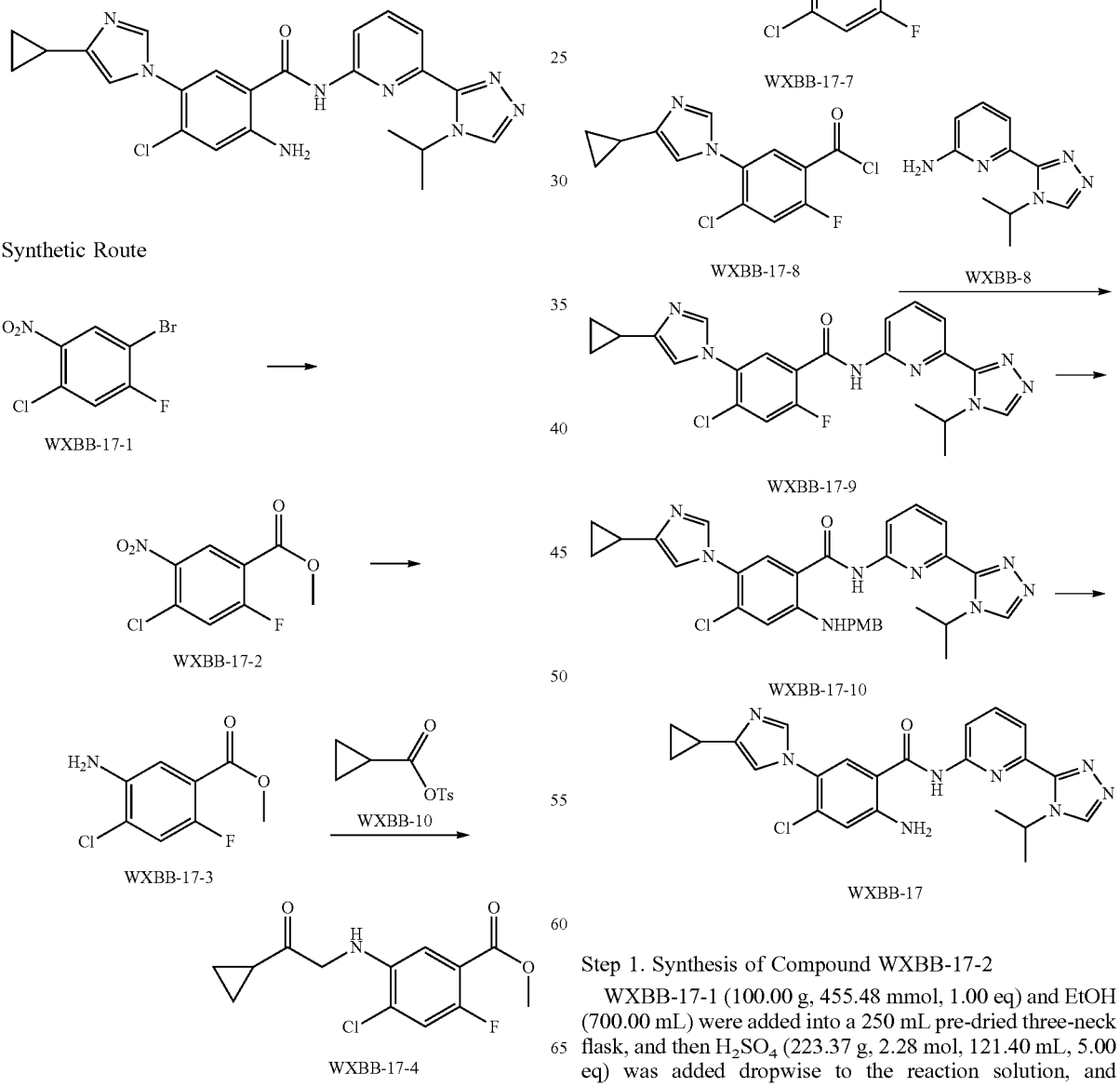

Synthetic Route

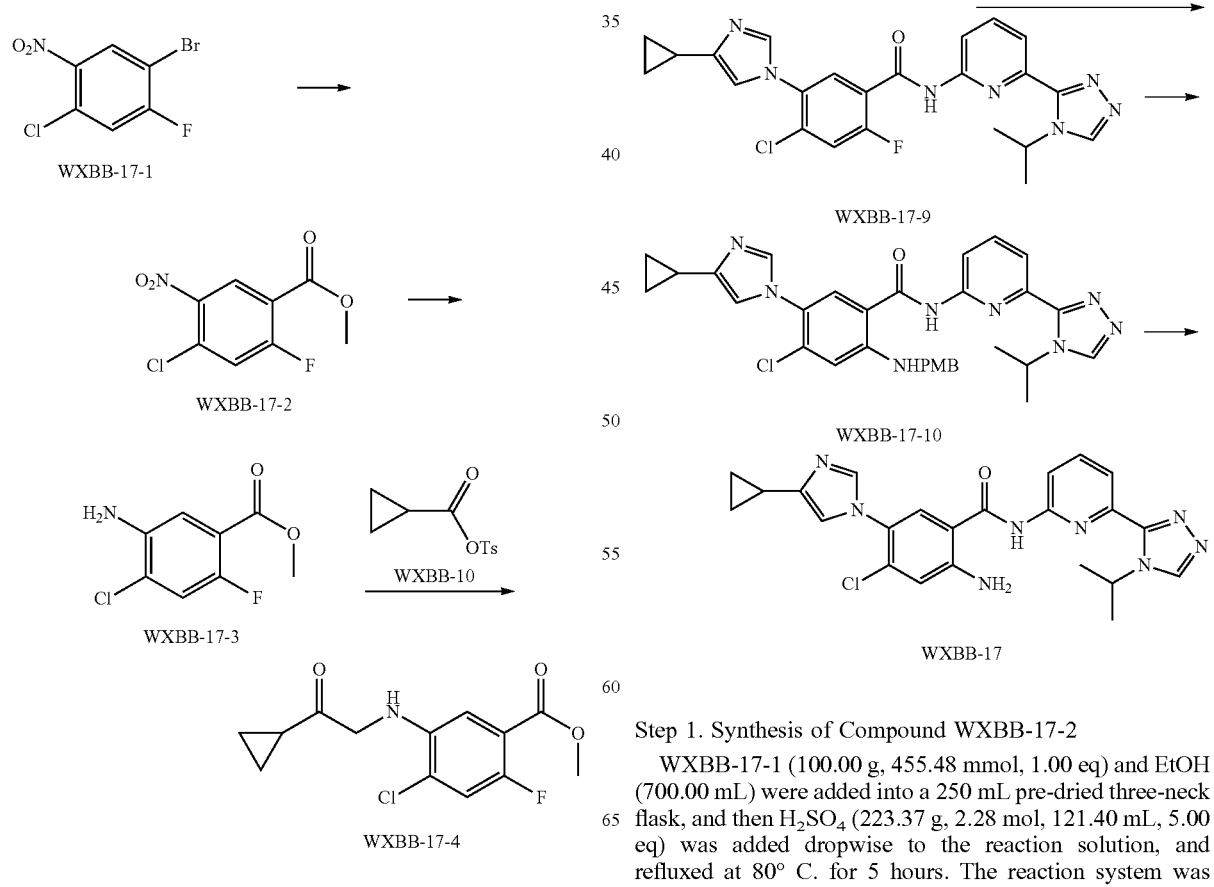

Step 1. Synthesis of Compound WXBB-17-2

WXBB-17-1 (100.00 g, 455.48 mmol, 1.00 eq) and EtOH (700.00 mL) were added into a 250 mL pre-dried three-neck flask, and then H$_2$SO$_4$ (223.37 g, 2.28 mol, 121.40 mL, 5.00 eq) was added dropwise to the reaction solution, and refluxed at 80° C. for 5 hours. The reaction system was cooled to room temperature, and diluted with 200 mL of EA. The obtained solution was layered, then the organic phase was collected and the aqueous phase was extracted with EA (2*100 mL). The organic phases were combined, washed successively with saturated aqueous sodium bicarbonate (2*100 mL), water (2*100 mL) and saturated brine (2*100 mL), dried over anhydrous sodium sulfate, and concentrated under reduced pressure to obtain residue WXBB-17-2.

Step 2. Synthesis of Compound WXBB-17-3

WXBB-17-2 (117.00 g, 472.52 mmol, 1.00 eq), Fe (65.98 g, 1.18 mol, 2.50 eq), $NH_4Cl$ (27.80 g, 519.77 mmol, 18.17 mL, 1.10 eq), and solvents $H_2O$ (345.00 mL) and EtOH (1.10 L) were added into a 2 L pre-dried round-bottom flask. The reaction solution was refluxed at 80° C. for 6 hours. The reaction solution was cooled to room temperature and passed through a Buchner funnel covered with celite. The filter cake was washed with dichloromethane (300 mL) and the filtrate was extracted with dichloromethane (2×400 mL). The organic phases were combined, washed with saturated brine (2×300 mL), dried over anhydrous sodium sulfate, and concentrated under reduced pressure to obtain residue WXBB-17-3.

Step 3. Synthesis of Compound WXBB-17-4

WXBB-17-3 (37.00 g, 170.02 mmol, 1.00 eq), WXBB-10 (47.56 g, 187.02 mmol, 1.10 eq) and DIEA (65.92 g, 510.06 mmol, 89.08 mL, 3.00 eq) were added into a 500 mL pre-dried round-bottom flask, then xylene (300.00 mL) was added and further stirred at 140° C. for 10 hours. The reaction system was cooled to room temperature, and diluted with 150 mL of water. The obtained solution was layered, then the organic phase was collected and the aqueous phase was extracted with EA (2*150 ml). The organic phases were combined, washed successively with saturated ammonium chloride (2*150 ml) and saturated brine (2*100 mL), dried over anhydrous sodium sulfate, and concentrated under reduced pressure to obtain WXBB-17-4.

Step 4. Synthesis of Compound WXBB-17-5

WXBB-17-4 (47.80 g, 159.48 mmol, 1.00 eq) and AcOH (250.00 mL) were added into a 500 mL pre-dried flask, and then potassium thiocyanate (31.00 g, 318.96 mmol, 31.00 mL, 2.00 eq) was added, and further stirred at 110° C. for 4 hours. After the reaction was completed, the reaction solution was dried directly on a rotary evaporator under reduced pressure to obtain a residue, which was re-dissolved in DCM (150 mL) and added with water (150 mL). The aqueous phase was extracted with DCM (2×100 mL). The organic phases were combined, dried over anhydrous sodium sulfate, then subjected to suction filtration, and dried on a rotary evaporator under reduced pressure. The residue was recrystallized from EA (15 ml) to give WXBB-17-5.

Step 5. Synthesis of Compound WXBB-17-6

Acetic acid (53.19 mL), water (10.00 mL) and hydrogen peroxide (4.49 g, 39.61 mmol, 3.81 mL, 30% purity, 3.00 eq) were added into a 250 mL pre-dried three-neck bottle. An internal thermometer was added to control the reaction temperature at 45° C., followed by addition of WXBB-17-5 (4.5 g, 13.20 mmol, 1.00 eq) in portions. The temperature was controlled below 55° C., and the mixture was reacted at this temperature for 30 min. Then the mixture was cooled to room temperature, and 20 mL of saturated sodium sulfite solution was added. No blue color was detected with a starch potassium iodide test paper. Then the mixture was subjected to ratory evaporation under reduced pressure, then dissolved in 100 mL of water, and adjusted to a pH of 10 with aqueous ammonia, and then extracted with dichloromethane (2×150 mL). The organic phases were combined, dried over anhydrous sodium sulfate, followed by rotary evaporation under reduced pressure. The crude product was purified by silica gel column (EA:PE=1:10-1:2) to obtain WXBB-17-6.

Step 6. Synthesis of Compound WXBB-17-7

WXBB-17-6 (3.85 g, 12.47 mmol, 1.00 eq), lithium hydroxide (895.97 mg, 37.41 mmol, 3.00 eq) and tetrahydrofuran (38.00 mL), and water (38.00 mL) were added into a 250 ml pre-dried round-bottom flask. The clear solution was stirred at 25° C. for 2 hours. Adjusted to pH 4-5 with 2N hydrochloric acid, and then extracted with chloroform:isopropyl alcohol (3:1, 5×50 mL). The organic phases were combined, dried over anhydrous sodium sulfate, followed by suction filtration and rotary evaporation under reduced pressure to obtain WXBB-17-7. m/z=281.1 [M+1].

Step 7. Synthesis of Compound WXBB-17-8

WXBB-17-7 (2.06 g, 7.34 mmol, 1.00 eq) was added into a 100 mL pre-dried round-bottom flask, purged with nitrogen three times, then dichloromethane (54.00 mL) was added, and then oxalyl chloride (1.86 g, 14.68 mmol, 1.29 mL, 2.00 eq) and N,N-dimethylformamide (53.65 mg, 734.00 μmol, 56.47 μL, 0.10 eq) were added dropwise under the protection of nitrogen atmosphere, followed by reaction at 25° C. for 1 hour. The reaction was directly evaporated on a ratory evaporator with a water pump. When the volume of the solution was reduced to about one-third, 10 mL of anhydrous dichloromethane was added. This process was repeated three times to obtain a solution of WXBB-17-8 in dichloromethane which was directly used for the next step. m/z=295.1 [M+14].

Step 8. Synthesis of Compound WXBB-17-9

A 100 mL round-bottom flask containing WXBB-17-8 (2.20 g, 7.35 mmol, 1.00 eq) was purged with nitrogen three times, then dichloromethane (20 mL) and diisopropylethylamine (950.52 mg, 7.35 mmol, 1.28 mL, 1.00 eq) were added, and WXBB-8 (1.49 g, 7.35 mmol, 1.00 eq) was added under the protection of nitrogen atmosphere. The clear solution was reacted at 25° C. for 1 hour. The reaction solution was directly dried on a rotary evaporator to obtain a dark yellow solid which was re-dissolved in dichloromethane (20 mL) and extracted with water (pH=2, 3×30 mL). The aqueous phase was adjusted to pH=10, and then extracted with dichloromethane (3×50 mL). The organic phases were combined, dried over anhydrous sodium sulfate, subjected to suction filtration, and dried on a rotary evaporator to obtain WXBB-17-9. m/z=466.3 [M+1] and 233.7 [M+2]/2.

Step 9. Synthesis of Compound WXBB-17-10

WXBB-17-9 (2.45 g, 5.26 mmol, 1 eq) and p-methoxybenzylamine (7.21 g, 52.59 mmol, 6.81 mL, 10 eq) and acetonitrile (25 mL) were added into a 100 ml pre-dried round-bottom flask, and then potassium carbonate (1.45 g, 10.52 mmol, 2 eq) was added. The system was reacted at 100° C. for 5 hours and then the reaction solution was diluted with 50 ml of water. The solution was layered, and then the organic phase was collected. The aqueous phase was washed with dichloromethane (3*50 mL). The organic phases were combined, washed with saturated brine (3*30 mL), dried over anhydrous sodium sulfate, and concentrated under reduced pressure. The residue was separated and purified by flash column chromatography (mobile phase dichloromethane:mobile phase methanol=10:1 to 1:1) to obtain WXBB-17-10. m/z=583.3 [M+1] and 292.2 [M+2]/2

Step 10. Synthesis of Compound WXBB-17

WXBB-17-10 (3.07 g, 5.27 mmol, 1 eq) and trifluoroacetic acid (15 mL) were added into a 100 mL pre-dried flask. The system was reacted at 25° C. for 10 hours. The reaction solution was directly concentrated under reduced pressure and the residue was diluted with 50 ml of water, adjusted to pH=10 with solid sodium carbonate, and added with 30 ml of dichloromethane. The solution was layered, and then the organic phase was collected. The aqueous phase was washed with dichloromethane (3*50 mL) and the organic phases were combined, washed successively with saturated sodium bicarbonate solution (1*30 ml) and saturated brine (2*30 mL), dried over anhydrous sodium sulfate, and concentrated under reduced pressure. The residue was separated and purified by flash column chromatography (mobile phase dichloromethane:mobile phase methanol=0-15:1) to obtain WXBB-17. m/z=463.3 [M+1] and 232.2 [M+2]/2

Example 001: WX001

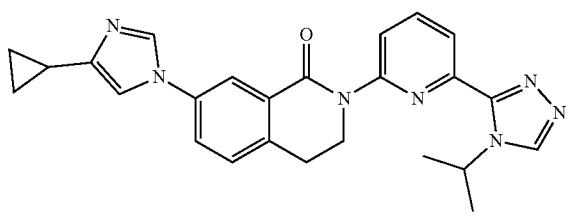 [SMILES: CC(C)n1cnnc1-c1cccc(N2CCc3ccc(-n4cnc(C5CC5)c4)cc3C2=O)n1]

Synthetic Route:

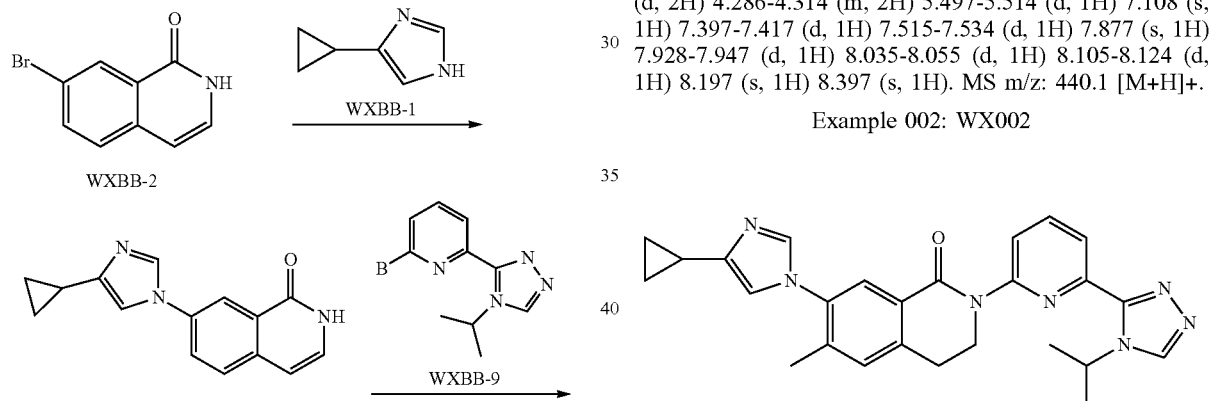

Step 1: Synthesis of Compound WX001-2

Compound WXBB-2 (1.00 g, 4.42 mmol, 1.00 eq), compound WXBB-1 (717.52 mg, 6.63 mmol, 1.50 eq), cuprous iodide (126.37 mg, 663.00 μmol, 0.15 eq), 8-hydroxyquinoline (96.32 mg, 663.00 μmol, 114.67 μL, 0.15 eq) and potassium carbonate (764.20 mg, 5.53 mmol, 1.25 eq) were dissolved in dimethyl sulfoxide (15.00 mL). The mixture was reacted at 130° C. for 24 hours under a nitrogen atmosphere. After the reaction was completed, the reaction solution was added with aqueous ammonia (50 mL), and then extracted with dichloromethane (80 mL*3). The organic phases were combined, and washed successively with water (100 mL) and saturated brine (100 mL), dried over anhydrous magnesium sulfate, and filtered, followed by concentration of the filtrate. Compound WX001-1 was obtained, $^1$H NMR (400 MHz, CHLOROFORM-d) δ ppm 0.821-0.829 (m, 2H) 0.886-0.906 (m, 2H) 1.912 (s, 1H) 3.04-3.073 (t, 2H) 3.605-3.636 (t, 2H) 7.093 (s, 1H) 7.322-7.342 (d, 1H) 7.442-7.463 (t, 1H) 7.784 (s, 1H) 8.077-8.083 (d, 1H). MS m/z: 254.1 [M+H]+.

Step 2: Synthesis of Compound WX001

Compound WX001-1 (800.00 mg, 2.50 mmol, 1.00 eq), compound WXBB-9 (667.92 mg, 2.50 mmol, 1.00 eq), xantphos (217.02 mg, 375.00 μmol, 0.15 eq), barium carbonate (2.44 g, 7.50 mmol, 3.00 eq) and pd$_2$(dba)$_3$ (114.48 mg, 125.00 μmol, 0.05 eq) were dissolved in dioxane (20.00 mL). The mixture was reacted at 120° C. for 16 hours under a nitrogen atmosphere. After the reaction was completed, the reaction solution was diluted with water (50 mL) and then extracted with dichloromethane (80 mL*3). The organic phases were combined, and washed successively with water (100 mL) and saturated brine (100 mL), dried over anhydrous magnesium sulfate, and filtered, followed by concentration of the filtrate. The crude product was separated and purified by prep-HPLC (column: Diamonsil 150*20 mm*5 μm; mobile phase: [water (0.225% FA)-ACN]; B %: 15%-45%, 11.5 min) to obtain compound WX001. $^1$H NMR (400 MHz, CHLOROFORM-d) δ ppm 0.839 (m, 2H) 0.908-0.926 (m, 2H) 1.56-1.576 (m, 6H) 1.926 (m, 1H) 3.21-3.26 (d, 2H) 4.286-4.314 (m, 2H) 5.497-5.514 (d, 1H) 7.108 (s, 1H) 7.397-7.417 (d, 1H) 7.515-7.534 (d, 1H) 7.877 (s, 1H) 7.928-7.947 (d, 1H) 8.035-8.055 (d, 1H) 8.105-8.124 (d, 1H) 8.197 (s, 1H) 8.397 (s, 1H). MS m/z: 440.1 [M+H]+.

Example 002: WX002

Synthetic Route:

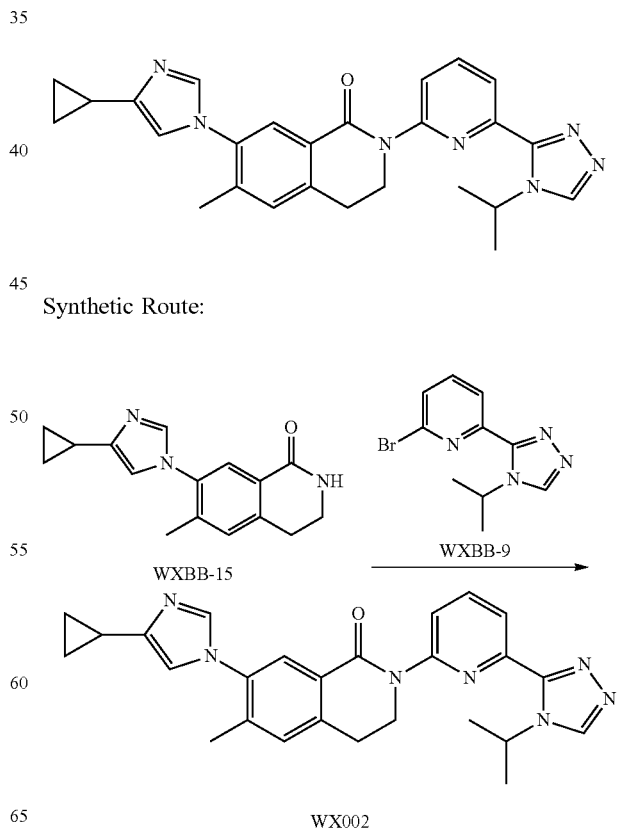

Step 1: Synthesis of Compound WX002

Compound WXBB-15 (50.00 mg, 187.03 μmol, 1.00 eq), compound WXBB-9 (59.95 mg, 224.44 μmol, 1.20 eq), cesium carbonate (182.81 mg, 561.09 μmol, 3.00 eq), Xantphos (16.23 mg, 28.05 μmol, 0.15 eq) and Pd$_2$(dba)$_3$ (8.56 mg, 9.35 μmol, 0.05 eq) were dissolved in dioxane (2.00 mL), and purged with nitrogen three times. The mixture was reacted at 120° C. for 16 hours under a nitrogen atmosphere. After the reaction was completed, the reaction solution was cooled to room temperature, added with water (15 mL), and extracted with dichloromethane (10 mL*3). The organic phases were combined, dried over anhydrous sodium sulfate (15 g), and filtered. The filtrate was dried on a rotary evaporator under reduced pressure. The crude product was separated and purified by prep-HPLC (column: Phenomenex Synergi C18 250*21.2 mm*4 μm; mobile phase: [water (0.05% HCl)-ACN]; B %: 10%-30%, 12 min) to obtain compound WX002. $^1$H NMR (400 MHz, METHANOL-d4) δ ppm 10.02 (s, 1H), 9.05 (s, 1H), 7.91-8.15 (m, 4H), 7.40-7.55 (m, 2H), 5.62 (br. s., 1H), 4.27 (br. s., 2H), 3.21 (br. s., 2H), 2.24 (s, 3H), 1.94-2.03 (m, 1H), 1.61 (d, J=6.0 Hz, 6H), 1.00-1.09 (m, 2H), 0.78-0.87 (m, 2H). MS m/z: 227.5 [M/2+H]+.

Example 003: WX003

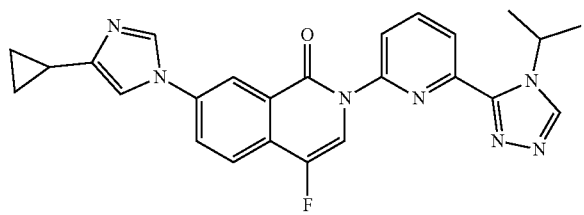 [SMILES: CC(C)n1cnnc1-c1cccc(-n2cc(F)c3ccc(-n4cnc(C5CC5)c4)cc3c2=O)n1]

Synthetic Route:

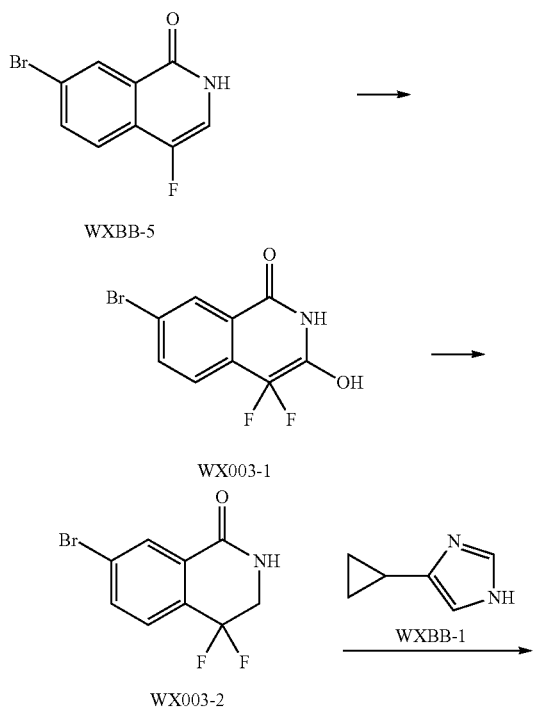

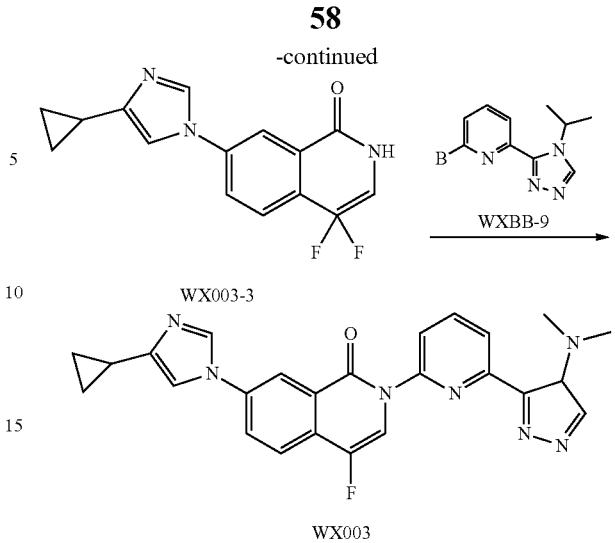

Step 1: Synthesis of Compound WX003-1

Compound WXBB-5 (2.50 g, 10.33 mmol, 1.00 eq) and 1-chloromethyl-4-fluoro-1,4-diazoniabicyclo[2.2.2]octane bis(tetrafluoroborate) (4.39 g, 12.40 mmol, 1.20 eq) were dissolved in acetonitrile (150.00 mL) and water (10.00 mL). The mixture was reacted at 20° C. for 16 hours. After the reaction was completed, the reaction solution was added with water (300 mL), and extracted with dichloromethane (DCM) (300 mL). The organic phases were combined, washed with saturated brine (30 mL), dried over anhydrous sodium sulfate, and filtered. The filtrate was dried on a rotary evaporator under reduced pressure. Compound WX003-1 was obtained, $^1$H NMR (400 MHz, DMSO-d6) δ ppm 5.06 (d, J=2.51 Hz, 1H) 5.33 (s, 1H) 7.72 (dd, J=8.28, 1.76 Hz, 1H) 7.85 (d, J=8.03 Hz, 1H) 7.99 (d, J=8.53 Hz, 1H) 8.06 (s, 1H) 8.15 (d, J=2.01 Hz, 1H) 9.25 (br. s., 1H).

Step 2: Synthesis of Compound WX003-2

A solution of compound WX003-1 (2.80 g, 10.07 mmol, 1.00 eq) in DCM (30.00 mL) was added to a mixture of methanesulfonic acid (3.87 g, 40.28 mmol, 2.87 mL, 4.00 eq) and triethylsilane (5.85 g, 50.35 mmol, 8.01 mL, 5.00 eq). The mixture was reacted at 15° C. for 32 hours. After the reaction was completed, the reaction solution was adjust to pH>7 by adding saturated sodium bicarbonate (100 mL), extracted with dichloromethane (50 mL), washed successively with water (50 mL) and saturated brine (50 mL), dried over anhydrous sodium sulfate, and filtered. The filtrate was dried on a rotary evaporator under reduced pressure to obtain a crude product. The crude product was purified by a column. Compound WX003-2 was obtained, $^1$H NMR (400 MHz, DMSO-d6) δ ppm 3.92 (td, J=13.30, 2.26 Hz, 2H) 7.70 (d, J=8.03 Hz, 1H) 7.91-8.03 (m, 1H) 8.06 (s, 1H) 8.61 (br. s., 1H).

Step 3: Synthesis of Compound WX003-3

Compound WX003-2 (400.00 mg, 1.53 mmol, 1.00 eq), compound WXBB-1 (248.18 mg, 2.30 mmol, 1.50 eq), potassium carbonate (634.38 mg, 4.59 mmol, 3.00 eq), cuprous iodide (145.69 mg, 765.00 μmol, 0.50 eq) and 8-hydroxyquinoline (111.05 mg, 765.00 μmol, 132.20 μL, 0.50 eq) were dissolved in dimethyl sulfoxide (4.00 mL). The mixture was reacted at 130° C. for 16 hours under a nitrogen atmosphere. After the reaction was completed, the reaction solution was added with water (30 mL), and extracted with dichloromethane (30 mL). The organic phase was washed successively with water (30 mL*3) and saturated brine (30 mL), dried over anhydrous sodium sulfate, and filtered. The filtrate was dried on a rotary evaporator under reduced pressure to obtain a crude product. The crude product was separated and purified by prep-TLC to obtain compound WX003-3, $^1$H NMR (400 MHz, CHLOROFORM-d) δ ppm 0.76-0.87 (m, 4H) 0.93 (d, J=6.02 Hz, 4H) 1.93 (br. s., 1H) 4.05 (t, J=4.64 Hz, 1H) 4.14-4.22 (m, 1H) 7.14 (d, J=4.77 Hz, 1H) 7.21 (d, J=6.02 Hz, 1H) 7.71 (dd, J=8.53, 2.01 Hz, 1H) 7.78-7.86 (m, 2H) 7.93 (d, J=8.53 Hz, 2H) 8.29 (s, 1H) 8.38 (s, 1H).

Step 4: Synthesis of Compound WX003

Compound WX003-3 (130.00 mg, 449.39 μmol, 1.00 eq), compound WXBB-9 (186.26 mg, 539.27 μmol, 1.20 eq) (purity 77.34%), cesium carbonate (439.26 mg, 1.35 mmol, 3.00 eq), Xantphos (39.00 mg, 67.41 μmol, 0.15 eq) and Pd$_2$(dba)$_3$ (20.58 mg, 22.47 μmol, 0.05 eq) were dissolved in anhydrous dioxane (10.00 mL). The mixture was reacted at 120° C. for 16 hours under a nitrogen atmosphere. After the reaction was completed, the reaction solution was cooled to room temperature, added with water (10 mL), and extracted with dichloromethane (10 mL*3). The organic phase was washed with water (300 mL) and saturated brine (300 mL), dried over anhydrous sodium sulfate, and filtered. The filtrate was dried on a rotary evaporator under reduced pressure to obtain a crude product. The crude product was separated and purified by pre-HPLC (column: Phenomenex Gemini 150*25 mm*10 μm; mobile phase: [water (0.05% HCl)-ACN]; B %: 15%-45%, 10 min) to obtain compound WX003. $^1$H NMR (400 MHz, METHANOL-d4) δ ppm 0.59-0.70 (m, 2H) 0.76-0.88 (m, 2H) 1.49 (d, J=6.53 Hz, 6H) 1.75-1.86 (m, 1H) 5.30-5.43 (m, 1H) 7.34 (s, 1H) 7.85 (dd, J=12.80, 7.78 Hz, 2H) 7.93-8.04 (m, 2H) 8.07 (d, J=3.51 Hz, 3H) 8.33 (s, 1H) 8.78 (s, 1H). MS m/z: 228.7[M/2+H]+.

Example 004: WX004

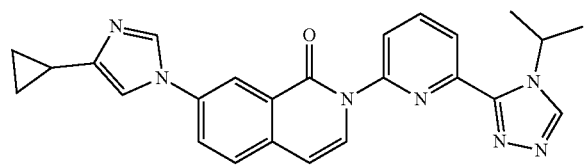 [SMILES: CC(C)n1cnnc1-c1cccc(-n2ccc3ccc(-n4cnc(C5CC5)c4)cc3c2=O)n1]

Synthetic Route:

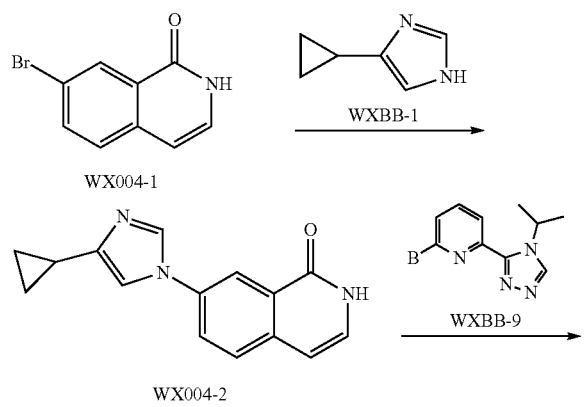

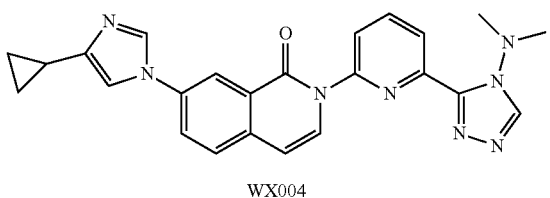

WX004

Step 1: Synthesis of Compound WX004-2

Compound WX004-1 (300.00 mg, 1.34 mmol, 1.00 eq), compound WXBB-1 (217.20 mg, 2.01 mmol, 1.50 eq), potassium carbonate (555.18 mg, 4.02 mmol, 3.00 eq), cuprous iodide (127.51 mg, 670.00 μmol, 0.50 eq) and 8-hydroxyquinoline (97.18 mg, 670.00 μmol, 115.69 μL, 0.50 eq) were dissolved in dimethyl sulfoxide (3.00 mL). The mixture was reacted at 130° C. for 16 hours under a nitrogen atmosphere. After the reaction was completed, dichloromethane (20 mL) and water (20 mL) were added to the reaction solution. The organic phase was washed successively with water (20 mL*3) and saturated brine (20 mL), dried over anhydrous sodium sulfate, and filtered. The filtrate was dried on a rotary evaporator under reduced pressure to obtain a crude product. The crude product was purified by a column. Compound WX004-2 was obtained, $^1$H NMR (400 MHz, METHANOL-d4) δ ppm 0.79 (d, J=3.26 Hz, 2H) 0.92 (d, J=8.03 Hz, 2H) 1.93 (d, J=4.52 Hz, 1H) 3.91 (t, J=5.14 Hz, 1H) 4.19 (t, J=5.14 Hz, 1H) 6.74 (d, J=7.28 Hz, 1H) 6.79 (d, J=7.03 Hz, 1H) 6.89 (d, J=7.28 Hz, 1H) 7.24 (d, J=7.03 Hz, 1H) 7.29 (d, J=7.03 Hz, 1H) 7.40-7.58 (m, 1H) 7.79-8.03 (m, 3H) 8.16 (br. s., 1H) 8.37 (s, 1H) 8.41-8.49 (m, 1H). MS m/z: 252.1 [M+H]+.

Step 2: Synthesis of Compound WX004

Compound WX004-2 (140.00 mg, 320.86 μmol, 1.00 eq), compound WXBB-9 (102.85 mg, 385.03 μmol, 1.20 eq), cesium carbonate (313.63 mg, 962.58 μmol, 3.00 eq), Xantphos (27.85 mg, 48.13 μmol, 0.15 eq) and Pd$_2$(dba)$_3$ (14.69 mg, 16.04 μmol, 0.05 eq) were dissolved in dioxane (10.00 mL). The mixture was reacted at 120° C. for 16 hours under a nitrogen atmosphere. After the reaction was completed, the reaction solution was cooled to room temperature, added with water (10 mL), and extracted with dichloromethane (10 mL*3). The organic phases were combined, washed with saturated brine (20 mL), dried over anhydrous sodium sulfate, and filtered. The filtrate was dried on a rotary evaporator under reduced pressure to obtain a crude product. The crude product was separated and purified by prep-HPLC (column: DuraShell 150*25 mm*5 μm; mobile phase: [water (0.05% HCl)-ACN]; B %: 6%-36%, 10 min) to obtain compound WX004. $^1$H NMR (400 MHz, METHANOL-d4) δ ppm 0.92-1.00 (m, 2H) 1.15-1.23 (m, 2H) 1.70 (d, J=6.78 Hz, 6H) 2.04-2.16 (m, 1H) 2.68 (s, 1H) 5.70 (dt, J=13.24, 6.56 Hz, 1H) 7.00 (d, J=7.53 Hz, 1H) 7.91-7.99 (m, 2H) 8.02 (d, J=8.53 Hz, 1H) 8.14 (dd, J=8.53, 2.01 Hz, 1H) 8.21 (dd, J=5.90, 2.63 Hz, 1H) 8.30-8.42 (m, 2H) 8.70 (d, J=1.76 Hz, 1H) 9.52 (s, 1H) 10.14 (br. s., 1H). MS m/z: 219.6[M/2+H]+.

Example 005: WX005

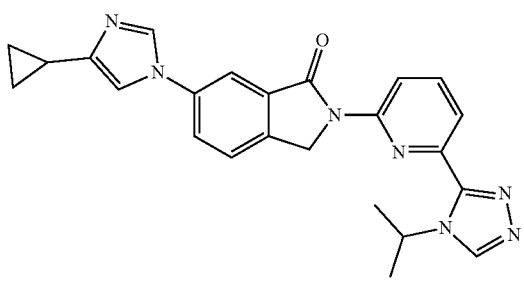 [SMILES: CC(C)n1cnnc1-c1cccc(N2Cc3ccc(-n4cnc(C5CC5)c4)cc3C2=O)n1]

Synthetic Route:

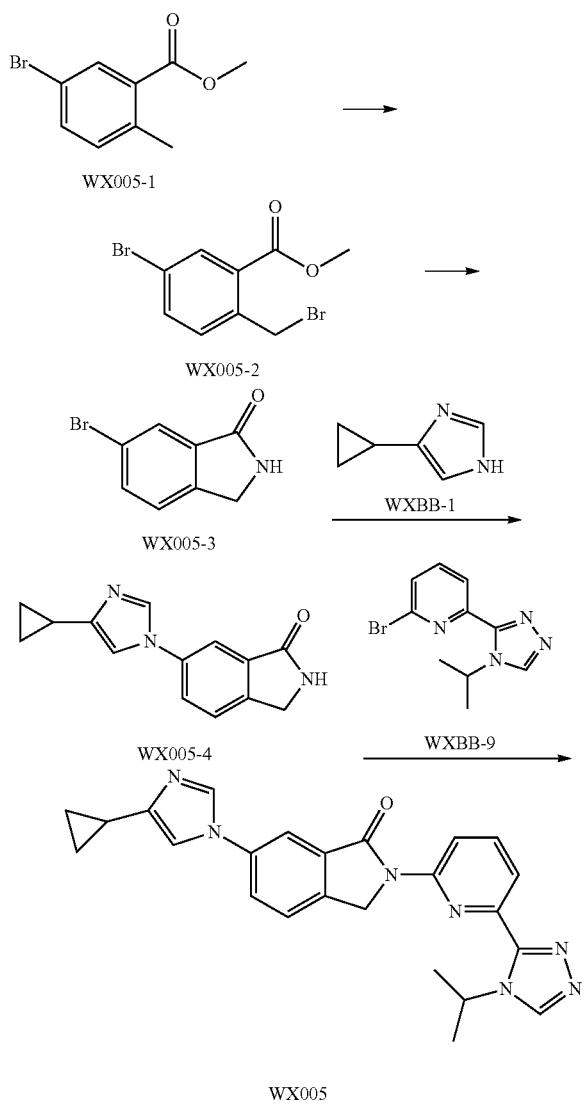

Step 1: Synthesis of Compound WX005-2

Compound WX005-1 (10.00 g, 43.65 mmol, 1.00 eq) was dissolved in carbon tetrachloride (200.00 mL), and NBS (7.77 g, 43.65 mmol, 1.00 eq) and AIBN (358.39 mg, 2.18 mmol, 0.05 eq) were added. The mixture was reacted at 80° C. for 16 hours. After the reaction was completed, 5% sodium thiosulfate (100 mL) was added to the reaction solution, and concentrated. After extraction with ethyl acetate (150 mL), the obtained organic phase was washed successively with water (100 mL) and saturated brine (100 mL), dried over anhydrous sodium sulfate (20 g), and filtered. The filtrate was dried on a rotary evaporator under reduced pressure. Compound WX005-2 was obtained, $^1$H NMR (400 MHz, CHLOROFORM-d) δ ppm 8.08-8.09 (s, 1H), 7.53-7.61 (d, 1H), 7.31-7.33 (d, 1H), 4.82-4.95 (s, 2H), 3.93-3.94 (s, 3H).

Step 2: Synthesis of Compound WX005-3

Compound WX005-2 (10.00 g, 32.47 mmol, 1.00 mL, 1.00 eq) was dissolved in tetrahydrofuran (80.00 mL), and aqueous ammonia (91.06 g, 2.60 mol, 100.07 mL, 80.01 eq) was added dropwise. The mixture was reacted at 70° C. for 3 hours. After the reaction was complete, a new point was generated. The reaction solution was cooled to 0° C. and filtered. The obtained filter cake was washed with n-hexane (20 mL) and dried. Compound WX005-3 was obtained, $^1$H NMR (400 MHz, DMSO-d6) δ ppm 8.72 (s., 1H), 7.76-7.79 (m, 2H), 7.55-7.57 (m, 1H), 4.29-4.36 (s, 2H). MS m/z: 212.0 [M+H]+.

Step 3: Synthesis of Compound WX005-4

Compound WX005-3 (1.00 g, 4.72 mmol, 1.00 eq), compound WXBB-1 (1.53 g, 14.15 mmol, 3.00 eq), cuprous iodide (89.82 mg, 471.61 μmol, 0.10 eq), potassium carbonate (1.96 g, 14.15 mmol, 3.00 eq), and tetramethylethylenediamine (54.81 mg, 471.61 μmol, 71.18 μL, 0.10 eq) were dissolved in toluene (10.00 mL). The mixture was purged with nitrogen three times, and then reacted at 130° C. for 16 hours under a nitrogen atmosphere. After the reaction was completed, the reaction solution was added with methanol (15 mL), and filtered, followed by concentrating of the filtrate. The crude product was separated and purified by prep-HPLC (column: Phenomenex Gemini 150*25 mm*10 μm; mobile phase: [water (0.05% HCl)-ACN]; B %: 0-30 (10 min) %-30-55 (4 min) %, 14 min). Compound WX005-4 was obtained, $^1$H NMR (400 MHz, METHANOL-d4) δ ppm 8.07 (s, 1H), 7.89 (s, 1H), 7.80-7.83 (m, 1H), 7.72-7.74 (m, 1H), 7.384 (s, 1H), 4.53 (s, 2H), 1.90-1.95 (m, 1H), 0.89-0.93 (m, 2H), 0.76-0.78 (m, 2H). MS m/z: 239.9 [M+H]+.

Step 4: Synthesis of Compound WX005

Compound WX005-4 (85.00 mg, 337.48 μmol, 1.00 eq) (purity 95%), compound WXBB-9 (180.30 mg, 506.23 μmol, 1.50 eq) (purity 75%), cuprous iodide (6.43 mg, 33.75 μmol, 0.10 eq), tetramethylethylenediamine (3.92 mg, 33.75 μmol, 5.09 μL, 0.10 eq), and potassium carbonate (46.64 mg, 337.48 μmol, 1.00 eq) were dissolved in toluene (15.00 mL). The mixture was purged with nitrogen three times, and then reacted at 130° C. for 16 hours under a nitrogen atmosphere. After the reaction was completed, the reaction solution was added with methanol (15 mL), and filtered, followed by concentration of the filtrate. The crude product was separated and purified by prep-HPLC (column: Phenomenex Gemini 150*25 mm*10 μm; mobile phase: [water (0.05% HCl)-ACN]; B %: 10%-40%, 10 min) to obtain compound WX005. $^1$H NMR (400 MHz, METHANOL-d4) δ ppm 9.85 (br s, 1H), 9.50 (d, J=1.8 Hz, 1H), 8.90 (br d, J=8.3 Hz, 1H), 8.14-8.25 (m, 2H), 7.99-8.10 (m, 3H), 7.96 (d, J=0.8 Hz, 1H), 5.82 (dt, J=13.4, 6.6 Hz, 1H), 5.27-5.39 (m, 2H), 2.02-2.16 (m, 1H), 1.77 (d, J=6.8 Hz, 6H), 1.11-1.23 (m, 2H), 0.87-1.01 (m, 2H). MS m/z: 213.7[M/2+H]+.

Example 006: WX006

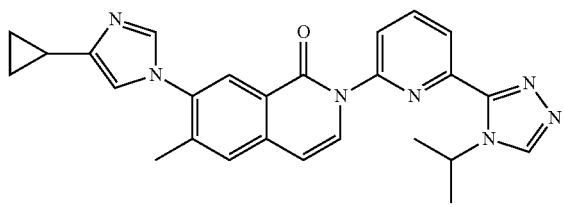 [SMILES: Cc1cc2ccn(-c3cccc(-c4nncn4C(C)C)n3)c(=O)c2cc1-n1cnc(C2CC2)c1]

Synthetic Route:

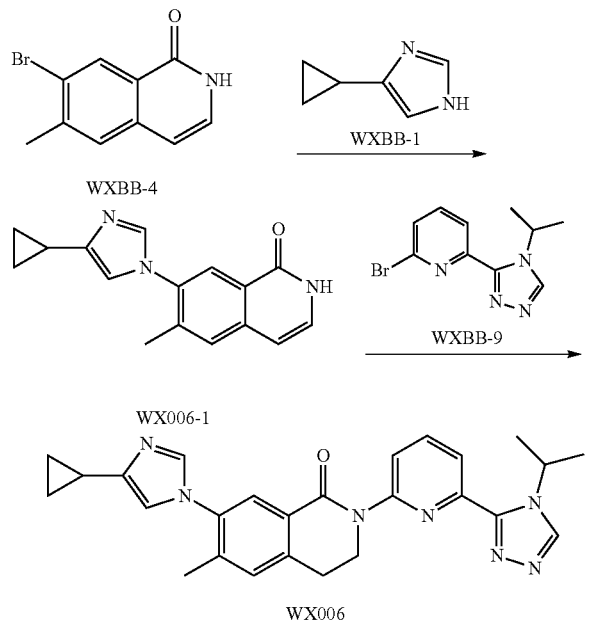

Step 1: Synthesis of Compound WX006-1

Compound WXBB-4 (5.00 g, 21.00 mmol, 1.00 eq), compound WXBB-1 (4.54 g, 42.00 mmol, 2.00 eq), potassium carbonate (8.71 g, 63.00 mmol, 3.00 eq), cuprous iodide (2.00 g, 10.50 mmol, 0.50 eq) and 8-hydroxyquinoline (1.52 g, 10.50 mmol, 1.81 mL, 0.50 eq) were dissolved in dimethyl sulfoxide (50.00 mL). The mixture was reacted at 130° C. for 16 hours under a nitrogen atmosphere. The reaction solution was cooled to room temperature and was poured slowly into water (20 mL) and filtered. The obtained filter cake was collected and dried. The obtained crude product was slurried with dichloromethane (150 mL) at 25° C. for 0.5 hour, filtered and the filtrate was concentrated. The crude product was purified by a column (MeOH/MeOH=0~2%~4%~10%) to obtain compound WX006-1. $^1$H NMR (400 MHz, CHLOROFORM-d) δ ppm 0.838-1.006 (m, 4H) 1.794 (s, 1H) 1.935 (s, 1H) 2.374 (s, 3H) 6.543-6.560 (d, 1H) 6.924 (s, 1H) 6.999 (s, 1H) 7.192-7.209 (d, 1H) 7.514 (s, 1H) 7.581 (s, 1H) 8.250 (s, 1H) 11.340 (s, 1H). MS m/z: 266.1 [M+H]+.

Step 2: Synthesis of Compound WX006

Compound WX006-1 (700.00 mg, 2.59 mmol, 1.00 eq) (purity 98.17%), Xantphos (224.81 mg, 388.50 μmol, 0.15 eq), compound WXBB-9 (982.08 mg, 3.11 mmol, 1.20 eq) (purity 84.54%), cesium carbonate (2.53 g, 7.77 mmol, 3.00 eq) and Pd$_2$(dba)$_3$ (118.59 mg, 129.50 μmol, 0.05 eq) were dissolved in dioxane (20.00 mL). The mixture was reacted at 120° C. for 16 hours. The reaction solution was cooled to room temperature, filtered, and the filtrate was concentrated. The crude product was separated and purified by prep-HPLC (column: Phenomenex Gemini 150*25 mm*10 μm; mobile phase: [water (0.05% HCl)-ACN]; B %: 10%-40%, 10 min) to obtain compound WX006. $^1$H NMR (400 MHz, CHLOROFORM-d) δ ppm 0.847-0.873 (m, 2H) 0.901-0.922 (m, 2H) 1.539-1.556 (d, 6H) 1.914-1.968 (m, 1H) 2.374 (s, 3H) 5.437-5.505 (m, 1H) 6.622-6.640 (d, 1H) 6.866 (s, 1H) 7.522 (s, 2H) 7.705-7.724 (d, 1H) 88.009-8.062 (m, 2H) 8.305-8.331 (m, 3H) 8.396 (s, 1H). MS m/z: 226.7[M/2+H]+.

Example 007: WX007

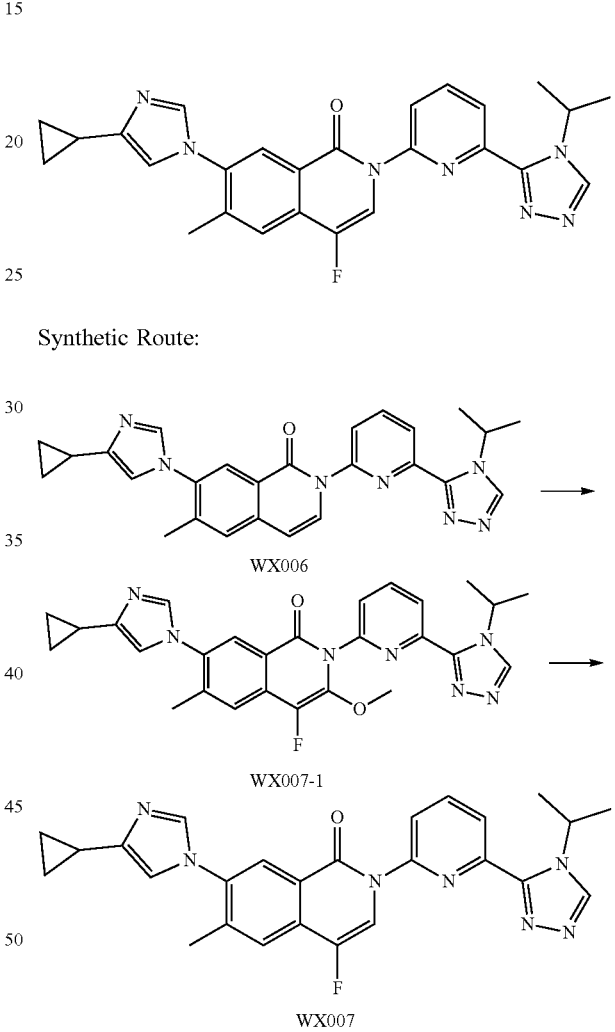

Step 1: Synthesis of Compound WX007-1

Compound WX006 (500.00 mg, 881.02 μmol, 79.56% purity, 1.00 eq) and N-fluoro-N'-(chloromethyl)triethylenediamine bis(tetrafluoroborate) (399.50 mg, 1.13 mmol, 1.28 eq) were dissolved in acetonitrile (15.00 mL) and methanol (15.00 mL). The mixture was reacted at 82° C. for 16 hours. The reaction solution was concentrated, added into water (30 mL) and extracted with dichloromethane (30 mL*3). The organic phases were combined, washed with saturated brine (30 mL), dried over anhydrous sodium sulfate, and filtered. The filtrate was dried on a rotary evaporator under reduced pressure. Compound WX007-1 was obtained, MSm/z: 251.7 [M/2+H]+.

Step 2: Synthesis of Compound WX007

Compound WX007-1 (400.00 mg, 188.14 μmol, 1.00 eq) (purity 23.59%) and hydrochloric acid/dioxane (4M, 470.34 μL, 10.00 eq) were dissolved in acetonitrile (6.00 mL). The mixture was reacted at 65° C. for 16 hours. The reaction solution was concentrated, adjusted to pH 7-8 with sodium carbonate and extracted with dichloromethane (30 mL*2). The organic phases were combined, washed with saturated brine (30 mL), dried over anhydrous sodium sulfate, and filtered. The filtrate was dried on a rotary evaporator under reduced pressure. The crude product was separated and purified by prep-HPLC (column: Agela ASB 150*25 mm*5 μm; mobile phase: [water (0.05% HCl)-ACN]; B %: 20%-50%, 10 min) to obtain compound WX007. $^1$H NMR (400 MHz, CHLOROFORM-d) δ=8.34 (br s, 1H), 8.29-8.20 (m, 2H), 8.08 (br d, J=8.0 Hz, 1H), 8.01-7.94 (m, 1H), 7.78 (br d, J=7.0 Hz, 1H), 7.70 (s, 1H), 7.48 (br s, 1H), 6.81 (br s, 1H), 5.49-5.35 (m, 1H), 2.36 (s, 3H), 1.87 (br s, 1H), 1.51 (br d, J=6.3 Hz, 6H). MS m/z: 235.5[M/2+H]+.

Example 008: WX008

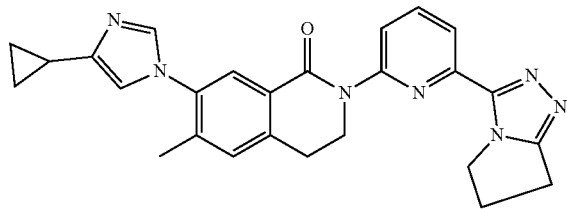 [SMILES: Cc1cc2c(cc1-n1cnc(C3CC3)c1)C(=O)N(c1cccc(-c3nnc4n3CCC4)n1)CC2]

Synthetic Route:

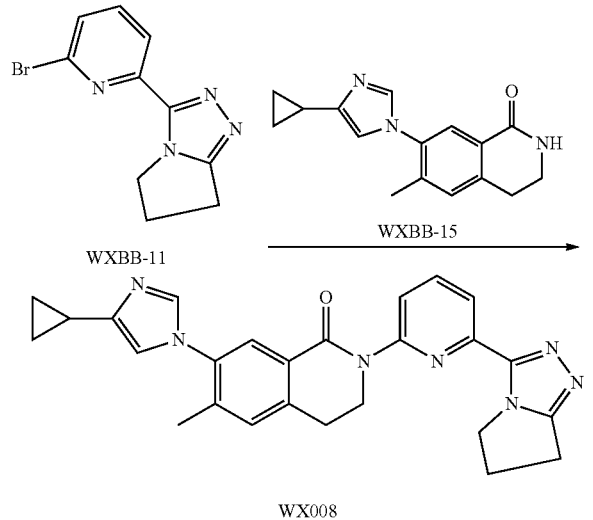

WX008

Step 1: Synthesis of Compound WX008

Compound WXBB-15 (262.02 mg, 754.40 μmol, 1.00 eq) (purity 76.33%), Xantphos (65.48 mg, 113.16 μmol, 0.15 eq), Pd$_2$(dba)$_3$ (34.54 mg, 37.72 μmol, 0.05 eq), and cesium carbonate (737.40 mg, 2.26 mmol, 3.00 eq) were dissolved in dioxane (5.00 mL) to form a suspension. Compound WXBB-11 (201.67 mg, 754.40 μmol, 1.00 eq) was added under nitrogen condition. The system was stirred at 120° C. for 16 hours under nitrogen atomosphere. The reaction solution was cooled to room temperature, added with water (50 mL), and extracted with dichloromethane (50 mL*3). The organic phase was washed with water (100 mL) and saturated brine (100 mL), dried over anhydrous sodium sulfate, and filtered. The filtrate was concentrated under reduced pressure to obtain a crude product. The crude product was separated and purified by prep-HPLC (column: Xtimate C18 150*25 mm*5 μm; mobile phase: [water (0.225% FA)-ACN]; B %: 20%-55%, 11.5 min) to obtain compound WX008. $^1$H NMR (400 MHz, CHLOROFORM-d) δ ppm 0.85 (br d, J=3.51 Hz, 2H) 0.91 (br d, J=7.78 Hz, 2H) 1.93 (br s, 1H) 2.29 (s, 3H) 2.77-2.89 (m, 2H) 3.04 (br d, J=8.03 Hz, 2H) 3.19 (t, J=6.15 Hz, 2H) 4.34 (t, J=6.40 Hz, 2H) 4.41 (t, J=7.15 Hz, 2H) 6.83 (br s, 1H) 7.26 (s, 1H) 7.53 (s, 1H) 7.85-7.91 (m, 1H) 8.00 (d, J=8.28 Hz, 1H) 8.04 (s, 1H) 8.12 (d, J=7.28 Hz, 1H). MS m/z: 226.7[M/2+H]+.

Example 009: WX009

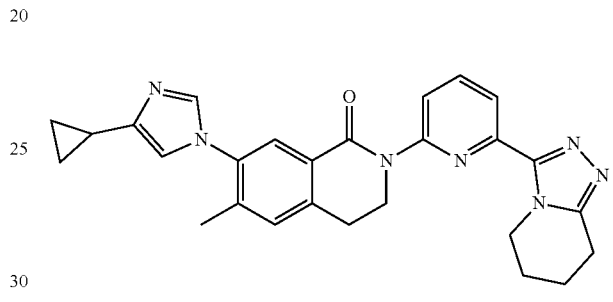

Synthetic Route:

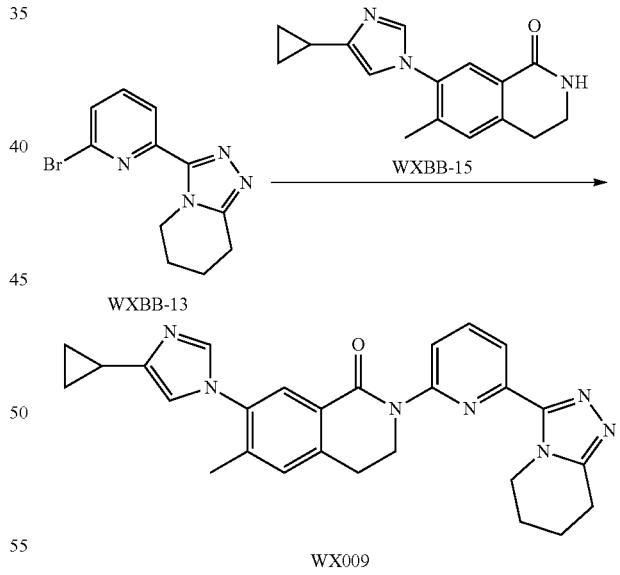

WX009

Step 1: Synthesis of Compound WX009

Compound WXBB-15 (100.00 mg, 374.07 μmol, 1.00 eq), Xantphos (32.47 mg, 56.11 μmol, 0.15 eq), and cesium carbonate (365.64 mg, 1.12 mmol, 3.00 eq) were dissolved in dioxane (2.00 mL), and Pd$_2$(dba)$_3$ (17.13 mg, 18.70 μmol, 0.05 eq) was added. Compound WXBB-13 (156.63 mg, 561.11 μmol, 1.50 eq) was added under nitrogen atomosphere. The system was stirred at 120° C. for 16 hours under nitrogen. The reaction solution was diluted with water (50 mL) and extracted with dichloromethane (50 mL*2). The organic phase was washed successively with water (50 mL) and saturated brine (50 mL), dried over anhydrous sodium sulfate, and filtered. The filtrate was dried on a rotary evaporator under reduced pressure to obtain a crude product. The crude product was separated and purified by prep-HPLC (column: Xtimate C18 150*25 mm*5 μm; mobile phase: [water (0.225% FA)-ACN]; B %: 10%-35%, 11.5 min) to obtain compound WX009. ¹H NMR (400 MHz, CHLOROFORM-d) δ ppm 0.79-0.85 (m, 2H) 0.86-0.92 (m, 2H) 1.87-2.06 (m, 5H) 2.27 (s, 3H) 3.08 (br t, J=6.27 Hz, 2H) 3.17 (br t, J=6.27 Hz, 2H) 4.29 (br t, J=6.27 Hz, 2H) 4.45 (br t, J=5.77 Hz, 2H) 6.80 (s, 1H) 7.25 (s, 1H) 7.48 (s, 1H) 7.83-7.90 (m, 1H) 7.97 (d, J=8.28 Hz, 1H) 8.02 (s, 1H) 8.10 (d, J=7.53 Hz, 1H). MS m/z: 233.6[M/2+H]+.

Example 010: WX010

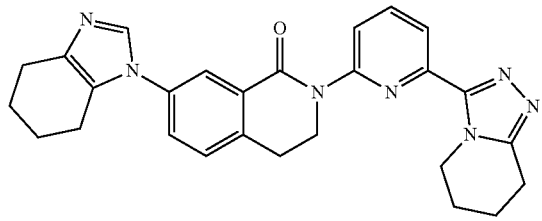 [SMILES: O=C1c2cc(-n3cnc4c3CCCC4)ccc2CCN1c1cccc(-c2nnc3n2CCCC3)n1]

Synthetic Route:

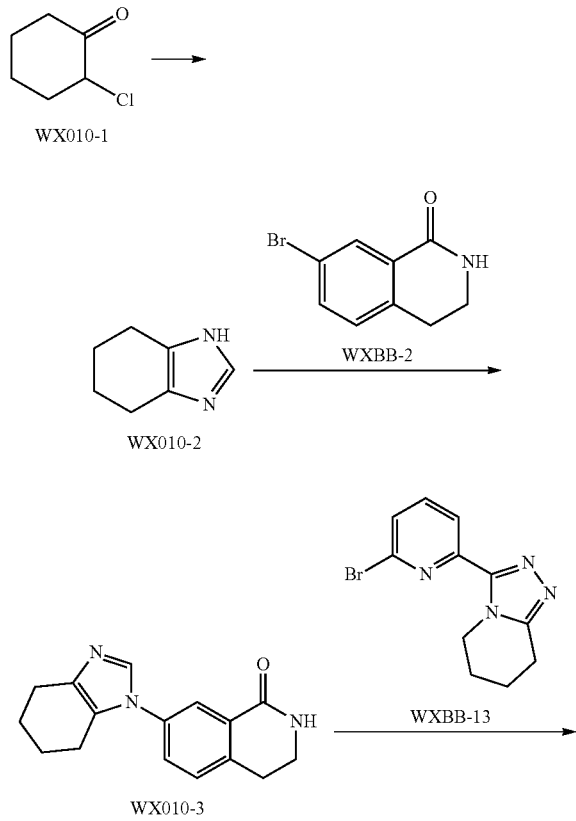

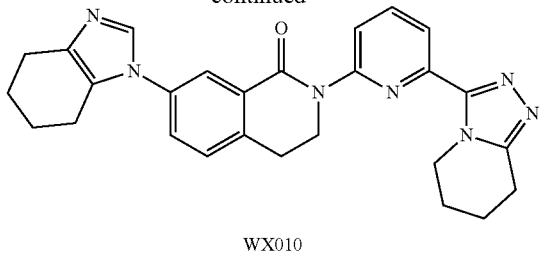

WX010

Step 1: Synthesis of Compound WX010-2

Compound WX010-1 (4.00 g, 30.17 mmol, 3.45 mL, 1.00 eq) was slowly added to formamide (13.59 g, 301.68 mmol, 12.02 mL, 10.00 eq). The reaction system was stirred at 170° C. for 4 hours. The reaction solution was cooled to room temperature, added slowly with water (50 mL), washed with toluene:cyclohexane (1:1, 40 mL*2), then adjusted to pH=8 by adding sodium bicarbonate, and extracted with dichloromethane (100 mL*3). The organic layer was washed with saturated brine (50 mL), dried over anhydrous sodium sulfate, filtered and dried on a rotary evaporator. Compound WX010-2 was obtained, ¹H NMR (400 MHz, DMSO-d6) δ ppm 1.66-1.72 (m, 4H) 2.41-2.47 (m, 4H) 7.35 (s, 1H).

Step 2: Synthesis of Compound WX010-3

Compound WXBB-2 (200.00 mg, 884.68 μmol, 1.00 eq), compound WX010-2 (200.00 mg, 1.64 mmol, 1.85 eq), 8-hydroxyquinoline (30.00 mg, 206.67 μmol, 35.71 μL, 0.23 eq) and potassium carbonate (160.00 mg, 1.16 mmol, 1.31 eq) were dissolved in dimethyl sulfoxide (2.00 mL), and cuprous iodide (40.00 mg, 210.03 μmol, 0.24 eq) was added. The system was stirred at 130° C. for 20 hours under nitrogen condition. The reaction solution was cooled to room temperature, added with water (30 mL), and extracted with dichloromethane (30 mL*2). The organic phase was washed successively with water (300 mL) and saturated brine (300 mL), dried over anhydrous sodium sulfate, and filtered. The filtrate was dried on a rotary evaporator under reduced pressure to obtain a crude product. The crude product was separated and purified by a TLC (DCM/MeOH=10/1) plate. Compound WX010-3 was obtained, MS m/z: 268.1 [M+H]+.

Step 3: Synthesis of Compound WX010

Compound WX010-3 (110.00 mg, 360.54 μmol, 1.00 eq) (purity 87.62%), compound WXBB-13 (130.00 mg, 465.72 μmol, 1.29 eq), Xantphos (32.00 mg, 55.30 μmol, 0.15 eq), Pd₂(dba)₃ (20.00 mg, 21.84 μmol, 0.06 eq), and cesium carbonate (350.00 mg, 1.07 mmol, 2.98 eq) were added to dioxane (2.00 mL). The system was stirred at 120° C. for 20 hours under nitrogen condition. The reaction solution was cooled to room temperature, added with water (30 mL), and extracted with dichloromethane (30 mL*2). The organic phase was washed successively with water (300 mL) and saturated brine (300 mL), dried over anhydrous sodium sulfate, and filtered. The filtrate was dried on a rotary evaporator under reduced pressure to obtain a crude product. The crude product was separated and purified by prep-HPLC (column: Xtimate C18 150*25 mm*5 μm; mobile phase: [water (0.225% FA)-ACN]; B %: 15%-40%, 11.5 min) to obtain compound WX010. ¹H NMR (400 MHz, CHLOROFORM-d) δ ppm 1.85 (br d, J=5.27 Hz, 4H) 1.94-2.09 (m, 4H) 2.53-2.62 (m, 3H) 2.66-2.75 (m, 2H) 3.10 (t, J=6.27 Hz, 2H) 3.24 (t, J=6.40 Hz, 2H) 4.34 (t, J=6.40 Hz, 2H) 4.47 (t, J=6.02 Hz, 2H) 7.39-7.53 (m, 2H) 7.70 (s, 1H) 7.84-7.94 (m, 1H) 8.01 (d, J=7.78 Hz, 1H) 8.08-8.18 (m, 2H). MS m/z: 233.7 [M/2+H]+.

Example 011: WX011

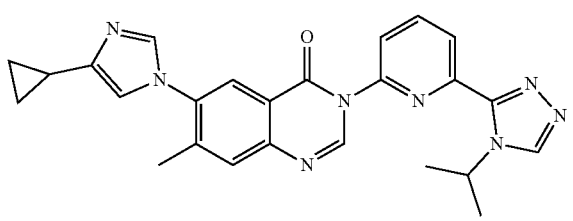 [SMILES: Cc1cc2ncn(-c3cccc(-c4nncn4C(C)C)n3)c(=O)c2cc1-n1cnc(C2CC2)c1]

Synthetic Route:

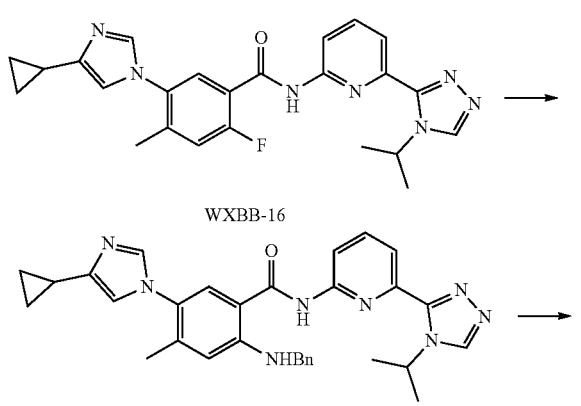

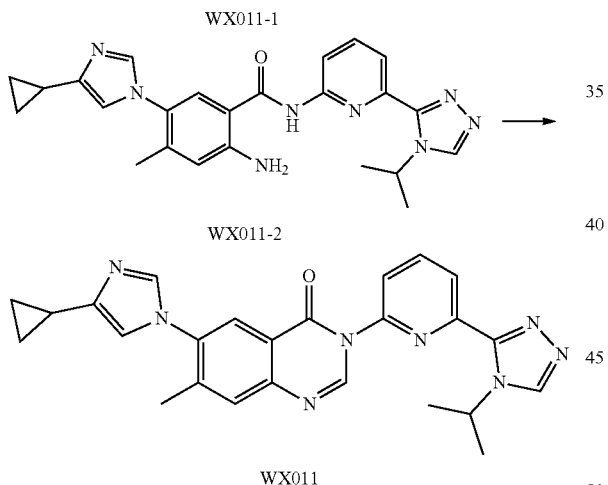

Step 1: Synthesis of Compound WX011-2

Compound WXBB-16 (740.00 mg, 1.27 mmol, 1.00 eq) (a purity of 76.2%), benzylamine (420.00 mg, 3.92 mmol, 428.57 μL, 3.09 eq), and potassium carbonate (550.00 mg, 3.98 mmol, 3.13 eq) were dissolved in acetonitrile (20.00 mL). Then the reaction was stirred at 90° C. for 48 hours. The reaction solution was added with water (30 mL), and then extracted with dichloromethane (30 mL*3). The organic phases were combined and dried over anhydrous sodium sulfate (15 g). The anhydrous sodium sulfate was filtered off, and the filtrate was dried on a rotary evaporator. The crude product was separated and purified by Prep-HPLC (column: Xtimate C18 150*25 mm*5 μm; mobile phase: [water (0.225% FA)-ACN]; B %: 25%-50%, 11.5 min) to obtain compound WX011-1. MS m/z: 533.2 [M+H]+.

Step 2: Synthesis of Compound WX011-2

Compound WX011-1 (150.00 mg, 281.62 μmol, 1.00 eq) (a purity of 100%) was dissolved in methanol (20.00 mL), and then dry Pd/C (50.00 mg, 10% purity) was added. Then the reaction was reacted at 25° C. for 32 hours under hydrogen (15 psi) condition. The Pd/C in the reaction solution was filtered off, and the filtrate was dried on a rotary evaporator. The crude product was separated and purified by Prep-HPLC (column: Xtimate C18 150*25 mm*5 μm; mobile phase: [water (0.225% FA)-ACN]; B %: 15%-30%, 11.5 min). Compound WX011-2 was obtained, MS m/z: 443.4 [M+H]+.

Step 3: Synthesis of Compound WX011

Compound WX011-2 (80.00 mg, 174.02 μmol, 1.00 eq) (a purity of 96.260%) was mixed with trimethyl orthoformate (9.23 g, 87.01 mmol, 9.52 mL, 500.00 eq). The reaction was stirred at 130° C. for 16 hours. The reaction solution was dried on a rotary evaporator. The crude product was separated and purified by Prep-HPLC (column: Xtimate C18 150*25 mm*5 μm; mobile phase: [water (0.225% FA)-ACN]; B %: 13%-30%, 11.5 min) to obtain compound WX011. $^1$H NMR (400 MHz, METHANOL-d4) δ ppm 8.92 (s, 1H), 8.75 (s, 1H), 8.23-8.33 (m, 2H), 8.20 (d, J=6.0 Hz, 1H), 8.04 (d, J=7.5 Hz, 1H), 7.78-7.88 (m, 2H), 7.17 (br s, 1H), 5.50 (dt, J=13.4, 6.6 Hz, 1H), 2.41 (s, 3H), 1.86-2.02 (m, 1H), 1.61 (d, J=6.8 Hz, 6H), 0.88-0.97 (m, 2H), 0.74-0.83 (m, 2H). MS m/z: 227.2[M/2+H]+.

Example 012: WX012

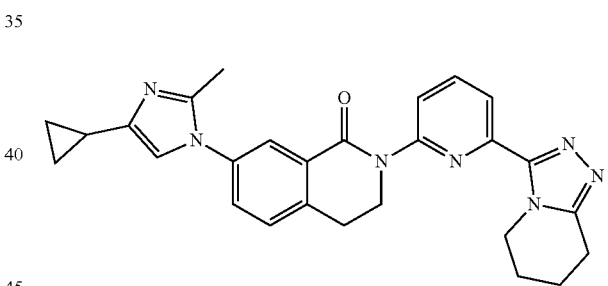

Synthetic Route:

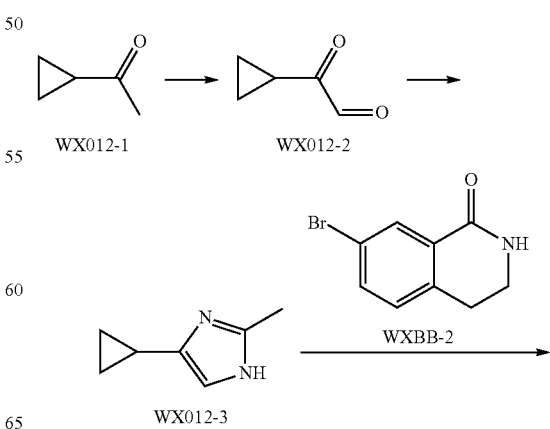

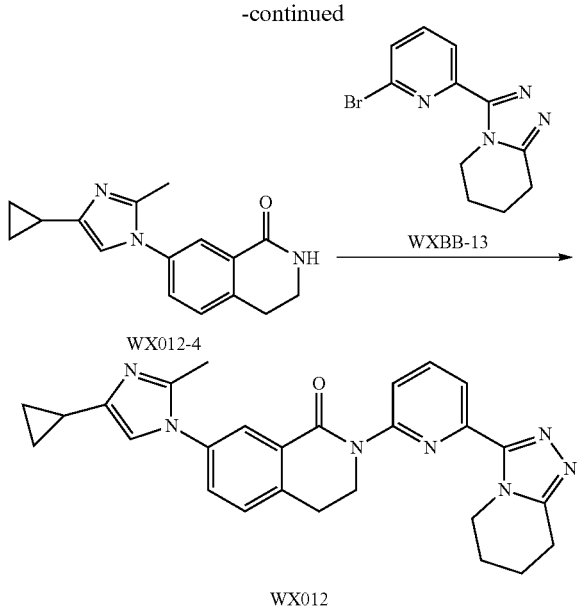

Step 1. Synthesis of Compound WX012-2

Selenium dioxide (55.00 g, 495.72 mmol, 53.92 mL, 1.39 eq), acetic acid (15.00 g, 249.64 mmol, 14.29 mL, 0.70 eq), and water (10.00 g, 554.94 mmol, 1.56 eq) were dissolved in dioxane (50.00 mL). The mixture was heated to 90° C., stirred for 1 hour, and then compound WX012-1 (30.00 g, 356.63 mmol, 35.29 mL, 1.00 eq) was added. The system was stirred at 90° C. for 16 hours. After the reaction was completed, the solid in the reaction solution was filtered off, and the filtrate was dried on a rotary evaporator. The resulting oil was separated by column chromatography (ethyl acetate/petroleum ether=0/1-1/1) to obtain product WX012-2. $^1$H NMR (400 MHz, CHLOROFORM-d) δ ppm 2.09-2.28 (m, 1H), 0.94-1.18 (m, 3H), 0.94-0.99 (m, 1H).

Step 2. Synthesis of Compound WX012-3

WX012-2 (1.00 g, 10.19 mmol, 1.00 eq) (crude), acetaldehyde (2.14 g, 15.29 mmol, 1.50 eq) (a purity of 40%), and aqueous ammonia (7.15 g, 50.95 mmol, 7.86 mL, 25% purity, 5.00 eq) were dissolved in methanol (20.00 mL). The system was stirred at 75° C. for 16 hours. After the reaction was completed, the reaction solution was dried on a rotary evaporator. 30 mL of water was added to the oil, and the pH of the reaction solution was adjusted to 1-2 with 6 mol/L hydrochloric acid solution (15 mL), and then extracted with dichloromethane (30 mL*3). The aqueous phase was retained and added with 0.5 g of sodium hydroxide to adjust the pH thereof to 10-11, and then extracted with dichloromethane (30 mL*3). The organic phases were combined, dried over anhydrous sodium sulfate (10 g), and filtered. The filtrate was dried on a rotary evaporator to obtain WX012-3. $^1$H NMR (400 MHz, CHLOROFORM-d) δ ppm 6.44-6.57 (m, 1H), 2.28 (s, 3H), 1.62-1.76 (m, 1H), 0.70-0.77 (m, 2H), 0.50-0.64 (m, 2H).

Step 3. Synthesis of Compound WX012-4

WXBB-2 (100.00 mg, 442.34 μmol, 1.00 eq), WX012-3 (110.00 mg, 900.38 μmol, 2.04 eq), cuprous iodide (43.00 mg, 225.78 μmol, 0.51 eq), 8-hydroxyquinoline (33.00 mg, 227.34 μmol, 39.29 μL, 0.51 eq), and potassium carbonate (92.00 mg, 665.65 μmol, 1.50 eq) were dissolved in dimethyl sulfoxide (15.00 mL), then purged with nitrogen three times, and the reaction was stirred at 130° C. for 16 hours. After the reaction was completed, the reaction solution was added with water (25 mL), and then extracted with dichloromethane (20 mL*3). The organic phases were combined, dried over anhydrous sodium sulfate (10 g), filtered and the filtrate was dried on a rotary evaporator. The obtained oil was separated and purified by Prep-TLC (ethyl acetate). Product WX012-4 was obtained, MSm/z: 268.1 [M+H]+.

Step 4. Synthesis of Compound WX012

WX012-4 (80.00 mg, 282.28 μmol, 1.00 eq) (a purity of 94.327%), WXBB-13 (120.00 mg, 429.89 μmol, 1.52 eq), Pd$_2$(dba)$_3$ (13.00 mg, 14.20 μmol, 0.05 eq), Xant-Phos (25.00 mg, 43.21 μmol, 0.15 eq), and cesium carbonate (280.00 mg, 859.37 μmol, 3.04 eq) were dissolved in anhydrous dioxane (15.00 mL), then purged with nitrogen three times, and the reaction was reacted at 120° C. for 16 hours. After the reaction was completed, the reaction solution was added with water (25 mL), and then extracted with dichloromethane (20 mL*3). The organic phases were combined, dried over anhydrous sodium sulfate (10 g), filtered and the filtrate was dried on a rotary evaporator. The resulting oil was separated and purified by Prep-TLC (methanol/dichloromethane=1/10) to obtain a brown oil, which was then separated and purified by Prep-HPLC (column: Xtimate C18 150*25 mm*5 μm; mobile phase: [water (0.225% FA)-ACN]; B %: 10%-35%, 11.5 min) to obtain product WX012. MS m/z: 466.2 [M+H]$^+$, $^1$H NMR (400 MHz, METHANOL-d4) δ ppm 8.25 (s, 1H), 8.12 (d, J=2.0 Hz, 1H), 8.02 (t, J=2.3 Hz, 2H), 7.60-7.68 (m, 2H), 7.16 (s, 1H), 4.57 (t, J=6.0 Hz, 2H), 4.40 (t, J=6.4 Hz, 2H), 3.29-3.32 (m, 2H), 3.06 (t, J=6.3 Hz, 2H), 2.43 (s, 3H), 2.09 (brd, J=4.5 Hz, 2H), 1.96-2.04 (m, 2H), 1.88-1.95 (m, 1H), 0.94-1.01 (m, 2H), 0.72-0.87 (m, 2H).

Example 013: WX013

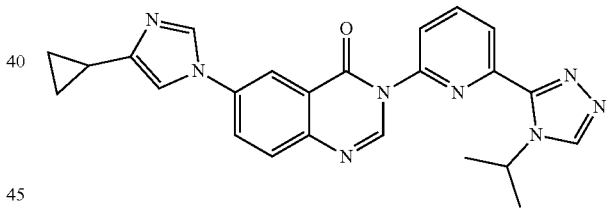

Synthetic Route:

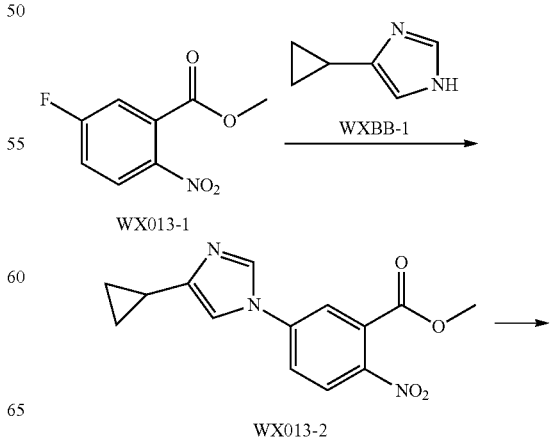

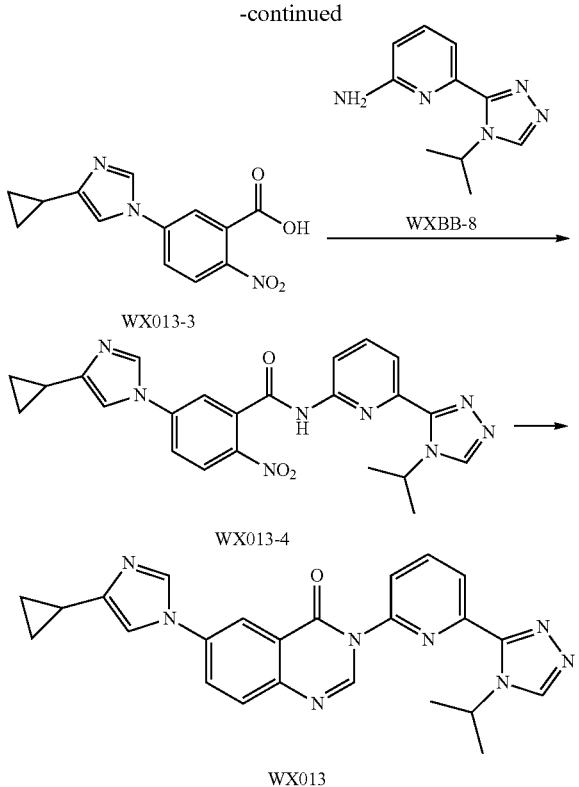

Step 1: Synthesis of Compound WX013-2

WX013-1 (9.00 g, 45.19 mmol, 1.00 eq) and WXBB-1 (5.86 g, 54.23 mmol, 1.20 eq) (crude) were dissolved in tetrahydrofuran (90.00 mL). The system was refluxed with stirring at 80° C. for 40 hours. After the reaction was completed, the reaction solution was dried on a rotary evaporator under reduced pressure to obtain a crude product. The crude product was purified by column (0~60% EA/PE) to obtain product WX013-2. MS m/z: 288.1 [M+H]+.

Step 2: Synthesis of Compound WX013-3

WX013-2 (4.50 g, 15.66 mmol, 1.00 eq) was dissolved in ethanol (30.00 mL), and sodium hydroxide solution (5M, 12.53 mL, 4.00 eq) was added. The system was stirred at 25° C. for 1 hour, and a large amount of precipitate was generated. The reaction solution was filtered, and the filter cake was dried to give product WX013-3. MS m/z: 274.1 [M+H]+.

Step 3: Synthesis of Compound WX013-4

WX013-3 (2.00 g, 7.32 mmol, 1.00 eq) and anhydrous N,N-dimethylformamide (26.75 mg, 365.98 µmol, 28.16 µL, 0.05 eq) were dissolved in anhydrous dichloromethane (20 mL), and oxalyl chloride (1.86 g, 14.64 mmol, 1.28 mL, 2.00 eq) was added dropwise under $N_2$ condition. The system was stirred at 25° C. for 1 hour. The reaction solution was then dried on a rotary evaporator under reduced pressure, and water (20 mL), WXBB-8 (1.50 g, 7.39 mmol, 1.01 eq), and diisopropylethylamine (1.89 g, 14.64 mmol, 2.56 mL, 2.00 eq) were added successively. The system was stirred at 25° C. for 16 hours. After the reaction was completed, the reaction solution was filtered, and the filter cake was dried to give product WX013-4. MS m/z: 459.2 [M+H]+.

Step 4. Synthesis of Compound WX013

WX013-4 (200.00 mg, 286.56 µmol, 1.00 eq) (purity 65.69%) was dissolved in formic acid (4.00 mL), and iron powder (160.04 mg, 2.87 mmol, 10.00 eq) was added. The system was refluxed with stirring at 100° C. for 2 h. After the reaction was completed, the reaction solution was cooled to room temperature, diluted with water (50 mL), adjusted to pH=8 with saturated sodium bicarbonate solution (50 mL), and extracted with ethyl acetate (100 mL*2). The organic phase was washed successively with water (200 mL) and saturated brine (200 mL), dried over anhydrous sodium sulfate, and filtered. The filtrate was dried on a rotary evaporator under reduced pressure to obtain a crude product. The crude product was washed sequentially with dimethyl sulfoxide (4 mL) and ethanol (4 mL) to afford product WX013. MS m/z: 439.3 [M+H]+, $^1$H NMR (400 MHz, DMSO-d6) δ ppm 0.69-0.77 (m, 2H) 0.79-0.89 (m, 2H) 1.49 (d, J=6.53 Hz, 6H) 1.79-1.94 (m, 1H) 5.30-5.42 (m, 1H) 7.71 (s, 1H) 7.91 (d, J=8.78 Hz, 1H) 7.96-8.01 (m, 1H) 8.20 (dd, J=8.78, 2.76 Hz, 1H) 8.29 (d, J=4.52 Hz, 2H) 8.32 (s, 1H) 8.33-8.38 (m, 1H) 8.71 (s, 1H) 8.95 (s, 1H).

Example 014: WX014

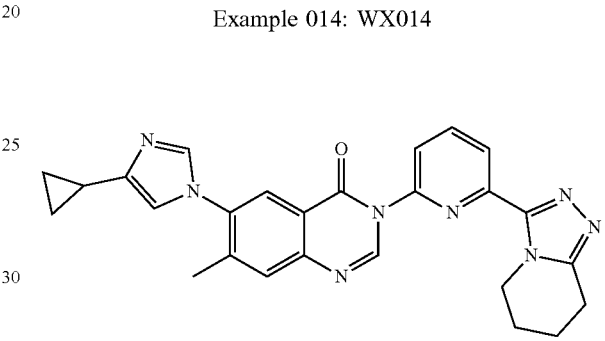

Synthetic Route:

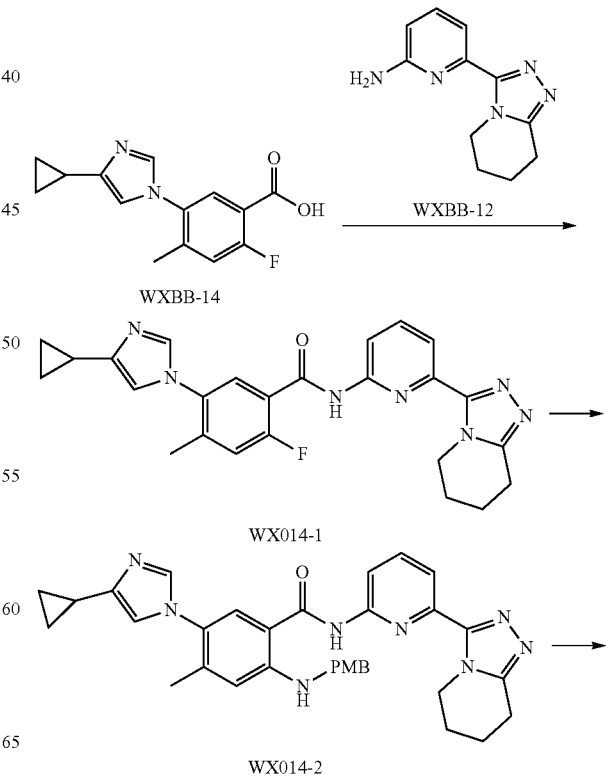

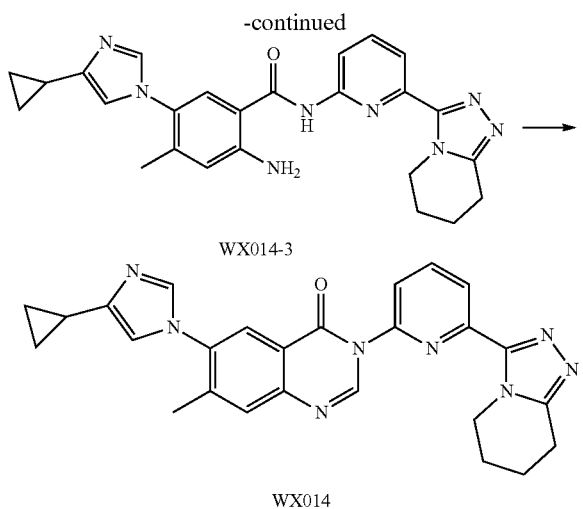

WX014-3

WX014

Step 1. Synthesis of Compound WX014-1

WXBB-14 (100.00 mg, 337.02 μmol, 1.21 eq, HCl) was dissolved in dichloromethane (5.00 mL), and oxalyl chloride (70.76 mg, 557.49 μmol, 48.80 μL, 2.00 eq) and N,N-dimethylformamide (20.37 mg, 278.75 μmol, 21.45 μL, 1.00 eq) were added under nitrogen condition. The system was stirred at 0° C. for 1 hour. The reaction solution was dried on a rotary evaporator under reduced pressure, and added successively with dichloromethane (5.00 mL), WXBB-12 (60.00 mg, 278.75 μmol, 1.00 eq) and DMAP (136.22 mg, 1.12 mmol, 4.00 eq). The system was stirred at 0° C. for 3 hours. The reaction solution was dried on a rotary evaporator under reduced pressure to obtain a crude product, which was separated with a prep-TLC (DCM:MeOH=20:1) plate to obtain WX014-1, $^1$H NMR (400 MHz, METHANOL-d4) ppm 9.17 (s, 1H), 8.47 (d, J=8.3 Hz, 1H), 8.16-8.08 (m, 1H), 8.06-7.96 (m, 2H), 7.63 (s, 1H), 7.50 (d, J=10.8 Hz, 1H), 4.82 (br. s., 2H), 3.27 (t, J=6.0 Hz, 2H), 2.36 (s, 3H), 2.20 (br. s., 2H), 2.15-2.04 (m, 3H), 1.22-1.12 (m, 2H), 0.98-0.89 (m, 2H).

Step 2. Synthesis of Compound WX014-2

WX014-1 (250 mg, 312.13 μmol, 1.00 eq) was dissolved in acetonitrile (2.00 mL), and p-methoxybenzylamine (128.45 mg, 936.39 μmol, 121.18 μL, 3.00 eq) and potassium carbonate (129.42 mg, 936.39 μmol, 3.00 eq) were added. The system was stirred at 100° C. for 88 hours. The reaction solution was cooled to room temperature, added with water (50 mL), and extracted with DCM (50 mL*2). The organic phase was washed successively with water (50 mL) and saturated brine (50 mL), dried over anhydrous sodium sulfate and filtered. The filtrate was dried on a rotary evaporator under reduced pressure to obtain a crude product. The crude product was purified by a column (0~6% MeOH/DCM) to obtain product WX014-2. MS m/z: 575.1 [M+H]$^+$.

Step 3. Synthesis of Compound WX014-3

WX014-2 (280.00 mg, 282.60 μmol, 1.00 eq) (purity 58.00%) was dissolved in trifluoroacetic acid (5.00 mL). The system was stirred at room temperature for 2 hours. The reaction solution was dried on a rotary evaporator under reduced pressure, added with DCM (20 mL), washed with water (20 mL*2), dried over anhydrous sodium sulfate, and then filtered. The filtrate was dried on a rotary evaporator under reduced pressure to obtain a crude product. The crude product was purified with prep-TLC (DCM/MeOH=10/1) to obtain product WX014-3. MS m/z: 455.2 [M+H]$^+$, $^1$H NMR (400 MHz, CHLOROFORM-d) δ ppm 0.78-0.84 (m, 2H) 0.86-0.92 (m, 2H) 1.89-2.03 (m, 5H) 2.10 (s, 3H) 3.01-3.11 (m, 2H) 4.42 (t, J=5.90 Hz, 2H) 5.83 (s, 2H) 6.64 (s, 1H) 6.75 (s, 1H) 7.36-7.43 (m, 2H) 7.79-7.90 (m, 1H) 8.01 (d, J=7.53 Hz, 1H) 8.25 (d, J=8.03 Hz, 1H) 8.36 (s, 1H).

Step 4. Synthesis of Compound WX014

WX014-3 (119.98 mg, 193.89 μmol, 1.00 eq) (purity 73.45%) was dissolved in trimethyl orthoformate (2.00 mL). The system was stirred at 110° C. for 2 hours. After the reaction was completed, the reaction solution was dried on a rotary evaporator under reduced pressure to obtain a crude product. The crude product was separated and purified by column (Xtimate C18 150*25 mm*5 μm; mobile phase: [water (10 mM NH$_4$HCO$_3$)-ACN]; B %: 28%-48%, 10 min) to obtain product WX014. MS m/z: 465.0 [M+H]$^+$, $^1$H NMR (400 MHz, CHLOROFORM-d) δ ppm 0.82-0.88 (m, 2H) 0.89-0.96 (m, 2H) 1.88-2.09 (m, 4H) 2.42 (s, 3H) 3.10 (t, J=6.40 Hz, 2H) 4.48 (t, J=6.02 Hz, 2H) 6.87 (s, 1H) 7.52 (s, 1H) 7.74 (s, 1H) 7.91 (d, J=7.78 Hz, 1H) 8.06 (t, J=8.03 Hz, 1H) 8.23 (s, 1H) 8.45 (d, J=7.53 Hz, 1H) 8.63 (s, 1H).

Example 015: WX015

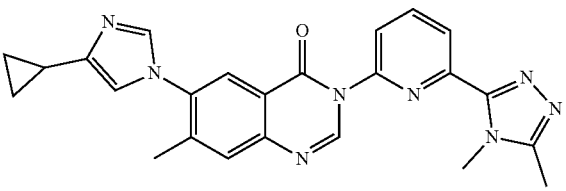 [SMILES: Cc1cc2ncn(-c3cccc(-c4nnc(C)n4C)n3)c(=O)c2cc1-n1cnc(C2CC2)c1]

Synthetic Route:

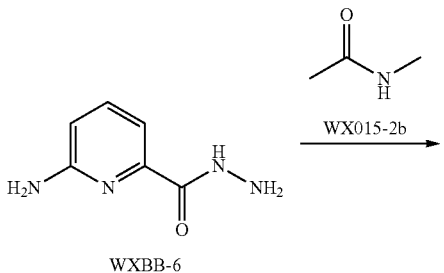

WXBB-6

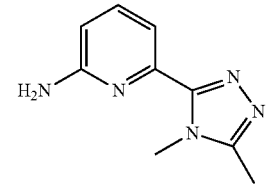

WX015-2

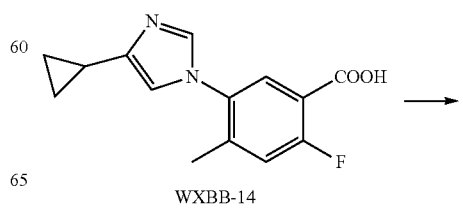

WXBB-14

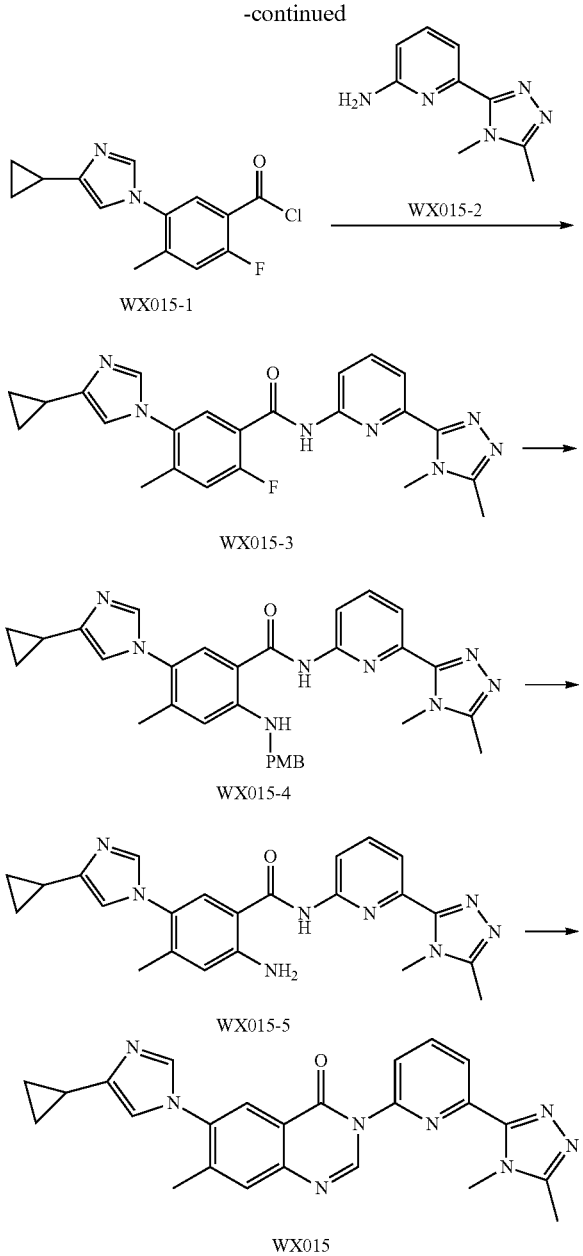

2,6-dimethylpyridine (2.11 g, 19.72 mmol, 2.30 mL, 1.00 eq) in anhydrous dichloromethane (30.00 mL) was added dropwise oxalyl chloride (2.50 g, 19.72 mmol, 1.73 mL, 1.00 eq) at 0° C., and the mixture was reacted at 0° C. for 1 hour. WXBB-6 (3.00 g, 19.72 mmol, 1.00 eq) was added to the reaction solution at 25° C. in one portion, and the reaction solution became cloudy, and anhydrous dichloromethane (10.00 mL) and anhydrous tetrahydrofuran (2.00 mL) were added. Stirred at 25° C. for 20 hours, and concentrated under reduced pressure with a water pump at 40° C. to obtain a yellow solid. 30 mL of saturated aqueous sodium bicarbonate solution was added to the yellow solid, and the white solid was dissolved. The solution was reacted at 100° C. for 17 hours. The reaction solution was cooled to 25° C., allowed to stand for 72 hours and a white precipitate was generated. The reaction solution was filtered, and the filtrate was lyophilized to give a brown-red oil, which was separated by prep-HPLC (column: Phenomenex luna (2) C18 250*50 mm 10 μm; mobile phase: [water (10 mM $NH_4HCO_3$)-ACN]; B %: 0%-15%, 20 min) to obtain WX015-2 as a brown-red oil. $^1$H NMR (400 MHz, CHLOROFORM-d) δ ppm 7.57 (dd, J=8.4 Hz, J=7.2 Hz, 1H) 7.20 (d, J=7.2 Hz, 1H) 6.64 (d, J=8.4 Hz, 1H) 3.93 (s, 3H) 2.48 (s, 3H).

Step 3. Synthesis of Compound WX015-3

WX015-1 (200.00 mg, 717.59 μmol, 1.00 eq) and anhydrous dichloromethane (5.00 mL) were added into a 40 mL pre-dried reaction bottle, and WX015-2 (135.78 mg, 717.59 μmol, 1.00 eq) was added under the protection of nitrogen atmosphere, then diisopropylethylamine (92.74 mg, 717.59 μmol, 125.32 μL, 1.00 eq) was added, and the mixture was reacted at 25° C. for 18 hours. After the reaction was completed, the reaction solution was added with dichloromethane (10 mL) and water (4 mL), and extracted. The aqueous phase was extracted with dichloromethane (4 mL*3), but was not extracted completely. The aqueous and organic phases were combined and dried on a ratory evaporator to give a yellow solid. The crude product was purified by Prep-TLC (DCM:MeOH=10:1) to obtain WX015-3 as a yellow oil. 216.7 (M/2+1).

Step 4. Synthesis of Compound WX015-4

WX015-3 (100.00 mg, 231.77 μmol, 1.00 eq) and p-methoxybenzylamine (2.00 mL) were added into a pre-dried thumb-bottle, and then potassium carbonate (62.46 mg, 451.95 μmol, 1.95 eq) and p-methoxybenzylamine (190.77 mg, 1.39 mmol, 179.97 μL, 6.00 eq) were added. The system was reacted at 100° C. for 20 hours. After the reaction was completed, the reaction solution was cooled to room temperature, diluted with water (2 mL), and extracted with dichloromethane (5 mL*3). The organic phase was washed with water (5 mL*3), dried over anhydrous sodium sulfate, and filtered. The filtrate was dried on a rotary evaporator under reduced pressure to obtain WX015-4 (1.50 g, crude) as a yellow oil. m/z=549.3 (M+1).

Step 5. Synthesis of Compound WX015-5

WX015-4 (127.00 mg, 231.48 μmol, 1.00 eq) and trifluoroacetic acid (5.00 mL) were added into a 40 mL pre-dried reaction bottle. The system was reacted at 25° C. for 24 hours. The reaction solution was dried on a rotary evaporator, and added with dichloromethane (15 mL) and aqueous saturated $NaHCO_3$ solution (10 mL). The organic phase was separated and washed successively with water (5 mL) and saturated brine (5 mL), dried over anhydrous sodium sulfate, and then filtered. The filtrate was dried on a rotary evaporator under reduced pressure to obtain WX015-5 as a yellow oil. m/z=429.2 [M+1].

Step 1. Synthesis of Compound WX015-1

WXBB-14 (200.00 mg, 768.46 mmol, 1.00 eq) and anhydrous dichloromethane (6.00 mL) were added into a 100 mL pre-dried single-neck bottle, purged with nitrogen three times, and then oxalyl chloride (165.82 mg, 1.31 mmol, 114.36 μL, 1.70 eq) was added, and then anhydrous N,N-dimethylformamide (5.62 mg, 76.85 μmol, 5.92 μL, 0.10 eq) was added. The reaction solution was reacted at 25° C. for 1.5 hours under the protection of nitrogen atmosphere. After the reaction was completed, the reaction solution was added with 3 mL of anhydrous dichloromethane, evaporated on a rotary evaporator with a water pump at room temperature until ~3 mL of anhydrous dichloromethane was remained. This process was repeated 3 times. Brown WX015-1 (200.00 mg, 717.59 μmol, 93.38% yield) in 3 mL anhydrous dichloromethane was obtained. m/z=275.1 (methyl ester).

Step 2. Synthesis of Compound WX015-2

Under the protection of nitrogen atmosphere, to a solution of WX015-2b (1.44 g, 19.72 mmol, 1.50 mL, 1.00 eq) and Step 6. Synthesis of Compound WX015

WX015-5 (150.00 mg, 350.07 µmol, 1.00 eq) and trimethyl orthoformate (2.00 mL) were added into a pre-dried thumb-bottle, and the mixture was reacted at 110° C. for 18 hours under the protection of nitrogen atmosphere. After the reaction was completed, the reaction solution was dried on a rotary evaporator to give a crude product, which was purified with prep-HPLC (column: Waters Xbridge 150*25 mm 5 µm; mobile phase: [water (10 mM NH$_4$HCO$_3$)-ACN]; B %: 10%-45%, 10.5 min) to obtain WX015, m/z=439.2 [M+1]. $^1$H NMR (400 MHz, CHLOROFORM-d) δ ppm 0.85-0.89 (m, 2H) 0.92 (br d, J=7.78 Hz, 2H) 1.94 (s, 1H) 2.42 (s, 3H) 2.56 (s, 3H) 3.98 (s, 3H) 6.87 (s, 1H) 7.52 (s, 1H) 7.75 (s, 1H) 7.92 (d, J=8.16 Hz, 1H) 8.08 (t, J=7.91 Hz, 1H) 8.24 (s, 1H) 8.44 (d, J=7.78 Hz, 1H) 8.63 (s, 1H).

Example 016: WX016

Synthetic Route:

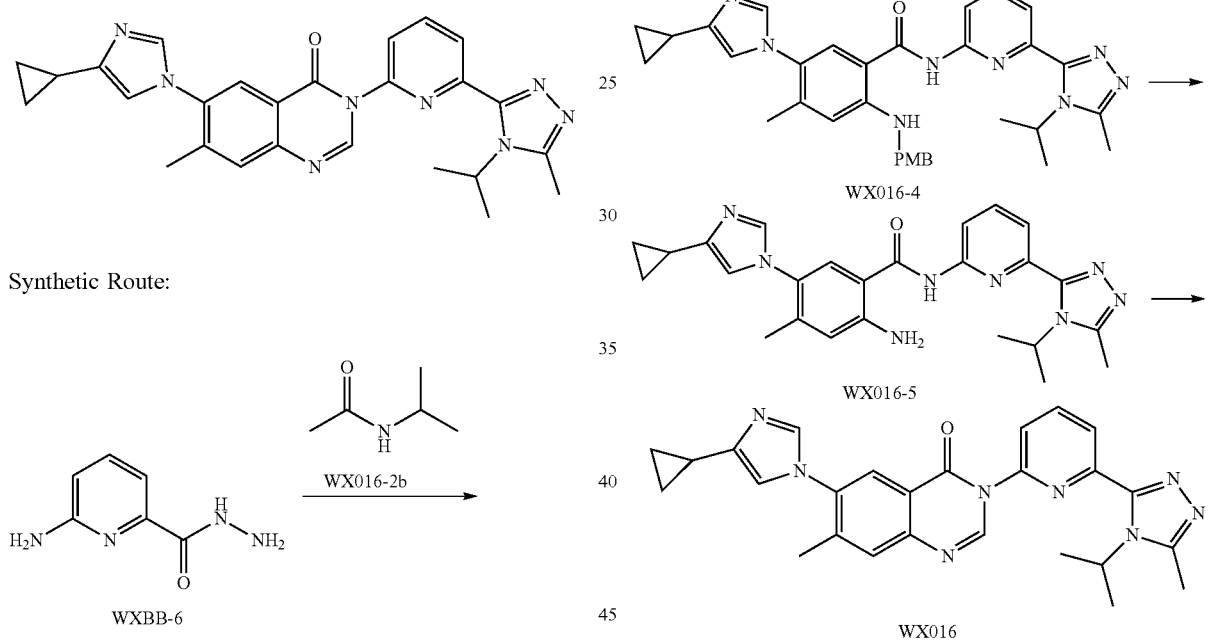

Step 1. Synthesis of Compound WX016

WXBB-14 (300.00 mg, 1.15 mmol, 1.00 eq) and anhydrous dichloromethane (3.00 mL) were added into a pre-dried thumb-bottle, purged with nitrogen three times, and oxalyl chloride (248.73 mg, 1.96 mmol, 171.54 µL, 1.70 eq) was added, and anhydrous N,N-dimethylformamide (8.43 mg, 115.27 µmol, 8.87 µL, 0.10 eq) was added. The reaction solution was reacted at 25° C. for 1 hour under the protection of nitrogen atmosphere. The reaction solution was added with 3 mL of anhydrous dichloromethane, evaporated on a rotary evaporator with a water pump at room temperature until about 2 mL of dichloromethane was remained. This process was repeated 3 times. A solution of brown WX016-1 in 2 mL of anhydrous DCM was obtained. m/z=275.1 (methyl ester MS).

Step 2. Synthesis of Compound WX016-2

WXBB-6 (1.90 g, 18.80 mmol, 1.00 eq), 2,6-dimethyl-pyridine (2.01 g, 18.80 mmol, 2.19 mL, 1.00 eq) and anhydrous dichloromethane (40.00 mL) were added into a 100 mL pre-dried three-necked bottle, purged with nitrogen three times and then the reaction system was cooled to 0° C. Oxalyl chloride (2.39 g, 18.80 mmol, 1.65 mL, 1.00 eq) was added slowly to the reaction system and the reaction system was reacted at 0° C. for 1 hour. WX016-2b (2.86 g, 18.80 mmol, 1.00 eq) was added to the reaction system in one portion at 25° C. The solution became cloudy and stirred at 25° C. for 20 hours. After the raw materials were consumed completely, the solution was concentrated under reduced pressure with a water pump at 40° C. to obtain a yellow solid. 50.00 mL of saturated sodium bicarbonate solution was added to the yellow solid. The yellow solid was dissolved, and the mixture was refluxed at 100° C. for 17 hours. After the reaction was completed, the reaction solution was poured into water (200 mL), and extracted with dichloromethane (200 mL*3). The organic phases were combined, washed successively with water (200 mL) and saturated brine (200 mL), dried over anhydrous sodium sulfate, and concentrated under reduced pressure with a water pump at 40° C. to obtain a yellow solid. The crude product was separated and purified by silica gel column chromatography to afford product WX016-2. $^1$H NMR (400 MHz, CHLOROFORM-d) δ ppm 1.52 (s, 3H) 1.54 (s, 3H) 2.62 (s, 3H) 4.49 (br s, 2H) 5.34-5.44 (m, 1H) 6.56 (d, J=8.16 Hz, 1H) 7.41 (d, J=7.53 Hz, 1H) 7.56 (t, J=7.78 Hz, 1H).

Step 3. Synthesis of Compound WX016-3

WX016-1 (300.00 mg, 1.08 mmol, 1.00 eq) and anhydrous dichloromethane (3.00 mL) were added into a pre-dried reaction bottle, and WX016-2 (233.87 mg, 1.08 mmol, 1.00 eq) was added, then diisopropylethylamine (139.11 mg, 1.08 mmol, 187.99 µL, 1.00 eq) was added, followed by purging with nitrogen, and the mixture was reacted at 25° C. for 18 hours under the protection of nitrogen atmosphere. The reaction solution was dried on a rotary evaporator and purified with prep-TLC (DCM:MeOH=10:1) to obtain WX016-3, m/z=460.0 (M+1).

Step 4. Synthesis of Compound WX016-4

WX016-3 (200.00 mg, 435.24 µmol, 1.00 eq) and p-methoxybenzylamine (2.00 mL) were added into a pre-dried thumb-bottle, and then potassium carbonate (117.30 mg, 848.71 µmol, 1.95 eq) and p-methoxybenzylamine (358.23 mg, 2.61 mmol, 337.96 µL, 6.00 eq) were added. The system was reacted at 100° C. for 18 hours. The reaction solution was cooled to room temperature, diluted with water (2 mL), and extracted with dichloromethane (5 mL*3). The organic phase was washed with water (5 mL*3), dried over anhydrous sodium sulfate, and filtered. The filtrate was dried on a rotary evaporator under reduced pressure to obtain WX016-4. m/z=577.3 (M+1).

Step 5. Synthesis of Compound WX016-5

WX016-4 (250.00 mg, 433.51 µmol, 1.00 eq) and trifluoroacetic acid (5.00 mL) were added into a pre-dried reaction bottle. The system was reacted at 25° C. for 20 hours. The reaction solution was dried on a rotary evaporator, added with dichloromethane (10 mL) and saturated aqueous NaHCO$_3$ solution (5 mL). The organic phase was separated and washed successively with water (5 mL) and saturated brine (5 mL), dried over anhydrous sodium sulfate, and then filtered. The filtrate was dried on a rotary evaporator under reduced pressure to obtain a product, which was purified with prep-TLC (DCM:MeOH=10:1) to obtain WX016-5. m/z=457.2 (M+1).

Step 6. Synthesis of Compound WX016

WX016-5 (150.00 mg, 328.56 µmol, 1.00 eq) and trimethyl orthoformate (3.00 mL) were added into a pre-dried reaction bottle, and the mixture was reacted at 110° C. for 18 hours under the protection of nitrogen atmosphere. The reaction solution was dried on a rotary evaporator and purified with prep-HPLC (column: Waters Xbridge 150*25 mm 5 µm; mobile phase: [water (10 mM NH$_4$HCO$_3$)-ACN]; B %: 20%-50%, 10.5 min) to obtain WX016. m/z=467.2 (M+1), $^1$H NMR (400 MHz, CHLOROFORM-d) δ ppm 0.82-0.95 (m, 4H) 1.54 (s, 3H) 1.57-1.59 (m, 1H) 1.82 (br s, 3H) 1.91-1.98 (m, 1H) 2.41 (s, 3H) 2.67 (s, 3H) 5.34-5.46 (m, 1H) 6.87 (s, 1H) 7.51 (s, 1H) 7.74 (s, 1H) 7.95 (d, J=8.03 Hz, 1H) 8.08 (t, J=7.91 Hz, 1H) 8.18-8.32 (m, 2H) 8.61 (s, 1H).

Example 017: WX017

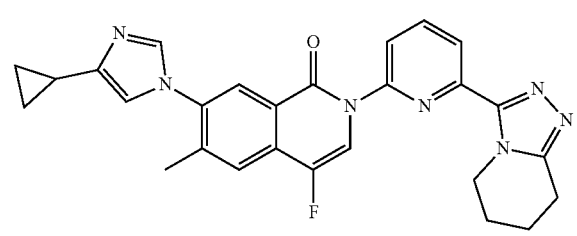 [SMILES: Cc1cc2c(F)cn(-c3cccc(-c4nnc5n4CCCC5)n3)c(=O)c2cc1-n1cnc(C2CC2)c1]

Synthetic Route:

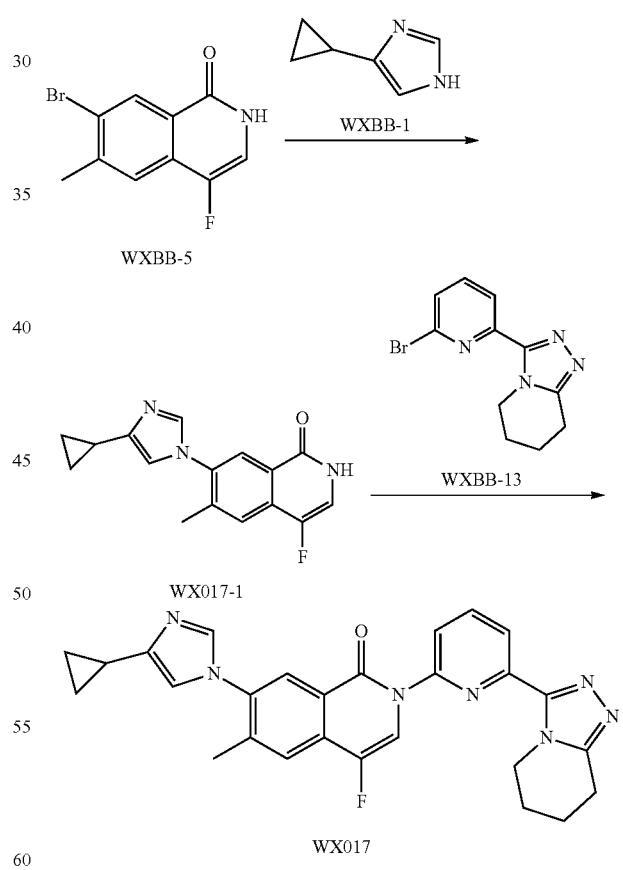

Step 1. Synthesis of Compound WX017-1

WXBB-5 (400.00 mg, 1.44 mmol, 1.00 eq), WXBB-1 (626.71 mg, 5.80 mmol, 4.03 eq), potassium carbonate (598.24 mg, 4.33 mmol, 3.01 eq), cuprous iodide (27.39 mg, 143.80 µmol, 0.10 eq), and 8-hydroxyquinoline (22.96 mg, 158.18 µmol, 27.34 µL, 0.11 eq) were added to dimethyl sulfoxide (5.00 mL). The system was filled with N₂, heated to 130° C. under microwave condition, and stirred for 10 h. The reaction solution was added with aqueous ammonia (30 mL), and extracted with dichloromethane (50 mL*2). The organic phase was washed successively with water (50 mL) and saturated brine (50 mL), dried over anhydrous sodium sulfate, and filtered. The filtrate was dried on a rotary evaporator under reduced pressure to obtain a crude product. The crude product was purified by column (0~10% MeOH/DCM) to obtain product WX017-1. m/z=284.1 [M+H]⁺, ¹H NMR (400 MHz, CHLOROFORM-d) δ ppm 0.83 (br d, J=3.26 Hz, 2H) 0.87-0.91 (m, 2H) 1.92 (br s, 1H) 2.40 (s, 3H) 6.86 (br s, 1H) 7.15 (br d, J=4.27 Hz, 1H) 7.53 (br s, 1H) 7.74 (s, 1H) 8.23 (br s, 1H).

Step 2. Synthesis of Compound WX017

WX017-1 (250.00 mg, 754.15 μmol, 1.00 eq) (purity 85.46%), WXBB-13 (315.77 mg, 1.13 mmol, 1.50 eq), Pd₂(dba)₃ (40.00 mg, 43.68 μmol, 0.06 eq), Xantphos (70.00 mg, 120.98 μmol, 0.16 eq), and cesium carbonate (750.00 mg, 2.30 mmol, 3.05 eq) were added to anhydrous dioxane (4.00 mL). The system was heated to 120° C. under microwave and stirred for 2 h. The reaction solution was filtered, and the filtrate was dried on a rotary evaporator under reduced pressure to obtain a crude product. The crude product was purified by prep-HPLC (Xtimate C18 150*25 mm*5 μm; mobile phase: [water (0.225% FA)-ACN]; B %: 10%-40%, 12 min) to obtain product WX017. ¹H NMR (400 MHz, CHLOROFORM-d) δ ppm 0.86 (br d, J=3.26 Hz, 2H) 0.90-0.97 (m, 2H) 1.93 (br d, J=5.27 Hz, 1H) 1.96-2.01 (m, 2H) 2.06 (br d, J=5.27 Hz, 2H) 2.44 (s, 3H) 3.12 (br t, J=6.27 Hz, 2H) 4.48 (t, J=5.77 Hz, 2H) 6.88 (s, 1H) 7.55 (s, 1H) 7.77 (s, 1H) 7.86 (d, J=6.78 Hz, 1H) 7.97-8.04 (m, 1H) 8.06-8.12 (m, 1H) 8.28-8.39 (m, 2H).

Example 018: WX018

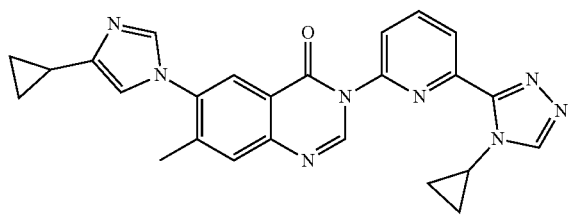 [SMILES: Cc1cc2ncn(-c3cccc(-c4nncn4C4CC4)n3)c(=O)c2cc1-n1cnc(C2CC2)c1]

Synthetic Route:

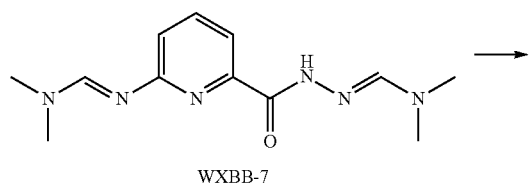

WXBB-7

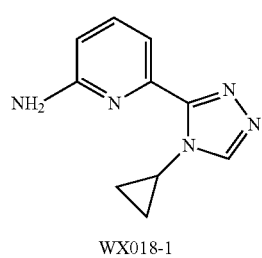

WX018-1

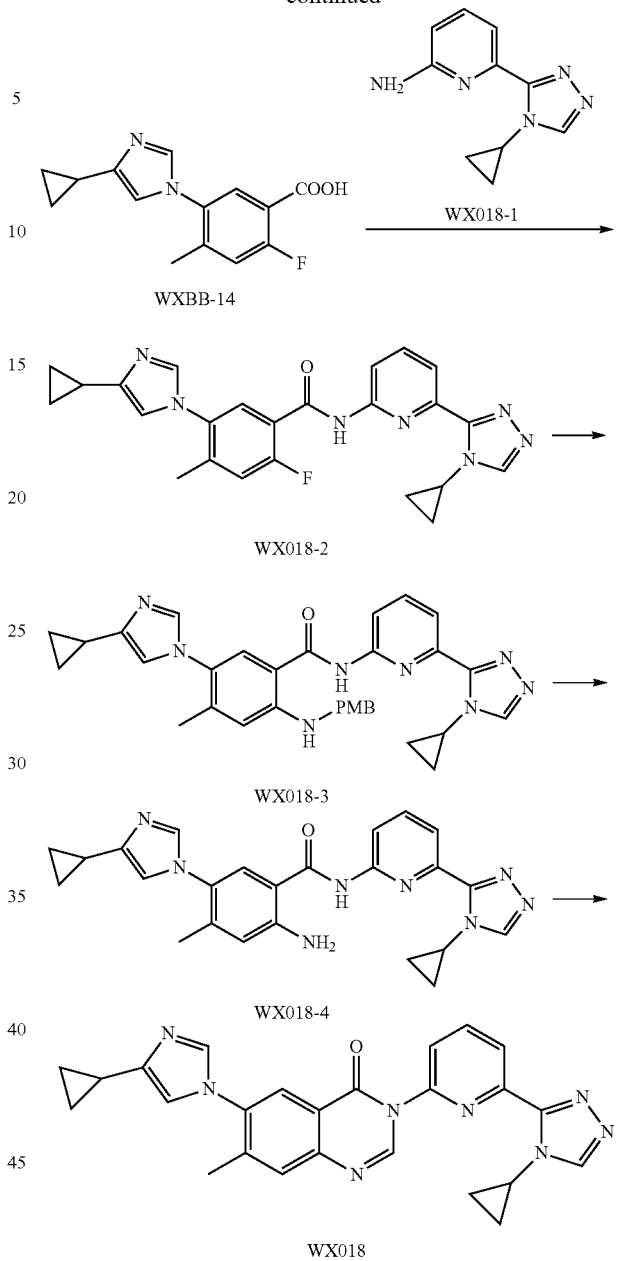

Step 1. Synthesis of Compound WX018-1

WXBB-7 (4.00 g, 15.25 mmol, 1.00 eq) was dissolved in a mixture of acetonitrile (32.00 mL) and acetic acid (8.00 mL), and cyclopropylamine (4.39 g, 76.86 mmol, 5.35 mL, 5.04 eq) was added. The system was stirred at 80° C. for 16 hours. The reaction solution was dried on a rotary evaporator under reduced pressure, diluted with water (100 mL), adjusted to pH=8 with saturated sodium bicarbonate solution (100 mL), and extracted with ethyl acetate (150 mL*4). The organic phase was dried over anhydrous sodium sulfate and filtered. The filtrate was dried on a rotary evaporator under reduced pressure to obtain a crude product. The crude product was purified by a column (0~10% MeOH/DCM) to obtain WX018-1, ¹H NMR (400 MHz, CHLOROFO RM-d) δ ppm 0.86-0.93 (m, 2H) 1.08 (q, J=6.53 Hz, 2H) 3.89 (tt, J=7.37, 3.80 Hz, 1H) 4.53 (br s, 2H) 6.58 (d, J=8.03 Hz, 1H) 7.48-7.54 (m, 1H) 7.54-7.60 (m, 1H) 8.16 (s, 1H).

Step 2. Synthesis of Compound WX018-2

WXBB-14 (500.00 mg, 1.92 mmol, 1.00 eq, HCl) was added to anhydrous dichloromethane (8 mL), and anhydrous N,N-dimethylformamide (14.03 mg, 192.00 μmol, 14.77 μL, 0.10 eq) was added, and oxalyl chloride (450.86 mg, 3.55 mmol, 310.93 μL, 1.85 eq) was added dropwise slowly under nitrogen condition. The system was stirred at 25° C. for 1 hour. The reaction solution was dried on a rotary evaporator, then dichloromethane (8 mL) was added, and WX018-1 (471.36 mg, 2.34 mmol, 1.22 eq) and diisopropylethylamine (500.00 mg, 3.87 mmol, 675.68 μL, 2.01 eq) were added successively with stirring. The system was stirred at 25° C. for 1 hour. The reaction solution was diluted with water (30 mL) and extracted with dichloromethane (30 mL*2). The organic phase was washed successively with water (30 mL) and saturated brine (30 mL), dried over anhydrous sodium sulfate, and filtered. The filtrate was dried on a rotary evaporator under reduced pressure to obtain a crude product. The crude product was purified by column (0~10% MeOH/DCM) to obtain product WX018-2, MS m/z: 444.2 [M+H]+ 1HNMR (400 MHz, CHLOROFORM-d) δ ppm 0.84 (br d, J=3.26 Hz, 2H) 0.88-0.92 (m, 2H) 0.97-1.05 (m, 2H) 1.18 (q, J=6.44 Hz, 2H) 1.89-1.94 (m, 1H) 2.30 (s, 3H) 3.77-3.87 (m, 1H) 6.80 (s, 1H) 7.19 (br d, J=12.55 Hz, 1H) 7.46 (s, 1H) 7.89-7.98 (m, 1H) 8.07 (dd, J=13.93, 7.40 Hz, 2H) 8.23 (s, 1H) 8.43 (d, J=8.28 Hz, 1H) 9.11 (br d, J=15.31 Hz, 1H).

Step 3. Synthesis of Compound WX018-3

WX018-2 (purity 71.36%) was dissolved in acetonitrile (8.00 mL), and potassium carbonate (130.00 mg, 940.60 μmol, 1.95 eq) and p-methoxybenzylamine (400.00 mg, 2.92 mmol, 377.36 μL, 6.04 eq) were added. The system was refluxed with stirring at 100° C. for 80 hours. The reaction solution was cooled to room temperature, diluted with water (20 mL), and extracted with dichloromethane (30 mL*2). The organic phase was washed with water (50 mL*2), dried over anhydrous magnesium sulfate, and filtered. The filtrate was dried on a rotary evaporator under reduced pressure to obtain product WX018-3, MS m/z: 561.2 [M+H]+.

Step 4. Synthesis of Compound WX018-4

WX018-3 (600.00 mg, 461.14 μmol, 1.00 eq) (purity 43.09%) was dissolved in TFA (4.00 mL). The system was stirred at 25° C. for 1 hour. The reaction solution was dried on a rotary evaporator under reduced pressure, added with dichloromethane (30 mL) and saturated sodium bicarbonate solution (20 mL). The organic phase was separated and washed successively with water (30 mL) and saturated brine (30 mL), dried over anhydrous sodium sulfate, and then filtered. The filtrate was dried on a rotary evaporator under reduced pressure to obtain product WX018-4, MS m/z: 441.2 [M+H]+.

Step 5. Synthesis of Compound WX018

WX018-4 (350.00 mg, 438.71 μmol, 1.00 eq) (purity 55.215%) was dissolved in trimethyl orthoformate (5.00 mL). The system was stirred at 110° C. for 16 hours. The reaction solution was dried on a rotary evaporator to obtain a crude product, which was purified by prep-HPLC (Xtimate C18 150*25 mm*5 μm; mobile phase: [water (0.225% FA)-ACN]; B %: 10%-40%, 12 min) to obtain product WX018. 1H NMR (400 MHz, CHLOROFORM-d) δ ppm 0.81-0.88 (m, 2H) 0.92-1.03 (m, 4H) 1.09-1.19 (m, 2H) 1.88-2.00 (m, 1H) 2.40 (s, 3H) 3.85 (tt, J=7.22, 3.83 Hz, 1H) 6.87 (d, J=0.75 Hz, 1H) 7.75 (s, 1H) 7.77-7.77 (m, 1H) 7.83 (s, 1H) 8.02 (d, J=7.78 Hz, 1H) 8.07-8.14 (m, 1H) 8.24 (s, 1H) 8.31 (s, 1H) 8.40 (d, J=7.53 Hz, 1H) 8.75 (s, 1H).

Example 019: WX019

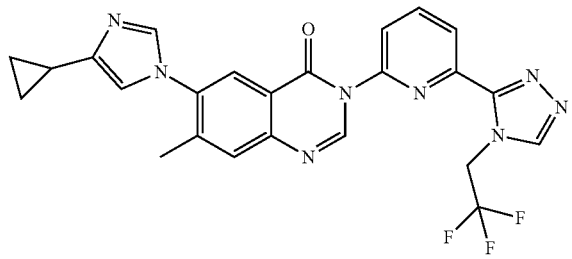 [SMILES: Cc1cc2ncn(-c3cccc(-c4nncn4CC(F)(F)F)n3)c(=O)c2cc1-n1cnc(C2CC2)c1]

Synthetic Route:

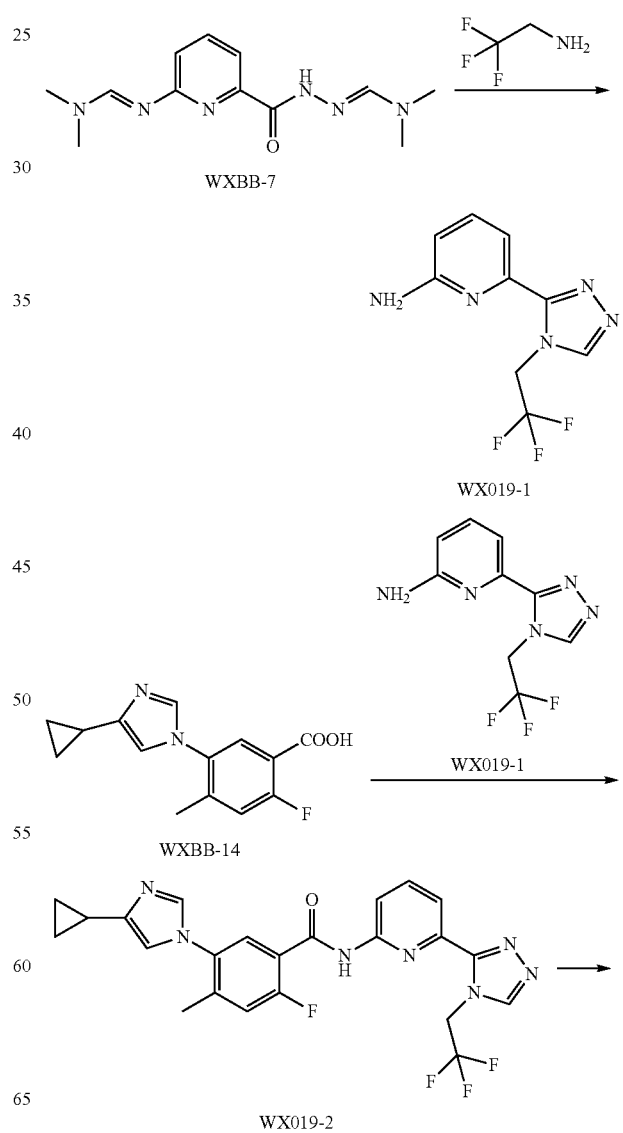

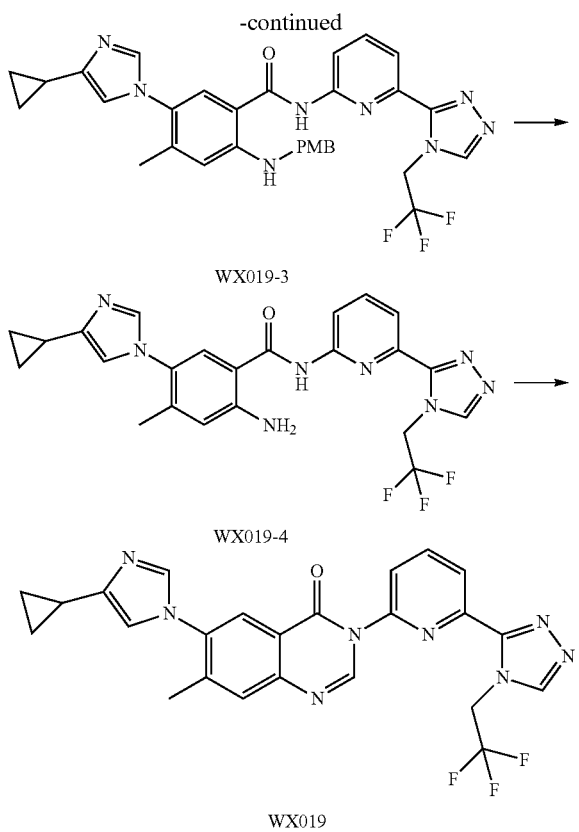

Step 1. Synthesis of Compound WX019-1

WXBB-7 (2.00 g, 7.62 mmol, 1.00 eq) and WX019-1a (3.77 g, 38.10 mmol, 3.00 mL, 5.00 eq) were added into acetic acid (5.00 mL) and acetonitrile (20.00 mL). The mixture was stirred at 80° C. for 16 hours. After the reaction was completed, the reaction solution was concentrated, adjusted to pH=8~9 by adding saturated sodium carbonate solution. A solid precipitated out and was filtered. The filter cake was dried on a rotary evaporator under reduced pressure to obtain WX019-1, $^1$H NMR (400 MHz, DMSO-d6) δ=8.69 (s, 1H), 7.54 (t, J=7.9 Hz, 1H), 7.28 (d, J=7.3 Hz, 1H), 6.54 (d, J=8.3 Hz, 1H), 6.32 (s, 2H), 5.88 (q, J=9.2 Hz, 2H).

Step 2. Synthesis of Compound WX019-2

WXBB-14 (500.00 mg, 1.33 mmol, 1.00 eq, HCl) (purity: 79.03%) was placed in anhydrous dichloromethane (10.00 mL), and oxalyl chloride (286.99 mg, 2.26 mmol, 197.92 μL, 1.70 eq) and anhydrous N,N-dimethylformamide (9.34 mg, 127.78 μmol, 9.83 μL, 0.10 eq) were added thereto. The mixture was stirred at 25° C. for 1 hour. The reaction solution was concentrated until a half volume thereof is left, then added with anhydrous dichloromethane (5 mL) to complement the other half volume. This process was repeated three times. Then diisopropylethylamine (515.67 mg, 3.99 mmol, 696.85 μL, 3.00 eq) and WX019-1 (323.00 mg, 1.33 mmol, 1.00 eq) were added thereto. The mixture was further reacted at 25° C. for 16 hours. The reaction solution was added with water (20 mL) and dichloromethane (10 mL), and layered by stirring. The aqueous phase was extracted with dichloromethane (10 mL) and the organic phases were combined, dried over anhydrous sodium sulfate, and filtered. The filtrate was dried on a rotary evaporator under reduced pressure. The crude product was purified by an automatic column (ISCO®; 24 g SepaFlash® Silica Flash Column, eluent 0~10% MeOH/DCM ethergradient @ 35 mL/min) to obtain WX019-2, m/z: 486.4 [M+H]$^+$, $^1$H NMR (400 MHz, CHLOROFORM-d) δ ppm 0.81-0.87 (m, 2H) 0.89-0.95 (m, 2H) 1.91-1.96 (m, 1H) 2.31 (s, 3H) 5.47 (q, J=8.28 Hz, 2H) 6.81 (d, J=1.00 Hz, 1H) 7.23 (d, J=12.30 Hz, 1H) 7.50 (d, J=1.25 Hz, 1H) 7.97 (t, J=8.03 Hz, 1H) 8.09 (d, J=7.28 Hz, 1H) 8.19 (d, J=7.03 Hz, 1H) 8.34 (s, 1H) 8.43 (d, J=8.03 Hz, 1H) 9.08 (br d, J=16.06 Hz, 1H).

Step 3. Synthesis of Compound WX019-3

WX019-2 (100.00 mg, 153.12 μmol, 1.00 eq) (purity: 74.33%), p-methoxybenzylamine (63.00 mg, 459.25 μmol, 59.43 μL, 3.00 eq) and potassium carbonate (63.00 mg, 455.83 μmol, 2.98 eq) were added to acetonitrile (5.00 mL). The mixture was stirred at 100° C. for 80 hours. The reaction solution was added with water (30 mL), and extracted with DCM (30 mL*2). The organic phase was washed with saturated brine (30 mL), dried over anhydrous sodium sulfate, and filtered. The filtrate was dried on a rotary evaporator under reduced pressure. The crude product was purified by an automatic column (ISCO®; 24 g SepaFlash® Silica Flash Column, eluent 0~8% MeOH/DCM ethergradient @ 35 mL/min) to obtain WX019-3, m/z: 603.6 [M+H]$^+$.

Step 4. Synthesis of Compound WX019-4

WX019-3 (280.00 mg, 66.54 μmol, 1.00 eq) (purity: 14.32%) and trifluoroacetic acid (2.00 mL) were stirred at 25° C. for 16 hours. The reaction solution was dried on a rotary evaporator, adjusted to pH=8~9 by adding saturated sodium carbonate, and extracted twice with DCM (20 mL*2). The organic phase was washed with saturated brine (20 mL), dried over anhydrous sodium sulfate, and filtered. The filtrate was dried on a rotary evaporator under reduced pressure to obtain WX019-4, which was used for the next step. MS m/z: 483.5 [M+H]$^+$.

Step 5. Synthesis of Compound WX019

WX019-4 (30.00 mg, 43.63 μmol, 1.00 eq) (purity: 70.17%) and trimethyl orthoformate (2.00 mL) were stirred at 110° C. for 1 hour. The reaction solution was dried on a rotary evaporator. The crude product was separated and purified by preparative high performance liquid chromatography (Xtimate C18 150*25 mm*5 μm; mobile phase: [water (0.225% FA)-ACN]; B %: 10%-40%, 12 min) to obtain WX019. MS m/z: 493.5 [M+H]$^+$, $^1$H NMR (400 MHz, CHLOROFORM-d) δ ppm 0.85 (br s, 2H) 0.92 (br d, J=7.53 Hz, 2H) 2.42 (s, 3H) 5.42 (q, J=7.95 Hz, 2H) 6.82-7.01 (m, 1H) 7.56 (br s, 1H) 7.77 (s, 1H) 7.94 (br d, J=7.78 Hz, 1H) 8.12-8.20 (m, 1H) 8.23 (s, 1H) 8.37 (s, 1H) 8.49 (s, 1H) 8.55 (br d, J=7.78 Hz, 1H).

Example 020: WX020

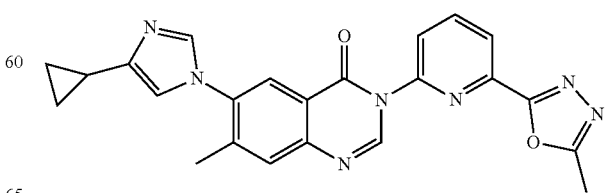

Synthetic Route:

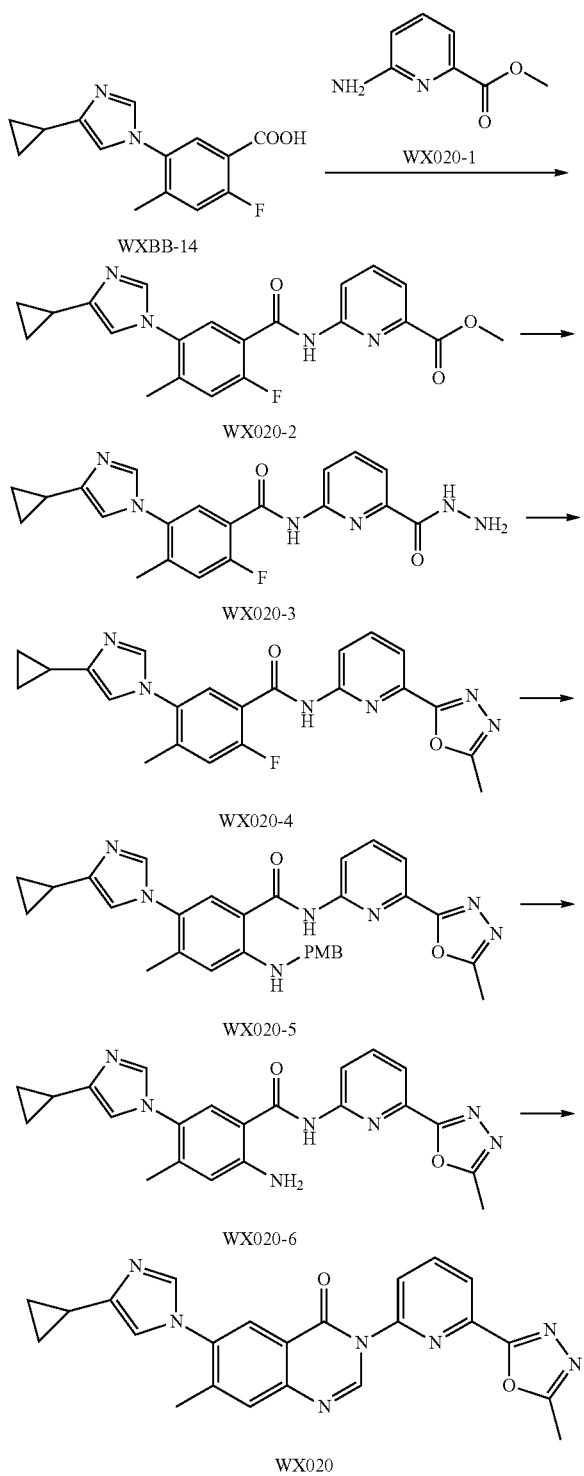

Step 1. Synthesis of Compound WX020-2

WXBB-14 (500.00 mg, 1.23 mmol, 1.00 eq, HCl) (purity 73.25%) and anhydrous N,N-dimethylformamide (5.00 mg, 68.41 μmol, 5.26 μL, 0.06 eq) were dissolved in anhydrous dichloromethane (8 mL) to form a suspension, and oxalyl chloride (310.00 mg, 2.44 mmol, 213.79 μL, 1.99 eq) was added dropwise slowly under $N_2$ condition. The system was stirred at 25° C. for 1 hour before the reaction solution was evaporated on a rotary evaporator under reduced pressure to become thick. Then anhydrous dichloromethane (5 mL) was added thereto and evaporated on a rotary evaporator under reduced pressure to become thick again. This process was repeated three times. Afterwards, anhydrous dichloromethane (8 mL), WX020-1 (220.00 mg, 1.45 mmol, 1.18 eq) and diisopropylethylamine (340.00 mg, 2.63 mmol, 459.46 μL, 2.14 eq) were added thereto successively. The system was stirred at 25° C. for 1 hour. After the reaction was completed, the reaction solution was poured into water (30 mL) and extracted with dichloromethane (30 mL*2). The organic phase was dried over anhydrous sodium sulfate and filtered. The obtained filtrate was dried on a rotary evaporator under reduced pressure to obtain a crude product WX020-2, NMR (400 MHz, CHLOROFORM-d) δ ppm 0.78-0.85 (m, 2H) 0.87-0.92 (m, 2H) 1.91-1.94 (m, 1H) 2.28 (s, 3H) 4.00-4.03 (m, 3H) 6.80 (br s, 1H) 7.19 (d, J=12.05 Hz, 1H) 7.40-7.51 (m, 1H) 7.91-7.95 (m, 2H) 7.98 (d, J=7.03 Hz, 1H) 8.53-8.60 (m, 1H) 9.16 (br d, J=11.80 Hz, 1H).

Step 2. Synthesis of Compound WX020-3

WX020-2 (450.00 mg, 936.17 μmol, 1.00 eq) (purity: 82.05%) was dissolved in methanol (10.00 mL), and hydrazine hydrate (91.00 mg, 1.82 mmol, 88.35 μL, 1.94 eq) was added. The mixture was stirred at 60° C. for 16 hours. The reaction solution was dried on a rotary evaporator to obtain product WX020-3, m/z: 395.4 [M+H]+.

Step 3. Synthesis of Compound WX020-4

WX020-3 (400.00 mg, 546.55 μmol, 1.00 eq) (purity: 53.859%) and triethyl orthoformate (4.45 g, 27.43 mmol, 5.00 mL, 50.19 eq) were stirred at 135° C. for 16 hours. After the reaction was completed, the reaction solution was dried on a rotary evaporator under reduced pressure. The crude product was purified by column (MeOH/DCM=0~8%) to obtain product WX020-4, $^1$H NMR (400 MHz, CHLOROFORM-d) δ=7.46 (d, J=8.0 Hz, 1H), 7.24 (d, J=1.5 Hz, 1H), 6.90 (dd, J=1.6, 8.2 Hz, 1H), 2.97-2.89 (m, 2H), 2.67 (t, J=6.9 Hz, 2H).

Step 4. Synthesis of Compound WX020-5

WX020-4 (180.00 mg, 430.19 μmol, 1.00 eq) (crude), potassium carbonate (178.00 mg, 1.29 mmol, 2.99 eq) and p-methoxybenzylamine (3.18 g, 23.18 mmol, 3.00 mL, 53.89 eq) were stirred at 100° C. for 16 hours followed by addition of water (30 mL) and extraction with DCM (30 mL*2). The organic phase was washed with saturated brine (30 mL), dried over anhydrous sodium sulfate, and filtered. The filtrate was dried on a rotary evaporator under reduced pressure. The crude product was purified by column (MeOH/DCM=0~8%) to obtain product WX020-5, MS m/z: 536.6 [M+H]±.

Step 5. Synthesis of Compound WX020-6

WX020-5 (150.00 mg, 280.06 μmol, 1.00 eq) (crude) was placed in trifluoroacetic acid (2.00 mL). The mixture was stirred at 25° C. for 1 hour. The reaction solution was dried on a rotary evaporator, adjusted to pH=8~9 by adding saturated sodium carbonate, and extracted twice with dichloromethane (20 mL*2). The organic phase was washed with saturated brine (20 mL), dried over anhydrous sodium sulfate, and filtered. The filtrate was dried on a rotary evaporator under reduced pressure to obtain WX020-6, MSm/z: 416.2 [M+H]±.

Step 6. Synthesis of Compound WX020

WX020-6 (100.00 mg, 121.00 μmol, 1.00 eq) (purity: 50.27%) was added to trimethyl orthoformate (2.00 mL). The mixture was stirred at 110° C. for 1 hour. The reaction solution was directly dried on a rotary evaporator. The crude product was separated by preparative HPLC (column: Xtimate C18 150*25 mm*5 μm; mobile phase: [water (0.225% FA)-ACN]; B %: 14%-24%, 12 min) to obtain product WX020. ¹H NMR (400 MHz, CHLOROFORM-d) δ=8.77 (br s, 1H), 8.33 (br d, J=6.3 Hz, 1H), 8.22 (br s, 1H), 8.12 (br d, J=8.3 Hz, 1H), 8.18-8.04 (m, 1H), 7.77 (br s, 1H), 7.65 (br s, 1H), 6.89 (br s, 1H), 2.71 (br s, 1H), 2.77-2.65 (m, 1H), 2.42 (br s, 3H), 1.96 (br s, 1H), 0.96 (br s, 2H), 0.87 (br s, 2H).
Example 021: WX021
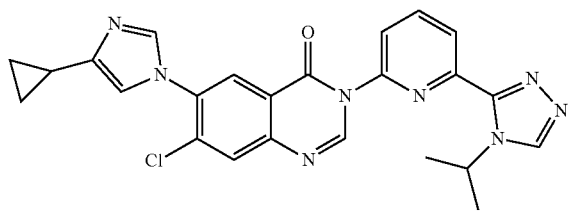 [SMILES: CC(C)n1cnnc1-c1cccc(-n2cnc3cc(Cl)c(-n4cnc(C5CC5)c4)cc3c2=O)n1]
Synthetic Route:
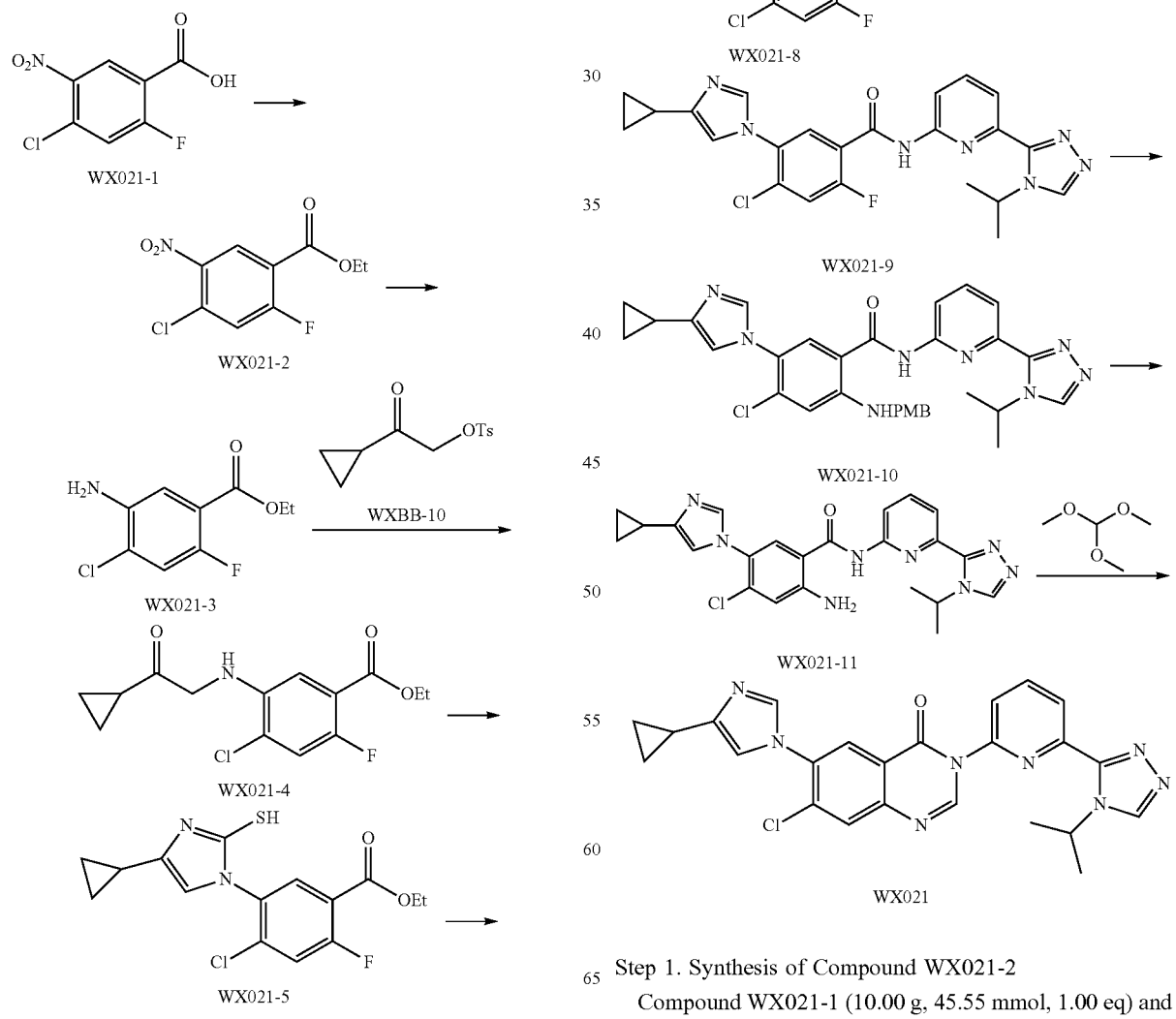
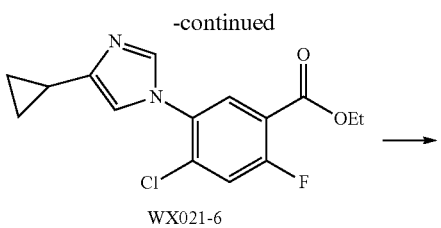
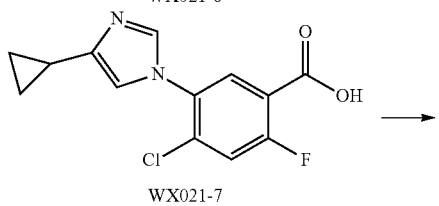
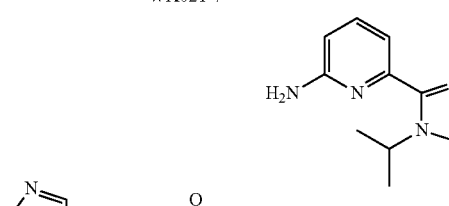
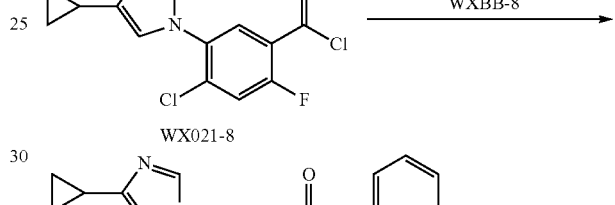
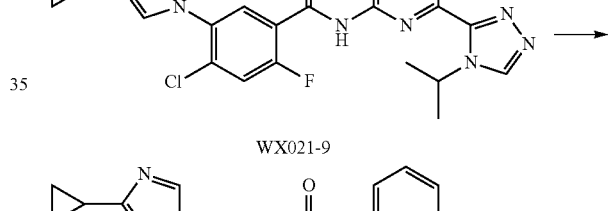
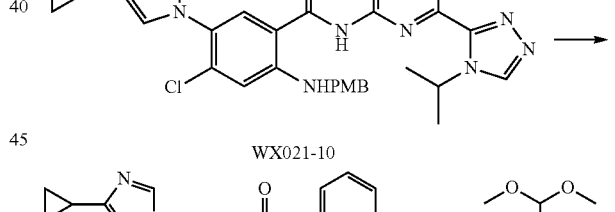
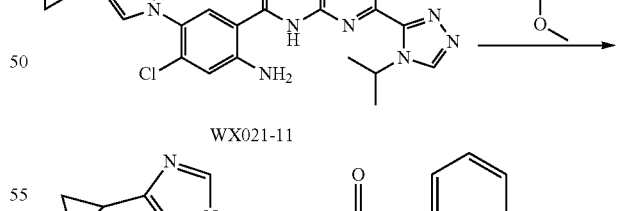
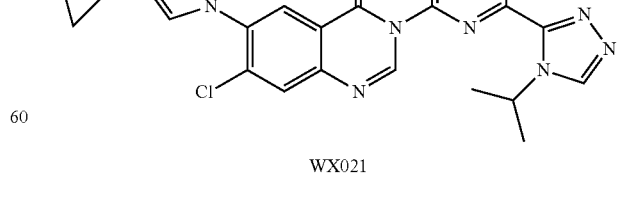
Step 1. Synthesis of Compound WX021-2
Compound WX021-1 (10.00 g, 45.55 mmol, 1.00 eq) and ethanol (100.00 mL) were added into a 250 mL pre-dried three-neck flask. To the reaction solution was added sulfuric acid (22.34 g, 227.75 mmol, 12.14 mL, 5.00 eq), and refluxed at 80° C. for 2 hours. The reaction system was cooled to room temperature, and diluted with 100 mL of ethyl acetate. The obtained solution was layered. Then the organic phase was collected and the aqueous phase was extracted with ethyl acetate (2*50 ml). The organic phases were combined, washed successively with saturated aqueous sodium bicarbonate (2*50 ml), water (2*50 ml) and saturated brine (2*50 mL), dried over anhydrous sodium sulfate, and concentrated under reduced pressure to obtain WX021-2. 1H NMR (400 MHz, CHLOROFORM-d) 1H NMR (400 MHz, CHLOROFORM-d) δ ppm 1.44 (t, J=7.03 Hz, 3H) 4.46 (q, J=7.03 Hz, 2H) 7.41 (d, J=9.54 Hz, 1H) 8.60 (d, J=7.03 Hz, 1H).

Step 2: Synthesis of Compound WX021-3

Compound WX021-2 (16.00 g, 64.62 mmol, 1.00 eq), iron powder (18.04 g, 323.10 mmol, 5.00 eq), ammonium chloride (3.80 g, 71.08 mmol, 2.48 mL, 1.10 eq), and solvents of water (130.00 mL) and ethanol (410.00 mL) were added into a 250 mL pre-dried eggplant-shaped bottle. The reaction solution was refluxed at 80° C. for 6 hours. The reaction solution was cooled to room temperature and passed through a Buchner funnel covered with celite. The obtained filter cake was washed with dichloromethane (30 mL) and the filtrate was extracted with dichloromethane (2×40 mL). The organic phases were combined, washed with saturated brine (2×50 mL), dried over anhydrous sodium sulfate, and concentrated under reduced pressure to obtain WX021-3.

Step 3: Synthesis of Compound WX021-4

Compound WX021-3 (10.00 g, 45.95 mmol, 1.00 eq), compound WXBB-10 (12.85 g, 50.55 mmol, 1.10 eq) and N,N-diisopropylethylamine (17.82 g, 137.85 mmol, 24.08 mL, 3.00 eq) were added into a pre-dried thumb-bottle. Then solvent was added, and further stirred at 140° C. for 10 hours. The reaction system was cooled to room temperature, and diluted with 100 mL of water. The obtained solution was layered, then the organic phase was collected and the aqueous phase was extracted with ethyl acetate (2*70 ml). The organic phases were combined, then washed successively with saturated ammonium chloride (2*100 ml) and saturated brine (2*100 mL), dried over anhydrous sodium sulfate, and concentrated under reduced pressure to obtain a crude product. The crude product was separated and purified by flash column chromatography (ethyl acetate:petroleum ether=1:9 to 1:4) to obtain WX021-4. m/z=300.1 [M+1].

Step 4: Synthesis of Compound WX021-5

Compound WX021-4 (12.00 g, 40.04 mmol, 1.00 eq) and acetic acid (150.00 mL) were added into a pre-dried thumb-bottle, and then potassium thiocyanate (7.78 g, 80.08 mmol, 7.78 mL, 2.00 eq) was added, and further stirred at 110° C. for 4 hours. After the reaction was completed, the reaction solution was dried directly on a rotary evaporator under reduced pressure to obtain a residue, which was re-dissolved in dichloromethane (100 mL) and added with water (100 mL). The aqueous phase was extracted with dichloromethane (2×80 mL). The organic phases were combined, dried over anhydrous sodium sulfate, then subjected to suction filtration, and dried on a rotary evaporator under reduced pressure. The residue was recrystallized from ethyl acetate (15 ml) to give WX021-5. $^1$H NMR (400 MHz, CHLOROFORM-d) δ ppm 0.60-0.67 (m, 2H) 1.32 (t, J=7.06 Hz, 3H) 1.65 (ddd, J=13.34, 8.38, 4.96 Hz, 2H) 4.31-4.40 (m, 2H) 6.33 (d, J=1.32 Hz, 1H) 7.31 (d, J=9.92 Hz, 1H) 8.00 (d, J=6.84 Hz, 1H) 10.55 (br s, 1H). m/z=341.0 [M+1].

Step 5: Synthesis of Compound WX021-6

Acetic acid (51.00 mL), water (9.80 mL) and hydrogen peroxide (4.94 g, 43.57 mmol, 4.19 mL, 30% purity, 3.00 eq) were added into a 50 mL pre-dried three-neck bottle, purged with nitrogen three times, then an internal thermometer was added to control the reaction temperature below 45° C., then compound WX021-5 (4.95 g, 14.52 mmol, 1.00 eq) was added in portions thereto under the protection of nitrogen atmosphere. The temperature was controlled below 55° C., and the mixture was reacted at this temperature for 30 min. The mixture was cooled to room temperature, and 10 mL of saturated sodium sulfite solution was added, then detected with a starch potassium iodide test paper. The mixture was subjected to ratory evaporation under reduced pressure, then dissolved in 250 mL of water, and adjusted to a pH of 10 with aqueous ammonia, followed by extraction with dichloromethane (2×200 mL). The organic phases were combined, dried over anhydrous sodium sulfate, followed by rotary evaporation under reduced pressure to obtain a dark yellow solid residue. The residue was separated and purified by flash column chromatography (ethyl acetate:petroleum ether=1:9 to 1:3) to obtain WX021-6. $^1$H NMR (400 MHz, CHLOROFORM-d) δ ppm 0.75-0.86 (m, 4H) 1.32 (t, J=7.03 Hz, 3H) 1.77-1.85 (m, 1H) 4.34 (q, J=7.36 Hz, 2H) 6.79 (d, J=1.00 Hz, 1H) 7.30 (d, J=10.04 Hz, 1H) 7.45 (d, J=1.00 Hz, 1H) 7.85 (d, J=7.03 Hz, 1H). m/z=309.1 [M+1].

Step 6: Synthesis of Compound WX021-7

Compound WX021-6 (2.48 g, 8.03 mmol, 1.00 eq), tetrahydrofuran (24.00 mL) and water (24.00 mL) were added into a pre-dried reaction bottle. The clear solution was stirred at 25° C. for 2 hours before adjusted to pH 4-5 with 2N hydrochloric acid, and then extracted with chloroform:isopropyl alcohol (3:1, 5×50 mL). The organic phases were combined, dried over anhydrous sodium sulfate, followed by suction filtration and rotary evaporation under reduced pressure to obtain WX021-7. $^1$H NMR (400 MHz, METHANOL-d4) δ ppm 0.75-0.80 (m, 1H) 0.88-0.98 (m, 2H) 1.84-1.96 (m, 1H) 7.16 (d, J=1.10 Hz, 1H) 7.57 (d, J=9.70 Hz, 1H) 7.94 (d, J=6.84 Hz, 1H) 8.02 (s, 1H).

Step 7: Synthesis of Compound WX021-8

Compound WX021-7 (500.00 mg, 1.78 mmol, 1.00 eq) was added into a 50 mL pre-dried round-bottom flask, purged with nitrogen three times, then dichloromethane (20.00 mL) was added, and then oxalyl chloride (452.22 mg, 3.56 mmol, 311.88 μL, 2.00 eq) and N,N-dimethylformamide (13.01 mg, 178.00 μmol, 13.69 μL, 0.10 eq) were added dropwise under the protection of nitrogen atmosphere. After addition, the mixture was reacted at 25° C. for 1 hour. The reaction solution was directly evaporated on a ratory evaporator with a water pump. When the volume of the solution was reduced to about one-third, 10 mL of anhydrous dichloromethane was added. This process was repeated three times to obtain WX021-8 which was directly used for the next step. m/z=295.1 [M+14].

Step 8: Synthesis of Compound WX021-9

A 100 mL round-bottom flask containing compound WX021-8 (532.00 mg, 1.78 mmol, 1.00 eq) was purged with nitrogen three times, then dichloromethane (20.00 mL) and N,N-diisopropylethylamine (230.05 mg, 1.78 mmol, 310.88 μL, 1.00 eq) were added. Afterwards, compound WXBB-8 (379.53 mg, 1.87 mmol, 1.05 eq) was added under the protection of nitrogen atmosphere. The clear solution was reacted at 30° C. for 3 hours. The reaction solution was directly dried on a rotary evaporator. The product was re-dissolved in ethyl acetate (20 mL) and extracted with water (pH=2, 3×30 mL). The aqueous phase was adjusted to pH=10, and then extracted with dichloromethane (3×50 mL). The organic phases were combined, dried over anhydrous sodium sulfate, subjected to suction filtration, and dried on a rotary evaporator to obtain WX021-9. $^1$H NMR (400 MHz, CHLOROFORM-d) δ ppm 0.71-0.90 (m, 4H) 1.52-1.54 (d, J=8 Hz, 6H) 1.79-1.92 (m, 1H) 5.41 (dt, J=13.55, 6.78 Hz, 1H) 6.84 (s, 1H) 7.41 (d, J=11.04 Hz, 1H) 7.48-7.55 (m, 1H) 7.81-7.91 (m, 1H) 8.03 (d, J=7.53 Hz, 1H) 8.14 (d, J=7.53 Hz, 1H) 8.25 (s, 1H) 8.28-8.37 (m, 1H) 8.30-8.32 (m, 1H) 8.31-8.32 (m, 1H) 8.94 (br d, J=15.06 Hz, 1H). m/z=466.2 [M+1].

Step 9: Synthesis of Compound WX021-10

Compound WX021-9 (400.00 mg, 858.53 μmol, 1.00 eq) and p-methoxybenzylamine (1.18 g, 8.59 mmol, 1.11 mL, 10.00 eq) were added into a pre-dried reaction bottle, and then potassium carbonate (237.32 mg, 1.72 mmol, 2.00 eq) was added. The system was reacted at 100° C. for 5 hours. The reaction solution was cooled to room temperature, diluted with water (5 mL), and extracted with dichloromethane (5 mL*3). The organic phase was washed with water (5 mL*3), dried over anhydrous sodium sulfate, and filtered. The filtrate was dried on a rotary evaporator under reduced pressure to obtain WX021-10, which was directly put into the next reaction. m/z=583.2 [M+1].

Step 10: Synthesis of Compound WX021-11

Compound WX021-10 (600.00 mg, 1.03 mmol, 1.00 eq) and trifluoroacetic acid (10.00 mL) were added into a 10 mL pre-dried reaction bottle. The system was reacted at 25° C. for 0.5 hour. The reaction solution was dried on a rotary evaporator under reduced pressure, added with dichloromethane (10 mL) and saturated aqueous sodium bicarbonate (5 mL). The organic phase was separated and washed successively with water (5 mL) and saturated brine (5 mL), dried over anhydrous sodium sulfate, and then filtered. The filtrate was dried on a rotary evaporator under reduced pressure to obtain WX021-11. m/z=463.2 [M+1].

Step 11: Synthesis of Compound WX021

Compound WX021-11 (200.00 mg, 432.02 μmol, 1.00 eq) and dimethyl orthoformate (2.91 g, 27.42 mmol, 3.00 mL, 63.47 eq) were added into a 10 mL pre-dried reaction bottle, and the mixture was reacted at 110° C. for 1 hour under the protection of nitrogen atmosphere. The reaction solution was dried on a rotary evaporator under reduced pressure and purified by preparative high performance liquid chromatography to obtain WX021. $^1$H NMR (400 MHz, CHLOROFORM-d) δ ppm 0.74-0.94 (m, 4H) 1.55 (d, J=6.84 Hz, 6H) 1.88-1.96 (m, 1H) 5.45 (dt, J=13.40, 6.64 Hz, 1H) 6.96 (s, 1H) 7.63 (s, 1H) 7.92 (d, J=7.94 Hz, 1H) 7.97 (s, 1H) 8.10 (t, J=7.94 Hz, 1H) 8.31 (s, 1H) 8.39 (s, 1H) 8.45 (d, J=7.72 Hz, 1H) 8.59 (s, 1H). m/z=473.1 [M+1].

Example 022: WX022

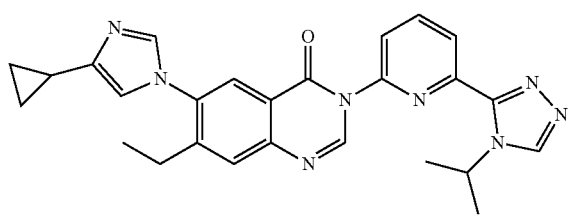 [SMILES: CCc1cc2ncn(-c3cccc(-c4nncn4C(C)C)n3)c(=O)c2cc1-n1cnc(C2CC2)c1]

Synthetic Route:

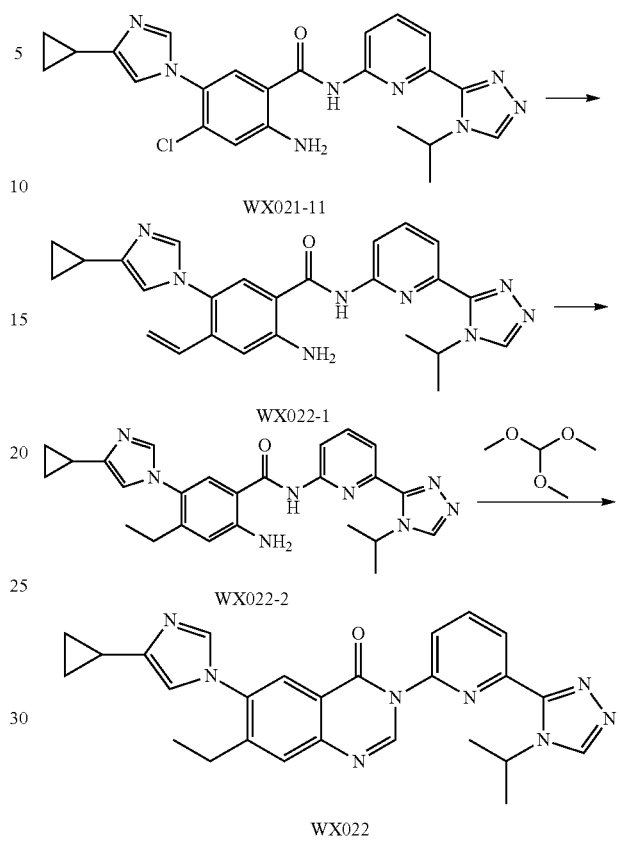

Step 1. Synthesis of Compound WX022-1

Compound WX021-11 (180.00 mg, 388.83 μmol, 1.00 eq), potassium vinyltrifluoroborate (104.17 mg, 777.66 μmol, 2.00 eq), palladium acetate (8.73 mg, 38.88 μmol, 0.10 eq), n-butyldi (1-adamantyl)phosphine (13.94 mg, 38.88 μmol, 0.10 eq) and potassium carbonate (161.22 mg, 1.17 mmol, 3.00 eq) were added into a 50 mL pre-dried flask, purged with nitrogen three times, and then water (500.00 μL) and 1,4-dioxane (5.00 mL) were added. Under the protection of nitrogen atmosphere, the reaction vessel was placed in an oil bath at 90° C. and stirred for 2 hours. The reaction solution was added with water (10 mL), and extracted with dichloromethane (3×15 mL). The organic phases were combined, washed with saturated brine (2×25 mL), dried over anhydrous sodium sulfate, and filtered under reduced pressure to obtain WX022-1. m/z=455.2 [M+1].

Step 2. Synthesis of Compound WX022-2

Compound WX022-1 (76.00 mg, 167.21 μmol, 1.00 eq), methanol (2.00 mL) and dry palladium carbon (20.00 mg, 188.68 μmol, 1.13 eq) were added into a 10 mL pre-dried reaction bottle, purged with hydrogen three times, and then reacted at 25° C. for 1 hour. The reaction solution was subjected to suction filtration under reduced pressure through a suction filtration funnel covered with celite, and then evaporated on a rotary evaporator under reduced pressure to afford WX022-2. m/z=455.2 [M+1].

Step 3. Synthesis of Compound WX022

Compound WX022-2 (76.00 mg, 166.47 μmol, 1.00 eq) and trimethyl orthoformate (2.91 g, 27.42 mmol, 3.00 mL, 164.73 eq) were added into a 10 mL pre-dried reaction bottle, and the mixture was reacted at 110° C. for 12 hours under the protection of nitrogen atmosphere. The reaction solution was directly subjected to rotary evaporation under reduced pressure and then purified by preparative high performance liquid chromatography to obtain WX022. ¹H NMR (400 MHz, CHLOROFORM-d) δ ppm 0.74-0.89 (m, 4H) 1.18 (t, J=7.53 Hz, 3H) 1.50 (d, J=6.53 Hz, 6H) 1.82-1.91 (m, 1H) 2.63 (q, J=7.53 Hz, 2H) 5.39-5.46 (m, 1H) 6.79 (d, J=1.00 Hz, 1H) 7.43 (d, J=1.51 Hz, 1H) 7.58 (d, J=1.00 Hz, 1H) 7.71 (s, 1H) 7.85-7.93 (m, 2H) 8.00-8.07 (m, 1H) 8.16 (s, 1H) 8.34 (s, 1H) 8.38 (d, J=8.03 Hz, 1H) 8.53-8.54 (m, 1H). m/z=467.2 [M+1].

Example 023: WX023

Synthetic Route:

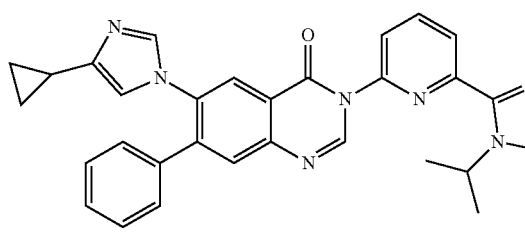

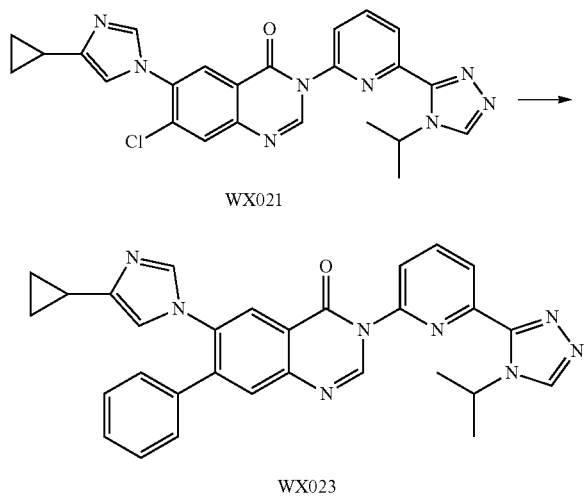

Step 1. Synthesis of Compound WX023

Compound WX021 (50.00 mg, 105.72 μmol, 1.00 eq), phenylboronic acid (25.78 mg, 211.44 mmol, 2.00 eq), palladium acetate (2.37 mg, 10.57 mmol, 0.10 eq), n-butyldi (1-adamantyl)phosphine (3.79 mg, 10.57 μmol, 0.10 eq) and potassium carbonate (43.83 mg, 317.16 μmol, 3.00 eq) were added into a 10 mL pre-dried thumb-bottle, purged with nitrogen three times, and then water (300.00 μL) and dioxane (3.00 mL) were added. Under the protection of nitrogen atmosphere, the reaction vessel was placed in an oil bath at 90° C. and stirred for 2 hours. The reaction solution was directly dried on a rotary evaporator, then rapidly passed through a short silica gel column, followed by separation with prep-HPLC to obtain WX023. ¹H NMR (400 MHz, CHLOROFORM-d) δ ppm 0.59-0.67 (m, 2H) 0.73-0.80 (m, 2H) 1.51 (d, J=7.03 Hz, 6H) 1.70-1.77 (m, 1H) 5.42 (dt, J=13.55, 6.78 Hz, 1H) 6.55 (d, J=1.51 Hz, 1H) 7.19-7.27 (m, 2H) 7.32 (dt, J=7.78, 1.88 Hz, 1H) 7.85 (s, 1H) 7.91 (dd, J=8.03, 1.00 Hz, 1H) 8.06 (t, J=7.78 Hz, 1H) 8.33 (s, 1H) 8.35 (s, 1H) 8.40 (d, J=8.53 Hz, 1H) 8.52 (d, J=1.51 Hz, 1H) 8.58 (s, 1H) 8.59 (m, 1H). m/z=515.1 [M+1].

Example 024: WX024

Synthetic Route:

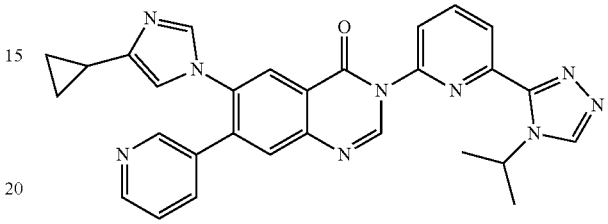

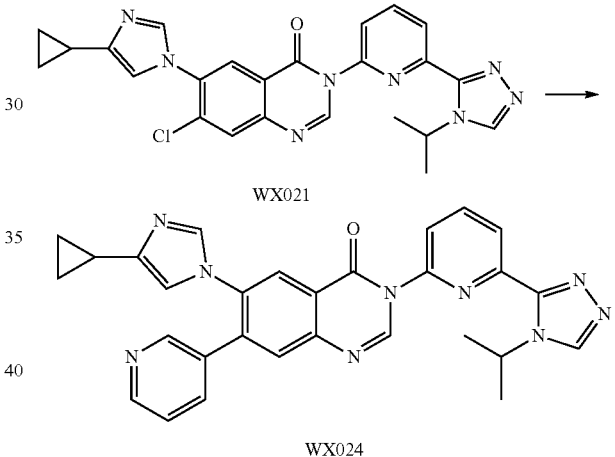

Step 1: Synthesis of Compound WX024

Compound WX021 (50.00 mg, 105.72 μmol, 1.00 eq), 3-pyridinylboronic acid (25.99 mg, 211.45 μmol, 2.00 eq), palladium acetate (2.37 mg, 10.57 μmol, 0.10 eq), n-butyldi (1-adamantyl)phosphine (3.79 mg, 10.57 μmol, 0.10 eq) and potassium carbonate (43.84 mg, 317.17 μmol, 3.00 eq) were added into a 10 mL pre-dried thumb-bottle, purged with nitrogen three times, and then water (300.00 μL) and dioxane (3.00 mL) were added. Under the protection of nitrogen atmosphere, the reaction vessel was placed in an oil bath at 90° C. and stirred for 2 hours. The reaction solution was directly dried on a rotary evaporator, then rapidly passed through a short silica gel column (MeOH:DCM=1:5), and then separated by prep-HPLC to obtain WX024. NMR (400 MHz, CHLOROFORM-d) δ ppm 0.60-0.66 (m, 2H) 0.73-0.80 (m, 2H) 1.51 (d, J=7.03 Hz, 6H) 1.69-1.77 (m, 1H) 5.38-5.48 (m, 1H) 6.55 (s, 1H) 7.18-7.27 (m, 2H) 7.32 (dt, J=8.03, 2.01 Hz, 1H) 7.85 (s, 1H) 7.91 (d, J=8.03 Hz, 1H) 8.06 (t, J=7.78 Hz, 1H) 8.33 (s, 1H) 8.35 (s, 1H) 8.40 (d, J=7.53 Hz, 1H) 8.52 (d, J=2.51 Hz, 1H) 8.58 (s, 1H), 8.59 (d, 1H). m/z=516.2 [M+1].

Example 025: WX025

Example 026: WX026

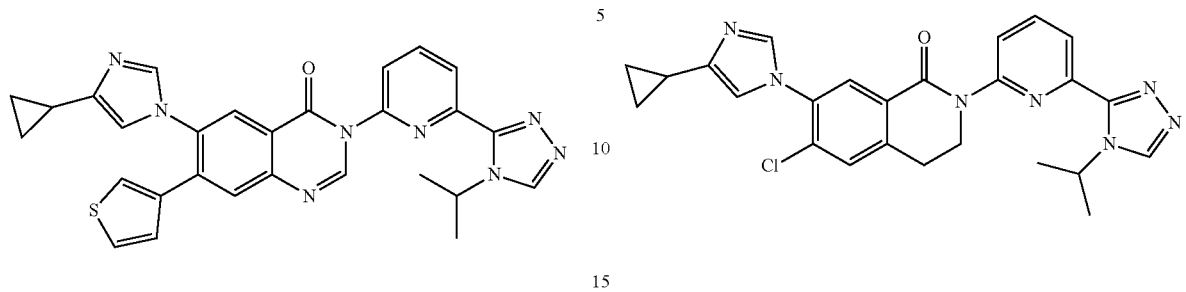

Synthetic Route:

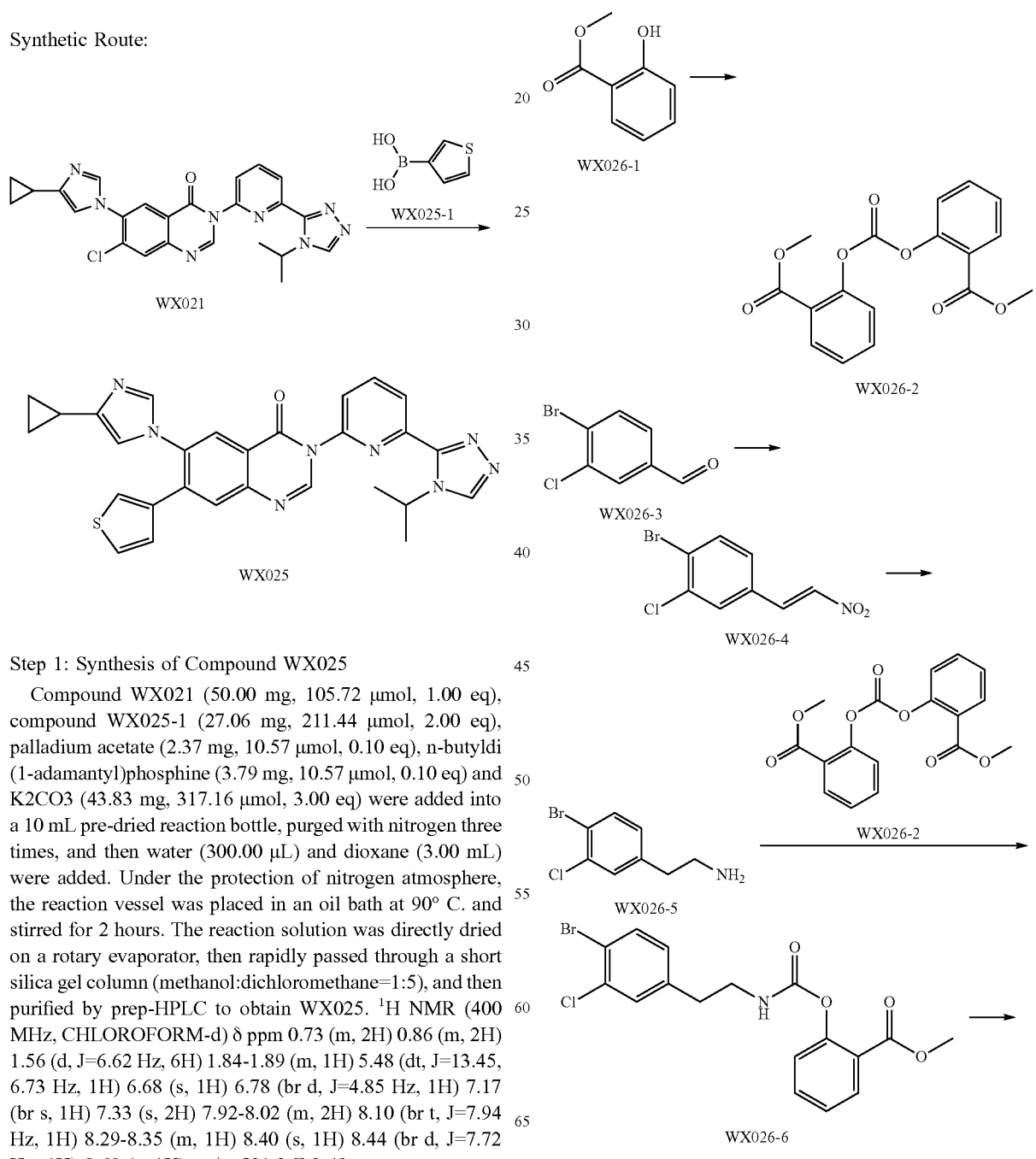

Step 1: Synthesis of Compound WX025

Compound WX021 (50.00 mg, 105.72 μmol, 1.00 eq), compound WX025-1 (27.06 mg, 211.44 μmol, 2.00 eq), palladium acetate (2.37 mg, 10.57 μmol, 0.10 eq), n-butyldi (1-adamantyl)phosphine (3.79 mg, 10.57 μmol, 0.10 eq) and K2CO3 (43.83 mg, 317.16 μmol, 3.00 eq) were added into a 10 mL pre-dried reaction bottle, purged with nitrogen three times, and then water (300.00 μL) and dioxane (3.00 mL) were added. Under the protection of nitrogen atmosphere, the reaction vessel was placed in an oil bath at 90° C. and stirred for 2 hours. The reaction solution was directly dried on a rotary evaporator, then rapidly passed through a short silica gel column (methanol:dichloromethane=1:5), and then purified by prep-HPLC to obtain WX025. $^1$H NMR (400 MHz, CHLOROFORM-d) δ ppm 0.73 (m, 2H) 0.86 (m, 2H) 1.56 (d, J=6.62 Hz, 6H) 1.84-1.89 (m, 1H) 5.48 (dt, J=13.45, 6.73 Hz, 1H) 6.68 (s, 1H) 6.78 (br d, J=4.85 Hz, 1H) 7.17 (br s, 1H) 7.33 (s, 2H) 7.92-8.02 (m, 2H) 8.10 (br t, J=7.94 Hz, 1H) 8.29-8.35 (m, 1H) 8.40 (s, 1H) 8.44 (br d, J=7.72 Hz, 1H) 8.60 (s, 1H). m/z=521.2 [M+1].

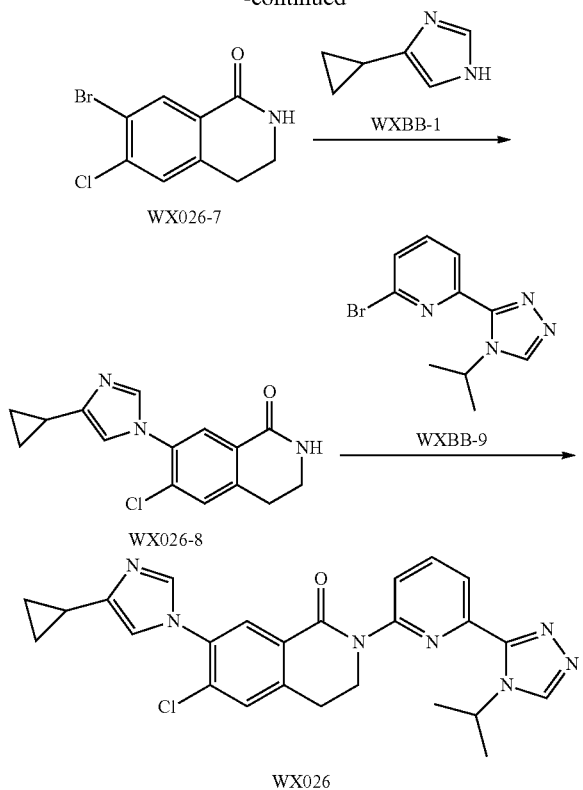

Step 1. Synthesis of Compound WX026-2

WX026-1 (5.00 g, 32.86 mmol, 4.27 mL, 1.00 eq) was dissolved in dichloromethane (20.00 mL). Triethylamine (33.25 mg, 328.60 μmol, 45.55 μL, 0.01 eq) was added dropwise, and then triphosgene (7.31 g, 24.65 mmol, 0.75 eq) was added slowly at 0° C., afterwards, sodium hydroxide (2M, 164.30 mL, 10.00 eq) was added to adjust to pH=12-13. The mixture was stirred at 25° C. for 2 hours. After the reaction was completed, 2M hydrochloric acid was added to the reaction solution to adjust the pH=7-8, and stirred. The organic phase was separated and the aqueous was extracted with dichloromethane (50 mL). The organic phases were combined, washed with saturated brine (50 mL), dried over anhydrous sodium sulfate, and filtered. The filtrate was dried on a rotary evaporator under reduced pressure to obtain WX026-2. $^1$H NMR (400 MHz, CHLOROFORM-d) δ=7.96 (dd, J=1.5, 7.8 Hz, 2H), 7.54 (dt, J=1.5, 7.8 Hz, 2H), 7.36-7.25 (m, 4H), 3.93-3.85 (m, 6H).

Step 2. Synthesis of Compound WX026-4

WX026-3 (10.00 g, 45.57 mmol, 1.00 eq) and nitromethane (14.00 g, 229.22 mmol, 12.39 mL, 5.03 eq) were dissolved in glacial acetic acid (60.00 mL), and ammonium acetate (9.00 g, 116.66 mmol, 2.56 eq) was added. The system was stirred at 90° C. for 3 hours. After the reaction was completed, the reaction solution was cooled to room temperature, added with water (200 mL), and extracted with ethyl acetate (300 mL*2). The organic phase was washed with water (300 mL*2) and saturated brine (300 mL), dried over anhydrous sodium sulfate, and filtered. The filtrate was dried on a rotary evaporator under reduced pressure to obtain WX026-4.

Step 3. Synthesis of Compound WX026-5

Lithium borohydride (660.00 mg, 30.33 mmol, 3.98 eq) was suspended in tetrahydrofuran (20 mL), and trimethylchlorosilane (6.62 g, 60.96 mmol, 7.70 mL, 8.00 eq) was added at 0° C. under the protection of nitrogen atmosphere, stirred for 10 min, and a solution of WX026-4 (2.00 g, 7.62 mmol, 1.00 eq) in tetrahydrofuran (10 mL) was added dropwise. The mixture was stirred at 80° C. for 2 hours. After the reaction was completed, the reaction solution was quenched with methanol (50 mL), dried on a rotary evaporator under reduced pressure, added with 20% potassium hydroxide solution (100 mL), and extracted with dichloromethane (100 mL*2). The organic phase was washed with brine (200 mL), dried over anhydrous sodium sulfate, and filtered. The filtrate was dried on a rotary evaporator under reduced pressure, then purified by a column (methanol/dichloromethane=10%~50%) to obtain WX026-5. $^1$H NMR (400 MHz, CHLOROFORM-d) δ=7.46 (d, J=8.0 Hz, 1H), 7.24 (d, J=1.5 Hz, 1H), 6.90 (dd, J=1.6, 8.2 Hz, 1H), 2.97-2.89 (m, 2H), 2.67 (t, J=6.9 Hz, 2H).

Step 4. Synthesis of Compound WX026-6

WX026-2 (1.41 g, 4.26 mmol, 1.00 eq) was dissolved in anhydrous THF (15 mL), and a solution of WX026-5 (1.00 g, 4.26 mmol, 1.00 eq) in anhydrous THF (5 mL) was added dropwise at 0° C. under the protection of nitrogen atmosphere. The mixture was stirred at 30° C. for 16 hours. After the reaction was completed, the reaction solution was directly dried on a rotary evaporator. The crude product was purified by a column (ethyl acetate/petroleum ether=0~10%~25%) to obtain WX026-6.

Step 5. Synthesis of Compound WX026-7

WX026-6 (1.10 g, 1.86 mmol, 1.00 eq) (purity: 69.6%) was dissolved in anhydrous dichloromethane (30.00 mL), and p-toluenesulfonic acid (2.79 g, 18.60 mmol, 1.64 mL, 10.00 eq) was added dropwise at 0° C. The mixture was stirred at 25° C. for 16 hours. The reaction solution was slowly poured into ice-water (100 mL), and extracted with dichloromethane (100 mL*2). The organic phase was washed with 2M aqueous sodium hydroxide (100 mL) and saturated brine (100 mL), dried over anhydrous sodium sulfate, and filtered. The filtrate was dried on a rotary evaporator under reduced pressure to obtain WX026-7. $^1$H NMR (400 MHz, CHLOROFORM-d) δ=10.69 (s, 1H), 8.22 (s, 1H), 7.77 (dd, J=1.5, 7.8 Hz, 1H), 7.42-7.36 (m, 1H), 7.27 (s, 1H), 6.91 (d, J=8.3 Hz, 1H), 6.81 (t, J=7.5 Hz, 1H), 6.36 (br s, 1H), 3.88 (s, 2H), 3.50 (dt, J=2.6, 6.6 Hz, 2H), 2.88 (t, J=6.5 Hz, 2H).

Step 6. Synthesis of Compound WX026-8

WX026-7 (250.00 mg, 959.66 μmol, 1.00 eq), WXBB-1 (208.00 mg, 1.92 mmol, 2.00 eq), potassium carbonate (400.00 mg, 2.89 mmol, 3.02 eq), cuprous iodide (20.00 mg, 105.01 μmol, 0.11 eq) and 8-hydroxyquinoline (14.00 mg, 96.45 μmol, 16.67 μL, 0.10 eq) were added to dimethyl sulfoxide (2.00 mL). The mixture was stirred at 130° C. for 5 hours under microwave and nitrogen atmosphere. After the reaction was completed, the reaction solution was poured into water (20 mL), and extracted with dichloromethane (20 mL*2). The organic phase was washed with saturated brine (20 mL), dried over anhydrous sodium sulfate, and filtered. The filtrate was dried on a rotary evaporator under reduced pressure. The crude product was purified by a column (methanol/dichloromethane=0~2%~4%~8%) to obtain WX026-8. m/z: 288.1 [M+H]+.

Step 7. Synthesis of Compound WX026

WX026-8 (50.00 mg, 173.77 μmol, 1.00 eq), WXBB-9 (60.00 mg, 203.98 μmol, 1.17 eq) (purity: 90.81%), Xantphos (15.00 mg, 25.92 μmol, 0.15 eq), Pd$_2$(dba)$_3$ (9.00 mg, 9.83 μmol, 0.06 eq) and cesium carbonate (170.00 mg, 521.76 μmol, 3.00 eq) were added to anhydrous dioxane (5.00 mL). The mixture was stirred at 120° C. for 16 hours under nitrogen. After the reaction was completed, added with water (20 mL), and extracted with dichloromethane (20 mL*2). The organic phase was washed with saturated sodium chloride (20 mL), dried over anhydrous sodium sulfate, and filtered. The filtrate was dried on a rotary evaporator under reduced pressure. The crude product was separated and purified with a prep.TLC (dichloromethane/methanol=20/1) plate to give WX026. $^1$H NMR (400 MHz, CHLOROFORM-d) δ=8.30 (s, 1H), 8.08 (s, 1H), 8.04 (br d, J=7.5 Hz, 1H), 7.94 (br d, J=8.3 Hz, 1H), 7.89-7.79 (m, 1H), 7.52 (s, 1H), 7.42 (s, 1H), 6.84 (s, 1H), 5.39 (td, J=6.6, 13.2 Hz, 1H), 4.23 (br t, J=6.0 Hz, 2H), 3.13 (br t, J=5.8 Hz, 2H), 1.85 (br d, J=4.5 Hz, 1H), 1.49 (br d, J=6.5 Hz, 6H), 0.87-0.72 (m, 4H).

Example 028: WX028

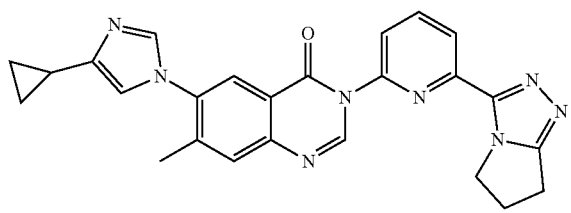 [SMILES: Cc1cc2ncn(-c3cccc(-c4nnc5n4CCC5)n3)c(=O)c2cc1-n1cnc(C2CC2)c1]

Synthetic Route:

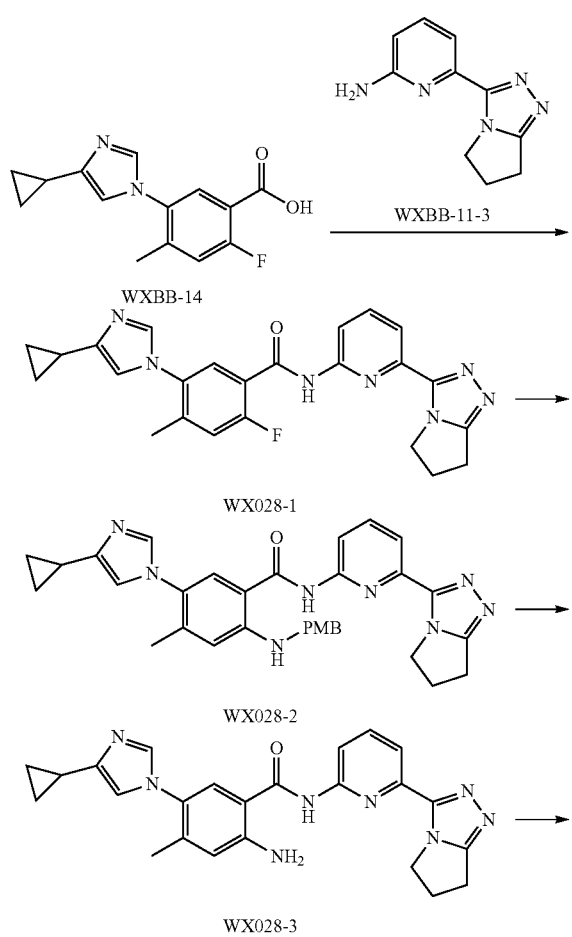

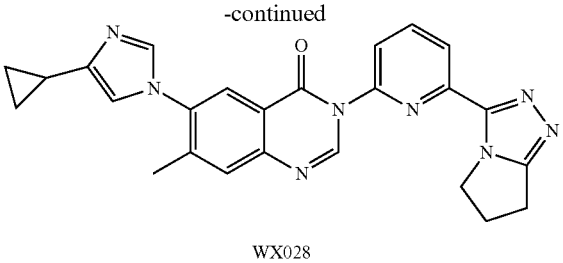

Step 1. Synthesis of Compound WX028-1

WXBB-14 (500.00 mg, 1.92 mmol, 1.00 eq) and anhydrous dichloromethane (10.00 mL) were added into a 100 mL pre-dried single-neck bottle, purged with nitrogen, then oxalyl chloride (414.55 mg, 3.26 mmol, 285.90 μL, 1.70 eq) was added, afterwards, N,N-dimethylformamide (14.04 mg, 192.00 μmol, 14.78 μL, 0.10 eq) was added, and the mixture was reacted at 25° C. for 0.5 hour under the protection of nitrogen atmosphere. After the reaction was completed, the reaction solution was added with 3 mL of anhydrous dichloromethane, evaporated on a rotary evaporator until ~5 mL of anhydrous dichloromethane was remained. This process was repeated 3 times to obtain a yellow solution. Dichloromethane (10.00 mL) was added, purged with nitrogen three times, and then diisopropylethylamine (254.47 mg, 1.97 mmol, 343.88 μL, 1.10 eq) was added. 5 min later, a solution of WXBB-11-3 (360.20 mg, 1.79 mmol, 1.00 eq) in anhydrous dichloromethane (5.00 mL) was added. The system was reacted at 25° C. for 18 hours under the protection of nitrogen atmosphere. After the reaction was completed, the reaction solution was dried on a rotary evaporator, added with 10 mL of water, adjusted to pH~2 with 2M hydrochloric acid, and the aqueous phase was washed with 20 mL ethyl acetate. The aqueous phase was adjusted to pH~10 (with anhydrous potassium carbonate solid), and extracted with dichloromethane (20 mL*3). The organic phases were combined, dried over anhydrous sulfuric acid, and dried on a rotary evaporator to give WX028-1. m/z=444.2 (M+1).

Step 2. Synthesis of Compound WX028-2

WX028-1 (500.00 mg, 1.13 mmol, 1.00 eq) and acetonitrile (4.00 mL) were added into a pre-dried reaction bottle, and then potassium carbonate (311.65 mg, 2.25 mmol, 2.00 eq) and p-methoxybenzylamine (1.55 g, 11.27 mmol, 1.46 mL, 10.00 eq) were added. The system was reacted at 100° C. for 22 hours. After the reaction was completed, the reaction solution was cooled to room temperature, dried on a rotary evaporator, and then diluted with water (10 mL), followed by extraction with dichloromethane (15 mL*3). The organic phase was washed with saturated brine (10 mL*3), dried over anhydrous sodium sulfate, and filtered. The filtrate was dried on a rotary evaporator under reduced pressure to obtain WX028-2. m/z=561.3 (M+1).

Step 3. Synthesis of Compound WX028-3

WX028-2 (630.00 mg, 1.12 mmol, 1.00 eq) and trifluoroacetic acid (15.00 mL) were added into a 50 mL pre-dried single-neck bottle. The system was reacted at 25° C. for 16 hours. After the reaction was completed, the reaction solution was dried on a rotary evaporator, added with 10 mL of dichloromethane, and washed with saturated sodium bicarbonate solution (20 mL*3). The organic phase was dried over anhydrous sodium sulfate and dried on a rotary evaporator to give WX028-3. m/z=441.3 (M+1).

Step 4. Synthesis of Compound WX028

WX028-3 (150.00 mg, 340.52 μmol, 1.00 eq) and trimethyl orthoformate (3.00 mL) were added into a pre-dried thumb-bottle, purged with nitrogen three times, and the mixture was reacted at 110° C. for 16 hours under the protection of nitrogen atmosphere. After the reaction was completed, the reaction solution was cooled to room temperature and dried on a rotary evaporator, and then separated and purified with prep-HPLC (column: Waters Xbridge 150*25 mm 5 μm; mobile phase: [water (0.225% FA)-ACN]; B %: 1%-30%, 12 min), then purified with prep-HPLC (column: Waters Xbridge 150*25 mm 5 μm; mobile phase: [water (10 mM $NH_4HCO_3$)-ACN]; B %: 15%-45%, 10.5 min) to obtain WX028, m/z=451.2 (M+1); 1H NMR (400 MHz, CHLOROFORM-d) δ ppm 0.83-0.89 (m, 2H) 0.89-0.94 (m, 2H) 1.87-2.00 (m, 1H) 2.42 (s, 3H) 2.77-2.89 (m, 2H) 3.03-3.11 (m, 2H) 4.43 (t, J=7.17 Hz, 2H) 6.88 (s, 1H) 7.52 (s, 1H) 7.74 (s, 1H) 7.94 (d, J=7.94 Hz, 1H) 8.02-8.11 (m, 1H) 8.24 (s, 1H) 8.42 (d, J=7.50 Hz, 1H) 8.68 (s, 1H).

Example 029: WX029

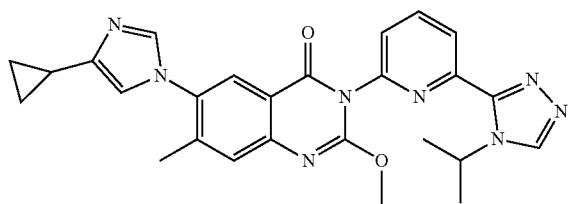 [SMILES: COc1nc2cc(C)c(-n3cnc(C4CC4)c3)cc2c(=O)n1-c1cccc(-c2nncn2C(C)C)n1]

Synthetic Route:

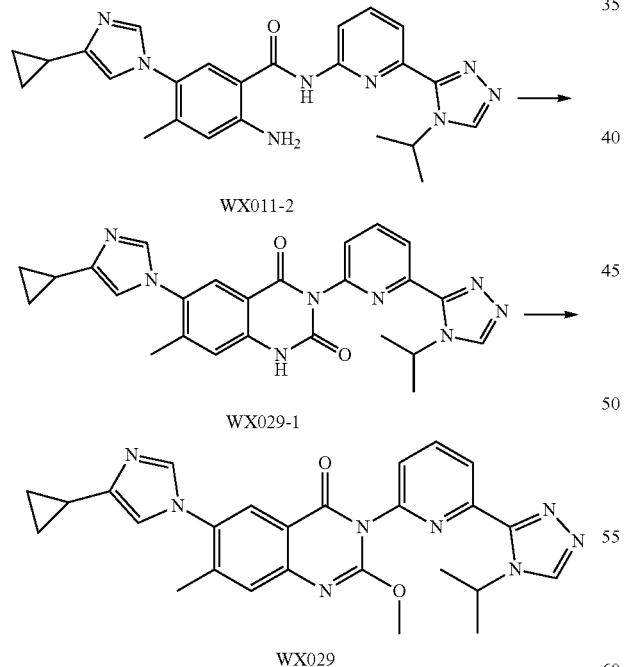

Step 1. Synthesis of Compound WX029-1

WX011-2 (50.00 mg, 112.99 umol, 1.00 eq) and dioxane (3 mL) were added into a 40 mL pre-dried reaction bottle. Then a solution of triphosgene (33.53 mg, 112.99 umol, 1.00 eq) in dioxane (2 mL) was added to a reaction bottle at 35° C., and the solution became cloudy. The system was reacted at 35° C. for 16 hours. After the reaction was completed, the reaction solution was cooled to room temperature, dried on a rotary evaporator, and purified with prep-HPLC (column: Waters Xbridge 150*25 mm 5 μm; mobile phase: [water (10 mM $NH_4HCO_3$)-ACN]; B %: 15%-45%, 10.5 min) to obtain WX029-1, m/z=469.2 (M+1); 1H NMR (400 MHz, CHLOROFORM-d) δ ppm 0.77-0.95 (m, 4H) 1.48 (d, J=6.65 Hz, 6H) 1.85-1.98 (m, 1H) 2.29 (s, 3H) 5.46 (dt, J=13.43, 6.59 Hz, 1H) 6.80 (s, 1H) 7.19 (s, 1H) 7.40-7.56 (m, 2H) 8.00 (s, 1H) 8.08 (t, J=7.84 Hz, 1H) 8.35-8.47 (m, 2H) 10.41 (br s, 1H).

Step 2. Synthesis of Compound WX029

WX029-1 (100.00 mg, 213.44 μmol, 1.00 eq) and dichloromethane (2.00 mL) were added into a pre-dried reaction bottle, then $Me_3OBF_4$ (94.71 mg, 640.33 μmol, 3.00 eq) was added, followed by purging with nitrogen three times, then the mixture was reacted at 20° C. for 16 hours under the protection of nitrogen atmosphere, and then supplemented with $Me_3OBF_4$ (94.71 mg, 640.32 μmol, 3.00 eq). The system was reacted at 40° C. for 16 hours. After the reaction was completed, the reaction solution was cooled to room temperature, adjusted to pH-8 with saturated aqueous sodium bicarbonate, and extracted with dichloromethane (3 mL*3). The organic phases were combined, dried and then dried on a rotary evaporator. The obtained crude product was purified with prep-HPLC (column: Waters Xbridge 150*25 mm 5 μm; mobile phase: [water (0.225% FA)-ACN]; B %: 1%-30%, 12 min) to obtain WX029, m/z=483.2 (M+1); $^1$H NMR (400 MHz, CHLOROFORM-d) δ ppm 0.76-0.93 (m, 4H) 1.52 (br d, J=5.65 Hz, 6H) 1.90 (br s, 1H) 2.29 (s, 3H) 4.24 (br s, 3H) 5.43-5.60 (m, 1H) 6.77 (s, 1H) 7.39-7.51 (m, 2H) 7.55 (s, 1H) 7.89 (s, 1H) 7.98-8.14 (m, 2H) 8.76 (br s, 1H) 11.64 (br s, 1H).

Example 030: WX030

Synthetic Route:

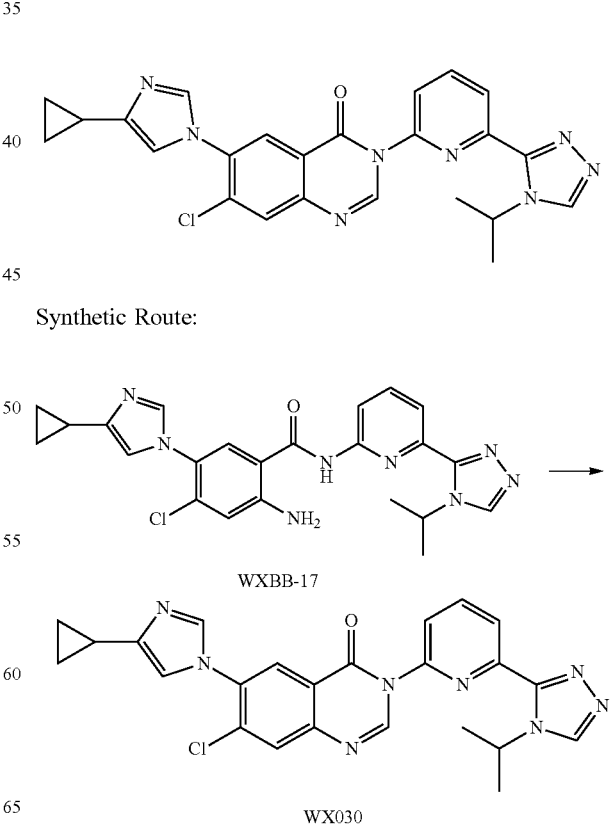

Step 1. Synthesis of Compound WX030

WXBB-17 (900.00 mg, 1.94 mmol, 1.00 eq) and trimethyl orthoformate (9.70 g, 91.41 mmol, 10.00 mL, 47.12 eq) were added into a 50 mL pre-dried round-bottom flask, and the mixture was reacted at 110° C. for 10 hours under the protection of nitrogen atmosphere. After the reaction was completed, the reaction solution was dried on a rotary evaporator. The residue was separated by flash column chromatography (methanol:dichloromethane=0 to 1:20) to obtain WX030. 1H NMR (400 MHz, DMSO-d6) δ ppm 0.63-0.69 (m, 2H) 0.73-0.82 (m, 2H) 1.48 (d, J=6.62 Hz, 6H) 1.76-1.86 (m, 1H) 2.51-2.52 (m, 1H) 5.32 (s, 2H) 7.06 (s, 1H) 7.11 (s, 1H) 7.60 (s, 1H) 7.67 (br s, 1H) 7.74 (s, 1H) 7.91 (dd, J=7.72, 1.76 Hz, 2H) 7.98-8.05 (m, 1H) 8.89 (s, 1H).

Example 031: WX031

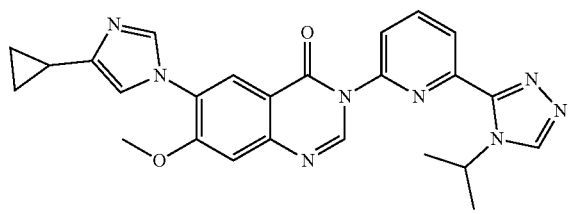 [SMILES: COc1cc2ncn(-c3cccc(-c4nncn4C(C)C)n3)c(=O)c2cc1-n1cnc(C2CC2)c1]

Synthetic Route:

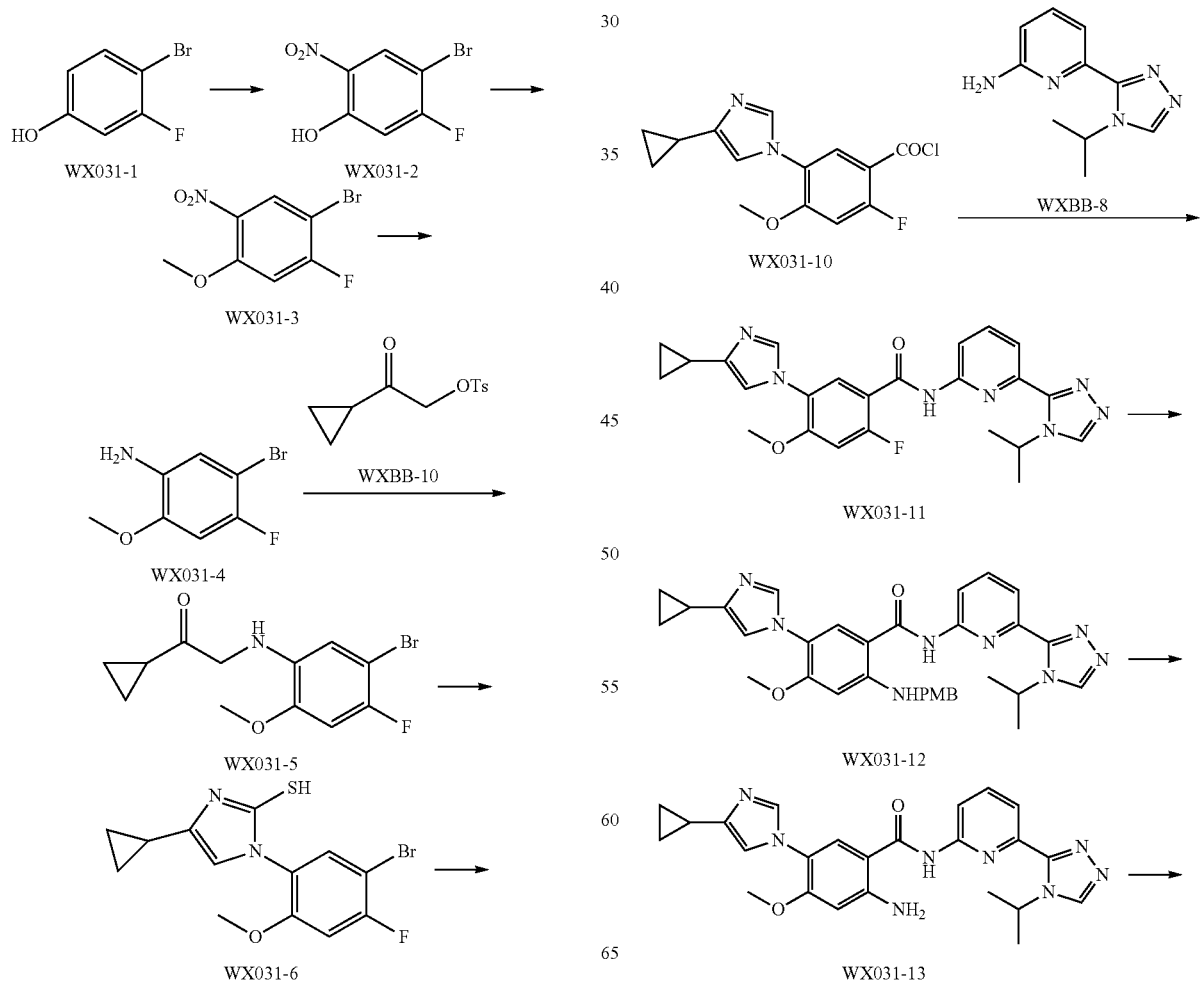

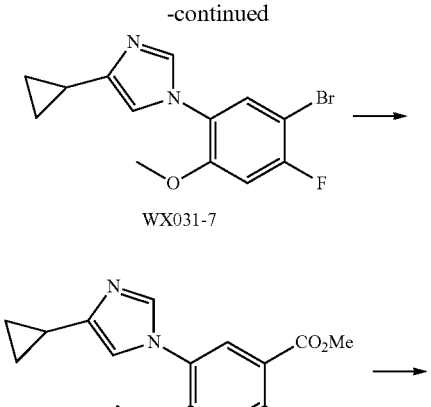

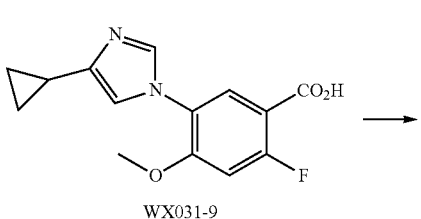

-continued

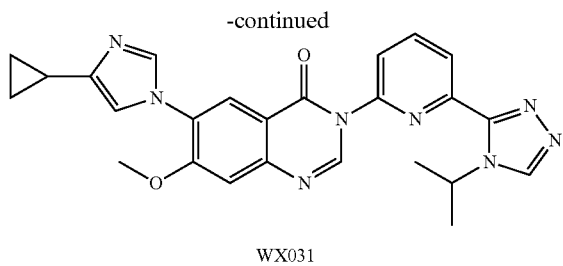

WX031

Step 1. Synthesis of Compound WX031-2

WX031-1 (30.00 g, 157.07 mmol, 1.00 eq), concentrated sulfuric acid (30.81 g, 314.14 mmol, 16.74 mL, 2.00 eq) and dichloromethane (310.00 mL) were added into a 1000 mL pre-dried flask. The reaction system was cooled to 0° C., and then concentrated nitric acid (15.23 g, 157.07 mmol, 10.88 mL, 65% purity, 1.00 eq) was added dropwise to the system. After the reaction was completed, ice water (200 mL) was added to the reaction solution. The organic and aqueous phases were separated. Then the aqueous phase was extracted with dichloromethane (3×100 mL). The organic phases were combined, washed with saturated brine (2×200 mL), dried over anhydrous sodium sulfate, and subjected to suction filtration and concentration to obtain a crude product, which was purified by flash silica gel column (ethyl acetate:petroleum ether=1:30) to obtain WX031-2. $^1$H NMR (400 MHz, CHLOROFORM-d) δ ppm 6.96 (d, J=9.03 Hz, 1H) 8.40 (d, J=7.03 Hz, 1H) 10.69 (d, J=1.51 Hz, 1H).

Step 2. Synthesis of Compound WX031-3

WX031-2 (22.01 g, 93.26 mmol, 1.00 eq) and acetone (250.00 mL) were added into a 250 mL pre-dried three-neck reaction bottle, purged with nitrogen three times, and then dimethyl sulfoxide (14.12 g, 111.91 mmol, 10.61 mL, 1.20 eq) was added. The reaction was refluxed at 50° C. for 10 hours. After the reaction was completed, the reaction solution was added with water (100 mL), and then stirred for 2 hours. The organic and aqueous phases were separated and the aqueous phase was extracted with ethyl acetate (3×80 mL). The organic phases were combined, washed with saturated brine (2×200 mL), dried over anhydrous sodium sulfate, and subjected to suction filtration and concentration to obtain a crude product. The crude product was slurried with methanol (20 mL), and then purified by flash silica gel column (ethyl acetate:petroleum ether=1:30) to obtain WX031-3.

Step 3. Synthesis of Compound WX031-4

WX031-3 (8.30 g, 33.20 mmol, 1.00 eq), iron powder (9.27 g, 166.00 mmol, 5.00 eq), ammonium chloride (1.95 g, 36.52 mmol, 1.28 mL, 1.10 eq), ethanol (192.00 mL) and water (64.00 mL) were added into a 100 mL pre-dried eggplant-shaped bottle. The reaction solution was refluxed at 80° C. for 6 hours. After the reaction was completed, the reaction solution was filtered through celite, then dried on a rotary evaporator, dissolved in dichloromethane (30 mL) and water (20 mL), and extracted with dichloromethane (2×20 mL). The organic phases were combined, washed with saturated brine (2×30 mL), dried, filtered and concentrated to obtain a crude product, which was purified by chromatography column (ethyl acetate:petroleum ether=1:20-1:4) to obtain WX031-4. $^1$H NMR (400 MHz, CHLOROFORM-d) δ ppm 3.57-3.73 (m, 2H) 3.81 (s, 4H) 6.59 (d, J=9.92 Hz, 1H) 6.79 (d, J=6.84 Hz, 1H).

Step 4. Synthesis of Compound WX031-5

WX031-4 (4.68 g, 21.27 mmol, 1.00 eq), WXBB-10 (5.95 g, 23.40 mmol, 1.10 eq) and toluene (50.00 mL) were added into a pre-dried long tube. The reaction was heated to 100° C., then diisopropylethylamine (5.50 g, 42.54 mmol, 7.43 mL, 2.00 eq) was added, and the mixture was reacted at 100° C. for 10 hours. After the reaction was completed, the mixture was dried directly on a rotary evaporator and then re-dissolved in dichloromethane (30 mL) followed by addition of water (30 mL), and the organic phase and the aqueous phase were separated. The aqueous phase was extracted with dichloromethane (2×20 mL). The organic phases were combined, washed with saturated ammonium chloride solution (2×30 mL) and saturated brine (2×30 mL) successively, dried over anhydrous sodium sulfate, and subjected to suction filtration and concentration to obtain a crude product, which was purified with chromatography column (ethyl acetate:petroleum ether=0-1:10) to obtain WX031-5.

Step 5. Synthesis of Compound WX031-6

WX031-5 (5.25 g, 17.38 mmol, 1.00 eq) and glacial acetic acid (200 mL) were added into a 500 mL pre-dried round-bottom flask, and then potassium thiocyanate (3.38 g, 34.76 mmol, 3.38 mL, 2.00 eq) was added. The reaction was warmed to 110° C. and reacted for 4 hours. After the reaction was completed, the reaction solution was dried directly on a rotary evaporator under reduced pressure to obtain a residue, which was re-dissolved in dichloromethane (30 mL) and added with water (30 mL). The aqueous phase was extracted with dichloromethane (2×25 mL). The organic phases were combined, dried over anhydrous sodium sulfate, then subjected to suction filtration, and dried on a rotary evaporator under reduced pressure to obtain a crude product, which was slurried with methanol (10 mL) to obtain WX031-6. $^1$H NMR (400 MHz, METHANOL-d4) δ ppm 0.60-0.72 (m, 2H) 0.82-0.95 (m, 2H) 1.67-1.76 (m, 1H) 4.83 (s, 3H) 6.61 (s, 1H) 7.10 (d, J=10.36 Hz, 1H) 7.55 (d, J=7.50 Hz, 1H).

Step 6. Synthesis of Compound WX031-7

Glacial acetic acid (70.00 mL), water (14.00 mL) and hydrogen peroxide (3.47 g, 30.59 mmol, 2.94 mL, 30% purity, 3.00 eq) were added into a 50 mL pre-dried three-neck flask, purged with nitrogen three times, then an internal thermometer was added to control the reaction temperature below 45° C., then WX031-6 (3.5 g, 10.20 mmol, 1.00 eq) was added in portions under the protection of nitrogen atmosphere. The temperature was controlled below 55° C. and the mixture was reacted at this temperature for 30 min. After the reaction was completed, the mixture was cooled to room temperature and 10 mL of saturated sodium sulfite solution was added, then detected with a starch potassium iodide test paper. The mixture was subjected to ratory evaporation under reduced pressure, then dissolved in 100 mL of water, and adjusted to a pH of 10 with aqueous ammonia, and then extracted with dichloromethane (2×100 mL). The organic phases were combined, dried over anhydrous sodium sulfate, followed by rotary evaporation under reduced pressure to obtain a crude product, which was purified by chromatography column (ethyl acetate:petroleum ether=1:10-1:1) to obtain WX031-7. m/z=311.0, 313.0 [M+1].

Step 7. Synthesis of Compound WX031-8

WX031-7 (2.23 g, 7.17 mmol, 1.00 eq) and triethylamine (1.45 g, 14.34 mmol, 1.99 mL, 2.00 eq) were added into a 250 mL hydrogenation bottle, and then methanol (30.00 mL) was added. After protection with nitrogen, Pd(dppf)Cl$_2$ (786.95 mg, 1.08 mmol, 0.15 eq) was added, the mixture was purged with carbon monoxide three times, and pressurized to 50 psi. The reaction vessel was placed in an oil bath at 70° C. (external temperature) and stirred for 10 hours. After the reaction was completed, the reaction solution was dried on a rotary evaporator, and then purified with column chromatography (ethyl acetate:petroleum ether=1:10-1:1) to obtain WX031-8. m/z=291.0 [M+1]; $^1$H NMR (400 MHz, CHLOROFORM-d) δ ppm 0.80-0.97 (m, 4H) 1.88-1.99 (m, 1H) 3.92 (s, 3H) 3.94 (s, 3H) 6.81 (d, J=11.92 Hz, 1H) 6.90 (d, J=0.88 Hz, 1H) 7.61 (d, J=1.13 Hz, 1H) 7.90 (d, J=7.40 Hz, 1H).

Step 8. Synthesis of Compound WX031-9

WX031-8 (1 g, 3.44 mmol, 1.00 eq), tetrahydrofuran (10 mL) and water (10 mL) were added into a 50 mL pre-dried round-bottom flask, and then lithium hydroxide (247.51 mg, 10.33 mmol, 3.00 eq) was added. The system was reacted at 25° C. for 2 hours. After the reaction was completed, it was dried directly on a rotary evaporator, and then toluene (5 mL×3) was added and dried on a rotary evaporator three times. The reaction was successful, and WX031-9 was obtained. m/z=277.2 [M+1].

Step 9. Synthesis of Compound WX031-10

WX031-9 (0.95 g, 3.44 mmol, 1.00 eq) and dichloromethane (15 mL) were added into a 50 mL pre-dried round-bottom flask, purged with nitrogen three times, and then oxalyl chloride (872.96 mg, 6.88 mmol, 602.04 μL, 2.00 eq) and N,N-dimethylformamide (25.13 mg, 343.88 μmol, 26.46 μL, 0.10 eq) were added. The system was reacted at 25° C. for 0.5 hour. After the reaction was completed, it was directly evaporated on a ratory evaporator. When the volume of the solvent was reduced to about one-third, dichloromethane (15 mL) was added. This process was repeated three times to obtain a solution of WX031-10 in dichloromethane which was directly put into the next reaction. m/z=291.2 [M+114].

Step 10. Synthesis of Compound WX031-11

Dichloromethane (20 mL) was added to a solution of WX031-10 in dichloromethane. The obtained solution was purged with nitrogen three times, then diisopropylethylamine (885.84 mg, 6.85 mmol, 1.20 mL, 2.00 eq) was added, and a solution of WXBB-8 (731.37 mg, 3.60 mmol, 1.05 eq) in dichloromethane (5 mL) was added slowly. The system was reacted at 20° C. for 10 hours. After the reaction was completed, the reaction solution was dried on a rotary evaporator and then re-dissolved in dichloromethane (30 mL). The organic phase was extracted with dilute hydrochloric acid (pH=2). The aqueous phase was adjusted to a pH of 10 with sodium carbonate, and then extracted with dichloromethane (3×30 mL). The organic phases were combined, dried over anhydrous sodium sulfate, subjected to suction filtration and concentration to obtain WX031-11. m/z=462.3 [M+1] and 231.7 [M+2]/2.

Step 11. Synthesis of Compound WX031-12

WX031-11 (1.1 g, 2.38 mmol, 1 eq) and potassium carbonate (329.43 mg, 2.38 mmol, 1 eq) were added into a pre-dried long tube, and then p-methoxybenzylamine (5 mL) was added. The reaction was heated to 100° C. and reacted at this temperature for 10 hours. After the reaction was completed, the reaction solution was cooled, and then dissolved in dichloromethane (20 mL) and water (15 mL). The organic and aqueous phases were separated and then the aqueous phase was extracted with dichloromethane (3×10 mL). The organic phases were combined, washed with saturated brine (2×20 mL), dried over anhydrous sodium sulfate, and subjected to suction filtration and concentration to obtain WX031-12. m/z=579.3[M+1] and 290.2 [M+2]/2.

Step 12. Synthesis of Compound WX031-13

WX031-12 (3.5 g, 6.05 mmol, 1.00 eq) and trifluoroacetic acid (689.64 mg, 6.05 mmol, 447.82 μL, 1.00 eq) were added into a 100 mL pre-dried round-bottom flask, and the mixture was reacted at 25° C. for 12 hours. After the reaction was completed, the reaction solution was dried on a rotary evaporator and then re-dissolved in dichloromethane (20 mL) and saturated aqueous sodium bicarbonate (20 mL). The organic and aqueous phases were separated and then the aqueous phase was washed with dichloromethane (2×15 mL). The organic phases were combined, washed with saturated aqueous sodium bicarbonate solution (2×20 mL) and saturated brine (2×20 mL) successively, dried over anhydrous sodium sulfate, and subjected to suction filtration and concentration to obtain a crude product, which was purified by chromatography column (methanol:dichloromethane=1:30-1:10), and then separated by flash preparative chromatography (column: Luna C18 100*30 mm 5 μm; mobile phase: [water (0.1% TFA)-ACN]; B %: 20%-40%, 10 min) to obtain WX031-13. m/z=459.3 [M+1] and 230.3 [M+2]/2

Step 14. Synthesis of Compound WX031

WX031-13 (0.055 g, 119.95 μmol, 1.00 eq) and trimethyl orthoformate (4.36 g, 41.13 mmol, 4.5 mL, 342.91 eq) were added into a 10 mL pre-dried thumb-bottle, and the mixture was reacted at 110° C. for 0.1 hour under the protection of nitrogen atmosphere. After the reaction was completed, the reaction solution was dried on a rotary evaporator under reduced pressure, and then separated by flash preparative chromatography (column: Agela Durashell C18 150*25 mm 5 μm; mobile phase: [water (10 mM NH$_4$HCO$_3$)-ACN]; B %: 25%-55%, 10.5 min}) to give WX031. $^1$H NMR (400 MHz, CHLOROFORM-d) δ ppm 0.78-0.84 (m, 2H) 0.84-0.90 (m, 2H) 1.53 (s, 3H) 1.55 (s, 3H) 1.86-1.94 (m, 1H) 4.01 (s, 3H) 5.46 (dt, J=13.45, 6.73 Hz, 1H) 7.01 (d, J=1.10 Hz, 1H) 7.30 (s, 1H) 7.74 (d, J=1.32 Hz, 1H) 7.93 (dd, J=8.05, 0.77 Hz, 1H) 8.07 (t, J=7.94 Hz, 1H) 8.22 (s, 1H) 8.37 (s, 1H) 8.41 (dd, J=7.83, 0.77 Hz, 1H) 8.55 (s, 1H).

Example 032: WX032

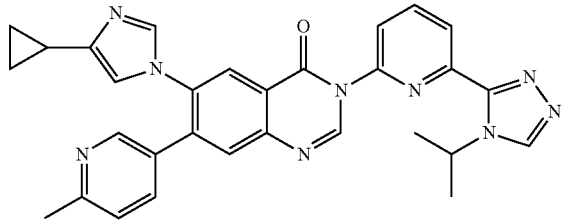 [SMILES: Cc1ccc(-c2cc3ncn(-c4cccc(-c5nncn5C(C)C)n4)c(=O)c3cc2-n2cnc(C3CC3)c2)cn1]

Synthetic Route:

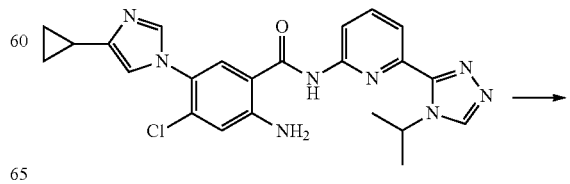

WXBB-17

113

-continued

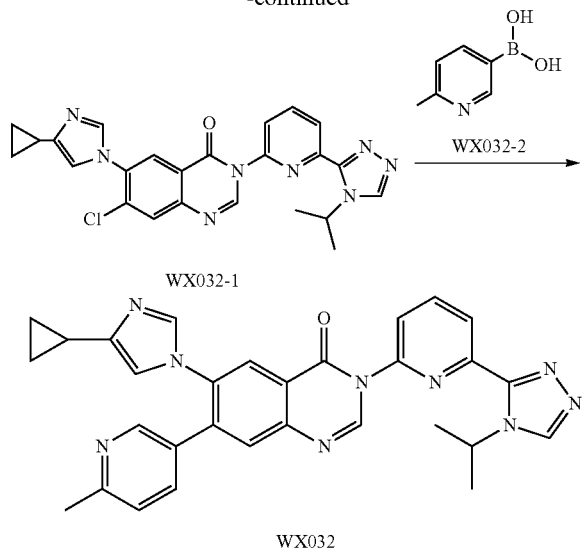

Step 1. Synthesis of Compound WX032-1

WXBB-17 (1.51 g, 3.26 mmol, 1 eq) and trimethyl orthoformate (9.68 g, 91.22 mmol, 10 mL, 27.97 eq) were added into a 100 mL pre-dried round-bottom flask, and the mixture was reacted at 110° C. for 1 hour under the protection of nitrogen atmosphere. After the reaction was completed, the reaction solution was directly concentrated under reduced pressure to give a residue, which was separated and purified by flash column chromatography (dichloromethane:methanol=0-10:1) to obtain WX032-1. m/z=473.2 [M+1] and 237.1 [M+2]/2

Step 2. Synthesis of Compound WX032

WX032-1 (0.06 g, 126.87 μmol, 1 eq), WX032-2 (17.37 mg, 126.87 μmol, 1 eq), palladium acetate (2.85 mg, 12.69 μmol, 0.1 eq), n-butyl-di(1-adamantyl)phosphine (4.55 mg, 12.69 μmol, 0.1 eq) and potassium carbonate 3 (52.60 mg,

114

380.61 μmol, 3 eq) were added into a pre-dried thumb-bottle, then water (0.3 mL) and dioxane (3 mL) were added, followed by purging with nitrogen three times, and the mixture was reacted at 90° C. for 2 hours under the protection of nitrogen atmosphere. After the reaction was completed, the reaction solution was directly concentrated under reduced pressure to give a residue. The residue was dissolved in 5 mL of dichloromethane, diluted with 5 mL of water. The obtained solution was layered and then the organic phase was collected. The aqueous phase was washed with dichloromethane (3*5 mL). The organic phases were combined, then washed with saturated brine (2×3 mL), dried over anhydrous sodium sulfate, and concentrated under reduced pressure to obtain a crude product, which quickly passed through a short silica gel column (dichloromethane: methanol=3:1) and then separated and purified by flash preparative chromatography (column: Agela DuraShell 150 mm_25 mm_5 μm; mobile phase: [water (10 mM $NH_4HCO_3$)-ACN]; B %: 25%-45%, 12 min) to obtain WX032. $^1$H NMR (400 MHz, CHLOROFORM-d) δ 8.66 (s, 1H), 8.48-8.53 (m, 2H), 8.44 (s, 1H), 8.40 (s, 1H), 8.15 (t, J=7.97 Hz, 1H), 8.00 (d, J=8.16 Hz, 1H), 7.92 (s, 1H), 7.29-7.30 (m, 1H), 7.28 (s, 1H), 7.15 (d, J=8.03 Hz, 1H), 5.52 (td, J=6.63, 13.46 Hz, 1H), 2.63 (s, 3H), 1.78-1.91 (m, 1H), 0.78-0.95 (m, 2H), 0.63-0.77 (m, 2H).

Example 033: WX033

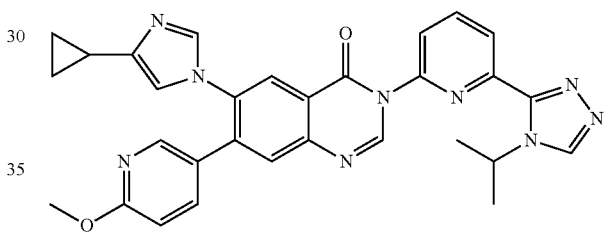

Synthetic Route:

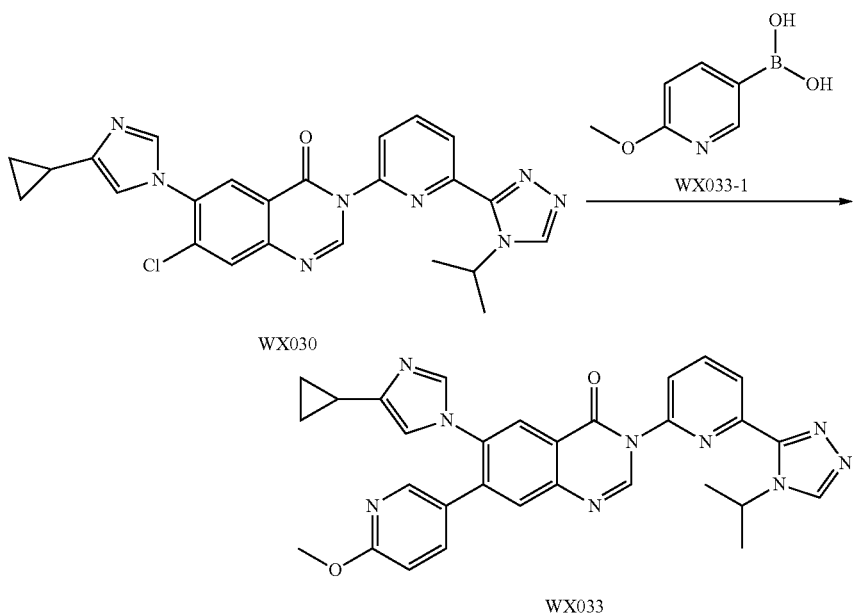

Step 1. Synthesis of Compound WX033

WX030 (0.05 g, 105.72 μmol, 1 eq), WX033-1 (32.34 mg, 211.45 μmol, 2 eq), acetic acid (2.37 mg, 10.57 μmol, 0.1 eq), n-butyl-di(1-adamantyl)phosphine (3.79 mg, 10.57 μmol, 0.1 eq) and potassium carbonate (43.84 mg, 317.17 μmol, 3 eq) were added into a pre-dried reaction bottle, then water (0.3 mL) and dioxane (3 mL) were added, followed by purging with nitrogen three times, and the mixture was reacted at 90° C. for 2 hours under the protection of nitrogen atmosphere. After the reaction was completed, the reaction solution was directly concentrated under reduced pressure to give a residue. The residue was dissolved in 5 mL of dichloromethane, diluted with 5 mL of water. The obtained solution was layered and then the organic phase was collected. The aqueous phase was washed with dichloromethane (3*5 mL). The organic phases were combined, then washed with saturated brine (2×3 mL), dried over anhydrous sodium sulfate, and concentrated under reduced pressure to obtain a crude product, which quickly passed through a short silica gel column (dichloromethane:methanol=3:1) and then separated and purified by flash preparative chromatography (column: Agela DuraShell 150 mm_25 mm_5 μm; mobile phase: [water (10 mM NH$_4$HCO$_3$)-ACN]; B %: 30%-55%, 12 min) to obtain WX033. $^1$H NMR (400 MHz, CHLOROFORM-d) δ 8.64 (s, 1H), 8.48 (d, J=7.53 Hz, 1H), 8.42 (s, 1H), 8.37 (s, 1H), 8.15 (d, J=2.64 Hz, 1H), 8.09-8.13 (m, 1H), 7.98 (d, J=7.91 Hz, 1H), 7.89 (s, 1H), 7.31 (s, 1H), 7.22 (dd, J=2.64, 8.66 Hz, 1H), 6.72 (d, J=8.78 Hz, 1H), 6.68 (s, 1H), 5.51 (td, J=6.76, 13.46 Hz, 1H), 3.99 (s, 3H), 1.78-1.89 (m, 1H), 1.59 (s, 6H), 0.82-0.90 (m, 2H), 0.70-0.77 (m, 2H).

Example 034: WX034

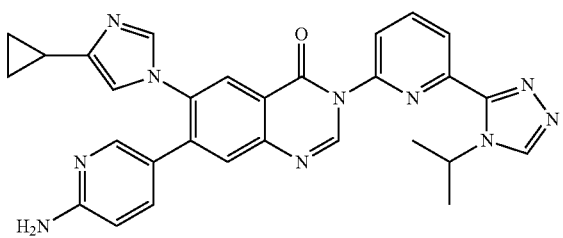 [SMILES: CC(C)n1cnnc1-c1cccc(-n2cnc3cc(-c4ccc(N)nc4)c(-n4cnc(C5CC5)c4)cc3c2=O)n1]

Synthetic Route:

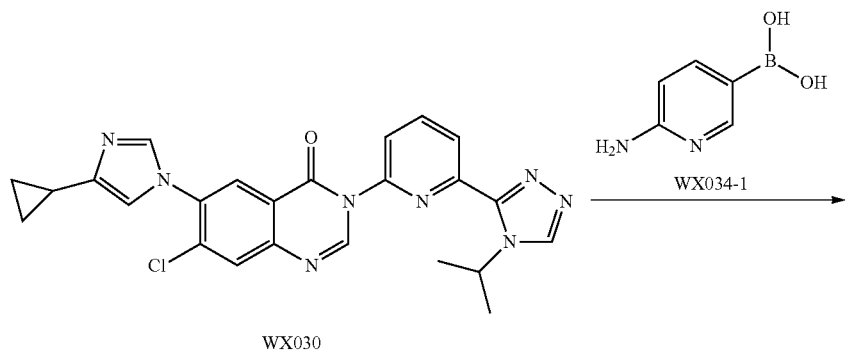

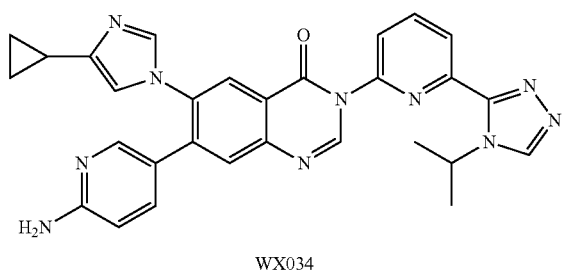

WX034

Step 1. Synthesis of Compound WX034

WX030 (0.05 g, 105.72 μmol, 1 eq), WX034-1 (29.17 mg, 211.45 μmol, 2 eq), caesium acetate (2.37 mg, 10.57 μmol, 0.1 eq), n-butyl-di(1-adamantyl)phosphine (3.79 mg, 10.57 μmol, 0.1 eq) and potassium carbonate (43.84 mg, 317.17 μmol, 3 eq) were added into a pre-dried thumb-bottle, then water (0.3 mL) and dioxane (3 mL) were added, followed by purging with nitrogen three times, and the mixture was reacted at 90° C. for 2 hours under the protection of nitrogen atmosphere. After the reaction was completed, the reaction solution was directly concentrated under reduced pressure to give a residue. The residue was dissolved in 5 ml of dichloromethane, diluted with 5 mL of water. The obtained solution was layered and then the organic phase was collected. The aqueous phase was washed with dichloromethane (3*5 mL). The organic phases were combined, then washed with saturated brine (2×3 mL), dried over anhydrous sodium sulfate, and concentrated under reduced pressure to obtain a crude product, which quickly passed through a short silica gel column (dichloromethane:methanol=3:1) and then separated and purified by flash preparative chromatography (column: Agela DuraShell 150 mm_25 mm_5 μm; mobile phase: [water (10 mM $NH_4HCO_3$)-ACN]; B %: 20%-45%, 12 min) to obtain WX034. $^1$H NMR (400 MHz, CHLOROFORM-d) δ 8.63 (s, 1H), 8.47 (d, J=7.03 Hz, 1H), 8.42 (s, 1H), 8.33 (s, 1H), 8.11-8.16 (m, 1H), 8.07-8.11 (m, 1H), 7.98 (d, J=7.40 Hz, 1H), 7.87 (s, 1H), 7.34 (d, J=1.25 Hz, 1H), 7.04 (dd, J=2.38, 8.66 Hz, 1H), 6.70 (d, J=1.13 Hz, 1H), 6.44 (d, J=8.53 Hz, 1H), 5.51 (quin, J=6.78 Hz, 1H), 4.64 (s, 2H), 1.78-1.92 (m, 1H), 1.58 (d, J=6.65 Hz, 6H), 0.83-0.91 (m, 2H), 0.72-0.78 (m, 2H).

Example 035: WX035

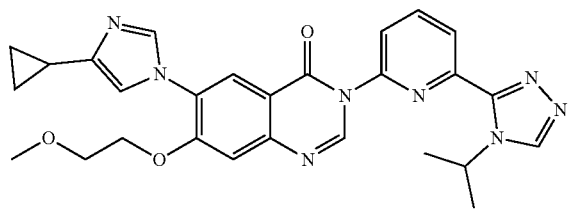 [SMILES: COCCOc1cc2ncn(-c3cccc(-c4nncn4C(C)C)n3)c(=O)c2cc1-n1cnc(C2CC2)c1]

Synthetic Route:

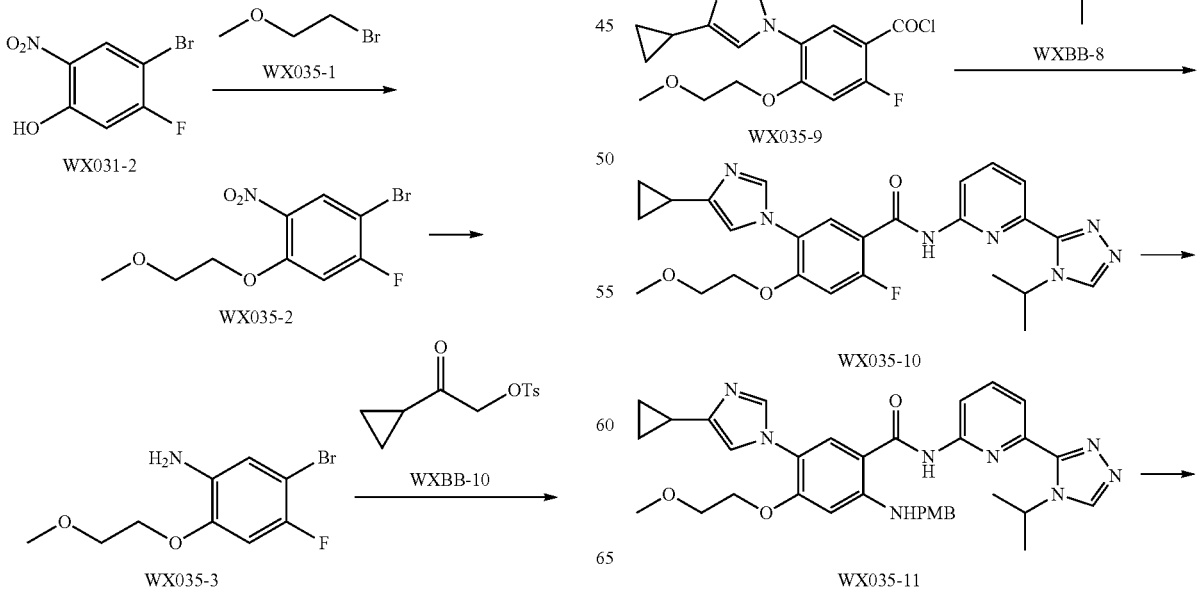

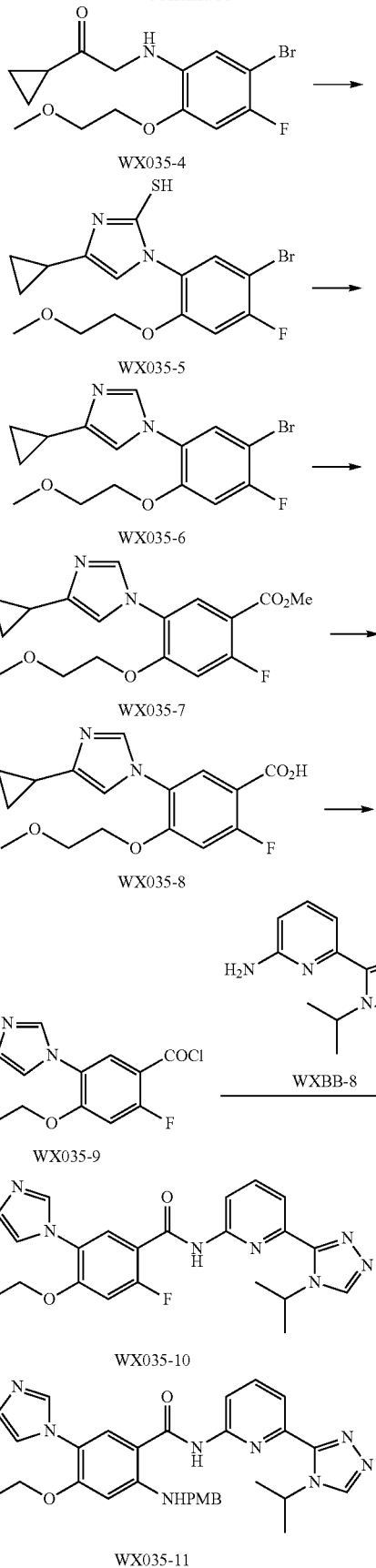

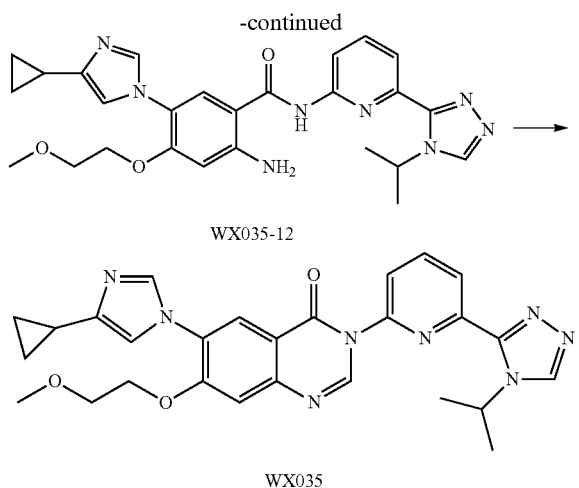

WX035-12

WX035

Step 1. Synthesis of Compound WX035-2

WX031-2 (20 g, 84.75 mmol, 1 eq) and N,N-dimethylformamide (150 mL) were added into a 250 ml pre-dried round-bottom flask, and then WX035-1 (14.13 g, 101.70 mmol, 9.55 mL, 1.2 eq) and potassium carbonate (23.43 g, 169.49 mmol, 2 eq) were added. The system was reacted at 50° C. for 20 hours. The reaction solution was dried on a rotary evaporator and then re-dissolved in ethyl acetate (100 mL) and water (100 mL). The organic and aqueous phases were separated and the aqueous phase was extracted with ethyl acetate (3×50 mL). The organic phases were combined, washed with saturated brine (2×150 mL), dried over anhydrous sodium sulfate, and subjected to suction filtration to obtain a crude product, which was purified by flash silica gel column (EA:PE=1:10-1:4) to obtain WX035-2. $^1$H NMR (400 MHz, CHLOROFORM-d) δ ppm 3.41 (s, 3H) 3.73-3.82 (m, 2H) 4.14-4.28 (m, 1H) 4.14-4.28 (m, 1H) 6.93 (d, J=9.92 Hz, 1H) 8.10 (d, J=7.28 Hz, 1H).

Step 2. Synthesis of Compound WX035-3

WX035-2 (22.3 g, 75.83 mmol, 1.00 eq), iron powder (12.71 g, 227.49 mmol, 3 eq), ammonium chloride (4.46 g, 83.41 mmol, 2.92 mL, 1.10 eq), water (130 mL) and ethanol (400 mL) were added into a 1000 mL pre-dried eggplant-shaped bottle. The reaction solution was refluxed at 80° C. for 6 hours. The reaction solution passed through celite, then was dried on a rotary evaporator, and dissolved in dichloromethane (100 mL) and water (80 mL). The aqueous phase was extracted with dichloromethane (2×50 mL). The organic phases were combined, washed with saturated brine (2×100 mL), dried, filtered and concentrated to obtain a crude product, which was purified by flash silica gel column (ethyl acetate:petroleum ether=1:8-1:1) to obtain WX035-3. $^1$H NMR (400 MHz, CHLOROFORM-d) δ ppm 3.41 (s, 3H) 3.71-3.77 (m, 4H) 4.06-4.10 (m, 2H) 6.62 (d, J=9.92 Hz, 1H) 6.80 (d, J=6.84 Hz, 1H).

Step 3. Synthesis of Compound WX035-4

WX035-3 (12.64 g, 47.86 mmol, 1.00 eq), WXBB-10 (13.39 g, 52.65 mmol, 1.10 eq) and toluene (120 mL) were added into a 500 mL pre-dried reaction bottle. The reaction was heated to 100° C., then diisopropylethylamine (12.37 g, 95.72 mmol, 16.67 mL, 2.00 eq) was added, and the mixture was reacted at 100° C. for 10 hours. After drying on a rotary evaporator, it was then purified with chromatography column (ethyl acetate:petroleum ether=0-1:10) to obtain WX035-4. m/z=346.1, 348.1 [M+1].

Step 4. Synthesis of Compound WX035-5

WX035-4 (14.85 g, 42.90 mmol, 1.00 eq) and glacial acetic acid (200 mL) were added into a 500 mL pre-dried round-bottom flask, and then potassium thiocyanate (8.34 g, 85.79 mmol, 8.34 mL, 2.00 eq) was added. The reaction was warmed to 110° C. and reacted for 3 hours. After the reaction was completed, the reaction solution was dried directly on a rotary evaporator under reduced pressure to obtain a residue, which was re-dissolved in dichloromethane (60 mL) and added with water (60 mL), and the aqueous phase was extracted with dichloromethane (2×40 mL). The organic phases were combined, washed with saturated brine (50 mL), dried over anhydrous sodium sulfate, and then subjected to suction filtration and dried on a rotary evaporator under reduced pressure. Purifying with chromatography column (ethyl acetate:petroleum ether=1:10-1:1) to obtain WX035-5. m/z=387.1, 389.1 [M+1].

Step 5. Synthesis of Compound WX035-6

Glacial acetic acid (100 mL), water (18 mL) and hydrogen peroxide (9.39 g, 82.80 mmol, 7.95 mL, 30% purity, 3.00 eq) were added into a 250 mL pre-dried three-neck flask. An internal thermometer was added to control the reaction temperature at 45° C., followed by addition of WX035-5 (10.69 g, 27.60 mmol, 1.00 eq) in portions. The temperature was controlled below 55° C. and the mixture was reacted at this temperature for 30 min. The reaction was cooled to room temperature, and 20 mL of saturated sodium sulfite solution was added. No blue color was detected with a starch potassium iodide test paper. Then the mixture was subjected to ratory evaporation under reduced pressure, then dissolved in 100 mL of water, and adjusted to a pH of 10 with aqueous ammonia, and then extracted with dichloromethane (2×150 mL). The organic phases were combined, dried over anhydrous sodium sulfate, followed by rotary evaporation under reduced pressure to obtain WX035-6. m/z=355.1, 357.1 [M+1].

Step 6. Synthesis of Compound WX035-7

WX035-6 (7.1 g, 19.99 mmol, 1.00 eq) and triethylamine (4.05 g, 39.98 mmol, 5.56 mL, 2.00 eq) were added into a 250 hydrogenation bottle, then methanol (100 mL) and Pd(dppf)Cl$_2$ (2.19 g, 3.00 mmol, 0.15 eq) were added, followed by purging with carbon monoxide three times and pressurizing to 50 psi. The reaction vessel was placed in an oil bath at 70° C. (external temperature) and stirred for 10 hours. The reaction solution was dried on a rotary evaporator, and then separated with chromatography column (ethyl acetate:petroleum ether=1:10-1:1) to obtain WX035-7. $^1$H NMR (400 MHz, CHLOROFORM-d) δ ppm 0.70-0.78 (m, 2H) 0.81-0.89 (m, 2H) 1.81-1.91 (m, 1H) 3.36 (s, 3H) 3.66-3.73 (m, 2H) 3.88 (s, 3H) 4.14-4.21 (m, 2H) 6.78 (d, J=11.69 Hz, 1H) 6.90 (s, 1H) 7.66 (s, 1H) 7.84 (d, J=7.50 Hz, 1H).

Step 7. Synthesis of Compound WX035-8

WX035-7 (2.5 g, 7.48 mmol, 1.00 eq), lithium hydroxide (537.25 mg, 22.43 mmol, 3.00 eq), tetrahydrofuran (25 mL) and water (25 mL) were added into a 100 mL pre-dried flask. The clear solution was stirred at 25° C. for 1 hour. After the reaction was completed, the reaction solution was dried directly on a ratory evaporator with a water pump, and then toluene (2×10 mL) was added to remove the un-evaporated water to obtain WX035-8. m/z=321.1 [M+1].

Step 8. Synthesis of Compound WX035-9

WX035-8 (2.4 g, 7.49 mmol, 1.00 eq) was added into a 100 mL pre-dried round-bottom flask, followed by purging with nitrogen three times, then dichloromethane (40 mL) was added, and then oxalyl chloride (1.90 g, 14.99 mmol, 1.31 mL, 2.00 eq) and N,N-dimethylformamide (54.76 mg, 749.26 μmol, 57.65 μL, 0.10 eq) were added dropwise under the protection of nitrogen atmosphere. After the addition, the mixture was reacted at 25° C. for 1 hour. After the reaction was completed, it was directly evaporated on a ratory evaporator with a water pump. When the volume of the solution was reduced to about one-third, 20 mL of anhydrous dichloromethane was added. This process was repeated three times to obtain a solution of WX035-9 in dichloromethane which was directly used for the next reaction. m/z=335.2 [M+14].

Step 9. Synthesis of Compound WX035-10

A 100 mL round-bottom flask containing WX035-9 (2.54 g, 7.50 mmol, 1.00 eq) was purged with nitrogen three times, then dichloromethane (40 mL) and diisopropylethylamine (1.94 g, 15.00 mmol, 2.61 mL, 2 eq) were added. Then WXBB-8 (1.60 g, 7.87 mmol, 1.05 eq) was added under the protection of nitrogen atmosphere. The clear solution was reacted at 25° C. for 4 hours. After the reaction was completed, the mixture was extracted with water (pH=2, 3×30 mL). The aqueous phase was adjusted to pH=10, and then extracted with dichloromethane (3×50 mL). The organic phases were combined, dried over anhydrous sodium sulfate, subjected to suction filtration and dried on a rotary evaporator to obtain WX035-10. m/z=506.4 [M+1] 253.8 [M+2]/2.

Step 10. Synthesis of Compound WX035-11

WX035-10 (1.2 g, 2.37 mmol, 1 eq), p-methoxybenzylamine (3.26 g, 23.74 mmol, 10 eq), potassium carbonate (656.13 mg, 4.75 mmol, 2 eq) were added into a pre-dried long tube, and then N-methylpyrrolidone (10 mL) was added. The reaction was heated to 100° C. and reacted at this temperature for 10 hours. After the reaction was completed, the reaction solution was cooled, and then ethyl acetate (20 mL) and water (20 mL) were added. The organic and aqueous phases were separated and the aqueous phase was extracted with ethyl acetate (3×20 mL). The organic phases were combined, then washed with water (5×30 mL) to remove N-methylpyrrolidone, dried over anhydrous sodium sulfate, and subjected to suction filtration and concentration to obtain WX035-11. m/z=623.3 [M+1] and 312.2 [M+2]/2.

Step 11. Synthesis of Compound WX035-12

WX035-11 (1.75 g, 2.81 mmol, 1 eq) and trifluoroacetic acid (30.80 g, 270.12 mmol, 20 mL, 96.12 eq) were added into a 100 mL pre-dried flask. The clear solution was stirred at 30° C. for 2 hours. After the reaction was completed, the reaction solution was dried directly on a rotary evaporator, then re-dissolved in dichloromethane (20 mL), and added with sodium bicarbonate (20 mL). The organic and aqueous phases were separated and then the aqueous phase was extracted with dichloromethane (3×20 mL). The organic phases were combined, then washed with saturated brine (2×25 mL), dried, and subjected to suction filtration and concentration to obtain a crude product, which was purified by a chromatography column (methanol:dichloromethane=1:30-1:10) to obtain WX035-12. m/z=503.3 [M+1] and 252.2 [M+2]/2.

Step 12. Synthesis of Compound WX035

WX035-12 (550.41 mg, 1.10 mmol, 1.00 eq) and trimethyl orthoformate (9.70 g, 91.41 mmol, 10 mL, 83.46 eq) were added into a 50 mL pre-dried round-bottom flask, and the mixture was reacted at 110° C. for 1 hour under the protection of nitrogen atmosphere. After the reaction was completed, the reaction solution was dried on a rotary evaporator under reduced pressure, separated by flash preparative chromatography (column: Agela Durashell C18 150*25 mm 5 μm; mobile phase: [water (10 mM NH$_4$HCO$_3$)-ACN]; B %: 25%-55%, 10.5 min) to give WX035. 1H NMR (400 MHz, METHANOL-d4) δ ppm 0.58-0.78 (m, 2H) 0.82-0.94 (m, 2H) 1.56 (s, 3H) 1.57 (s, 3H) 1.83-1.96 (m, 1H) 3.40 (s, 3H) 3.76-3.84 (m, 2H) 4.39 (br d, J=3.53 Hz, 2H) 5.46 (dt, J=13.62, 6.75 Hz, 1H) 7.24 (s, 1H) 7.42 (s, 1H) 7.96-8.03 (m, 2H) 8.18-8.30 (m, 3H) 8.67 (s, 1H) 8.86 (s, 1H).

Example 036: WX036

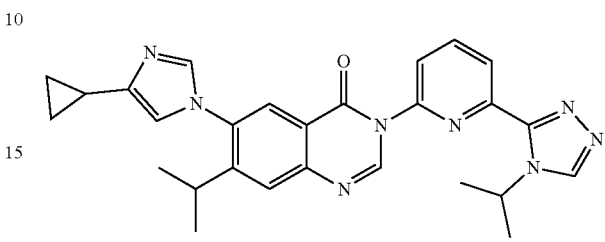

Synthetic Route:

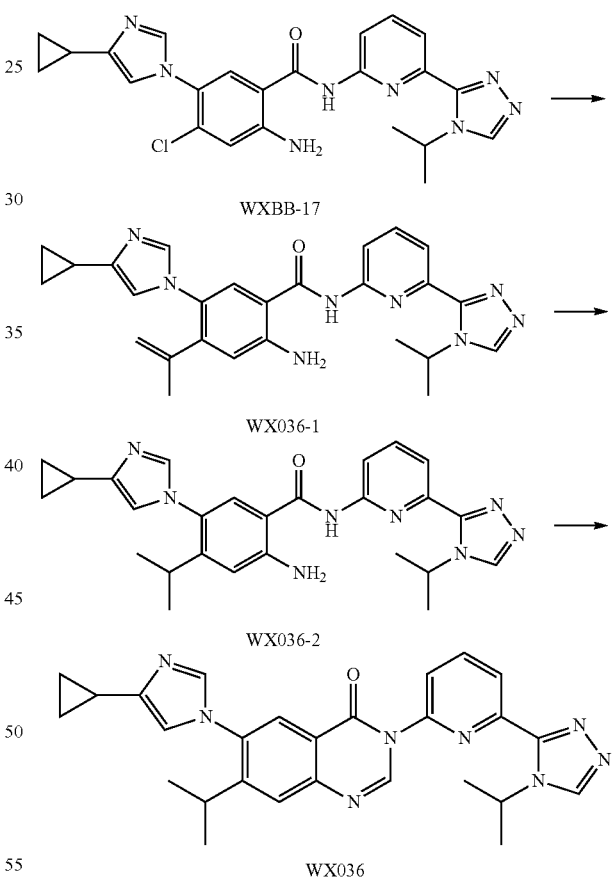

Step 1. Synthesis of Compound WX036-1

Isopropenyl potassium fluoroborate (235.19 mg, 2.16 mmol, 2 eq), compound WXBB-17 (0.5 g, 1.08 mmol, 1.00 eq), n-butyldi (1-adamantyl)phosphine (38.72 mg, 108.01 μmol, 0.10 eq), palladium acetate (24.25 mg, 108.01 μmol, 0.10 eq) and potassium carbonate (447.83 mg, 3.24 mmol, 3.00 eq) were added into a 10 mL pre-dried reaction bottle, followed by purging with nitrogen three times, and then water (0.7 mL) and dioxane (7 mL) were added. Under the protection of nitrogen atmosphere, the reaction vessel was placed in an oil bath at 90° C. and stirred for 2 hours. After the reaction was completed, the reaction solution was added with water (10 mL), and extracted with dichloromethane (3×15 mL). The organic phases were combined, washed with saturated brine (2×25 mL), dried over anhydrous sodium sulfate, and filtered under reduced pressure to obtain WX036-1. MS: m/z=235.3[M+1]/2.

Step 2. Synthesis of Compound WX036-2

Compound WX036-1 (257.72 mg, 550.02 μmol, 1.00 eq), methanol (8 mL) and palladium carbon (65.88 mg) were added into a 50 mL pre-dried flask, followed by purging with hydrogen three times, and then the mixture was reacted at 25° C. for 1 hour. After the reaction was completed, the reaction solution was subjected to suction filtration under reduced pressure through a suction filtration funnel covered with celite, and then evaporated on a rotary evaporator under reduced pressure to afford WX036-2. MS: m/z=236.4[M+1]/2.

Step 3. Synthesis of Compound WX036

Compound WX036-2 (0.14 g, 297.51 μmol, 1.00 eq) and trimethyl orthoformate (5.20 g, 49.01 mmol, 5.37 mL, 164.73 eq) were added into a 50 mL pre-dried reaction bottle, and the mixture was reacted at 110° C. for 2 hours under the protection of nitrogen atmosphere. After the reaction was completed, the reaction solution passed through flash silica gel column (methanol/dichloromethane=0~20%), and then separated and purified by flash preparative chromatography (column: Agela Durashell C18 150*25 mm 5 μm; mobile phase: [water (10 mM NH₄HCO₃)-ACN]; B %: 27%-57%, 10.5 min) to give WX036. ¹HNMR (400 MHz, CHLOROFORM-d) δ ppm 0.83-0.89 (m, 2H) 0.89-0.95 (m, 2H) 1.27 (d, J=6.84 Hz, 6H) 1.56 (d, J=6.84 Hz, 6H) 1.89-1.97 (m, 1H) 2.99 (dt, J=13.67, 6.84 Hz, 1H) 5.49 (dt, J=13.45, 6.73 Hz, 1H) 6.84 (s, 1H) 7.48 (s, 1H) 7.84 (s, 1H) 7.94 (d, J=8.16 Hz, 1H) 8.06-8.14 (m, 1H) 8.22 (s, 1H) 8.40 (s, 1H) 8.45 (d, J=7.72 Hz, 1H) 8.60 (s, 1H).

Example 037: WX037

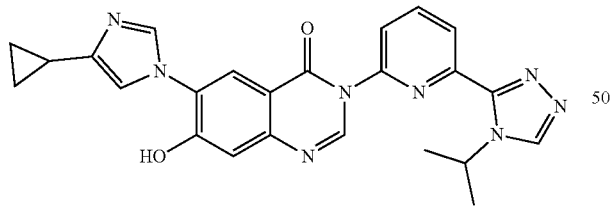

Synthetic Route:

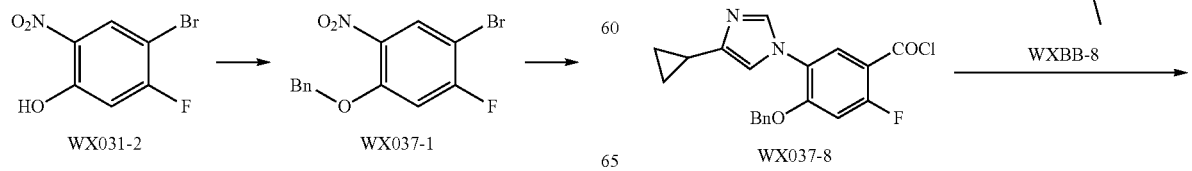

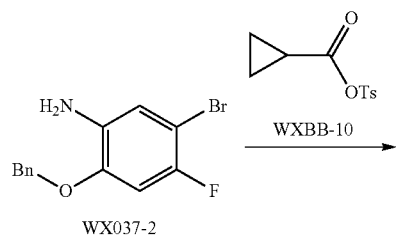
WX037-2

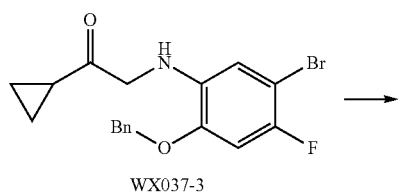
WX037-3

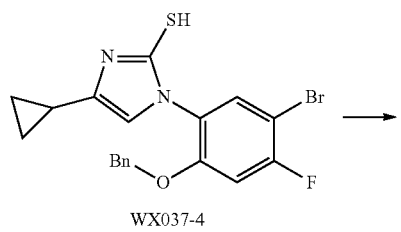
WX037-4

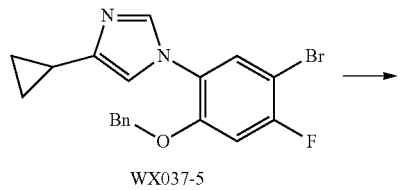
WX037-5

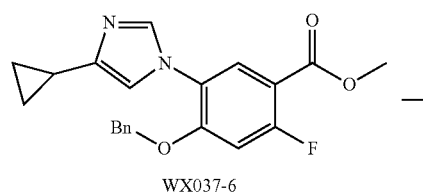
WX037-6

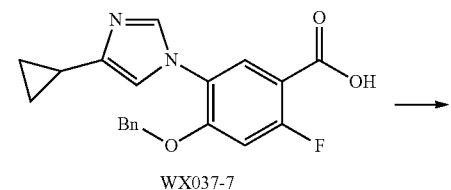
WX037-7

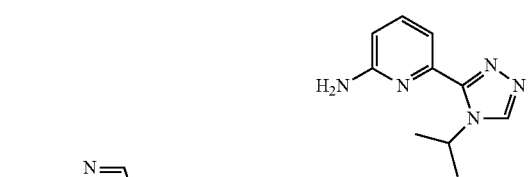
WX037-8

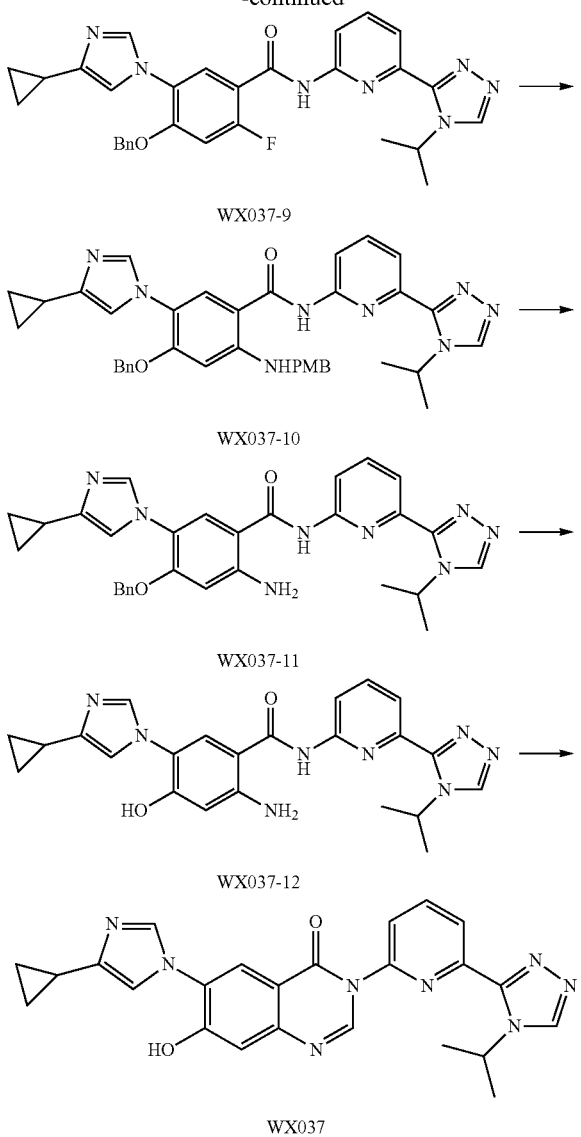

Step 1. Synthesis of Compound WX037-1

WX031-2 (28 g, 118.65 mmol, 1 eq) was dissolved in anhydrous DMF (200 mL), and $K_2CO_3$ (32.80 g, 237.29 mmol, 2 eq) and BnBr (24.35 g, 142.38 mmol, 16.91 mL, 1.2 eq) were added. The mixture was stirred at 20° C. for 16 hours. The reaction solution was poured into water (600 mL), and extracted with EA (300 mL*2). The organic phase was washed with water (300 mL) and saturated brine (300 mL), dried over anhydrous sodium sulfate, and filtered. The filtrate was dried on a rotary evaporator under reduced pressure. The crude product was slurried with PE/EA (5/1, 120 mL) at 20° C. for 0.5 hour, filtered, and the filter cake was dried under reduced pressure to obtain WX037-1. $^1$H NMR (400 MHz, CHLOROFORM-d) δ=8.20 (d, J=7.3 Hz, 1H), 7.50-7.38 (m, 5H), 6.94 (d, J=9.8 Hz, 1H), 5.25 (s, 2H).

Step 2: Synthesis of Compound WX037-2

WX037-1 (26.5 g, 81.26 mmol, 1 eq) was dissolved in MeOH (500 mL), and $NiCl_2 \cdot 6H_2O$ (69.53 g, 292.53 mmol, 3.6 eq) was added in portions. Then $NaBH_4$ (15.37 g, 406.26 mmol, 5 eq) was added in portions at 0° C. The mixture was stirred at 25° C. for 0.5 hour. To the reaction solution was added a saturated ammonium chloride solution (500 mL). Then it was evaporated on a ratory evaporator to remove the methanol, added with EA (500 mL), and stirred for 10 minutes. The insoluble solid was filtered off, then the filterate was separated to obtain a organic phase, and the aqueous phase was then extracted with EA (250 mL). The organic phases were combined, washed with saturated brine (250 mL), dried over anhydrous sodium sulfate, and filtered. The filtrate was dried on a rotary evaporator under reduced pressure to obtain WX037-2. $^1$H NMR (400 MHz, CHLOROFORM-d) δ=7.43 (br s, 5H), 6.87 (br d, J=5.0 Hz, 1H), 6.70 (br d, J=9.5 Hz, 1H), 5.07 (br s, 2H), 3.75 (br s, 2H).

Step 3: Synthesis of Compound WX037-3

WX037-2 (22 g, 63.81 mmol, 1 eq) (purity: 85.59%) was added to anhydrous toluene (200 mL), and WXBB-10 (17.04 g, 67.00 mmol, 1.05 eq) and DIEA (16.49 g, 127.62 mmol, 22.23 mL, 2 eq) were added. The mixture was stirred at 100° C. for 16 hours. The reaction solution was dried on a rotary evaporator, added with water (200 mL), and extracted with EA (200 mL*2). The organic phase was washed with saturated brine (100 mL), dried over anhydrous sodium sulfate, and filtered. The filtrate was dried on a rotary evaporator under reduced pressure. The crude product was added with PE/EA (5/1, 60 mL), slurried at 20° C. for 0.5 hour and filtered. The filter cake was dried on a rotary evaporator under reduced pressure to obtain WX037-3. $^1$H NMR (400 MHz, CHLOROFORM-d) δ=7.38-7.23 (m, 5H), 6.58 (d, J=9.8 Hz, 1H), 6.48 (d, J=6.8 Hz, 1H), 5.02 (br d, J=4.8 Hz, 1H), 5.00 (s, 2H), 4.06 (d, J=5.0 Hz, 2H), 1.98-1.88 (m, 1H), 1.08 (quin, J=3.8 Hz, 2H), 0.96-0.87 (m, 2H).

Step 4: Synthesis of Compound WX037-4

WX037-3 (15 g, 35.58 mmol, 1 eq) (purity: 89.71%) was added to AcOH (120 mL), and KSCN (6.91 g, 71.15 mmol, 6.91 mL, 2 eq) was added. The mixture was stirred at 110° C. for 4 hours under nitrogen. The reaction solution was cooled to room temperature, poured into water (300 mL), and stirred for 15 minutes. A solid precipitated out and was filtered, and the filter cake was dried on a rotary evaporator under reduced pressure to obtain WX037-4. $^1$H NMR (400 MHz, CHLOROFORM-d) δ=11.56 (br s, 1H), 7.60 (d, J=7.3 Hz, 1H), 7.30-7.21 (m, 5H), 6.79 (d, J=9.8 Hz, 1H), 6.31 (s, 1H), 5.02 (s, 2H), 1.67-1.58 (m, 1H), 0.84-0.77 (m, 2H), 0.61-0.53 (m, 2H).

Step 5: Synthesis of Compound WX037-5

WX037-4 was dissolved in a mixture of AcOH (150 mL) and $H_2O$ (15 mL), and $H_2O_2$ (12.97 g, 114.42 mmol, 10.99 mL, 30% purity, 3.22 eq) was added dropwise. The system was stirred at 45° C. for 0.5 hour. After cooling to room temperature, the reaction solution was added slowly to an aqueous solution (300 mL) of sodium sulfite (30 g), and extracted with EA (300 mL*2). The organic layer was washed with saturated sodium bicarbonate (300 mL), dried over anhydrous sodium sulfate, and filtered. The filtrate was dried on a rotary evaporator under reduced pressure. The crude product was purified by column (EA/PE=0~10%~20%) to obtain WX037-5. 1H NMR (400 MHz, CHLOROFORM-d) δ=7.64 (d, J=1.0 Hz, 1H), 7.48 (d, J=7.0 Hz, 1H), 7.42-7.34 (m, 3H), 7.33-7.29 (m, 2H), 6.94-6.88 (m, 2H), 5.11 (s, 2H), 1.95-1.86 (m, 1H), 0.92-0.86 (m, 2H), 0.83-0.77 (m, 2H).

Step 6: Synthesis of Compound WX037-6

WX037-5 (6 g, 14.56 mmol, 1 eq) (purity 93.95%) was dissolved in anhydrous MeOH (100 mL), and $Pd(dppf)Cl_2$ (1.07 g, 1.46 mmol, 0.1 eq) and $Et_3N$ (2.95 g, 29.11 mmol, 4.05 mL, 2 eq) were added. The system was stirred at 80° C. for 4 hours under CO (50 psi) condition. The reaction solution was filtered and the filtrate was dried on a rotary evaporator under reduced pressure. The crude product was purified by a column (EA/PE=0~10%~20%~40%) to obtain WX037-6. $^1$H NMR (400 MHz, CHLOROFORM-d) δ=7.92 (d, J=7.5 Hz, 1H), 7.67 (d, J=0.8 Hz, 1H), 7.44-7.31 (m, 5H), 6.93 (d, J=0.8 Hz, 1H), 6.87 (d, J=11.8 Hz, 1H), 5.19 (s, 2H), 3.94 (s, 3H), 1.96-1.86 (m, 1H), 0.93-0.86 (m, 2H), 0.84-0.78 (m, 2H).

Step 7: Synthesis of Compound WX037-7

WX037-6 (2.7 g, 7.37 mmol, 1 eq) was dissolved in anhydrous THF (20 mL), and a solution of LiOH (530 mg, 22.13 mmol, 3 eq) dissolved in H$_2$O (10 mL) was added. The mixture was stirred at 20° C. for 1 hour. The reaction solution was dried directly to obtain a crude product. The crude product was slurried with DCM:MeOH (10:1, 44 mL) at 20° C. for 0.5 hour, and filtered. The filtrate was dried on a rotary evaporator under reduced pressure to obtain WX037-7. $^1$H NMR (400 MHz, DMSO-d$_6$) δ ppm 0.59-0.65 (m, 2H) 0.69-0.78 (m, 2H) 1.73-1.83 (m, 1H) 5.15 (s, 2H) 6.99 (d, J=11.80 Hz, 1H) 7.08 (s, 1H) 7.33 (br dd, J=7.78, 4.77 Hz, 1H) 7.36 (d, J=1.51 Hz, 2H) 7.37 (br s, 2H) 7.57 (d, J=7.78 Hz, 1H) 7.64 (s, 1H).

Step 8: Synthesis of Compound WX037-8

Compound WX037-7 (2.5 g, 7.10 mmol, 1.00 eq) was added into a 100 mL pre-dried round-bottom flask, followed by purging with nitrogen three times, then dichloromethane (35 mL) was added. Oxalyl chloride (1.80 g, 14.19 mmol, 1.24 mL, 2.00 eq) and N, N-dimethylformamide (51.86 mg, 709.51 μmol, 54.59 μL, 0.10 eq) were added dropwise under the protection of nitrogen atmosphere. After the addition, the mixture was reacted at 25° C. for 1 hour. After the reaction was completed, it was directly evaporated on a ratory evaporator with a water pump. When the volume of the solution was reduced to about one-third, 15 mL of anhydrous dichloromethane was added. This process was repeated three times to obtain a solution of WX037-8 in dichloromethane which was directly used for the next step. MS: m/z=367.3[M+14].

Step 9: Synthesis of Compound WX037-9

A 100 mL round-bottom flask containing compound WX037-8 (2.6 g, 7.01 mmol, 1.00 eq) was purged with nitrogen three times, then dichloromethane (35 mL) and diisopropylethylamine (1.81 g, 14.02 mmol, 2.44 mL, 2 eq) were added. Compound WXBB-8 (1.50 g, 7.36 mmol, 1.05 eq) was added under the protection of nitrogen atmosphere. The clear solution was reacted at 25° C. for 3 hours. After the reaction was completed, the reaction solution was dried on a rotary evaporator. The product was re-dissolved in dichloromethane (40 mL) and extracted with water (pH=2, 3×30 mL). The aqueous phase was adjusted to pH=10, and then extracted with dichloromethane (3×50 mL). The organic phases were combined, dried over anhydrous sodium sulfate, subjected to suction filtration, and dried on a rotary evaporator to obtain WX037-9. MS: m/z=269.8 [M+1]/2.

Step 10: Synthesis of Compound WX037-10

Compound WX037-9 (3.5 g, 6.51 mmol, 1.00 eq) and p-methoxybenzylamine (8.93 g, 65.11 mmol, 8.43 mL, 10.00 eq) were added into a 100 ml pre-dried round-bottom flask, and then potassium carbonate (1.80 g, 13.02 mmol, 2.00 eq) was added. The system was reacted at 100° C. for 2 hours. After the reaction was completed, the reaction solution was dried on a rotary evaporator, then added with water (30 mL), adjusted to a pH of about 6 with 2N HCl, and extracted with dichloromethane (3×25 mL) to remove the unreacted p-methoxybenzylamine. The organic phases were combined and then purified by column chromatography (methanol:methylene chloride=1:30-1:10) to afford WX037-10. 1H NMR (400 MHz, CHLOROFORM-d) δ ppm 0.55-0.65 (m, 2H) 0.72 (br d, J=8.38 Hz, 2H) 1.28 (dt, J=6.62, 1.87 Hz, 6H) 1.67-1.81 (m, 1H) 1.90 (br s, 1H) 3.76-3.84 (m, 3H) 4.32 (d, J=5.51 Hz, 2H) 4.94 (s, 2H) 5.51 (dt, J=13.40, 6.64 Hz, 1H) 6.21 (s, 1H) 6.73 (s, 1H) 6.85 (s, 1H) 6.87 (s, 1H) 7.11-7.18 (m, 2H) 7.22-7.29 (m, 5H) 7.38 (s, 1H) 7.59 (d, J=1.76 Hz, 1H) 7.77-7.86 (m, 1H) 7.91-7.99 (m, 1H) 8.13 (d, J=8.16 Hz, 1H) 8.21 (s, 1H) 8.49 (br t, J=5.40 Hz, 1H) 9.46 (br d, J=14.77 Hz, 1H).

Step 11: Synthesis of Compound WX037-11

Compound WX037-10 (2 g, 3.05 mmol, 1 eq) and trifluoroacetic acid (20 mL) were added into a 100 mL pre-dried round-bottom flask. The system was reacted at 25° C. for 1 hour. After the reaction was completed, the reaction solution was dried on a rotary evaporator, then added to 40 mL of water, and adjusted to pH 8 by adding a saturated sodium bicarbonate solution. The aqueous phase was extracted with dichloromethane (3×40 mL). The organic phases were combined, then washed with saturated brine (2×40 mL), dried over anhydrous sodium sulfate, and subjected to suction filtration and concentration to obtain a crude product, which was purified by a automatic column (dichloromethane: methanol=20:1-10:1) to obtain WX037-11. MS: m/z=268.2 [M+1]/2.

Step 12: Synthesis of Compound WX037-12

Compound WX037-11 (1.33 g, 2.49 mmol, 1 eq), palladium carbon (1.33 g, 2.49 mmol, 10% purity, 1 eq) and methanol (40 mL) were added into a 250 mL hydrogenation bottle, followed by purging with hydrogen three times, and then reacted at 25° C. for 2 hours. After the reaction was completed, the reaction solution passed through celite. Then, the filtrate was dried on a rotary evaporator to obtain WX037-12. MS: m/z=223.3[M+1]/2.

Step 13: Synthesis of Compound WX037

Compound WX037-12 and trimethyl orthoformate (9.68 g, 91.22 mmol, 10 mL, 41.80 eq) were added into a 50 mL pre-dried round-bottom flask, and the mixture was reacted at 110° C. for 2 hours under the protection of nitrogen atmosphere. After the reaction was completed, the product precipitated out directly, and was filtered to obtain a crude product. 100 mg of crude product was separated by flash preparative chromatography {column: Agela Durashell C18 150*25 mm 5 μm; mobile phase: [water (10 mM NH$_4$HCO$_3$)-ACN]; B %: 10%-40%, 10.5 min} and purified to obtain WX037. $^1$H NMR (400 MHz, DMSO-d6) δ ppm 0.59-0.72 (m, 2H) 0.71-0.80 (m, 2H) 1.44 (d, J=6.62 Hz, 6H) 1.78-1.88 (m, 1H) 5.29 (dt, J=13.45, 6.73 Hz, 1H) 7.23 (s, 1H) 7.30 (d, J=1.10 Hz, 1H) 7.88 (s, 1H) 7.89-7.92 (m, 1H) 8.02 (s, 1H) 8.17 (br d, J=3.75 Hz, 1H) 8.19-8.25 (m, 1H) 8.60 (s, 1H) 8.90 (s, 1H).

Example 038: WX038

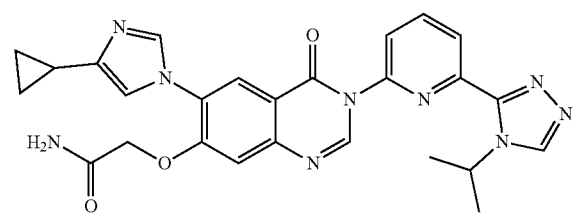 [SMILES: CC(C)n1cnnc1-c1cccc(-n2cnc3cc(OCC(N)=O)c(-n4cnc(C5CC5)c4)cc3c2=O)n1]

Synthetic Route:

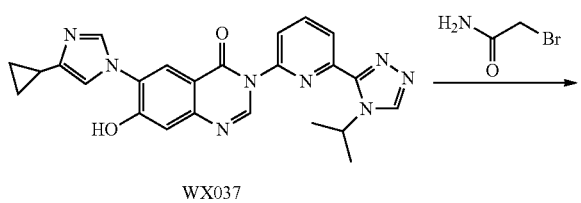

WX037

Synthetic Route:

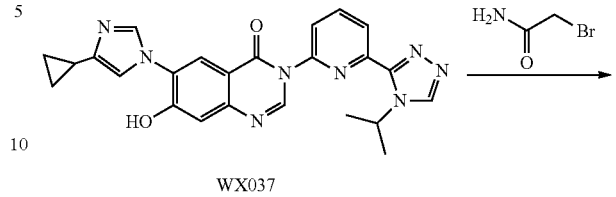

WX037

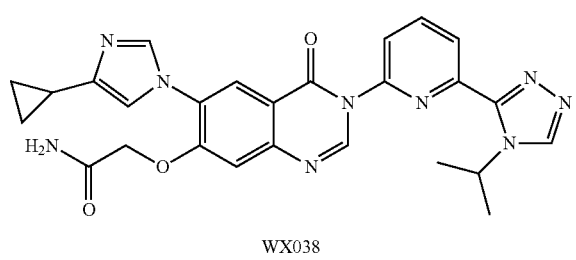

WX038

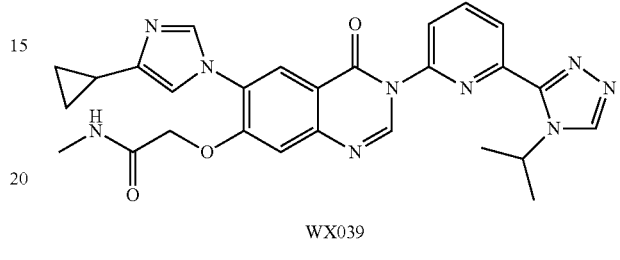

WX039

Step 1. Synthesis of Compound WX038

Compound WX037 (0.08 g, 176.02 μmol, 1 eq), 2-bromoacetamide (36.43 mg, 264.04 μmol, 1.5 eq) and potassium carbonate (48.66 mg, 352.05 μmol, 2 eq) were added into a 40 mL pre-dried reaction bottle, and then N,N-dimethylformamide (5 mL) was added. The system was reacted at 25° C. for 2 hours. After the reaction was completed, dichloromethane (10 mL) and water (10 mL) were added to the reaction solution. The organic and aqueous phases were separated and then the aqueous phase was extracted with dichloromethane (2×10 mL). The organic phases were combined, washed with saturated brine (2×30 mL), dried over anhydrous sodium sulfate, subjected to suction filtration, and then concentrated by a water pump. The concentrated N,N-dimethylformamide solution was separated by flash chromatography {column: Agela Durashell C18 150*25 mm 5 μm; mobile phase: [water (10 mM NH$_4$HCO$_3$)-ACN]; B %: 15%-45%, 10.5 min} to give WX038. $^1$H NMR (400 MHz, DMSO-d6) δ ppm 0.64-0.73 (m, 2H) 0.74-0.82 (m, 2H) 1.45 (d, J=6.62 Hz, 6H) 1.80-1.90 (m, 1H) 4.79 (s, 2H) 5.30 (dt, J=13.34, 6.56 Hz, 1H) 7.30 (s, 1H) 7.40 (s, 1H) 7.87-7.94 (m, 1H) 7.99 (s, 1H) 8.08 (s, 1H) 8.17-8.26 (m, 2H) 8.68 (s, 1H) 8.90 (s, 1H).

Step 1. Synthesis of Compound WX039

Compound WX037 (0.06 g, 132.02 μmol, 1 eq), 2-chloro-N-methyl-acetamide (21.30 mg, 198.03 μmol, 1.5 eq) and potassium carbonate (36.49 mg, 264.04 μmol, 2 eq) were added into a 8 mL pre-dried reaction bottle, and then N,N-dimethylformamide (3 mL) was added. The system was reacted at 25° C. for 2 hours. After the reaction was completed, water (5 mL) and dichloromethane (5 mL) were added to the reaction solution. The organic and aqueous phases were separated and then the aqueous phase was extracted with dichloromethane (3×5 mL). The organic phases were combined, washed with saturated brine (2×10 mL), dried over anhydrous sodium sulfate, and subjected to suction filtration and concentration to obtain a N,N-dimethylformamide solution, which was separated by flash preparative chromatography (column: Waters Xbridge 150*25 mm 5 μm; mobile phase: [water (10 mM NH$_4$HCO$_3$)-ACN]; B %: 15%-40%, 12 min) to obtain WX039. $^1$H NMR (400 MHz, DMSO-d6) δ ppm 0.63-0.73 (m, 2H) 0.72-0.82 (m, 2H) 1.44 (d, J=6.62 Hz, 6H) 1.83 (ddd, J=13.23, 8.27, 4.96 Hz, 1H) 2.64 (d, J=4.63 Hz, 2H) 4.82 (s, 3H) 5.22-5.24 (m, 1H) 7.29 (s, 1H) 7.41 (d, J=1.10 Hz, 1H) 7.89-7.94 (m, 1H) 8.00 (d, J=1.10 Hz, 1H) 8.09 (s, 1H) 8.17-8.27 (m, 2H) 8.68 (s, 1H) 8.91 (s, 1H).

Example 039: WX039

Example 040: WX040

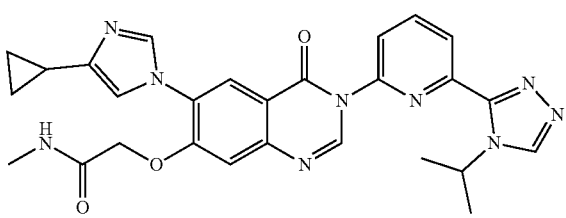 [SMILES: CNC(=O)COc1cc2ncn(-c3cccc(-c4nncn4C(C)C)n3)c(=O)c2cc1-n1cnc(C2CC2)c1]

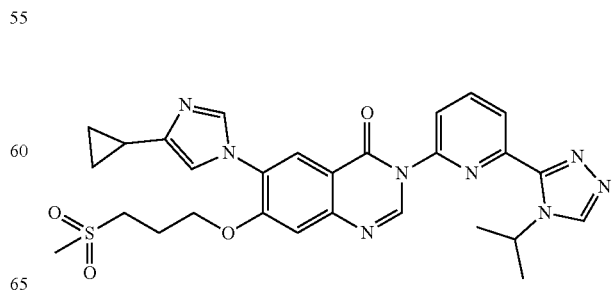

Synthetic Route:

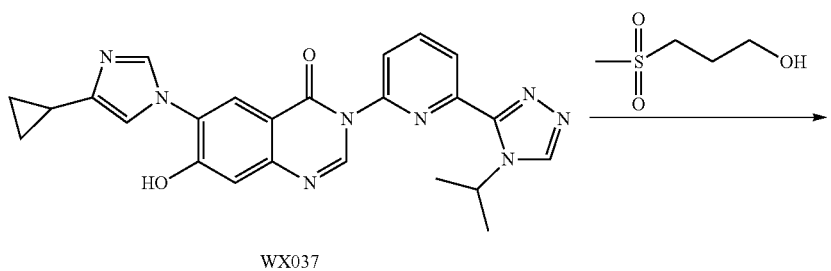

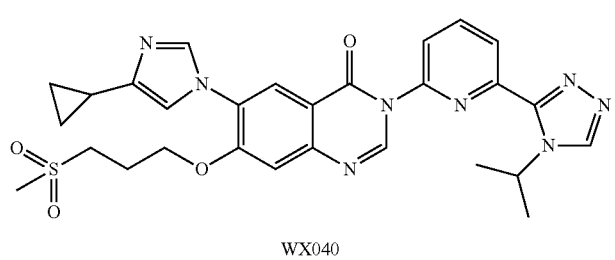

Step 1. Synthesis of Compound WX040

Compound WX037 (0.1 g, 220.03 μmol, 1 eq), 3-methanesulfonic acid-1-propanol (33.45 mg, 242.03 μmol, 1.1 eq), triphenylphosphine (86.57 mg, 330.05 μmol, 1.5 eq) were added into a 8 mL pre-dried reaction bottle, and then anhydrous tetrahydrofuran (7 mL) was added. The bottle was purged with nitrogen for 3 minutes, and then diisopropyl azodicarboxylate (66.74 mg, 330.05 μmol, 64.17 μL, 1.5 eq) was added slowly. The system was reacted at 25° C. for 1 hour. After the reaction was completed, the reaction solution was directly dried on a rotary evaporator to give a crude product, which was separated by flash chromatography (column: Agela Durashell C18 150*25 mm 5 μm; mobile phase: [water (10 mM NH$_4$HCO$_3$)-ACN]; B %: 25%-45%, 10.5 min) to give WX040. 1H NMR (400 MHz, DMSO-d6) δ ppm 0.67-0.77 (m, 2H) 0.78-0.89 (m, 2H) 1.48 (d, J=6.65 Hz, 6H) 1.85-1.94 (m, 1H) 2.19-2.31 (m, 2H) 3.02 (s, 3H) 3.18-3.28 (m, 2H) 4.39 (br t, J=6.27 Hz, 2H) 5.33 (quin, J=6.65 Hz, 1H) 7.35 (d, J=1.13 Hz, 1H) 7.49 (s, 1H) 7.90-7.94 (m, 1H) 7.94-8.00 (m, 1H) 8.11 (s, 1H) 8.24-8.30 (m, 2H) 8.74 (s, 1H) 8.95 (s, 1H).

Example 041: WX041

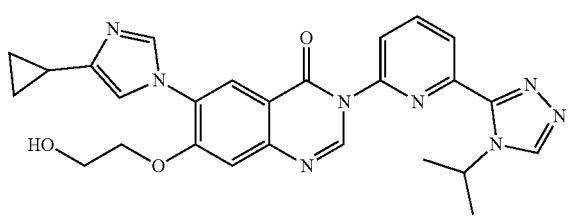 [SMILES: CC(C)n1cnnc1-c1cccc(-n2cnc3cc(OCCO)c(-n4cnc(C5CC5)c4)cc3c2=O)n1]

Synthetic Route:

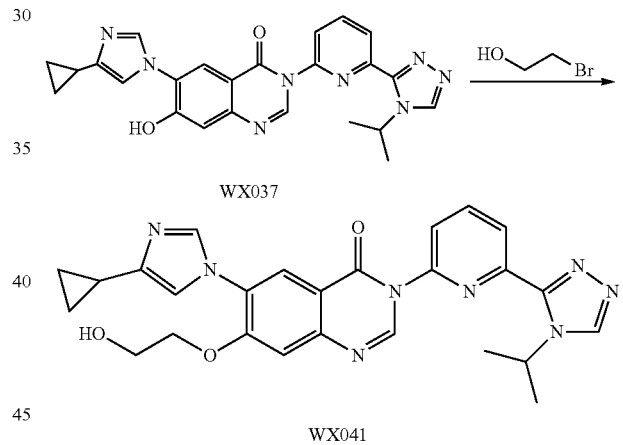

Step 1. Synthesis of Compound WX041

Compound WX037 (100 mg, 220.03 μmol, 1 eq), potassium carbonate (60.82 mg, 440.06 μmol, 2 eq), N,N-dimethylformamide (4 mL) and 2-bromoethanol (54.99 mg, 440.06 μmol, 31.25 μL, 2 eq) were added into a 40 mL pre-dried reaction vial. The reaction solution was stirred at 100° C. for 16 hours. After the reaction was completed, the reaction solution was filtered to give a clear N,N-dimethylformamide solution. The clear solution (5 ml/N,N-dimethylformamide) was separated and purified by preparative HPLC {column: Agela Durashell C18 150*25 mm 5 μm; mobile phase: [water (10 mM NH$_4$HCO$_3$)-ACN]; B %: 20%-50%, 10.5 min} to give WX041. 1H NMR (400 MHz, CHLOROFORM-d) δ=8.58 (s, 1H), 8.45 (d, J=7.3 Hz, 1H), 8.42 (s, 1H), 8.28 (s, 1H), 8.11 (t, J=7.9 Hz, 1H), 7.97 (d, J=7.7 Hz, 1H), 7.91 (s, 1H), 7.35 (s, 1H), 7.06 (s, 1H), 5.60-5.42 (m, 1H), 4.38-4.29 (m, 2H), 4.11-4.01 (m, 2H), 1.98-1.89 (m, 1H), 1.59 (s, 3H), 1.57 (s, 3H), 0.91 (td, J=2.8, 8.4 Hz, 2H), 0.87-0.80 (m, 2H).

Example 042: WX042

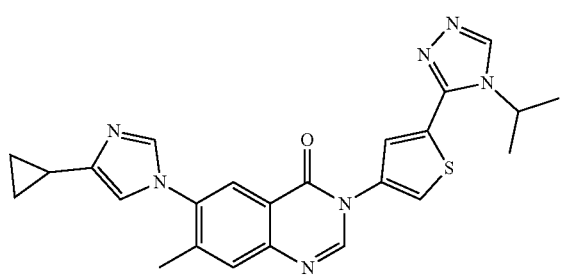 [SMILES: Cc1cc2ncn(-c3csc(-c4nncn4C(C)C)c3)c(=O)c2cc1-n1cnc(C2CC2)c1]

Synthetic Route:

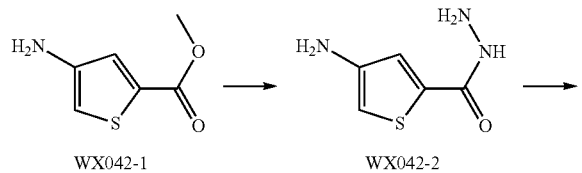

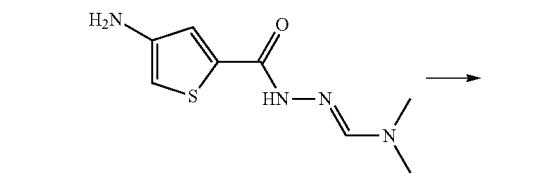

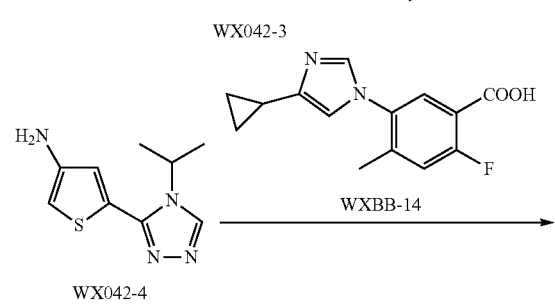

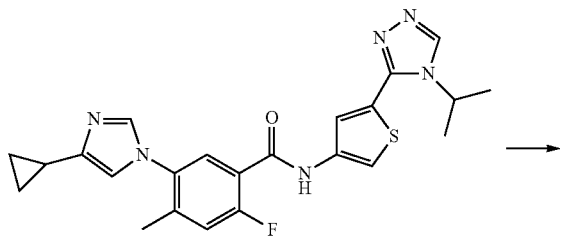

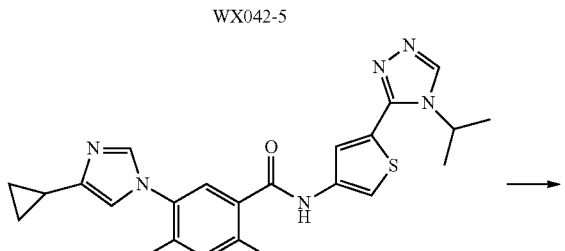

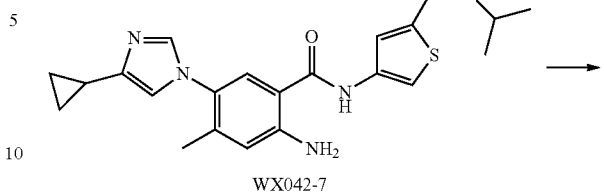

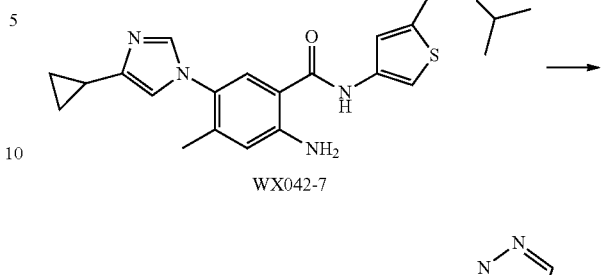

WX042

Step 1. Synthesis of Compound WX042-2

WX042-1 (850.00 mg, 5.41 mmol, 1.00 eq) was dissolved in methanol (10.00 mL), and hydrazine hydrate (1.35 g, 27.05 mmol, 1.31 mL, 5.00 eq) was added. The mixture was stirred at 70° C. for 2 hours. The reaction solution was directly dried on a rotary evaporator to obtain WX042-2. $^1$H NMR (400 MHz, DMSO-d6) δ=9.59 (s, 1H), 7.13 (d, J=1.8 Hz, 1H), 6.18 (d, J=1.8 Hz, 1H), 4.89 (br s, 2H), 4.39 (br s, 2H).

Step 2. Synthesis of Compound WX042-3

WX042-2 (850.00 mg, 5.41 mmol, 1.00 eq) and dimethylformamide dimethyl acetal (1.29 g, 10.82 mmol, 1.43 mL, 2.00 eq) were stirred at 110° C. for 16 hours. The reaction solution was dried on a rotary evaporator under reduced pressure. The crude product was added with ethyl acetate (20 mL), slurried at 15° C. for 0.5 hour, filtered and the filter cake was dried under reduced pressure to obtain WX042-3. $^1$H NMR (400 MHz, DMSO-d$_6$) δ=10.48 (s, 1H), 7.90-7.80 (m, 2H), 7.45 (d, J=1.3 Hz, 1H), 6.82 (d, J=1.3 Hz, 1H), 3.35 (s, 12H).

Step 3. Synthesis of Compound WX042-4

WX042-3 (500.00 mg, 1.87 mmol, 1.00 eq) and isopropyl amine (552.68 mg, 9.35 mmol, 800.99 μL, 5.00 eq) were added to glacial acetic acid (1.00 mL) and acetonitrile (4.00 mL). The mixture was stirred at 85° C. for 16 hours. The reaction solution was dried on a rotary evaporator under reduced pressure, adjusted to pH=8 by adding saturated sodium carbonate solution, and extracted with dichloromethane (20 mL*3). The organic phases were combined, dried over anhydrous sodium sulfate, and filtered. The filtrate was dried on a rotary evaporator under reduced pressure to obtain WX042-4, $^1$H NMR (400 MHz, DMSO-d$_6$) δ=8.79 (s, 1H), 6.99 (d, J=1.5 Hz, 1H), 6.20 (d, J=1.5 Hz, 1H), 4.67-4.55 (m, 1H), 1.47 (s, 3H), 1.45 (s, 3H).

Step 4. Synthesis of Compound WX042-5

WXBB-14 (320.81 mg, 672.17 μmol, 1.00 eq, HCl) (purity: 62.17%) was added to anhydrous dichloromethane (5 mL), and oxalyl chloride (102.38 mg, 806.60 μmol, 70.61 μL, 1.20 eq) and anhydrous N,N-dimethylformamide (2.95 mg, 40.33 μmol, 3.10 μL, 0.06 eq) were added dropwise. The mixture was stirred at 15° C. for 1 hour. The reaction solution was evaporated on a rotary evaporator to become thick, added with anhydrous dichloromethane (5 mL), evaporated on a rotary evaporator to become thick again. This process was repeated three times. Then anhydrous dichloromethane (5 mL) was added, and WX042-4 (140.00 mg, 672.17 μmol, 1.00 eq) and diisopropylethylamine (260.61 mg, 2.02 mmol, 352.18 μL, 3.00 eq) were added successively. The mixture was further stirred at 15° C. for 1 hour. The reaction solution was added with water (20 mL), and extracted with dichloromethane (20 mL*3). The organic phases were combined, washed with saturated brine (20 mL), dried over anhydrous sodium sulfate, and filtered. The filtrate was dried on a rotary evaporator under reduced pressure. The crude product was purified by column (methanol/dichloromethane=0~2%~4%~8%) to obtain WX042-5, ¹H NMR (400 MHz, CHLOROFORM-d) δ=8.70 (br d, J=16.1 Hz, 1H), 8.25 (s, 1H), 7.99 (d, J=7.3 Hz, 1H), 7.78 (d, J=1.5 Hz, 1H), 7.56 (d, J=1.5 Hz, 1H), 7.38 (d, J=1.3 Hz, 1H), 7.12 (d, J=12.3 Hz, 1H), 6.72 (d, J=1.0 Hz, 1H), 4.68 (td, J=6.7, 13.4 Hz, 1H), 2.22 (s, 3H), 1.53-1.52 (m, 3H), 1.50-1.49 (m, 3H), 0.88-0.80 (m, 2H), 0.78-0.72 (m, 2H).

Step 5. Synthesis of Compound WX042-6

WX042-5 (200.00 mg, 443.92 μmol, 1.00 eq), p-methoxybenzylamine (609.00 mg, 4.44 mmol, 574.53 μL, 10.00 eq) and potassium carbonate (184.00 mg, 1.33 mmol, 3.00 eq) were added to acetonitrile (1.00 mL). The mixture was stirred at 100° C. for 16 hours. The reaction solution was added with water (20 mL), and extracted with dichloromethane (20 mL*3). The organic phases were combined, washed with saturated brine (20 mL), dried over anhydrous sodium sulfate, and filtered. The filtrate was dried on a rotary evaporator under reduced pressure. The crude product was added with 25 mL of petroleum ether/ethyl acetate (5/1), and slurried at 15° C. for 0.5 hour. The supernatant liquid was filtered off, and the lower layer of oil was dried on a rotary evaporator under reduced pressure to give WX042-6.

Step 6. Synthesis of Compound WX042-7

WX042-6 (400.00 mg, 279.37 μmol, 1.00 eq) (purity: 39.65%) was added to trifluoroacetic acid (3.00 mL). The mixture was stirred at 15° C. for 16 hours. LCMS showed the reaction was completed. The reaction solution was dried on a rotary evaporator under reduced pressure, adjusted to pH=7-8 with saturated sodium carbonate solution, extracted with dichloromethane (20 mL*2), dried over anhydrous magnesium sulfate, and filtered. The filtrate was dried on a rotary evaporator under reduced pressure to obtain WX042-7.

Step 7. Synthesis of Compound WX042

WX042-7 (180.00 mg, 273.45 μmol, 1.00 eq) (purity: 67.99%) and trimethyl orthoformate (2.00 mL) were stirred at 110° C. for 16 hours. The reaction solution was dried on a rotary evaporator under reduced pressure. The crude product was separated and purified by flash preparative HPLC (column: Xtimate C18 150*25 mm*5 um; mobile phase: [water (0.225% FA)-ACN]; B %: 16%-26%, 12 min) to obtain WX042. ¹H NMR (400 MHz, DMSO-d₆) δ=8.90 (s, 1H), 8.57 (s, 1H), 8.16-8.11 (m, 2H), 8.02 (s, 1H), 7.92 (s, 1H), 7.85-7.80 (m, 2H), 7.32 (d, J=1.0 Hz, 1H), 4.79-4.67 (m, 1H), 2.37 (s, 3H), 1.93-1.85 (m, 1H), 1.50 (s, 3H), 1.48 (s, 3H), 0.88-0.82 (m, 2H), 0.77-0.71 (m, 2H).

Example 043: WX043

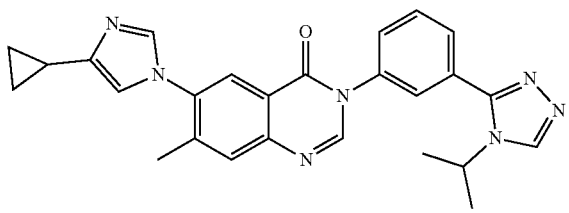 [SMILES: Cc1cc2ncn(-c3cccc(-c4nncn4C(C)C)c3)c(=O)c2cc1-n1cnc(C2CC2)c1]

Synthetic Route:

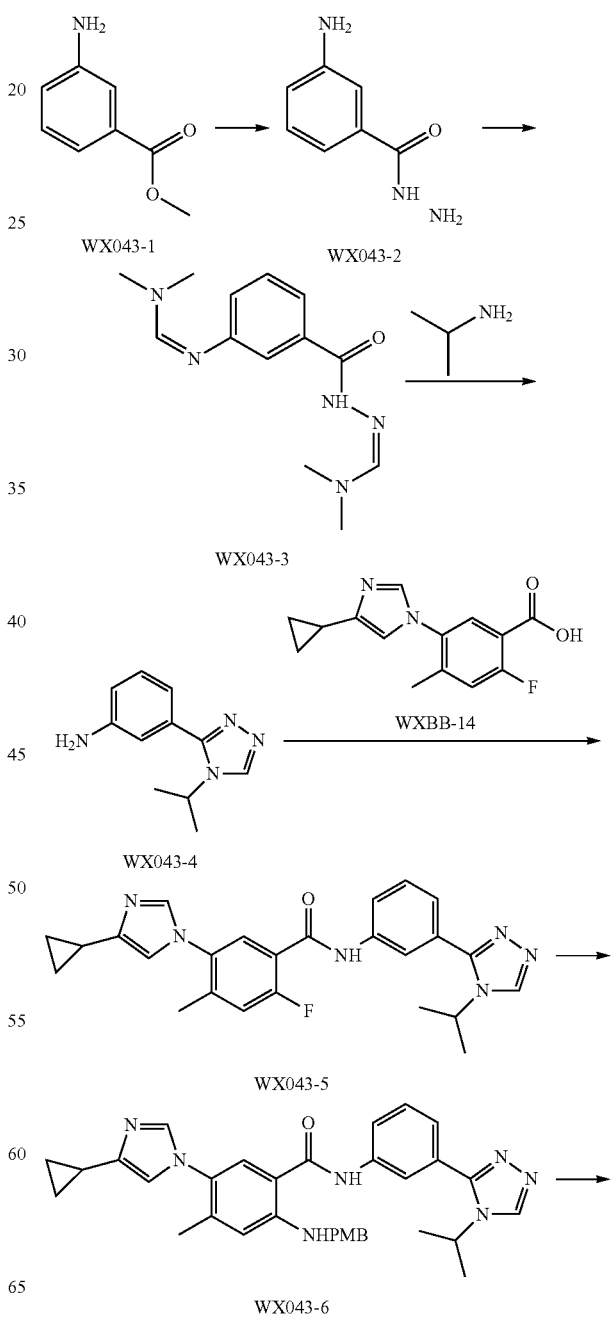

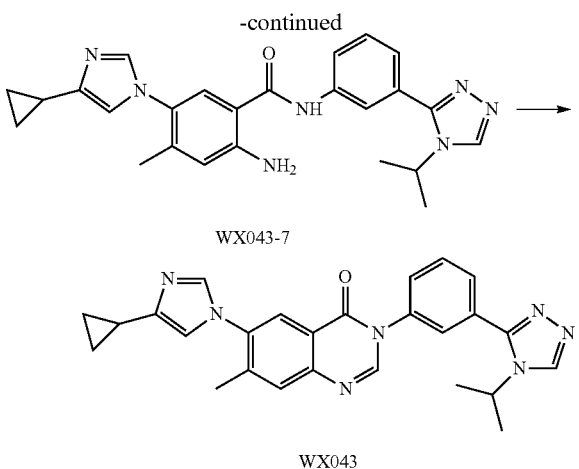

WX043-7

WX043

Step 1: Synthesis of Compound WX043-2

Compound WX043-1 (4.50 g, 29.77 mmol, 1.00 eq) was dissolved in methanol (40.00 mL), and hydrazine hydrate (3.51 g, 59.54 mmol, 3.40 mL, 85% purity, 2.00 eq) was added. The mixture was reacted at 80° C. for 3 hours, and added with hydrazine hydrate (1.75 g, 29.77 mmol, 1.70 mL, 85% purity, 1.00 eq). The mixture was reacted at 80° C. for 16 hours. The reaction solution was directly dried on a rotary evaporator under reduced pressure to obtain compound WX043-2. $^1$H NMR (400 MHz, DMSO-d6) δ ppm 5.22 (s, 2H) 6.66 (dd, J=7.78, 1.76 Hz, 1H) 6.92 (d, J=7.53 Hz, 1H) 7.00-7.04 (m, 1H) 7.04-7.07 (m, 1H) 9.52 (br s, 1H).

Step 2: Synthesis of Compound WX043-3

Compound WX043-2 (9.00 g, 59.54 mmol, 1.00 eq) (crude) was dissolved in N,N-dimethylformamide dimethyl acetal (90.00 mL). The mixture was reacted at 110° C. for 16 hours. The reaction solution was cooled to room temperature and the solvent was dried on a rotary evaporator. Then it was slurried with ethyl acetate (100 mL) at 20° C. for 0.5 hour, and filtered. The filter cake was dried under reduced pressure to obtain WX043-3. $^1$H NMR (400 MHz, DMSO-d6) δ ppm 2.83 (s, 6H) 2.90-3.07 (m, 6H) 7.02 (d, J=8.78 Hz, 1H) 7.26 (t, J=7.65 Hz, 1H) 7.31 (d, J=1.76 Hz, 1H) 7.32-7.36 (m, 1H) 7.77 (s, 1H) 7.90 (s, 1H) 10.48 (s, 1H).

Step 3: Synthesis of Compound WX043-4

Compound WX043-3 (3.00 g, 11.48 mmol, 1.00 eq) was dissolved in a mixture of acetonitrile (24.00 mL) and acetic acid (6.00 mL) (volume ratio of 4:1, 30 mL), and isopropyl amine (3.39 g, 57.40 mmol, 4.91 mL, 5.00 eq) was added. The mixture was stirred at 80-90° C. for 16 hours. Then it was evaporated on a rotary evaporator to remove the solvent, adjusted to pH=8 with saturated sodium bicarbonate (50 mL), and extracted with dichloromethane (30 mL*3). The organic phases were combined, washed with saturated sodium chloride (20 mL), dried over anhydrous sodium sulfate, and filtered. The filtrate was dried on a rotary evaporator under reduced pressure to obtain WX043-4. $^1$H NMR (400 MHz, DMSO-d6) δ ppm 1.39 (s, 3H) 1.41 (s, 3H) 4.41 (dt, J=13.36, 6.74 Hz, 1H) 5.32-5.39 (m, 2H) 6.62-6.66 (m, 1H) 6.68-6.73 (m, 1H) 6.74 (t, J=1.76 Hz, 1H) 7.17 (t, J=7.78 Hz, 1H) 8.78 (s, 1H).

Step 4: Synthesis of Compound WX043-5

Compound WXBB-14 (800.00 mg, 1.68 mmol, 1.00 eq, HCl) (purity 62.17%) and compound WX043-4 (386.00 mg, 1.91 mmol, 1.14 eq) were dissolved in pyridine (8.00 mL), and 2-(7-azabenzotriazol)-tetramethyluronium hexafluorophosphate (637.34 mg, 1.68 mmol, 1.00 eq) was added. The mixture was stirred at 20° C. for 16 hours, and then dried on a rotary evaporator to remove the solvent. Afterwards, it was added with water (10 mL) and extracted with dichloromethane (10 mL*3). The organic phases were combined, washed with saturated sodium chloride (20 mL), dried over anhydrous sodium sulfate, and filtered. The filtrate was dried on a rotary evaporator under reduced pressure. The residue was purified by column (methanol/dichloromethane=0~10%) to obtain a crude product. The obtained crude product was dissolved in dichloromethane (5 mL), adjusted to pH=8 by adding saturated sodium bicarbonate, and extracted with dichloromethane (10 mL*3). The organic phases were combined, washed with saturated sodium chloride (10 mL), dried over anhydrous sodium sulfate, and filtered. The filtrate was dried on a rotary evaporator under reduced pressure to obtain WX043-5. $^1$H NMR (400 MHz, DMSO-d$_6$) δ ppm 0.68-0.72 (m, 2H) 0.78-0.83 (m, 2H) 1.43 (s, 3H) 1.45 (s, 3H) 1.81-1.89 (m, 1H) 2.25 (s, 3H) 4.46 (dt, J=13.36, 6.74 Hz, 1H) 7.19 (d, J=1.00 Hz, 1H) 7.36 (d, J=7.78 Hz, 1H) 7.48 (d, J=11.04 Hz, 1H) 7.56 (t, J=7.91 Hz, 1H) 7.64 (d, J=6.52 Hz, 1H) 7.70 (d, J=1.00 Hz, 1H) 7.87 (br d, J=8.03 Hz, 1H) 8.00 (s, 1H) 8.87 (s, 1H) 10.64 (br s, 1H).

Step 5: Synthesis of Compound WX043-6

Compound WX043-5 (500.00 mg, 1.12 mmol, 1.00 eq) was dissolved in acetonitrile (3.00 mL), and p-methoxybenzylamine (1.54 g, 11.25 mmol, 1.46 mL, 10.00 eq) and potassium carbonate (310.00 mg, 2.24 mmol, 2.00 eq) were added. The mixture was stirred at 100° C. for 16 hours. The reaction solution was added with water (10 mL), and extracted with dichloromethane (10 mL*3). The organic phases were combined, washed with saturated sodium chloride (20 mL), dried over anhydrous sodium sulfate, and filtered. The filtrate was dried on a rotary evaporator under reduced pressure. The crude product was purified by column (methanol/dichloromethane=0~6%). A mixture of petroleum ether/ethyl acetate (5/1, 5 mL) was poured into the obtained product, stirred for 5 minutes, and left to stand. The supernatant was poured, and the underlayer oil matter was retained and dried on a ratory evaporator to obtain WX043-6. MS: m/z=281.6 [M+1]/2.

Step 6: Synthesis of Compound WX043-7

Compound WX043-6 (500.00 mg, 717.01 μmol, 1.00 eq) (purity 80.546%) was dissolved in trifluoroacetic acid (5.00 mL). The mixture was stirred at 20° C. for 1 hour. LCMS showed that only 57.974% of the target product was formed, and 31.046% of the starting material remained. The mixture was further stirred at 20° C. for 1 hour. The reaction solution was adjusted to pH=8 by adding slowly saturated sodium carbonate (20 mL), and extracted with dichloromethane (20 mL*3). The organic phases were combined, washed with saturated sodium chloride 1 (20 mL), dried over anhydrous sodium sulfate, and filtered. The filtrate was dried on a rotary evaporator under reduced pressure to obtain WX043-7. MS: m/z=442.2 [M+1].

Step 7. Synthesis of Compound WX043

Compound WX043-7 (250.00 mg, 424.69 μmol, 1.00 eq) (purity 75.006%) was dissolved in trimethyl orthoformate (3.00 mL). The mixture was stirred at 110° C. for 1 hour and then cooled to room temperature. Afterwards, the reaction solution was directly dried on a rotary evaporator. The crude product was separated and purified by flash preparative chromatography (column: Xtimate C18 150*25 mm*5 μm; mobile phase: [water (0.225% FA)-ACN]; B %: 15%-25%, 12 min) to obtain WX043. $^1$H NMR (400 MHz, DMSO-d6) δ ppm 0.73 (br d, J=5.02 Hz, 2H) 1.43 (s, 3H) 1.45 (s, 3H)

1.87 (s, 1H) 2.37 (s, 3H) 4.52 (s, 1H) 7.26 (s, 1H) 7.77 (s, 4H) 7.83 (s, 2H) 7.98 (s, 1H) 8.16 (s, 1H) 8.51 (s, 1H) 8.91 (s, 1H).

Example 044: WX044

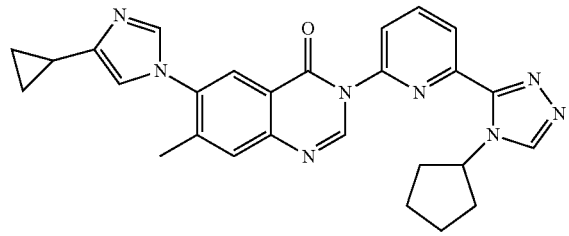 [SMILES: Cc1cc2ncn(-c3cccc(-c4nncn4C4CCCC4)n3)c(=O)c2cc1-n1cnc(C2CC2)c1]

Synthetic Route:

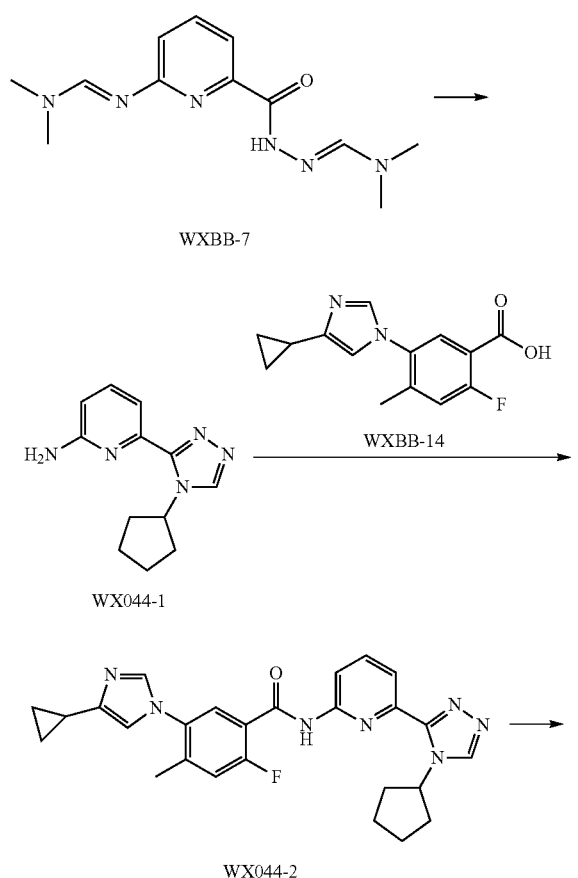

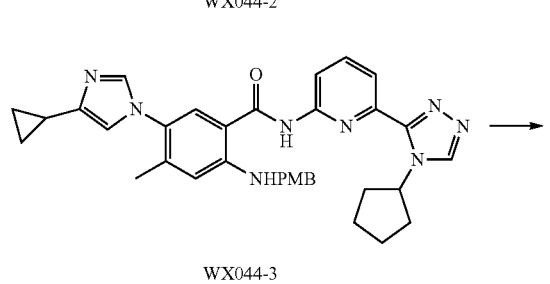

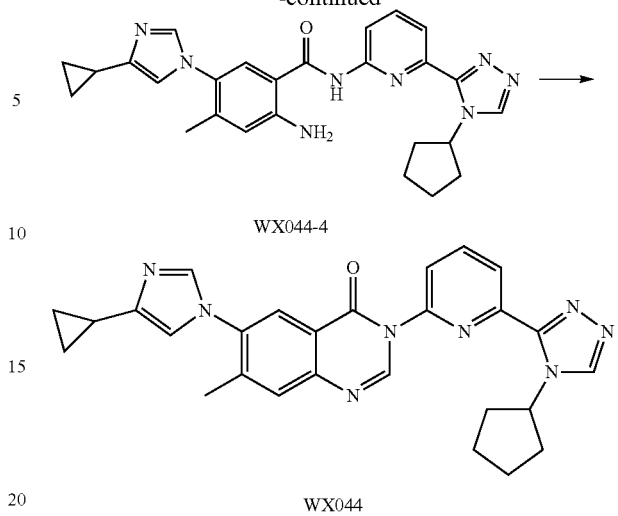

Step 1. Synthesis of Compound WX044-1

WXBB-7 (2.46 g, 9.40 mmol, 1.00 eq) and cyclopentylamine (4.00 g, 46.98 mmol, 4.65 mL, 5.00 eq) were added to a mixture of acetonitrile (40.00 mL) and glacial acetic acid (10.00 mL). The system was stirred at 80° C. for 20 hours. The reaction solution was concentrated under reduced pressure, adjusted to pH 10 with sodium hydroxide (1M, 100 mL), and extracted with ethyl acetate (100 mL*2). The organic phase was dried over anhydrous sodium sulfate and filtered. The filtrate was dried on a rotary evaporator under reduced pressure to obtain a crude product, which was purified by column (0~10% methanol/dichloromethane) to obtain product WX044-1, $^1$H NMR (400 MHz, CHLOROFORM-d) δ ppm 1.76-1.87 (m, 6H) 2.22-2.27 (m, 2H) 4.56 (br s, 2H) 5.53-5.65 (m, 1H) 6.55-6.59 (m, 1H) 7.53-7.60 (m, 2H) 8.29 (s, 1H).

Step 2. Synthesis of Compound WX044-2

WXBB-14 (1.00 g, 2.10 mmol, 1.00 eq, HCl) (purity 62.17%) was dissolved in anhydrous dichloromethane (10 mL) to form a suspension, and anhydrous N,N-dimethylformamide (10.00 mg, 136.82 μmol, 10.53 μL, 0.07 eq) was added, and oxalyl chloride (530.00 mg, 4.18 mmol, 365.52 μL, 1.99 eq) was added under N2 condition. The system was stirred at 20° C. for 1 hour. The reaction solution was then evaporated on a rotary evaporator under reduced pressure to become thick, added with anhydrous dichloromethane (10 mL), and evaporated on a rotary evaporator to become thick again. This process was repeated three times, then added successively with anhydrous dichloromethane (10 mL), WX044-1 (480.00 mg, 2.09 mmol, 1.00 eq), and diisopropylethylamine (600.00 mg, 4.64 mmol, 810.81 μL, 2.21 eq). The system was stirred at 20° C. for 1 hour. The reaction solution was added with water (25 mL), and extracted with dichloromethane (25 ml*2). The organic phase was washed with water (50 mL) and saturated brine (50 mL), dried over anhydrous sodium sulfate, and filtered. The filtrate was dried on a rotary evaporator under reduced pressure to obtain a crude product. The crude product was dissolved in dichloromethane (25 mL), and hydrochloric acid (2M, 25 mL) was added. Then the obtained solution was layered. The aqueous phase was retained and adjusted to pH 9-10 with sodium hydroxide solution (2M) and extracted with dichloromethane (25 mL*2). The organic phase was washed with water (50 mL) and saturated brine (50 mL), dried over anhydrous magnesium sulfate, and filtered. The filtrate was dried on a rotary evaporator under reduced pressure to obtain WX044-2.

Step 3. Synthesis of Compound WX044-3

WX044-2 (600.00 mg, 1.20 mmol, 1.00 eq) (purity 94.09%) was dissolved in acetonitrile (2.00 mL), and p-methoxybenzylamine (1.65 g, 12.00 mmol, 1.55 mL, 10.00 eq) and potassium carbonate (350.00 mg, 2.53 mmol, 2.11 eq) were added. The system was stirred at 100° C. for 16 hours. The reaction solution was cooled to room temperature, diluted with water (30 mL), and extracted with dichloromethane (30 mL*2). The organic phase was washed with water (50 mL) and saturated brine (50 mL), dried over anhydrous magnesium sulfate, and filtered. The filtrate was dried on a rotary evaporator under reduced pressure to obtain a crude product, which was purified by a column (0~6% methanol/dichloromethane), and then separated and purified with a prep-TLC (dichloromethane/methanol=10/1) plate to give product WX044-3, $^1$H NMR (400 MHz, CHLOROFORM-d) δ ppm 0.75-0.83 (m, 2H) 0.83-0.89 (m, 2H) 1.68-1.75 (m, 2H) 1.80-1.87 (m, 4H) 2.11 (s, 3H) 2.14-2.24 (m, 2H) 3.49 (s, 1H) 3.82 (s, 3H) 4.41 (d, J=5.52 Hz, 2H) 5.39-5.49 (m, 1H) 6.63 (s, 1H) 6.73 (d, J=1.00 Hz, 1H) 6.91 (d, J=8.53 Hz, 2H) 7.31 (d, J=8.53 Hz, 2H) 7.38 (d, J=1.00 Hz, 1H) 7.41 (s, 1H) 7.83-7.91 (m, 1H) 7.91-7.96 (m, 1H) 8.16 (br t, J=5.27 Hz, 1H) 8.22 (d, J=7.53 Hz, 1H) 8.29 (s, 1H) 8.40 (s, 1H).

Step 4. Synthesis of Compound WX044-4

WX044-3 (250.00 mg, 399.86 μmol, 1.00 eq) (purity 94.16%) was dissolved in trifluoroacetic acid (3.00 mL). The system was stirred at 20° C. for 1 hour. The reaction solution was added dropwise with saturated aqueous sodium bicarbonate (25 mL) with stirring, and extracted with dichloromethane (25 mL*2). The organic phase was washed with water (50 mL) and saturated brine (50 mL), dried over anhydrous sodium sulfate, and filtered. The filtrate was dried on a rotary evaporator under reduced pressure to obtain WX044-4.

Step 5. Synthesis of Compound WX044

WX044-4 (180.00 mg, 384.16 μmol, 1.00 eq) was dissolved in trimethyl orthoformate (2.00 mL). The system was stirred at 110° C. for 1 hour. LCMS showed the reaction was completed. The reaction solution was dried on a rotary evaporator under reduced pressure to obtain a crude product, which was separated and purified by prep-HPLC column: Waters Xbridge 150*25 mm 5 μm; mobile phase: [water (10 mM NH$_4$HCO$_3$)-ACN]; B %: 26%-46%, 8 min to obtain product WX044, $^1$H NMR (400 MHz, CHLOROFORM-d) δ ppm 0.83-0.89 (m, 2H) 0.89-0.96 (m, 2H) 1.77 (br s, 2H) 1.85-1.98 (m, 5H) 2.26 (br d, J=7.03 Hz, 2H) 2.42 (s, 3H) 5.52 (br d, J=5.02 Hz, 1H) 6.87 (d, J=1.00 Hz, 1H) 7.52 (d, J=1.25 Hz, 1H) 7.75 (s, 1H) 7.96 (d, J=7.53 Hz, 1H) 8.10 (t, J=7.91 Hz, 1H) 8.24 (s, 1H) 8.36 (s, 1H) 8.43 (d, J=7.78 Hz, 1H) 8.61 (s, 1H).

Example 045: WX045

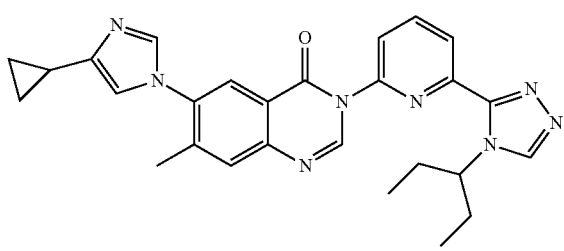 [SMILES: CCC(CC)n1cnnc1-c1cccc(-n2cnc3cc(C)c(-n4cnc(C5CC5)c4)cc3c2=O)n1]

Synthetic Route:

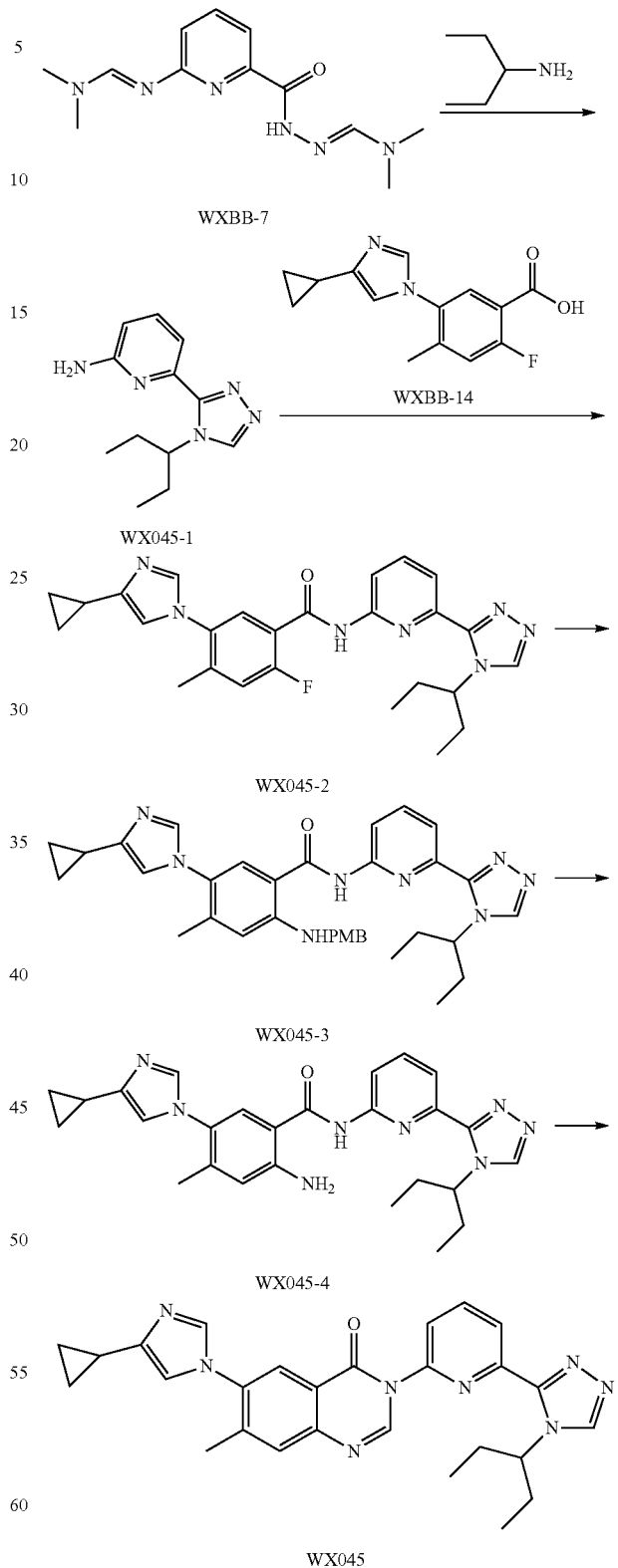

Step 1. Synthesis of Compound WX045-1

WXBB-7 (2.00 g, 7.62 mmol, 1.00 eq) was dissolved in a mixture of acetonitrile (8.00 mL) and glacial acetic acid (2.00 mL), and 3-pentylamine (2.99 g, 34.29 mmol, 3.99 mL, 4.50 eq) was added. The system was stirred at 80° C. for 18 hours. The reaction solution was dried on a rotary evaporator under reduced pressure, diluted with water (50 mL), adjusted to pH 8-9 with saturated sodium bicarbonate solution (100 mL), and extracted with ethyl acetate (100 mL*2). The organic phase was dried over anhydrous sodium sulfate and filtered. The filtrate was dried on a rotary evaporator under reduced pressure to obtain a crude product. To the crude product was added a mixture of PE/ethyl acetate=1/1 (20 mL), stirred for 10 min at room temperature and filtered. The filter cake was dried to give WX045-1. $^1$H NMR (400 MHz, CHLOROFORM-d) δ ppm 0.85 (t, J=7.40 Hz, 6H) 1.76-1.92 (m, 4H) 4.51 (br s, 2H) 5.24-5.38 (m, 1H) 6.57 (dd, J=7.15, 1.88 Hz, 1H) 7.52-7.62 (m, 2H) 8.24 (s, 1H).

Step 2. Synthesis of Compound WX045-2

WXBB-14 (1.00 g, 2.10 mmol, 1.00 eq, HCl) (purity 62.17%) was dissolved in anhydrous dichloromethane (10 mL) to form a suspension, then anhydrous N,N-dimethylformamide (10.00 mg, 136.82 μmol, 10.53 μL, 0.07 eq) was added, and oxalyl chloride (530.00 mg, 4.18 mmol, 365.52 μL, 1.99 eq) was added under N2 condition. The system was stirred at 20° C. for 1 hour. The reaction solution was then evaporated on a rotary evaporator under reduced pressure to become thick, added with anhydrous dichloromethane (10 mL), and evaporated on a rotary evaporator to become thick again. This process was repeated three times. Then anhydrous dichloromethane (10 mL), WX045-1 (480.00 mg, 2.09 mmol, 1.00 eq), and diisopropylethylamine (600.00 mg, 4.64 mmol, 810.81 μL, 2.21 eq) were added successively. The system was stirred at 20° C. for 1 hour. The reaction solution was added with water (25 mL), and extracted with dichloromethane (25 ml*2). The organic phase was washed with water (50 mL) and saturated brine (50 mL), dried over anhydrous sodium sulfate, and filtered. The filtrate was dried on a rotary evaporator under reduced pressure to obtain a crude product. The crude product was dissolved in dichloromethane (25 mL), and hydrochloric acid (2M, 25 mL) was added. Then the obtained solution was layered. The aqueous phase was retained and adjusted to pH 9-10 with sodium hydroxide solution (2M) and extracted with dichloromethane (25 mL*2). The organic phase was washed with water (50 mL) and saturated brine (50 mL), dried over anhydrous magnesium sulfate, and filtered. The filtrate was dried on a rotary evaporator under reduced pressure to obtain WX045-2.

Step 3. Synthesis of Compound WX045-3

WX045-2 (600.00 mg, 1.01 mmol, 1.00 eq) (purity 79.71%) was dissolved in acetonitrile (2.00 mL), and p-methoxybenzylamine (1.39 g, 10.10 mmol, 1.31 mL, 10.00 eq) and potassium carbonate (300.00 mg, 2.17 mmol, 2.15 eq) were added. The system was stirred at 100° C. for 16 hours. The reaction solution was cooled to room temperature, diluted with water (30 mL), and extracted with dichloromethane (30 mL*2). The organic phase was washed with water (50 mL) and saturated brine (50 mL), dried over anhydrous magnesium sulfate, and filtered. The filtrate was dried on a rotary evaporator under reduced pressure to obtain a crude product. The crude product was first purified by a column (0~6% methanol/dichloromethane), and then separated and purified with a prep-TLC (dichloromethane/methanol=10/1) plate to give product WX045-3. $^1$H NMR (400 MHz, CHLOROFORM-d) δ ppm 0.81-0.88 (m, 10H) 1.85 (s, 1H) 1.87-1.94 (m, 4H) 2.11 (s, 3H) 3.82 (s, 3H) 4.41 (d, J=5.52 Hz, 2H) 5.01-5.08 (m, 1H) 6.63 (s, 1H) 6.73 (d, J=1.00 Hz, 1H) 6.88-6.94 (m, 3H) 7.31 (d, J=8.53 Hz, 2H) 7.36-7.40 (m, 2H) 7.85-7.91 (m, 1H) 7.96-8.01 (m, 1H) 8.17 (s, 1H) 8.23 (d, J=8.53 Hz, 1H) 8.28 (s, 1H).

Step 4. Synthesis of Compound WX045-4

WX045-3 (300.00 mg, 450.38 μmol, 1.00 eq) (purity 88.683%) was dissolved in trifluoroacetic acid (3.00 mL). The system was stirred at 20° C. for 1 hour. The reaction solution was added dropwise with saturated aqueous sodium bicarbonate (25 mL) with stirring, and extracted with dichloromethane (25 mL*2). The organic phase was washed with water (50 mL) and saturated brine (50 mL), dried over anhydrous sodium sulfate, and filtered. The filtrate was dried on a rotary evaporator under reduced pressure to obtain a crude product WX045-4.

Step 5. Synthesis of Compound WX045

WX045-4 (220.00 mg, 406.39 μmol, 1.00 eq) (purity 86.924%) was dissolved in trimethyl orthoformate (2.00 mL). The system was stirred at 110° C. for 1 hour. The reaction solution was dried on a rotary evaporator under reduced pressure to obtain a crude product, which was separated and purified with prep-HPLC (Waters Xbridge 150*25 mm 5 μm; mobile phase: [water (10 mM NH$_4$HCO$_3$)-ACl]; B %: 25%-45%, 8 min) to obtain WX045. $^1$H NMR (400 MHz, CHLOROFORM-d) δ ppm 0.81-0.87 (m, 8H) 0.89-0.93 (m, 2H) 1.83-1.94 (m, 5H) 2.41 (s, 3H) 5.19 (br d, J=5.27 Hz, 1H) 6.87 (s, 1H) 7.51 (s, 1H) 7.75 (s, 1H) 7.95 (br d, J=7.78 Hz, 1H) 8.10 (br t, J=7.91 Hz, 1H) 8.23 (s, 1H) 8.34 (s, 1H) 8.43 (br d, J=7.78 Hz, 1H) 8.57 (s, 1H).

Example 046: WX046

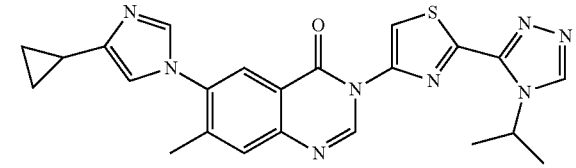 [SMILES: Cc1cc2ncn(-c3csc(-c4nncn4C(C)C)n3)c(=O)c2cc1-n1cnc(C2CC2)c1]

Synthetic Route:

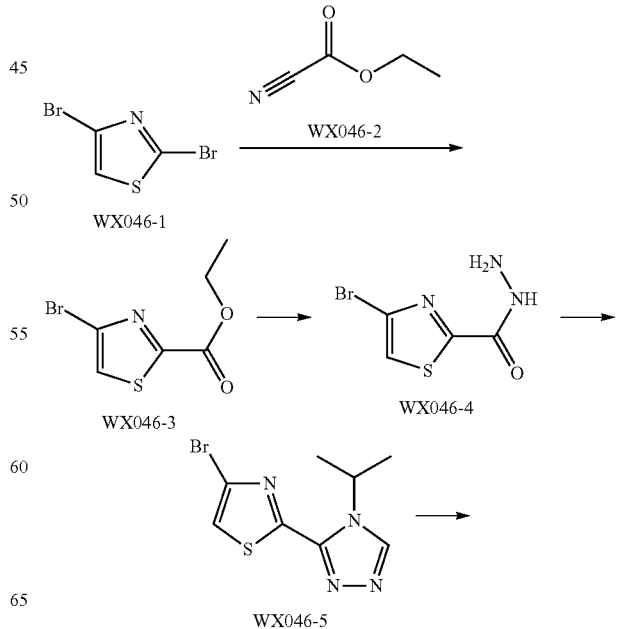

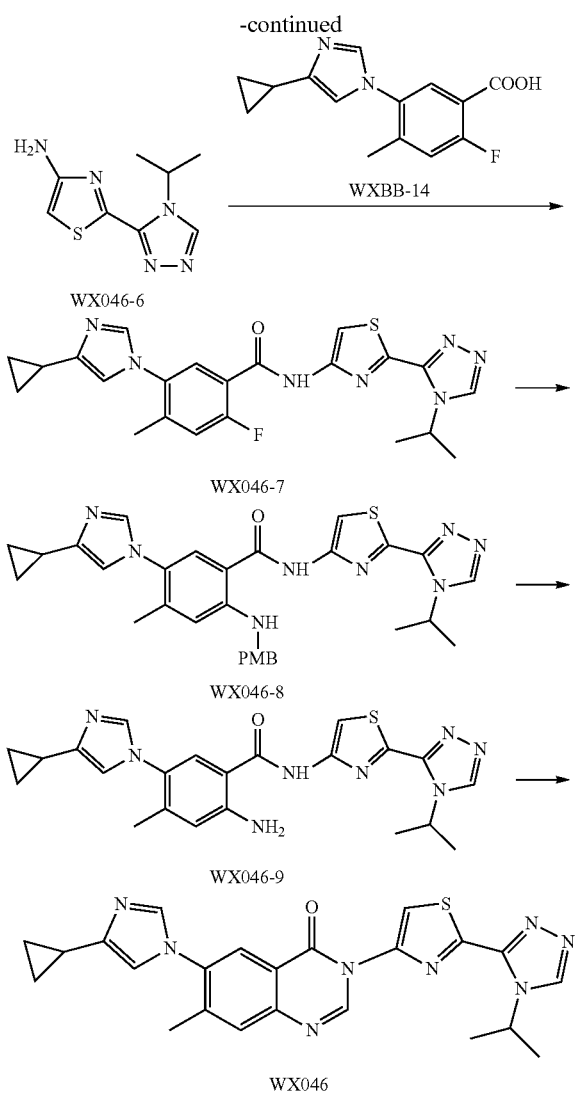

Step 1. Synthesis of Compound WX046-3

WX046-1 (10.00 g, 41.17 mmol, 1.00 eq) was added to anhydrous tetrahydrofuran (100.00 mL), then isopropyl magnesium chloride (2M, 22.64 mL, 1.10 eq) was added dropwise at 0° C. under the protection of nitrogen atmosphere. The mixture was stirred at 0° C. for 0.5 hour, and WX046-2 (10.20 g, 102.92 mmol, 10.10 mL, 2.50 eq) was added. The mixture was stirred at 15° C. for 1 hour. The reaction solution was quenched with saturated aqueous ammonium chloride (150 mL), and extracted with dichloromethane (150 mL*2). The organic phase was dried over anhydrous sodium sulfate and filtered. The filtrate was dried on a rotary evaporator under reduced pressure. The crude product was purified by column (ethyl acetate/petroleum ether=0~5%~10%~20%) to obtain WX046-3.

Step 2. Synthesis of Compound WX046-4

WX046-3 (1.70 g, 7.20 mmol, 1.00 eq) was dissolved in methanol (17.00 mL), and hydrazine hydrate (2.12 g, 36.00 mmol, 2.06 mL, 5.00 eq) (purity: 85%) was added. The mixture was stirred at 70° C. for 2 hours. After the reaction was completed, the reaction solution was added with methanol/ethyl acetate (1/1, 10 ml), slurried at 15° C. for 10 min and filtered. The filter cake was dried under reduced pressure to obtain WX046-4, $^1$H NMR (400 MHz, DMSO-d6) δ=8.15 (s, 1H).

Step 3. Synthesis of Compound WX046-5

WX046-4 (550.00 mg, 2.48 mmol, 1.00 eq), dimethylformamide dimethyl acetal (1.18 g, 9.93 mmol, 1.31 mL, 4.01 eq), isopropyl amine (364.55 mg, 6.17 mmol, 528.33 μL, 2.49 eq), and glacial acetic acid (148.73 mg, 2.48 mmol, 141.65 μL, 1.00 eq) were placed in anhydrous toluene (5.00 mL). The mixture was stirred at 140° C. for 1 hour under microwave condition. After the reaction was completed, the reaction solution was dried on a rotary evaporator under reduced pressure, adjusted to pH=7-8 with saturated sodium bicarbonate, and extracted with dichloromethane (20 mL*2). The organic phase was dried over anhydrous sodium sulfate and filtered. The filtrate was dried on a rotary evaporator under reduced pressure to obtain WX046-5. $^1$H NMR (400 MHz, CHLOROFORM-d) δ=8.29 (s, 1H), 7.29 (s, 1H), 5.51 (spt, J=6.7 Hz, 1H), 1.52 (s, 3H), 1.50 (s, 3H).

Step 4. Synthesis of Compound WX046-6

WX046-5 (800.00 mg, 2.73 mmol, 1.00 eq) (purity: 93.19%), acetylacetone (112.00 mg, 1.12 mmol, 114.29 μL, 0.41 eq), aqueous ammonia (682.50 mg, 5.45 mmol, 750.00 μL, 28% purity, 2.00 eq), caesium carbonate (1.78 g, 5.46 mmol, 2.00 eq) and bis[(Z)-1-methyl-3-oxo-but-1-enyloxy] copper (71.00 mg, 271.24 μmol, 0.10 eq) were added to N,N-dimethylformamide (5.00 mL). The mixture was stirred at 90° C. for 4 hours under microwave condition under nitrogen protection. After the reaction was completed, the reaction solution was dried on a rotary evaporator under reduced pressure, added with dichloromethane/methanol=10/1 (33 mL), stirred at 15° C. for 10 minutes and filtered. The filtrate was dried on a rotary evaporator under reduced pressure. The crude product was purified by an automatic column (methanol/dichloromethane=0~2%~4%) to obtain WX046-6, $^1$H NMR (400 MHz, CHLOROFORM-d) δ=8.24 (s, 1H), 6.03 (s, 1H), 5.61-5.48 (m, 1H), 4.10 (br s, 2H), 1.49 (s, 3H), 1.47 (s, 3H).

Step 5. Synthesis of Compound WX046-7

WXBB-14 (126.00 mg, 424.64 μmol, 1.00 eq, HCl) was added to anhydrous dichloromethane (5 mL), and oxalyl chloride (108.00 mg, 850.86 μmol, 74.48 μL, 1.99 eq) and anhydrous N,N-dimethylformamide (2.00 mg, 27.36 μmol, 2.11 μL, 0.06 eq) were added dropwise. The mixture was stirred at 15° C. for 1 hour. The reaction solution was evaporated on a rotary evaporator to become thick, added with anhydrous dichloromethane (5 mL), and evaporated on a rotary evaporator to become thick again. This process was repeated three times. Then, anhydrous dichloromethane (5 mL) was added. Afterwards, WX046-6 (100.00 mg, 426.58 μmol, 1.00 eq) (purity: 89.27%) and diisopropylethylamine (165.00 mg, 1.28 mmol, 222.97 μL, 2.99 eq) were added successively. The mixture was further stirred at 15° C. for 1 hour. After the reaction was completed, the reaction solution was added with water (20 mL), and extracted with dichloromethane (20 mL*3). The organic phases were combined, washed with saturated brine (20 mL), dried over anhydrous sodium sulfate, and filtered. The filtrate was dried on a rotary evaporator under reduced pressure. The crude product was purified by column (methanol/dichloromethane=0~2%~4%~8%) to obtain WX046-7, $^1$H NMR (400 MHz, CHLOROFORM-d) δ=8.29 (s, 1H), 8.25 (s, 1H), 8.16 (s, 1H), 7.89 (s, 1H), 6.73 (s, 1H), 6.54 (s, 1H), 5.60-5.46 (m, 2H), 3.02 (s, 7H), 1.88-1.79 (m, 2H), 1.53 (s, 3H), 1.51 (s, 3H), 1.51 (s, 3H), 1.49 (s, 3H), 0.87-0.79 (m, 3H), 0.79-0.70 (m, 3H).

Step 6. Synthesis of Compound WX046-8

WX046-7 (180.00 mg, 235.52 μmol, 1.00 eq) (purity: 58.69%), potassium carbonate (97.87 mg, 708.15 μmol, 3.00 eq) and p-methoxybenzylamine (1.06 g, 7.73 mmol, 1.00 mL, 32.81 eq) were added to acetonitrile (1.00 mL). The mixture was stirred at 100° C. for 16 hours. After the reaction was completed, the reaction solution was added with water (20 mL), and extracted with dichloromethane (20 mL*3). The organic phases were combined, washed with saturated brine (20 mL), dried over anhydrous sodium sulfate, and filtered. The filtrate was dried on a rotary evaporator under reduced pressure. The crude product was added with 18 mL of petroleum ether/ethyl acetate (5/1), and slurried at 15° C. for 0.5 hour, then the supernatant liquid was poured out. This process was repeated three times and the underlayer oil matter was dried on a rotary evaporator under reduced pressure. The crude product was purified by Silica gel column chromatography (methanol/dichloromethane=0~2%~4%~8%) to obtain WX046-8, $^1$H NMR (400 MHz, CHLOROFORM-d) δ=8.28 (s, 1H), 8.25 (s, 1H), 7.77 (s, 1H), 7.33 (d, J=10.8 Hz, 1H), 7.24 (br d, J=8.5 Hz, 2H), 7.16 (d, J=8.5 Hz, 5H), 6.85 (s, 2H), 6.81 (d, J=8.5 Hz, 5H), 6.71 (s, 1H), 6.54 (s, 1H), 5.59-5.51 (m, 1H), 4.35 (d, J=5.3 Hz, 2H), 3.75-3.74 (m, 1H), 3.75 (br s, 3H), 3.74 (s, 9H), 1.88-1.77 (m, 1H), 1.51 (s, 3H), 1.49 (s, 3H), 0.87-0.81 (m, 2H), 0.79-0.73 (m, 2H).

Step 7. Synthesis of Compound WX046-9

WX046-8 (220.00 mg, 386.85 μmol, 1.00 eq) was added to trifluoroacetic acid (3.00 mL). The mixture was stirred at 15° C. for 16 hours. After the reaction was completed, adjusted to pH=7~8 with saturated sodium carbonate solution, extracted with dichloromethane (20 mL*2), dried over anhydrous sodium sulfate, and filtered. The filtrate was dried on a rotary evaporator under reduced pressure. The crude product was purified with preparative TLC (dichloromethane/methanol=20/1) to give product WX046-9.

Step 8. Synthesis of Compound WX046

WX046-9 (50.00 mg, 96.15 μmol, 1.00 eq) (purity: 86.25%) and trimethyl orthoformate (2.00 mL) were stirred at 110° C. for 6 hours. After the reaction was completed, the reaction solution was dried on a rotary evaporator under reduced pressure. The crude product was purified by preparative HPLC (column: Xtimate C18 150*25 mm*5 μm; mobile phase: [water (0.225% FA)-ACN]; B %: 10%-40%, 12 min) to obtain WX046. $^1$H NMR (400 MHz, DMSO-d6) δ=9.02 (s, 1H), 8.93 (s, 1H), 8.36 (s, 1H), 8.15 (s, 1H), 8.04 (s, 1H), 7.84 (s, 1H), 7.79 (d, J=1.3 Hz, 1H), 7.28 (d, J=1.3 Hz, 1H), 5.41 (td, J=6.8, 13.2 Hz, 1H), 2.37 (s, 3H), 1.91-1.84 (m, 1H), 1.54 (s, 3H), 1.52 (s, 3H), 0.86-0.78 (m, 2H), 0.75-0.70 (m, 2H).

Example 047: WX047

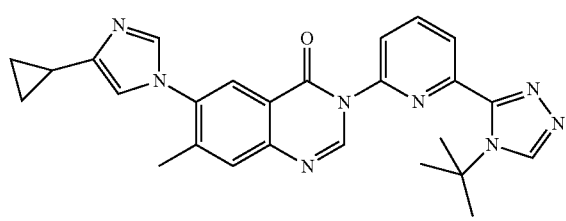 [SMILES: Cc1cc2ncn(-c3cccc(-c4nncn4C(C)(C)C)n3)c(=O)c2cc1-n1cnc(C2CC2)c1]

Synthetic Route:

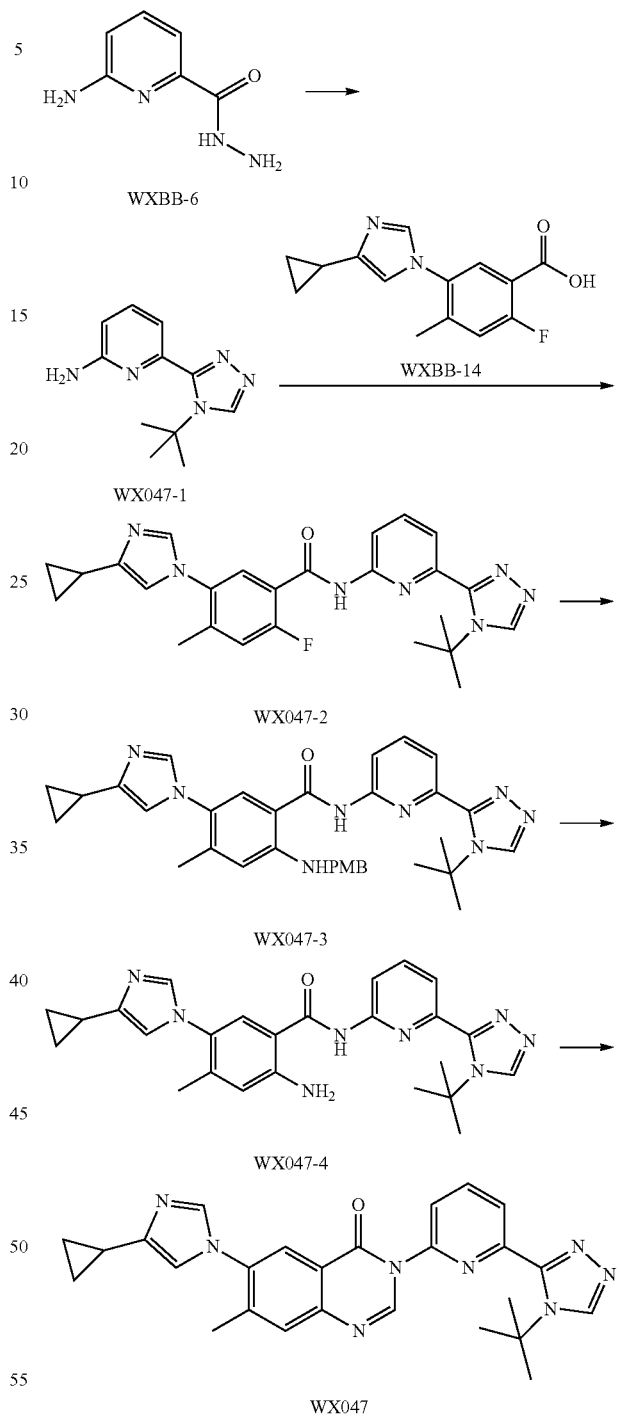

Step 1. Synthesis of Compound WX047-1

WXBB-6 (1.00 g, 6.57 mmol, 1.00 eq) was dissolved in toluene (10.00 mL) in a microwave tube, and dimethylformamide dimethyl acetal (1.96 g, 16.43 mmol, 2.18 mL, 2.50 eq) was added. The system was stirred at 20° C. for 5 min, and tert-butylamine (2.40 g, 32.86 mmol, 3.43 mL, 5.00 eq) and glacial acetic acid (500.00 mg, 8.33 mmol, 476.19 μL, 1.27 eq) were added. The system was heated to 140° C. under microwave and stirred for 30 min After the reaction was completed, the reaction solution was added into ethyl acetate (50 mL), stirred for 5 min and filtered. The filter cake was collected and dried to give a crude product. To the crude product was added dichloromethane (20 mL), stirred for 5 min, allowed to stand, filtered, and the filter cake was dried to give WX047-1, ¹HNMR (400 MHz, DMSO-d6) δ ppm 1.52 (s, 9H) 6.16 (s, 2H) 6.54 (d, J=8.53 Hz, 1H) 6.73 (d, J=7.03 Hz, 1H) 7.49 (t, J=7.78 Hz, 1H) 8.62 (s, 1H).

Step 2. Synthesis of Compound WX047-2

WXBB-14 (1.00 g, 3.37 mmol, 1.00 eq, HCl) was dissolved in anhydrous dichloromethane (10 mL) to form a suspension, then anhydrous DMF (10.00 mg, 136.82 μmol, 10.53 μL, 0.04 eq) was added, and oxalyl chloride (900.00 mg, 7.09 mmol, 620.69 μL, 2.10 eq) was added under N2 condition. The system was stirred at 20° C. for 1 hour. The reaction solution was then evaporated on a rotary evaporator under reduced pressure to become thick, added with anhydrous dichloromethane (10 mL), and evaporated on a rotary evaporator to become thick again. This process was repeated three times. Then anhydrous dichloromethane (10 mL), WX047-1 (700.00 mg, 3.22 mmol, 0.96 eq), and diisopropylethylamine (1.00 g, 7.75 mmol, 1.35 mL, 2.30 eq) were added successively. The system was stirred at 20° C. for 1 hour. After the reaction was completed, the reaction solution was added with water (50 mL), and extracted with dichloromethane (20 mL*2). The organic phase was dried over anhydrous sodium sulfate and filtered. The filtrate was dried on a rotary evaporator under reduced pressure to obtain a crude product., which was purified by column (0~8% methanol/dichloromethane) to obtain WX047-2, ¹H NMR (400 MHz, CHLOROFORM-d) δ ppm 0.81-0.85 (m, 2H) 0.88-0.92 (m, 2H) 1.68 (s, 9H) 1.88-1.92 (m, 1H) 2.29 (s, 3H) 6.80 (s, 1H) 7.19 (d, J=12.55 Hz, 1H) 7.45 (s, 1H) 7.68 (d, J=7.53 Hz, 1H) 7.92 (t, J=8.03 Hz, 1H) 8.07 (d, J=7.28 Hz, 1H) 8.37 (s, 1H) 8.46 (d, J=8.28 Hz, 1H) 9.11 (br d, J=15.06 Hz, 1H).

Step 3. Synthesis of Compound WX047-3

WX047-2 (500.00 mg, 903.41 μmol, 1.00 eq) (purity 83.027%) was dissolved in acetonitrile (1.00 mL), and potassium carbonate (250.00 mg, 1.81 mmol, 2.00 eq) and p-methoxybenzylamine (2.48 g, 18.07 mmol, 2.34 mL, 20.00 eq) were added. The system was stirred at 100° C. for 16 hours. After the reaction was completed, the reaction solution was cooled to room temperature, diluted with water (30 mL), and extracted with dichloromethane (30 mL*2). The organic phase was dried on a rotary evaporator under reduced pressure to obtain a crude product, which was separated and purified with prep-TLC (dichloromethane/methanol=10/1) to give product WX047-3.

Step 4. Synthesis of Compound WX047-4

WX047-3 (140.00 mg, 223.54 μmol, 1.00 eq) (purity 92.081%) was dissolved in trifluoroacetic acid (2.00 mL). The system was stirred at 20° C. for 0.5 hour. After the reaction was completed, the reaction solution was added with saturated aqueous sodium bicarbonate (30 mL) with stirring, and extracted with dichloromethane (30 mL*2). The organic phase was dried over anhydrous sodium sulfate and filtered. The filtrate was dried on a rotary evaporator under reduced pressure to obtain WX047-4.

Step 5. Synthesis of Compound WX047

WX047-4 (80 mg, 145.78 μmol, 1.00 eq) (purity 83.193%) was dissolved in anhydrous ethanol (2 mL), and trimethyl orthoformate (0.1 g, 942.33 μmol, 103.31 μL, 6.46 eq) and glacial acetic acid (9 mg, 149.87 μmol, 8.57 μL, 1.03 eq) were added. The system was stirred at 80° C. for 1.5 hour. After the reaction was completed, the reaction solution was cooled to room temperature, added with saturated sodium bicarbonate solution (20 mL) with stirring, and extracted with dichloromethane (15 mL*2). The organic phase was washed with water (20 mL) and saturated brine (20 mL), dried over anhydrous sodium sulfate, and filtered. The filtrate was dried on a rotary evaporator under reduced pressure to obtain a crude product, which was separated and purified with prep-HPLC (column: Waters Xbridge 150*25 mm 5 μm; mobile phase: [water (10 mM NH₄HCO₃)-ACN]; B %: 27%-47%, 8 mM) to obtain WX047. ¹H NMR (400 MHz, CHLOROFOR M-d) δ ppm 0.86 (br d, J=3.51 Hz, 2H) 0.92 (br d, J=8.03 Hz, 2H) 1.67 (s, 9H) 1.93 (br s, 1H) 2.40 (s, 3H) 6.87 (s, 1H) 7.51 (s, 1H) 7.74 (s, 1H) 7.99 (br d, J=7.53 Hz, 1H) 8.03-8.15 (m, 2H) 8.23 (s, 1H) 8.41 (s, 1H) 8.60 (s, 1H).

Example 048: WX048

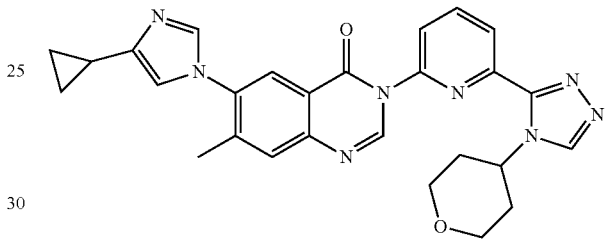

Synthetic Route:

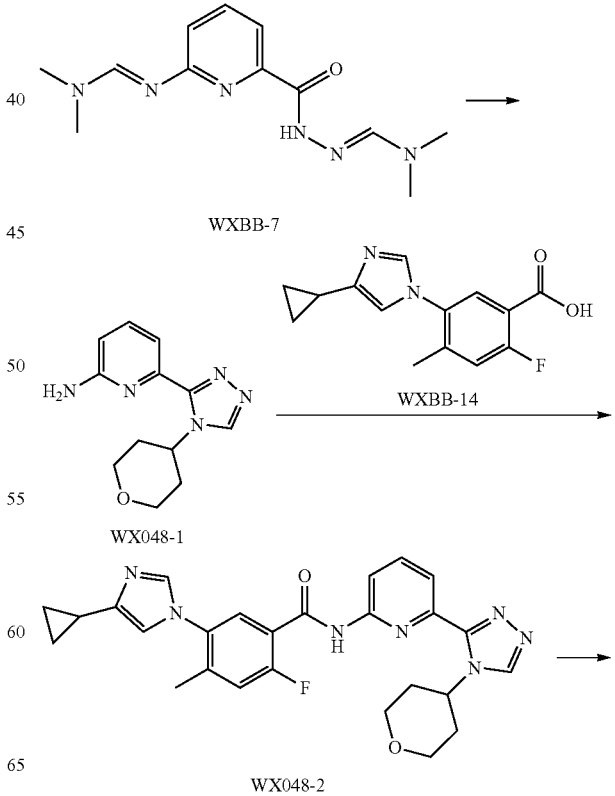

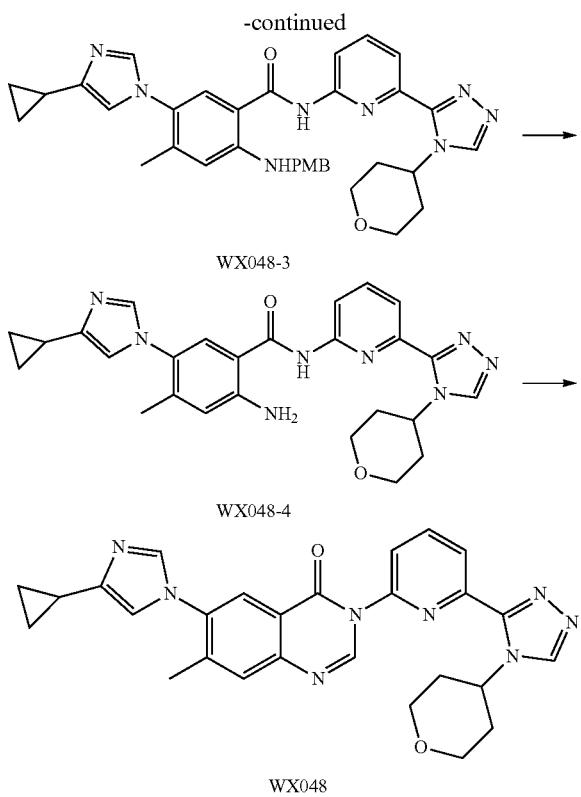

Step 1. Synthesis of Compound WX048-1

WXBB-7 (4 g, 39.55 mmol, 5.19 eq) was added to a mixture of acetonitrile (20 mL) and glacial acetic acid (5 mL). The system was stirred at 80° C. for 18 hours. The reaction solution was cooled to room temperature, added slowly with saturated sodium bicarbonate solution (200 mL) with stirring, and extracted with ethyl acetate (100 mL*3). The organic phase was dried over anhydrous sodium sulfate and filtered. The filtrate was dried on a rotary evaporator under reduced pressure to obtain a crude product. To the crude product was added ethyl acetate (10 mL), stirred for 5 min, allowed to stand and filtered. The filter cake was collected and dried to give product WX048-1. $^1$H NMR (400 MHz, DMSO-d6) δ ppm 1.91-2.04 (m, 4H) 3.50 (br t, J=11.17 Hz, 2H) 3.94 (br d, J=10.54 Hz, 2H) 5.25-5.51 (m, 1H) 6.19 (br s, 2H) 6.52 (d, J=8.28 Hz, 1H) 7.21 (d, J=7.28 Hz, 1H) 7.52 (t, J=7.91 Hz, 1H) 8.81 (s, 1H).

Step 2. Synthesis of Compound WX048-2

WXBB-14 (0.9 g, 3.03 mmol, 0.93 eq, HCl) was dissolved in anhydrous dichloromethane (10 mL) to form a suspension, and anhydrous DMF (10 mg, 136.81 µmol, 10.53 µL, 4.19e-2 eq) was added, followed by addition of oxalyl chloride (0.8 g, 6.30 mmol, 551.72 µL, 1.93 eq) under N2 condition. The system was stirred at 20° C. for 1 hour to obtain a clear solution. The reaction solution was then evaporated on a rotary evaporator under reduced pressure to become thick, added with anhydrous dichloromethane (10 mL), and evaporated on a rotary evaporator under reduced pressure to become thick again. This process was repeated three times. Then anhydrous dichloromethane (10 mL), WX048-1 (0.8 g, 3.26 mmol, 1 eq), and diisopropylethylamine (0.9 g, 6.96 mmol, 1.21 mL, 2.14 eq) were added successively. The system was stirred at 20° C. for 1 hour. The reaction solution was added with water (50 mL), and extracted with dichloromethane (50 mL*2). The organic phase was washed with water (50 mL) and saturated brine (50 mL), dried over anhydrous sodium sulfate, and filtered. The filtrate was dried on a rotary evaporator under reduced pressure to obtain a crude product. The crude product was added with acetonitrile (2 mL) to a complete dissolution and cooled in ice-water. A solid precipitated out and was filtered. The filter cake was collected and dried to give WX048-2.

Step 3. Synthesis of Compound WX048-3

WX048-2 (0.8 g, 1.32 mmol, 1 eq) (purity 80.152%) was dissolved in acetonitrile (2 mL), and potassium carbonate (0.36 g, 2.60 mmol, 1.98 eq) and p-methoxybenzylamine (3.61 g, 26.30 mmol, 3.40 mL, 20 eq) were added. The system was stirred at 100° C. for 16 hours. The reaction solution was cooled to room temperature, added with water (50 mL), and extracted with dichloromethane (50 mL*2). The organic phase was dried on a rotary evaporator under reduced pressure to obtain a crude product. A mixture of petroleum ether/ethyl acetate (5/1, 100 mL) was poured into the crude product, stirred for 5 min, and left to stand. Then the supernatant was poured, and the underlayer oil matter was retained. This process was reparted three times and then the underlayer oil matter was purified by a column (0~6% methanol/dichloromethane) to obtain WX048-3.

Step 4. Synthesis of Compound WX048-4

WX048-3 (0.8 g, 1.32 mmol, 1 eq) was dissolved in trifluoroacetic acid (10 mL). The system was stirred at 20° C. for 1 hour. To the reaction solution was added dropwise water (15 mL) with stirring to precipitate a solid, allowed to stand, and filtered. The filtrate was adjusted to pH 8~9 with saturated sodium bicarbonate solution (150 mL), and extracted with dichloromethane (50 mL*2). The organic phase was washed with water (100 mL) and saturated brine (100 mL), dried over anhydrous sodium sulfate, and filtered. The filtrate was dried on a rotary evaporator under reduced pressure to obtain WX048-4.

Step 5. Synthesis of Compound WX048

WX048-4 (0.4 g, 626.07 µmol, 1 eq) (purity 75.841%) was dissolved in trimethyl orthoformate (5 mL). The system was stirred at 110° C. for 1 hour. The reaction solution was dried on a rotary evaporator under reduced pressure to obtain a crude product, which was separated and purified with prep-HPLC (column: Waters Xbridge 150*25 mm 5 µm; mobile phase: [water (10 mM NH$_4$HCO$_3$)-ACN]; B %: 17%-47%, 10 min) to obtain WX048. $^1$H NMR (400 MHz, CHLOROFORM-d) δ ppm 0.84-0.90 (m, 2H) 0.90-0.96 (m, 2H) 1.90-1.98 (m, 1H) 1.99-2.11 (m, 2H) 2.14-2.23 (m, 2H) 2.43 (s, 3H) 3.45 (t, J=11.04 Hz, 2H) 4.11 (br dd, J=11.67, 4.39 Hz, 2H) 5.33-5.45 (m, 1H) 6.88 (d, J=1.00 Hz, 1H) 7.53 (d, J=1.25 Hz, 1H) 7.77 (s, 1H) 7.92 (d, J=7.53 Hz, 1H) 8.13 (t, J=8.03 Hz, 1H) 8.24 (s, 1H) 8.42 (s, 1H) 8.50 (d, J=7.28 Hz, 1H) 8.53 (s, 1H).

Example 049: WX049

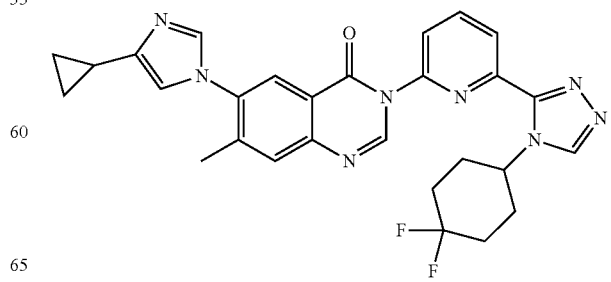

Synthetic Route:

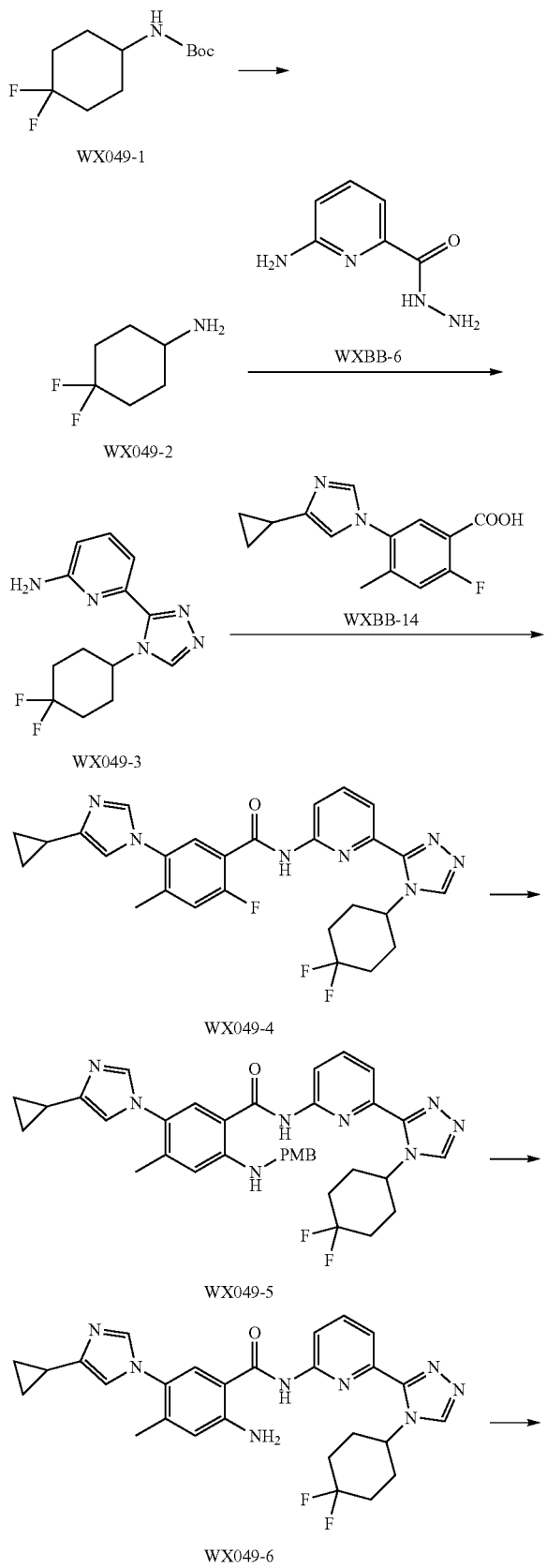

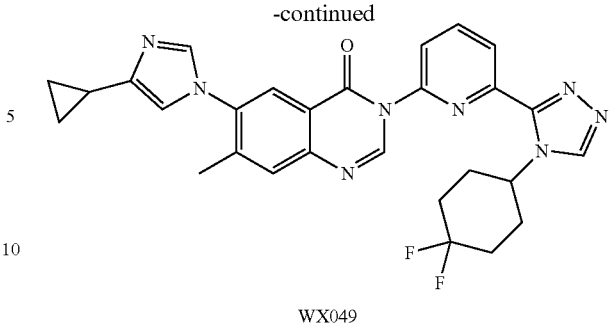

WX049

Step 1. Synthesis of Compound WX049-2

WX049-1 (4 g, 17.00 mmol, 1 eq) was dissolved in ethyl acetate (30 mL), and hydrochloric acid/ethyl acetate (4M, 21.25 mL, 5 eq) was added. The system was stirred at 20° C. for 1 hour. The reaction solution was allowed to stand and filtered, and the filter cake was dried to give WX049-2. $^1$H NMR (400 MHz, DMSO-d6) δ ppm 1.50-1.68 (m, 2H) 1.83-2.12 (m, 6H) 3.18 (br d, J=4.77 Hz, 1H).

Step 2. Synthesis of Compound WX049-3

WXBB-6 (0.6 g, 3.94 mmol, 1.35 eq) was dissolved in anhydrous toluene (10 mL), and dimethylformamide dimethyl acetal (1 g, 8.39 mmol, 1.11 mL, 2.88 eq) was added. The system was stirred at 20° C. for 5 min, and glacial acetic acid (0.2 g, 3.33 mmol, 190.48 µL, 1.14 eq), WX049-2 (2 g, 11.65 mmol, 4 eq, hydrochloric acid) were added. The system was heated to 140° C. under microwave and stirred for 0.5 h. The reaction solution was dried on a rotary evaporator under reduced pressure to obtain a crude product. Ethyl acetate (10 mL) was added to the crude product to dissolve all the crude product, and petroleum ether was added dropwise thereto with stirring to form a precipitate. Then the mixture was stirred for 5 min, allowed to stand, filtered, and the filter cake was dried to obtain WX049-3. $^1$H NMR (400 MHz, DMSO-d6) δ ppm 1.92-1.98 (m, 2H) 2.08-2.17 (m, 6H) 5.50 (br t, J=12.17 Hz, 1H) 6.24 (s, 2H) 6.50-6.53 (m, 1H) 7.27 (d, J=6.78 Hz, 1H) 7.51-7.55 (m, 1H) 8.82 (s, 1H).

Step 3. Synthesis of Compound WX049-4

WXBB-14 (0.5 g, 1.69 mmol, 1 eq, hydrochloric acid) was dissolved in anhydrous dichloromethane (5 mL) to form a suspension, and anhydrous N,N-dimethylformamide (12.50 mg, 171.01 µmol, 13.16 µL, 1.01e-1 eq) was added. Then oxalyl chloride (425.00 mg, 3.35 mmol, 293.10 µL, 1.99 eq) was added under nitrogen condition. The system was stirred at 15° C. for 1 hour to obtain a clear solution. The reaction solution was then evaporated on a rotary evaporator under reduced pressure to become thick, added with anhydrous dichloromethane (5 mL), and evaporated on a rotary evaporator to become thick again. This process was repeated three times. Anhydrous dichloromethane (5 mL), WX049-3 (0.4 g, 1.43 mmol, 0.85 eq), and diisopropylethylamine (500.00 mg, 3.87 mmol, 673.85 µL, 2.30 eq) were added successively. The system was stirred at 15° C. for 1 hour. The reaction solution was added with water (50 mL), and extracted with dichloromethane (50 mL*2). The organic phase was washed with water (50 mL) and saturated brine (50 mL), dried over anhydrous sodium sulfate, and filtrated. The filtrate was dried on a rotary evaporator under reduced pressure to obtain a crude product, which was purified by column (0~6% methanol/dichloromethane) to obtain product WX049-4.

Step 4. Synthesis of Compound WX049-5

WX049-4 (0.4 g, 693.53 μmol, 1 eq) (purity 90.426%) was dissolved in acetonitrile (1 mL), and p-methoxybenzylamine (1.90 g, 13.87 mmol, 1.80 mL, 20 eq) and potassium carbonate (0.2 g, 1.45 mmol, 2.09 eq) were added. The system was stirred at 100° C. for 20 hour. The reaction solution was cooled to room temperature, added with water (50 mL), and extracted with dichloromethane (50 mL*2). The organic phase was dried on a rotary evaporator under reduced pressure to obtain a crude product. A mixture of petroleum ether/ethyl acetate (5/1, 15 mL) was poured into the crude product, stirred for 1 min, left to stand, and the underlayer oil matter was retained. This process was reputed three times and then the underlayer oil matter was separated and purified by a rep-TLC (dichloromethane/methanol=10/1) plate to obtain WX049-5. $^1$H NMR (400 MHz, CHLOROFORM-d) δ ppm 0.71-0.80 (m, 2H) 0.81-0.89 (m, 2H) 1.81-1.93 (m, 3H) 2.10 (s, 3H) 2.14-2.29 (m, 6H) 3.82 (s, 3H) 4.41 (d, J=5.52 Hz, 2H) 5.17 (br t, J=11.04 Hz, 1H) 6.64 (s, 1H) 6.69-6.74 (m, 1H) 6.91 (d, J=8.53 Hz, 2H) 7.31 (d, J=8.53 Hz, 2H) 7.35-7.37 (m, 1H) 7.42 (s, 1H) 7.84-7.91 (m, 1H) 8.03 (d, J=7.03 Hz, 1H) 8.12 (d, J=8.28 Hz, 1H) 8.19 (br t, J=5.27 Hz, 1H) 8.31 (s, 1H) 8.64 (br s, 1H).

Step 5. Synthesis of Compound WX049-6

WX049-5 (0.25 g, 318.50 μmol, 1 eq) (purity 81.371%) was dissolved in trifluoroacetic acid (3 mL). The system was stirred at 20° C. for 1 hour. The reaction solution was added dropwise with water (3 mL) under stirring to generate a precipitate, allowed to stand, and filtered. The filtrate was adjusted to pH 8-9 with saturated sodium bicarbonate solution (150 mL), and extracted with dichloromethane (50 mL*2). The organic phase was washed with water (50 mL) and saturated brine (50 mL), dried over anhydrous sodium sulfate, and filtered. The filtrate was dried on a rotary evaporator under reduced pressure to obtain WX049-6.

Step 6. Synthesis of Compound WX049

WX049-6 (0.160 g, 308.55 μmol, 1 eq) was dissolved in trimethyl orthoformate (2 mL). The system was stirred at 110° C. for 0.5 hour. The reaction solution was dried on a rotary evaporator under reduced pressure to obtain a crude product. Ethyl acetate (3 mL) was added to the crude product to dissolve all the crude product, and petroleum ether was added dropwise thereto with stirring to form a precipitate. The obtained mixture was stirred for 5 min, allowed to stand, filtered, and the filter cake was dried to obtain WX049. $^1$H NMR (400 MHz, CHLOROFORM-d) δ ppm 0.85-0.90 (m, 2H) 0.90-0.95 (m, 2H) 1.80-1.99 (m, 3H) 2.01-2.13 (m, 2H) 2.29 (br s, 4H) 2.42-2.47 (m, 3H) 5.21-5.31 (m, 1H) 6.88 (d, J=1.00 Hz, 1H) 7.54 (s, 1H) 7.78 (s, 1H) 7.90 (d, J=8.03 Hz, 1H) 8.14 (t, J=7.91 Hz, 1H) 8.23 (s, 1H) 8.41 (s, 1H) 8.45-8.52 (m, 2H).

Example 050: WX050

Synthetic Route:

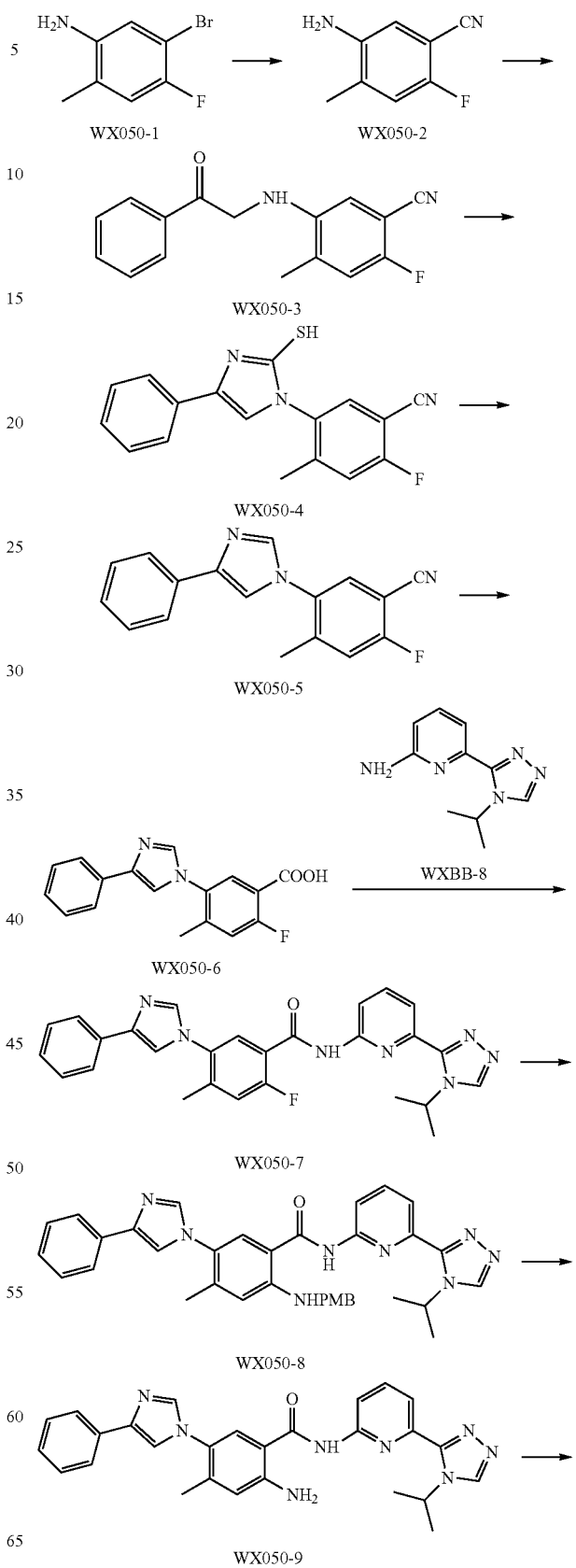

-continued

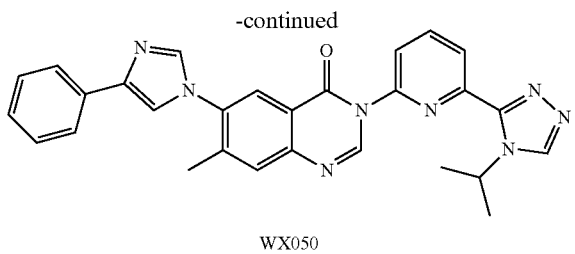

WX050

Step 1. Synthesis of Compound WX050-2

Compound WX050-1 (50.00 g, 245.05 mmol, 1.00 eq) was dissolved in N-methyl-2-pyrrolidone (400.00 mL), and cuprous cyanide (43.89 g, 490.10 mmol, 107.05 mL, 2.00 eq) was added. The reaction system was stirred at 180° C. for 3 hours. The reaction solution was cooled to room temperature, added with water (400 mL) and aqueous ammonia (400 mL, purity 30%), and stirred at 20° C. for 1 hour. The solid impurities were filtered off, and the filtrate was extracted with ethyl acetate (500 mL*3). The organic phase was washed with saturated sodium chloride (300 mL), dried over anhydrous sodium sulfate, and filtered. The filtrate was dried on a rotary evaporator under reduced pressure (water bath temperature of 40° C.). The crude product was purified by column (ethyl acetate/petroleum ether=0~30%) to obtain WX050-2. $^1$H NMR (400 MHz, CHLOROFORM-d) δ ppm 2.21 (s, 3H) 3.67 (br s, 2H) 6.77-6.83 (m, 1H) 6.91 (d, J=9.29 Hz, 1H).

Step 2. Synthesis of Compound WX050-3

Compound WX050-2 (4 g, 23.26 mmol, 1 eq) (purity 87.329%) was dissolved in anhydrous N,N-dimethylformamide (40 mL), potassium carbonate (3.86 g, 27.92 mmol, 1.2 eq) and potassium iodide (4.25 g, 25.59 mmol, 1.1 eq) were added, followed by purging with nitrogen three times, and 2-bromo-1-phenyl-ethanone (9.26 g, 46.53 mmol, 2 eq) was added. The mixture was stirred at 60° C. for 3 hours under a nitrogen atmosphere. The reaction solution was cooled to room temperature, added with water (30 mL), and extracted with ethyl acetate (30 mL*3). The organic phase was washed with saturated sodium chloride (50 mL), dried over anhydrous sodium sulfate, and filtered. The filtrate was dried on a rotary evaporator under reduced pressure. The crude product was purified by column (ethyl acetate/petroleum ether=0~25%) to obtain WX050-3. $^1$H NMR (400 MHz, DMSO-d6) δ ppm 2.27 (s, 3H) 4.80 (d, J=5.27 Hz, 2H) 5.39-5.46 (m, 1H) 7.00 (d, J=5.52 Hz, 1H) 7.26 (d, J=9.79 Hz, 1H) 7.56-7.64 (m, 2H) 7.68-7.74 (m, 1H) 8.11 (d, J=7.03 Hz, 2H).

Step 3. Synthesis of Compound WX050-4

Compound WX050-3 (3 g, 9.94 mmol, 1.00 eq) (purity 88.905%) was dissolved in acetic acid (25 mL), followed by purging with nitrogen 3 times, and potassium thiocyanate (1.93 g, 19.88 mmol, 1.93 mL, 2.00 eq) was added. The mixture was stirred at 110° C. for 16 hours under a nitrogen atmosphere. The reaction solution was cooled to room temperature, concentrated under reduced pressure, adjusted to pH=8 by adding saturated sodium bicarbonate (10 mL), and extracted with dichloromethane (20 mL*3). The organic phase was washed with saturated sodium chloride (30 mL), dried over anhydrous sodium sulfate, and filtered. The filtrate was dried on a rotary evaporator under reduced pressure. The crude product was purified by column (ethyl acetate/petroleum ether=0~30%) to obtain WX050-4. $^1$H NMR (400 MHz, DMSO-d6) δ ppm 2.25 (s, 3H) 7.30-7.36 (m, 1H) 7.44 (t, J=7.65 Hz, 2H) 7.68-7.72 (m, 1H) 7.73-7.77 (m, 2H) 8.11 (d, J=6.02 Hz, 1H) 13.09 (br s, 1H).

Step 4. Synthesis of Compound WX050-5

Hydrogen peroxide (2.05 g, 18.11 mmol, 1.74 mL, 30% purity, 3.00 eq) was dissolved in acetic acid (15 mL) and water (3 mL). The reaction system was stirred at 45° C. for 1 hour under nitrogen atmosphere. Then compound WX050-4 (2.1 g, 6.04 mmol, 1.00 eq) (purity 88.932%) was slowly added. The reaction system was stirred at 55° C. for 2 hours under nitrogen atmosphere. Then the reaction solution was cooled to room temperature, and added with saturated sodium sulfite solution until no blue color was detected with a starch potassium iodide test paper. Part of solvent was evaporated on a ratory evaporator. The starch potassium iodide test paper showed no hydrogen peroxide remained. The mixture was adjusted pH=8 with sodium bicarbonate (20 mL) and extracted with dichloromethane (20 mL*3). The organic phase was washed with saturated sodium chloride (30 mL), dried over anhydrous sodium sulfate, and filtered. The filtrate was dried on a rotary evaporator under reduced pressure to obtain compound WX050-5. $^1$H NMR (400 MHz, DMSO-d6) δ ppm 2.33 (s, 3H) 7.23-7.29 (m, 1H) 7.40 (br t, J=7.65 Hz, 2H) 7.73 (br d, J=10.04 Hz, 1H) 7.84 (br d, J=7.53 Hz, 2H) 7.97 (d, J=6.53 Hz, 2H) 8.14 (d, J=6.02 Hz, 1H).

Step 5. Synthesis of Compound WX050-6

Compound WX050-5 (1.6 g, 5.28 mmol, 1.00 eq) (purity 91.482%) was dissolved in concentrated hydrochloric acid (16.32 g, 170.09 mmol, 16 mL, 38% purity, 32.22 eq). The mixture was stirred at 100° C. for 5 hours. The reaction solution was directly dried on a rotary evaporator, and then slurried with dichloromethane/methanol (10/1, 22 mL) at 20° C. for 0.5 hour and filtered. The filtrate was dried on a rotary evaporator under reduced pressure to obtain compound WX050-6. $^1$H NMR (400 MHz, DMSO-d6) δ ppm 2.36 (s, 3H) 7.47-7.52 (m, 1H) 7.53-7.63 (m, 3H) 7.98 (br d, J=7.53 Hz, 2H) 8.16 (br d, J=6.78 Hz, 1H) 8.54 (s, 1H) 9.58 (s, 1H).

Step 6. Synthesis of Compound WX050-7

Compound WX050-6 (1.6 g, 4.32 mmol, 1 eq, HCl) (purity 89.813%) was dissolved in anhydrous dichloromethane (15 mL), and anhydrous N,N-dimethylformamide (32 mg, 437.79 μmol, 33.68 μL, 0.1 eq) and oxalyl chloride (932 mg, 7.34 mmol, 642.76 μL, 1.7 eq) were added. The mixture was stirred at 20° C. for 1 hour. The solvent was evaporated on a rotary evaporator to become thick mixture, then 3 mL of anhydrous dichloromethane was added. This process was reapeated three times. Compound WXBB-8 (1.05 g, 5.16 mmol, 1.2 eq) and diisopropylethylamine (558 mg, 4.32 mmol, 752.02 μL, 1 eq) were added. The mixture was stirred at 20° C. for 15 hours. The reaction solution was added with water (30 mL), and extracted with dichloromethane (30 mL*3). The organic phase was washed with saturated sodium chloride (50 mL), dried over anhydrous sodium sulfate, and filtered. The filtrate was dried on a rotary evaporator under reduced pressure. The crude product was purified by column (methanol/dichloromethane=0~10%) to obtain compound WX050-7. $^1$H NMR (400 MHz, DMSO-d6) δ ppm 1.43 (br d, J=6.53 Hz, 6H) 2.32 (s, 3H) 5.61-5.68 (m, 1H) 7.20-7.29 (m, 1H) 7.39 (br t, J=7.28 Hz, 2H) 7.55 (br d, J=11.29 Hz, 1H) 7.78 (br d, J=6.53 Hz, 1H) 7.86 (br d, J=7.28 Hz, 2H) 7.89 (br d, J=7.78 Hz, 1H) 7.95-8.00 (m, 2H) 8.04 (br t, J=8.16 Hz, 1H) 8.21 (br d, J=8.03 Hz, 1H) 8.87 (s, 1H).

Step 7. Synthesis of Compound WX050-8

Compound WX050-7 (1.2 g, 1.76 mmol, 1 eq) (purity 70.627%) was dissolved in acetonitrile (10 mL), and p-methoxybenzylamine (2.41 g, 17.60 mmol, 2.28 mL, 10 eq) and potassium carbonate (487 mg, 3.52 mmol, 2 eq)

were added. The mixture was stirred at 100° C. for 16 hours. The mixture was further stirred at 100° C. for 8 hours. The reaction solution was added with water (20 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure. The crude product was purified by column (methanol/dichloromethane=0~6%) to obtain compound WX050-8. MS: m/z=300.2[M+1]/2.

Step 8. Synthesis of Compound WX050-9

Compound WX050-8 (1.8 g, 3.01 mmol, 1 eq) (crude) was dissolved in trifluoroacetic acid (15 mL). The mixture was stirred at 20° C. for 1 hour. The reaction solution was adjusted to pH=8 by adding slowly saturated sodium carbonate (40 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure and slurried with petroleum ether/ethyl acetate (5/1, 12 mL) at 20° C. for 20 min. The solvent was slowly decanted and the oil was dried on a rotary evaporator under reduced pressure to obtain compound WX050-9. MS: m/z=240.1[M+1]/2.

Step 9. Synthesis of Compound WX050

Compound WX050-9 (250.00 mg, 424.69 μmol, 1.00 eq) (purity 75.006%) was dissolved in trimethyl orthoformate (3.00 mL). The mixture was stirred at 110° C. for 1 hour, and then cooled to room temperature. The reaction solution was directly dried on a rotary evaporator. The crude product was separated and purified by flash preparative chromatography (column: Xtimate C18 150*25 mm*5 μm; mobile phase: [water (0.225% FA)-ACN]; B %: 15%-25%, 12 min) to obtain compound WX050. $^1$H NMR (400 MHz, DMSO-d6) δ ppm 0.73 (br d, J=5.02 Hz, 2H) 1.43 (s, 3H) 1.45 (s, 3H) 1.87 (s, 1H) 2.37 (s, 3H) 4.52 (s, 1H) 7.26 (s, 1H) 7.77 (s, 4H) 7.83 (s, 2H) 7.98 (s, 1H) 8.16 (s, 1H) 8.51 (s, 1H) 8.91 (s, 1H).

Example 051: WX051

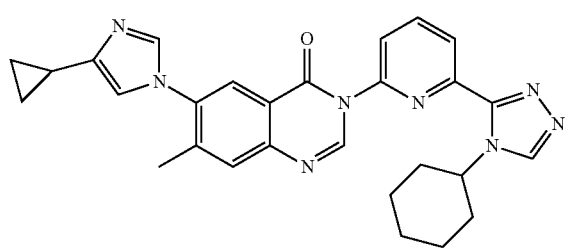 [SMILES: Cc1cc2ncn(-c3cccc(-c4nncn4C4CCCCC4)n3)c(=O)c2cc1-n1cnc(C2CC2)c1]

Synthetic Route:

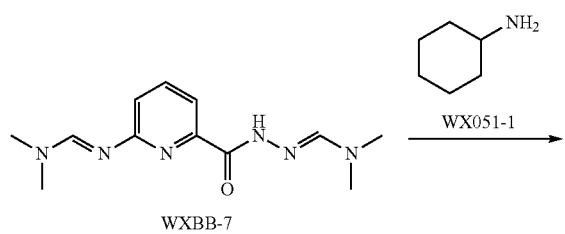

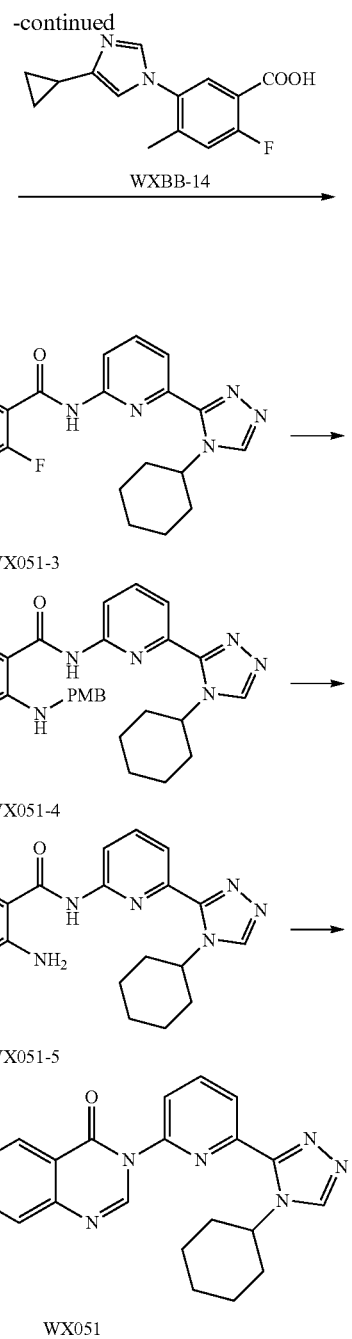

Step 1. Synthesis of Compound WX051-2

Compound WXBB-7 (0.5 g, 1.91 mmol, 1 eq) was dissolved in a mixture of acetonitrile (8 mL) and acetic acid (2 mL), and compound WX051-1 (0.95 g, 9.58 mmol, 1.10 mL, 5.03 eq) was added. The system was stirred at 80° C. for 16 hours. The reaction solution was cooled to room temperature, added with saturated sodium bicarbonate solution (200 mL) with stirring to a pH of 8~9, and extracted with ethyl acetate (50 mL*2). The organic phase was dried over anhydrous sodium sulfate and filtered. The filtrate was dried on a rotary evaporator under reduced pressure to obtain compound WX051-2. $^1$H NMR (400 MHz, CHLOROFORM-d) δ ppm 1.41 (br s, 2H) 1.61 (br d, J=3.26 Hz, 2H) 1.78 (br d, J=9.29 Hz, 2H) 2.21 (br s, 2H) 4.49 (br s, 2H) 5.14 (tt, J=11.86, 3.70 Hz, 1H) 6.57 (dd, J=7.53, 1.51 Hz, 1H) 7.55-7.62 (m, 2H) 8.31 (s, 1H).

Step 2. Synthesis of Compound WX051-3

Compound WXBB-14 (0.5 g, 1.69 mmol, 1 eq, HCl) was dissolved in anhydrous dichloromethane (10 mL) to form a suspension, then anhydrous N,N-dimethylformamide (0.01 g, 136.82 μmol, 10.53 μL, 8.10e-2 eq) was added, and oxalyl chloride (0.43 g, 3.39 mmol, 296.55 μL, 2.00 eq) was added under nitrogen condition. The system was stirred at 15° C. for 1 hour to obtain a clear solution. The reaction solution was then evaporated on a rotary evaporator under reduced pressure to become thick, added with anhydrous dichloromethane (5 mL), and evaporated on a rotary evaporator to become thick again. This process was repeated three times. Anhydrous dichloromethane (10 mL), compound WX051-2 (0.52 g, 2.14 mmol, 1.26 eq) (crude), and diisopropylethylamine (0.5 g, 3.87 mmol, 673.85 μL, 2.29 eq) were added successively. The system was stirred at 15° C. for 1 hour. The reaction solution was added with water (50 mL), and extracted with dichloromethane (50 mL*2). The organic phase was washed with water (50 mL) and saturated brine (50 mL), dried over anhydrous sodium sulfate and filtrated. The filtrate was dried on a rotary evaporator under reduced pressure to obtain a crude product. The crude product was purified by column (0~6% methanol/dichloromethane) to obtain compound WX051-3. MS: m/z=243.6 [M+1]/2.

Step 3. Synthesis of Compound WX051-4

Compound WX051-3 (0.45 g, 726.66 μmol, 1 eq) (purity 78.408%) was dissolved in acetonitrile (1 mL), and p-methoxybenzylamine (1.99 g, 14.53 mmol, 1.88 mL, 20 eq) and potassium carbonate (214.83 mg, 1.55 mmol, 2.14 eq) were added. The system was stirred at 100° C. for 20 hours. The reaction solution was cooled to room temperature, diluted with water (50 mL), and extracted with dichloromethane (50 mL*2). The organic phase was dried on a rotary evaporator under reduced pressure to obtain a crude product. A mixture of petroleum ether/ethyl acetate (5/1, 15 mL) was poured into the crude product, stirred for 1 minute, left to stand, and the underlayer oil matter was retained. This process was reputed three times and then the underlayer oil matter was separated and purified by a prep-TLC (dichloromethane/methanol=10/1) plate to obtain compound WX051-4. MS: m/z=603.1 [M+1].

Step 4: Synthesis of Compound WX051-5

Compound WX051-4 (0.15 g, 223.87 μmol, 1 eq) (purity 89.955%) was dissolved in trifluoroacetic acid (3 mL). The system was stirred at 20° C. for 1 hour. The reaction solution was added dropwise with water (3 mL) under stirring to generate a precipitate, allowed to stand, and filtered. The filtrate was adjusted to pH 8~9 with saturated sodium bicarbonate solution (150 mL), and extracted with dichloromethane (50 mL*2). The organic phase was washed with water (50 mL) and saturated brine (50 mL), dried over anhydrous sodium sulfate, and filtered. The filtrate was dried on a rotary evaporator under reduced pressure to obtain compound WX051-5. MS: m/z=242.1 [M+1]/2.

Step 5. Synthesis of Compound WX051

Compound WX051-5 (0.1 g, 207.22 μmol, 1 eq) was dissolved in trimethyl orthoformate (2 mL). The system was stirred at 110° C. for 0.5 hour. The reaction solution was dried on a rotary evaporator under reduced pressure to obtain a crude product. HPLC (ES5345-244-P1B) showed a product content of 82.17%. The crude product was separated and purified with prep-HPLC:column: Waters Xbridge 150*25 mm 5 μm; mobile phase: [water (10 mM NH$_4$HCO$_3$)-ACN]; B %: 35%-55%, 10 min to obtain compound WX051. $^1$H NMR (400 MHz, CHLOROFORM-d) δ ppm 0.85-0.89 (m, 2H) 0.92 (dt, J=8.41, 2.57 Hz, 2H) 1.24-1.44 (m, 4H) 1.61-1.70 (m, 2H) 1.88-1.97 (m, 3H) 2.26 (br d, J=10.79 Hz, 2H) 2.42 (s, 3H) 5.02-5.13 (m, 1H) 6.88 (d, J=1.00 Hz, 1H) 7.52 (d, J=1.25 Hz, 1H) 7.77 (s, 1H) 7.96 (d, J=7.53 Hz, 1H) 8.10 (t, J=7.91 Hz, 1H) 8.24 (s, 1H) 8.40 (s, 1H) 8.47 (d, J=7.03 Hz, 1H) 8.61 (s, 1H).

Example 052: WX052

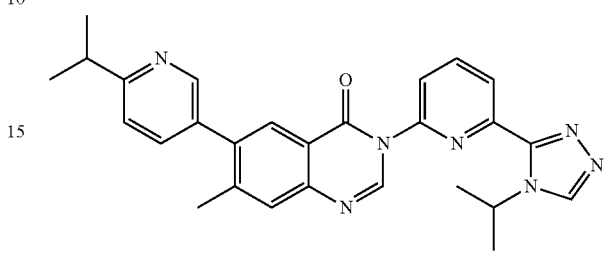

Synthetic Route:

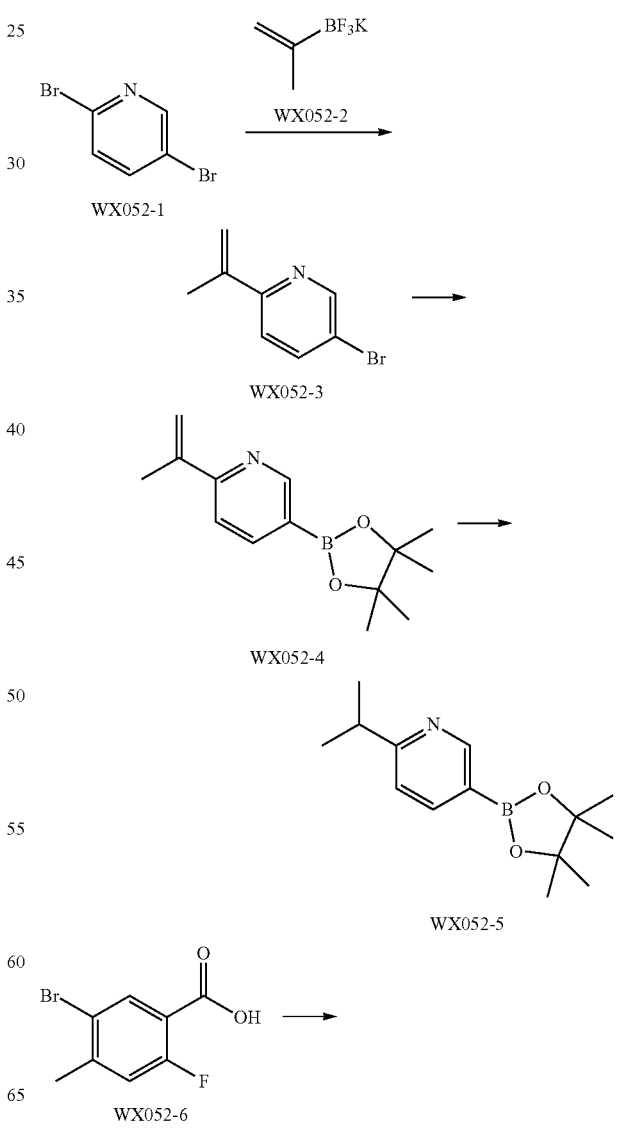

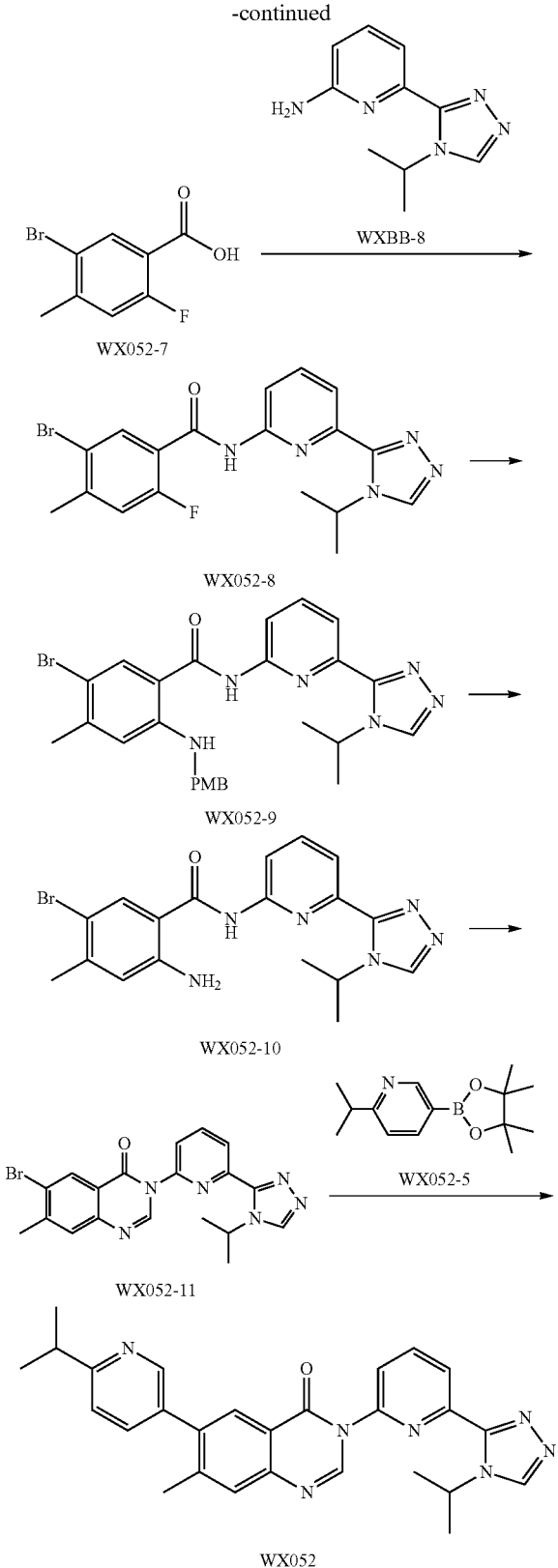

Step 1. Synthesis of Compound WX052-3

WX052-1 (4 g, 16.89 mmol, 1 eq), WX052-2 (2.50 g, 16.89 mmol, 1 eq), potassium carbonate (7.00 g, 50.65 mmol, 3 eq) and Pd(dppf)Cl₂ (371 mg, 507.03 μmol, 0.03 eq) were added into dioxane (40 mL) and water (8 mL). The mixture was stirred at 90° C. for 16 hours under nitrogen. The reaction solution was added to water (50 mL), and extracted with dichloromethane (50 mL*2). The organic phase was dried over anhydrous sodium sulfate and filtered. The filtrate was dried on a rotary evaporator under reduced pressure. The crude product was purified by column (ethyl acetate/petroleum ether=0~2%~4%~8%) to obtain WX052-3. ¹H NMR (400 MHz, CHLOROFORM-d) δ=8.58 (d, J=2.0 Hz, 1H), 7.72 (dd, J=2.3, 8.5 Hz, 1H), 7.35-7.32 (m, 1H), 5.82 (s, 1H), 5.31-5.26 (m, 1H), 2.15 (d, J=1.3 Hz, 3H).

Step 2. Synthesis of Compound WX052-4

WX052-3 (0.5 g, 2.52 mmol, 1 eq), diboron pinacol ester (769 mg, 3.03 mmol, 1.2 eq), potassium acetate (743 mg, 7.57 mmol, 3 eq) and Pd(dppf)Cl₂ (92 mg, 125.73 μmol, 4.98e-2 eq) were added to anhydrous dioxane (10 mL). The mixture was stirred at 80° C. for 16 hours under nitrogen. The reaction solution was directly dried on a rotary evaporator, added with dichloromethane (30 mL), slurried at 15° C. for 10 minutes and filtered. The filtrate was dried on a rotary evaporator under reduced pressure to obtain WX052-4 (1 g, crude). ¹H NMR (400 MHz, CHLOROFORM-d) δ=8.88 (s, 1H), 7.98 (br d, J=7.8 Hz, 1H), 7.41 (br d, J=8.0 Hz, 1H), 5.87 (s, 1H), 5.29 (s, 1H), 2.18 (s, 3H), 1.31 (s, 12H).

Step 3. Synthesis of Compound WX052-5

Wet palladium carbon (0.2 g) was added to methanol (15 mL) under the protection of nitrogen atmosphere, and WX052-4 (1 g, 4.08 mmol, 1 eq) (crude) was added. The mixture was purged with hydrogen three times. The mixture was stirred at 15° C. for 16 hours under hydrogen (15 PSI) condition. The reaction solution was filtered (with celite). The filtrate was dried on a rotary evaporator under reduced pressure to obtain WX052-5, 1H NMR (400 MHz, CHLOROFORM-d) δ=8.89 (s, 1H), 8.00 (br d, J=7.8 Hz, 1H), 7.19 (br d, J=7.8 Hz, 1H), 3.09 (td, J=6.8, 13.7 Hz, 1H), 1.36 (s, 12H), 1.32 (br d, J=7.0 Hz, 6H).

Step 4: Synthesis of Compound WX052-7

WX052-6 (10.00 g, 64.88 mmol, 1.00 eq) was dissolved in concentrated sulfuric acid (50.00 mL) (purity 98%), and bromosuccinimide (11.55 g, 64.88 mmol, 1.00 eq) was added. The system was stirred at 50° C. for 1 hour under N2 condition. The reaction solution was slowly added to ice water (500 mL) with stirring, allowed to stand and filtered, and the filter cake was dried to give product WX052-7. ¹H NMR (400 MHz, CHLOROFORM-d) δ ppm 2.46 (s, 3H) 7.09 (d, J=11.29 Hz, 1H) 8.19 (d, J=7.03 Hz, 1H).

Step 5: Synthesis of Compound WX052-8

WX052-7 (2.00 g, 8.58 mmol, 1.00 eq) was dissolved in anhydrous dichloromethane (20 mL) to form a suspension, and N,N-dimethylformamide (40.00 mg, 547.27 μmol, 42.11 μL, 0.06 eq) was added, and oxalyl chloride (2.07 g, 16.30 mmol, 1.43 mL, 1.90 eq) was added under N2 condition. The system was stirred at 15° C. for 1 hour. The reaction solution was then evaporated on a rotary evaporator under reduced pressure to become thick, added with anhydrous dichloromethane (20 mL), and evaporated on a rotary evaporator to become thick again. This process was repeated three times, and then anhydrous dichloromethane (20 mL), WXBB-8 (1.66 g, 8.15 mmol, 0.95 eq), diisopropylethylamine (2.22 g, 17.16 mmol, 3.00 mL, 2.00 eq) were added successively. The system was stirred at 15° C. for 0.5 hour. The reaction solution was filtered, and the filter cake was washed with n-hexane (10 mL) and collected. The filtrate was dried on a ratory evaporator under reduced pressure to give brown oil, which was dissolved in acetonitrile (2 mL). The solution was cooled to 0° C., allowed to stand for 10 min, and filtered. The filter cake was washed with n-hexane (10 mL) and collected. The filter cakes obtained by two filtrations were combined, and dried to give product WX052-8. $^1$H NMR (400 MHz, DMSO-d6) δ ppm 1.43 (d, J=6.78 Hz, 6H) 2.42 (s, 3H) 5.64 (dt, J=13.30, 6.65 Hz, 1H) 7.47 (d, J=10.79 Hz, 1H) 7.90 (t, J=7.53 Hz, 2H) 8.03 (t, J=7.91 Hz, 1H) 8.18 (d, J=8.03 Hz, 1H) 8.87 (s, 1H) 10.90 (br s, 1H).

Step 6: Synthesis of Compound WX052-9

WX052-8 (1.30 g, 3.11 mmol, 1.00 eq), p-methoxybenzylamine (4.26 g, 31.08 mmol, 4.02 mL, 10.00 eq) and potassium carbonate (1.28 g, 9.29 mmol, 2.99 eq) were added to acetonitrile (3.00 mL). The mixture was stirred at 100° C. for 32 hours. The reaction solution was added with water (20 mL), and extracted with dichloromethane (20 mL*3). The organic phases were combined, washed with saturated brine (20 mL), dried over anhydrous sodium sulfate, and filtered. The filtrate was dried on a rotary evaporator under reduced pressure. 25 mL of petroleum ether/ethyl acetate (5/1) was added, and slurried at 15° C. for 0.5 hour. The supernatant liquid was filtered out. 25 mL of petroleum ether/ethyl acetate (5/1) was added to the underlayer solid, and slurried at 15° C. for 0.5 hour. A solid precipitated out and was filtered, and the filter cake was dried on a rotary evaporator under reduced pressure to obtain WX052-9. $^1$H NMR (400 MHz, DMSO-d6) δ=8.87 (s, 1H), 8.00-7.98 (m, 1H), 8.01-7.96 (m, 1H), 7.92 (s, 1H), 7.84 (dd, J=2.5, 6.0 Hz, 1H), 7.75 (br t, J=5.3 Hz, 1H), 7.31 (d, J=8.5 Hz, 2H), 6.92 (d, J=8.5 Hz, 2H), 6.79 (s, 1H), 5.73-5.62 (m, 1H), 4.34 (br d, J=5.3 Hz, 2H), 3.76-3.73 (m, 3H), 2.29 (s, 3H), 1.43 (d, J=6.8 Hz, 6H).

Step 7: Synthesis of Compound WX052-10

WX052-9 (1.60 g, 2.73 mmol, 1.00 eq) (purity 91.48) was dissolved in trifluoroacetic acid (15.00 mL). The system was stirred at 20° C. for 1 hour. The reaction solution was added dropwise with saturated aqueous sodium bicarbonate (100 mL) with stirring, and extracted with DCM (50 mL*2). The organic phase was washed with water (100 mL) and saturated brine (100 mL), dried over anhydrous magnesium sulfate, and filtered. The filtrate was dried on a rotary evaporator under reduced pressure to obtain a product WX052-10. $^1$H NMR (400 MHz, CHLOROFORM-d) δ ppm 1.56 (d, J=6.78 Hz, 6H) 2.35 (s, 3H) 5.39-5.71 (m, 3H) 6.66 (s, 1H) 7.66 (s, 1H) 7.85-7.93 (m, 1H) 8.00 (d, J=7.53 Hz, 1H) 8.28 (br d, J=7.78 Hz, 2H) 8.37 (s, 1H).

Step 8: Synthesis of Compound WX052-11

WX052-10 (1.25 g, 2.45 mmol, 1.00 eq) (purity 81.465%) was dissolved in HCOOH (10.00 mL). The system was stirred at 100° C. for 1 hour. The reaction solution was dried on a ratory evaporator under reduced pressure to give yellow oil, which was diluted with water (20 mL), added with saturated NaCO$_3$ solution (50 mL) with stirring and extracted with DCM (50 mL*2). The organic phase was washed with water (100 mL) and saturated brine (100 mL), dried over anhydrous sodium sulfate, and filtered. The filtrate was dried on a rotary evaporator under reduced pressure to obtain a product WX052-11. $^1$H NMR (400 MHz, DMSO-d$_6$) δ ppm 1.47 (d, J=6.78 Hz, 6H) 2.54 (s, 3H) 5.32 (dt, J=13.36, 6.74 Hz, 1H) 7.80 (s, 1H) 7.93-7.97 (m, 1H) 8.24-8.29 (m, 2H) 8.35 (s, 1H) 8.71 (s, 1H) 8.94 (s, 1H).

Step 9. Synthesis of Compound WX052

WX052-11 (0.1 g, 214.03 μmol, 1 eq) (purity: 91.024%), WX052-5 (80 mg, 323.70 μmol, 1.51 eq), potassium carbonate (89 mg, 643.97 μmol, 3.01 eq) and Pd(dppf)Cl$_2$ (8 mg, 10.93 μmol, 5.11e-2 eq) were added to dioxane (5 mL) and water (1 mL). The mixture was stirred at 80° C. for 16 hours under nitrogen. The reaction solution was dried on a rotary evaporator, added with dichloromethane (200 mL), stirred at 15° C. for 10 minutes and filtered. The filtrate was dried on a rotary evaporator under reduced pressure. The crude product was purified with preparative TLC (dichloromethane/methanol=20/1) to give WX052, $^1$H NMR (400 MHz, CHLOROFORM-d) δ=8.51 (s, 1H), 8.50 (s, 1H), 8.36 (dd, J=0.8, 7.8 Hz, 1H), 8.33 (s, 1H), 8.18 (s, 1H), 8.02 (t, J=8.0 Hz, 1H), 7.89 (dd, J=0.8, 8.0 Hz, 1H), 7.64 (s, 1H), 7.58 (dd, J=2.3, 8.0 Hz, 1H), 7.23 (d, J=8.0 Hz, 1H), 5.44 (quin, J=6.7 Hz, 1H), 3.09 (spt, J=6.9 Hz, 1H), 2.41 (s, 3H), 1.50 (s, 3H), 1.49 (s, 3H), 1.32 (s, 3H), 1.30 (s, 3H).

Example 053: WX053

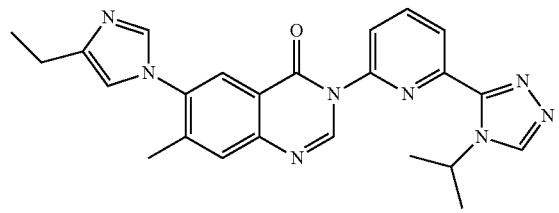 [SMILES: CCc1cn(-c2cc3c(=O)n(-c4cccc(-c5nncn5C(C)C)n4)cnc3cc2C)cn1]

Synthetic Route:

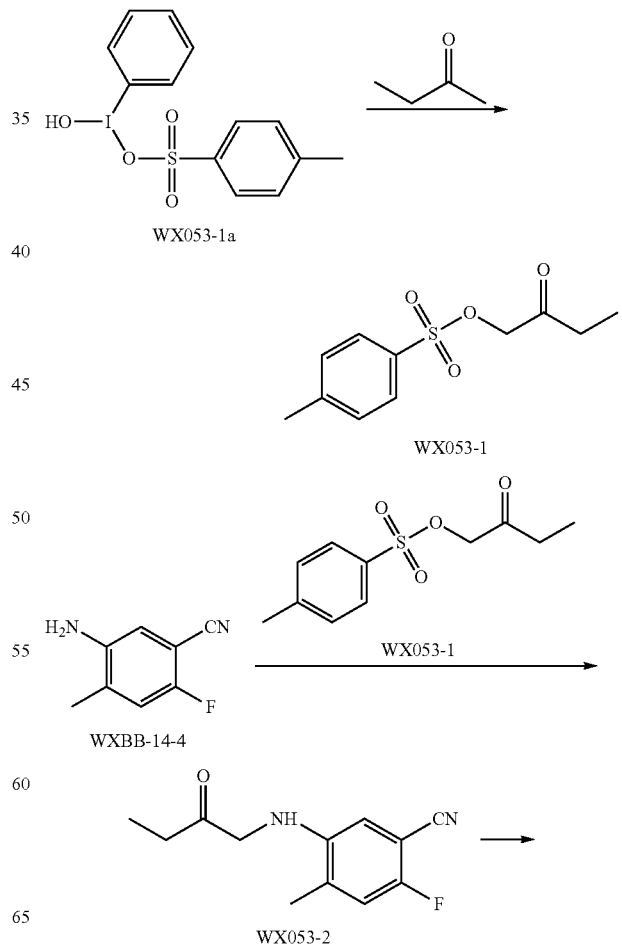

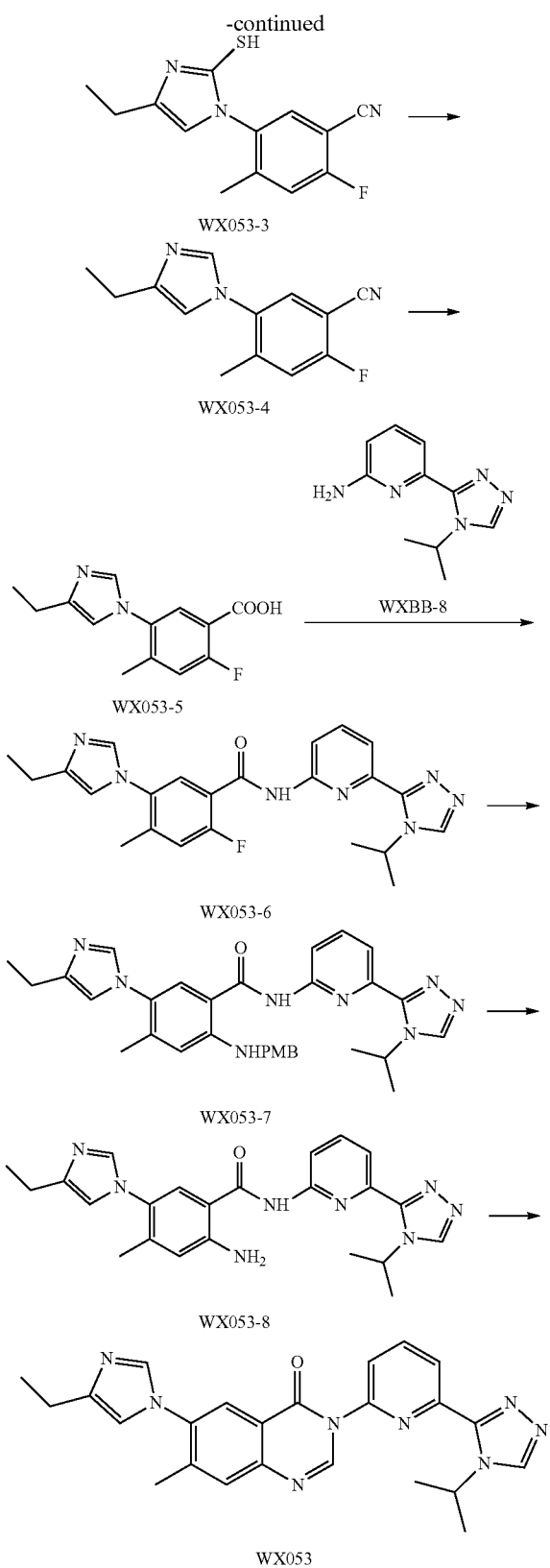

Step 1: Synthesis of Compound WX053-1

Compound WX053-1a (50 g, 127.48 mmol, 1.00 eq) was dissolved in acetonitrile (300 mL), and 2-butanone (9.19 g, 127.48 mmol, 11.35 mL, 1.00 eq) was added. The mixture was stirred at 75° C. for 3 hours. The reaction solution was cooled to room temperature, evaporated on a rotary evaporator to remove the solvent, added with water (100 mL), and extracted with dichloromethane (50 mL*3). The organic phase was washed with saturated sodium chloride (100 mL), dried over anhydrous sodium sulfate, and filtered. The filtrate was dried on a rotary evaporator under reduced pressure. The product was washed with n-hexane (50 mL*2) and dried to obtain compound WX053-1. $^1$H NMR (400 MHz, DMSO-d6) δ ppm 0.90 (t, J=7.28 Hz, 1H) 1.28 (d, J=7.03 Hz, 2H) 2.11 (s, 2H) 2.40-2.45 (m, 3H) 4.82 (s, 1H) 4.99 (q, J=6.86 Hz, 1H) 7.46-7.53 (m, 2H) 7.80-7.87 (m, 2H).

Step 2: Synthesis of Compound WX053-2

Compound WXBB-14-4 (15 g, 87.24 mmol, 1.00 eq) (purity 87.329%) and compound WX053-1 (25.37 g, 104.69 mmol, 1.2 eq) (crude) were dissolved in anhydrous toluene (150 mL), and diisopropylethylamine (22.56 g, 174.57 mmol, 30.49 mL, 2.00 eq) was added. The mixture was stirred at 90-100° C. for 16 hours. The reaction solution was cooled to room temperature, evaporated on a rotary evaporator to remove the solvent, added with water (50 mL), and extracted with dichloromethane (50 mL*3). The organic phase was washed with saturated sodium chloride (50 mL), dried over anhydrous sodium sulfate, and filtered. The filtrate was dried on a rotary evaporator under reduced pressure. The crude product was purified by column (ethyl acetate/petroleum ether=0~20%) to obtain compound WX053-2. $^1$H NMR (400 MHz, CHLOROFORM-d) δ ppm 1.18-1.25 (m, 2H) 1.49 (d, J=7.03 Hz, 3H) 2.26-2.29 (m, 6H) 2.30 (s, 3H) 2.60 (q, J=7.36 Hz, 1H) 2.59-2.60 (m, 1H) 2.59-2.60 (m, 1H) 4.01 (s, 2H) 4.62 (br s, 2H) 6.50-6.55 (m, 2H) 6.96 (d, J=9.29 Hz, 2H).

Step 3: Synthesis of Compound WX053-3

Compound WX053-2 (2.34 g, 10.62 mmol, 1 eq) was dissolved in acetic acid (20 mL), purged with nitrogen 3 times, and potassium thiocyanate (2.07 g, 21.25 mmol, 2.07 mL, 2 eq) was added. The mixture was stirred at 110° C. for 4 hours. The reaction solution was cooled to room temperature, evaporated on a rotary evaporator to remove part of solvent, adjusted to pH=8 by adding saturated sodium bicarbonate (30 mL), and extracted with dichloromethane (10 mL*3). The organic phases were combined, washed with saturated sodium chloride (15 mL), dried over anhydrous sodium sulfate, and filtered. The filtrate was dried on a rotary evaporator under reduced pressure. The crude product was purified by column (ethyl acetate/petroleum ether=0~30%) to obtain compound WX053-3. $^1$H NMR (400 MHz, CHLOROFORM-d) δ ppm 1.24-1.29 (m, 3H) 2.13 (s, 3H) 2.55 (q, J=7.53 Hz, 2H) 6.36-6.42 (m, 1H) 7.46 (d, J=6.02 Hz, 1H) 7.55-7.60 (m, 1H).

Step 4: Synthesis of Compound WX053-4

Hydrogen peroxide (2.73 g, 24.11 mmol, 2.32 mL, 30% purity, 3 eq) was dissolved in acetic acid (15 mL) and water (3 mL). The system was stirred at 45° C. for 1 hour under nitrogen atmosphere. Then WX053-3 (2.1 g, 8.04 mmol, 1 eq) was slowly added. The reaction system was stirred at 55° C. for 1 hour under nitrogen atmosphere. Then the reaction solution was cooled to room temperature, and added with saturated sodium sulfite solution until no blue color was detected with a starch potassium iodide test paper. Part of solvent was evaporated on a ratory evaporator. The starch potassium iodide test paper showed no hydrogen peroxide remained. The mixture was adjusted pH=8 with sodium bicarbonate (20 mL) and extracted with dichloromethane (20 mL*3). The organic phase was washed with saturated sodium chloride (30 mL), dried over anhydrous sodium sulfate, and filtered. The filtrate was dried on a rotary evaporator under reduced pressure. The crude product was purified by column (methanol/dichloromethane=0~5%) to obtain compound WX053-4. ¹H NMR (400 MHz, CHLOROFORM-d) δ ppm 1.22 (t, J=7.53 Hz, 3H) 2.20 (s, 3H) 2.56-2.67 (m, 2H) 6.66 (d, J=0.75 Hz, 1H) 7.14 (d, J=9.03 Hz, 1H) 7.39 (d, J=1.25 Hz, 1H) 7.44 (d, J=6.02 Hz, 1H).

Step 5: Synthesis of Compound WX053-5

Compound WX053-4 (0.8 g, 2.76 mmol, 1 eq) (purity 78.964%) was dissolved in concentrated hydrochloric acid (8.16 g, 85.04 mmol, 8 mL, 38% purity, 30.86 eq). The mixture was stirred at 100° C. for 5 hours. The reaction solution was dried directly and slurried with dichloromethane/methanol (10/1, 22 mL) at 20° C. for 0.5 hour and filtered. The filtrate was dried on a rotary evaporator under reduced pressure to obtain compound WX053-5. ¹H NMR (400 MHz, DMSO-d6) δ ppm 1.27 (t, J=7.53 Hz, 3H) 2.26 (s, 3H) 2.66-2.78 (m, 2H) 7.53-7.60 (m, 1H) 7.80 (s, 1H) 8.03 (d, J=6.78 Hz, 1H) 9.36 (d, J=1.51 Hz, 1H).

Step 6: Synthesis of Compound WX053-6

Compound WX053-5 (750 mg, 1.73 mmol, 1 eq, HCl) (purity 65.548%) was dissolved in anhydrous dichloromethane (5 mL), and anhydrous N,N-dimethylformamide (13 mg, 177.85 μmol, 13.68 μL, 0.1 eq) and oxalyl chloride (373 mg, 2.94 mmol, 257.24 μL, 1.7 eq) were added. The mixture was stirred at 20° C. for 1 hour. The solvent was evaporated on a rotary evaporator to become thick mixture, and then 5 mL of anhydrous dichloromethane was added. This process was reapeated three times. Compound WXBB-8 (421 mg, 2.07 mmol, 1.2 eq) and diisopropylethylamine (223 mg, 1.73 mmol, 300.54 μL, 9.99e-1 eq) were added. The mixture was stirred at 20° C. for 2 hours. The reaction solution was added with water (30 mL), and extracted with dichloromethane (30 mL*3). The organic phase was washed with saturated sodium chloride (40 mL), dried over anhydrous sodium sulfate, and filtered. The filtrate was dried on a rotary evaporator under reduced pressure. The crude product was purified by column (methanol/dichloromethane=0~10%) to obtain compound WX053-6. 1H NMR (400 MHz, DMSO-d6) δ ppm 1.18-1.22 (m, 3H) 1.44 (d, J=6.78 Hz, 6H) 2.26 (s, 3H) 2.90 (s, 2H) 5.64 (dt, J=13.30, 6.65 Hz, 1H) 7.15 (s, 1H) 7.51 (t, J=10.16 Hz, 1H) 7.66 (d, J=6.78 Hz, 1H) 7.76 (d, J=1.25 Hz, 1H) 7.89 (d, J=7.03 Hz, 1H) 7.96 (s, 1H) 8.04 (t, J=8.03 Hz, 1H) 8.20 (d, J=8.28 Hz, 1H) 8.87 (s, 1H).

Step 7: Synthesis of Compound WX053-7

Compound WX053-6 (500 mg, 899.12 μmol, 1 eq) (purity 77.95%) was dissolved in acetonitrile (1 mL), and p-methoxybenzylamine (1.23 g, 8.99 mmol, 1.16 mL, 10 eq) and potassium carbonate (249 mg, 1.80 mmol, 2 eq) were added. The mixture was stirred at 100° C. for 16 hours. The reaction solution was added with water (20 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure. The crude was purified by a column (methanol/dichloromethane=0~5%). A mixture of petroleum ether/ethyl acetate (5/1, 6 mL) was poured into the obtained product, stirred for 5 min, and left to stand. The supernatant was poured, and the underlayer oil matter was retained and dried on a ratory evaporator. The obtained oil was purified by prep-TLC (methanol/dichloromethane=1/10) to obtain compound WX053-7. MS: m/z=276.2 [M+1]/2.

Step 8: Synthesis of Compound WX053-8

Compound WX053-7 (150 mg, 246.05 μmol, 1 eq) (purity 90.324%) was dissolved in trifluoroacetic acid (2 mL). The mixture was stirred at 20° C. for 2 hours. The reaction solution was adjusted to pH=8 by adding slowly saturated sodium carbonate (20 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure. The crude product was purified by prep-TLC (methanol/dichloromethane=1/10) to obtain compound WX053-8. ¹H NMR (400 MHz, CHLOROFORM-d) δ ppm 1.24 (br t, J=7.40 Hz, 3H) 1.46 (br d, J=6.53 Hz, 6H) 2.09 (s, 3H) 2.62 (q, J=7.36 Hz, 2H) 5.46 (dt, J=13.30, 6.65 Hz, 1H) 5.82 (br s, 2H) 6.66 (s, 1H) 6.71 (s, 1H) 7.42 (s, 1H) 7.47 (s, 1H) 7.84-7.91 (m, 1H) 7.92-7.98 (m, 1H) 8.24 (br d, J=8.28 Hz, 1H) 8.32 (s, 1H) 8.80 (br s, 1H).

Step 9: Synthesis of Compound WX053

Compound WX053-8 (50 mg, 116.14 μmol, 1 eq) was dissolved in formic acid (1 mL). The mixture was stirred at 110° C. for 1 hour. The reaction was dried directly. The resulting crude product was subjected to HPLC and found to have a purity of 87.59%. The crude product was separated and purified by flash preparative chromatography (column: Xtimate C18 150*25 mm*5 μm; mobile phase: [water (0.225% FA)-ACN]; B %: 15%-25%, 12 min) to obtain compound WX053. ¹H NMR (400 MHz, CHLOROFORM-d) δ ppm 1.34 (br t, J=7.28 Hz, 3H) 1.56 (br s, 3H) 1.58 (br s, 3H) 2.42 (s, 3H) 2.77 (br d, J=7.28 Hz, 2H) 5.44-5.54 (m, 1H) 6.90 (br s, 1H) 7.77 (s, 1H) 7.91 (br s, 1H) 7.95 (br d, J=8.03 Hz, 1H) 8.11 (br t, J=7.91 Hz, 1H) 8.27 (s, 1H) 8.45 (br d, J=8.03 Hz, 2H) 8.61 (s, 1H).

Example 054: WX054

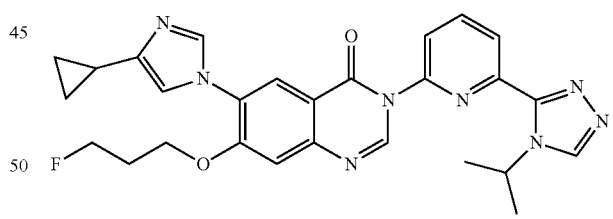

Synthetic Route:

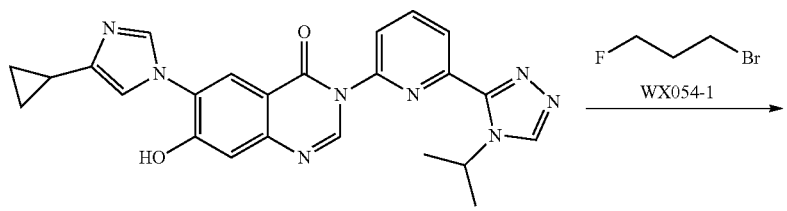

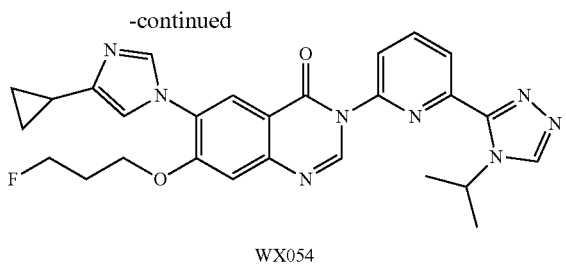

WX054

Step 1. Synthesis of Compound WX054

WX037 (0.05 g, 110.01 μmol, 1 eq) was dissolved in anhydrous DMF (2 mL), and potassium carbonate (0.03 g, 217.07 μmol, 1.97 eq) and WX054-1 (0.02 g, 141.86 μmol, 1.29 eq) were added. The system was stirred at 50° C. for 3 hour. The crude product was separated and purified with prep-HPLC (column: Waters Xbridge 150*25 mm 5 μm; mobile phase: [water (10 mM NH$_4$HCO$_3$)-ACN]; B %: 20%-45%, 10 min) to obtain product WX054. $^1$H NMR (400 MHz, CHLOROFORM-d) δ ppm 0.81-0.87 (m, 2H) 0.88-0.94 (m, 2H) 1.58 (d, J=6.78 Hz, 6H) 1.88-1.98 (m, 1H) 2.22 (br t, J=6.02 Hz, 1H) 2.26-2.34 (m, 1H) 4.35 (t, J=6.02 Hz, 2H) 4.56 (t, J=5.40 Hz, 1H) 4.68 (t, J=5.52 Hz, 1H) 5.50 (dt, J=13.24, 6.56 Hz, 1H) 7.03 (s, 1H) 7.35 (s, 1H) 7.78 (s, 1H) 7.97 (d, J=8.03 Hz, 1H) 8.11 (t, J=7.91 Hz, 1H) 8.27 (s, 1H) 8.38-8.50 (m, 2H) 8.58 (s, 1H).

Example 055: WX055

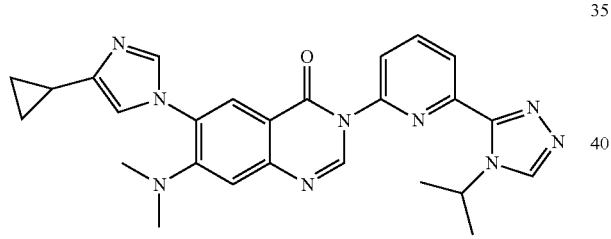

Synthetic Route:

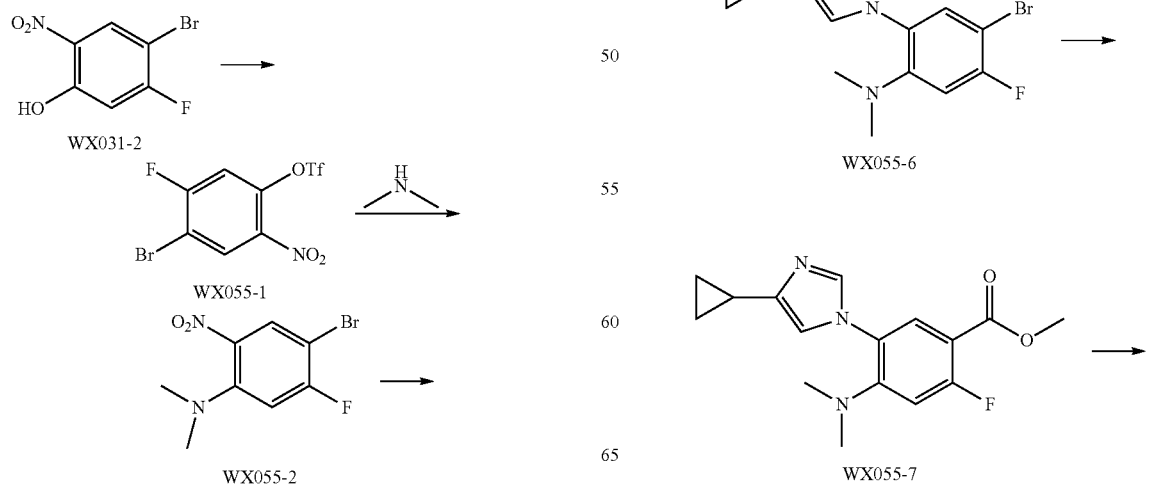

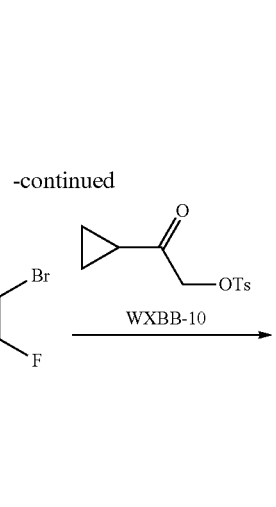

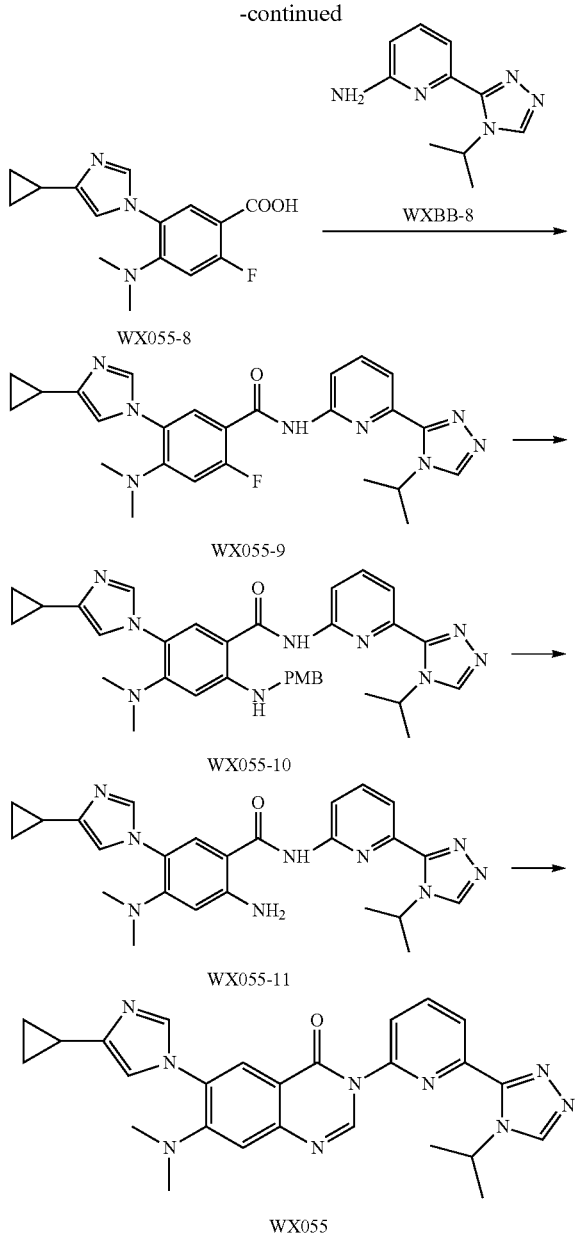

Step 1: Synthesis of Compound WX055-1

Compound WX031-2 (24 g, 101.70 mmol, 1 eq) was dissolved in anhydrous dichloromethane (200 mL), and dimethylaminopyridine (0.65 g, 5.32 mmol, 0.05 eq) and diisopropylethylamine (26.29 g, 203.39 mmol, 35.43 mL, 2 eq) were added. The system was cooled to 0° C., trifluoromethanesulfonic anhydride (43.04 g, 152.55 mmol, 25.17 mL, 1.5 eq) was slowly added at 0° C., and then warmed to 20° C. and stirred for 2 hours. To the reaction solution was added water (200 mL) with stirring. The organic phase was dried on a rotary evaporator under reduced pressure to obtain a crude product. The crude product was purified by column (ethyl acetate/petroleum ether=0~5%) to obtain WX055-1. $^1$H NMR (400 MHz, CHLOROFORM-d) δ ppm 7.29 (d, J=7.53 Hz, 1H) 8.51 (d, J=6.52 Hz, 1H).

Step 2: Synthesis of Compound WX055-2

Compound WX055-1 (24 g, 65.21 mmol, 1 eq) was dissolved in anhydrous toluene (200 mL), purged with nitrogen 3 times, and dimethylamine (4.80 g, 58.86 mmol, 5.39 mL, 0.9 eq, HCl), sodium tert-butoxide (9.36 g, 97.39 mmol, 1.49 eq) and Pd$_2$(dba)$_3$ (4.80 g, 5.24 mmol, 0.08 eq) were added. The mixture was stirred at 105° C. for 12 hours under a nitrogen atmosphere. The reaction solution was cooled to room temperature, added with water (400 mL), and extracted with ethyl acetate (200 mL*3). The organic phases were combined, washed with saturated sodium chloride (300 mL), dried over anhydrous sodium sulfate, and filtered. The filtrate was dried on a rotary evaporator under reduced pressure. The crude product was purified by column (ethyl acetate/petroleum ether=0~5%) to obtain WX055-2. $^1$H NMR (400 MHz, CHLOROFORM-d) δ ppm 2.91 (s, 6H) 6.75 (d, J=11.04 Hz, 1H) 8.02-8.07 (m, 1H).

Step 3: Synthesis of Compound WX055-3

Compound WX055-2 (9 g, 28.59 mmol, 1 eq) (purity 83.568%) was dissolved in acetic acid (80 mL), and iron powder (6.39 g, 114.36 mmol, 4 eq) was added in portions. The mixture was stirred at 20° C. for 16 hours. The reaction solution was added dropwise to saturated NaOH (100 mL), and extracted with ethyl acetate (50 mL*3). The organic phase was washed with sodium chloride (100 mL), dried over anhydrous sodium sulfate, and filtered. The filtrate was dried on a rotary evaporator under reduced pressure. The crude product was purified by column (ethyl acetate/petroleum ether=0~25%) to obtain WX055-3. $^1$H NMR (400 MHz, CHLOROFORM-d) δ ppm 2.65 (s, 6H) 6.80 (d, J=10.29 Hz, 1H) 6.86 (d, J=6.78 Hz, 1H).

Step 4: Synthesis of Compound WX055-4

Compound WX055-3 (1.1 g, 3.42 mmol, 1 eq) (purity 72.474%) was dissolved in anhydrous toluene (10 mL), and compound WXBB-10 (3 g, 11.80 mmol, 3.45 eq) and diisopropylethylamine (928.29 mg, 7.18 mmol, 1.25 mL, 2.1 eq) were added. The mixture was reacted at 140° C. for 0.5 hour under microwave condition. The reaction solution was cooled to room temperature, added with water (50 mL), and extracted with ethyl acetate (50 mL*3). The organic phases were combined, washed with sodium chloride (50 mL), dried over anhydrous sodium sulfate, and filtered. The filtrate was dried on a rotary evaporator under reduced pressure. The crude product was purified by column (ethyl acetate/petroleum ether=0~10%) to obtain WX055-4. $^1$H NMR (400 MHz, CHLOROFORM-d) δ ppm 0.93 (dq, J=7.47, 3.70 Hz, 2H) 1.09 (quin, J=3.83 Hz, 2H) 1.90-1.99 (m, 1H) 2.56 (s, 6H) 4.07 (d, J=3.51 Hz, 2H) 6.49 (d, J=6.53 Hz, 1H) 6.73 (d, J=10.04 Hz, 1H).

Step 5: Synthesis of Compound WX055-5

Compound WX055-4 (750 mg, 2.38 mmol, 1 eq) was dissolved in acetic acid (8 mL), purged with nitrogen 3 times, and potassium thiocyanate (463 mg, 4.76 mmol, 463.00 µL, 2 eq) was added. The mixture was stirred at 110° C. for 4 hours under a nitrogen atmosphere. The reaction solution was cooled to room temperature, concentrated under reduced pressure, adjusted to pH=8 by adding saturated sodium bicarbonate (20 mL), and extracted with dichloromethane (20 mL*3). The organic phase was washed with saturated sodium chloride (30 mL), dried over anhydrous sodium sulfate, and filtered. The filtrate was dried on a rotary evaporator under reduced pressure. The product was used directly for the next step without purification to obtain compound WX055-5. $^1$H NMR (400 MHz, DMSO-d6) δ ppm 0.64-0.71 (m, 2H) 0.78-0.89 (m, 2H) 1.67-1.76 (m, 1H) 2.57 (s, 6H) 6.75 (d, J=1.51 Hz, 1H) 7.00 (d, J=11.80 Hz, 1H) 7.40 (d, J=7.53 Hz, 1H) 12.28 (br s, 1H).

Step 6: Synthesis of Compound WX055-6

Compound WX055-5 (500 mg, 1.40 mmol, 1 eq) was dissolved in acetic acid (5 mL), and water (1 mL) and hydrogen peroxide (477 mg, 4.21 mmol, 404.24 µL, 30% purity, 3 eq) were added. The mixture was stirred at 45° C. for 1 hour. Then the reaction solution was cooled to room temperature, and added with saturated sodium sulfite solution until no blue color was detected with a starch potassium iodide test paper. Part of solvent was evaporated on a ratory evaporator. The starch potassium iodide test paper showed no hydrogen peroxide remained. The mixture was adjusted to pH=8 with sodium bicarbonate (20 mL) and extracted with dichloromethane (20 mL*3). The organic phase was washed with saturated sodium chloride (50 mL), dried over anhydrous sodium sulfate, and filtered. The filtrate was dried on a rotary evaporator under reduced pressure. The product was used directly for the next step without purification to obtain compound WX055-6. 1H NMR (400 MHz, DMSO-d6) δ ppm 0.62-0.71 (m, 2H) 0.77-0.82 (m, 2H) 2.32-2.34 (m, 1H) 2.43 (s, 6H) 7.08 (d, J=11.29 Hz, 1H) 7.14 (s, 1H) 7.56 (d, J=7.53 Hz, 1H) 7.69 (s, 1H).

Step 7: Synthesis of Compound WX055-7

Compound WX055-6 (400 mg, 1.09 mmol, 1 eq) (purity 88.522%) was dissolved in methanol (4 mL), then Pd(dppf)Cl$_2$ (120 mg, 164.00 µmol, 0.15 eq) and triethylamine (221 mg, 2.18 mmol, 303.99 µL, 2 eq) were added, and carbon monoxide (50 Psi) was introduced. The mixture was stirred at 70° C. for 16 hours. The reaction solution was dried directly. The crude product was purified by column (ethyl acetate/petroleum ether=0~30%). The product was further purified by prep-TLC (ethyl acetate) to obtain compound WX055-7. $^1$H NMR (400 MHz, CHLOROFORM-d) δ ppm 0.77-0.83 (m, 2H) 0.85-0.92 (m, 2H) 1.86-1.95 (m, 1H) 2.61 (s, 6H) 3.89 (s, 3H) 6.63 (d, J=13.30 Hz, 1H) 6.86 (d, J=1.00 Hz, 1H) 7.54 (d, J=1.00 Hz, 1H) 7.73 (d, J=7.78 Hz, 1H).

Step 8: Synthesis of Compound WX055-8

Compound WX055-7 (200 mg, 566.13 µmol, 1 eq) (purity 85.863%) was dissolved in a mixture of tetrahydrofuran (1 mL) and water (1 mL) (volume ratio of 1:1), and lithium hydroxide (41 mg, 1.71 mmol, 3.02 eq) was added. The mixture was stirred at 20° C. for 1 hour. The reaction was dried directly to obtain compound WX055-8. $^1$H NMR (400 MHz, DMSO-d6) δ ppm 0.65-0.71 (m, 2H) 0.75-0.81 (m, 2H) 1.79-1.88 (m, 1H) 2.41 (s, 6H) 6.67 (d, J=12.30 Hz, 1H) 7.06 (s, 1H) 7.44 (d, J=8.03 Hz, 1H) 7.61 (s, 1H).

Step 9: Synthesis of Compound WX055-9

Compound WX055-8 (500 mg, 1.73 mmol, 1 eq) (crude) and compound WXBB-8 (700 mg, 3.44 mmol, 1.99 eq) were dissolved in pyridine (5 mL), and phosphorus oxychloride (530.00 mg, 3.46 mmol, 321.21 µL, 2 eq) was added. The mixture was stirred at 20° C. for 6 hours and then added with water (50 mL) and extracted with dichloromethane (50 mL*3). The organic phases were combined, washed with saturated sodium chloride (100 mL), dried over anhydrous sodium sulfate, and filtered. The filtrate was dried on a rotary evaporator under reduced pressure. The crude product was purified by column (methanol/dichloromethane=0~10%) to obtain compound WX055-9. $^1$H NMR (400 MHz, CHLOROFORM-d) δ ppm 0.79-0.84 (m, 2H) 0.88-0.93 (m, 2H) 1.60 (s, 3H) 1.62 (s, 3H) 1.88-1.96 (m, 1H) 2.65 (s, 6H) 5.51 (dt, J=13.55, 6.78 Hz, 1H) 6.70 (d, J=15.06 Hz, 1H) 6.89 (s, 1H) 7.59 (s, 1H) 7.89-7.94 (m, 1H) 7.99 (d, J=8.53 Hz, 1H) 8.05 (d, J=7.28 Hz, 1H) 8.38 (s, 1H) 8.40 (d, J=8.03 Hz, 1H) 9.03 (br d, J=16.81 Hz, 1H).

Step 10: Synthesis of Compound WX055-10

Compound WX055-9 (250 mg, 526.83 µmol, 1 eq) was dissolved in acetonitrile (2 mL), and p-methoxybenzylamine (723 mg, 5.27 mmol, 682.08 µL, 10 eq) and potassium carbonate (73 mg, 528.20 µmol, 1 eq) were added. The mixture was stirred at 100° C. for 40 hours. The reaction solution was added with water (20 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure. The crude product was purified by prep-TLC (methanol/dichloromethane=1/10) to obtain compound WX055-10. MS: m/z=296.7 [M+1]/2.

Step 11: Synthesis of Compound WX055-11

Compound WX055-10 (180 mg, 177.77 µmol, 1 eq) (purity 58.436%) was dissolved in trifluoroacetic acid (1 mL). The mixture was stirred at 20° C. for 3 hours. The reaction solution was adjusted to pH=8 by adding slowly saturated sodium carbonate (20 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure to obtain compound WX055-11. MS: m/z=236.5 [M+1]/2.

Step 12 Synthesis of Compound WX055

Compound WX055-11 (80 mg, 118.44 µmol, 1 eq) (purity 69.816%) was dissolved in trimethyl orthoformate (1 mL). The mixture was stirred at 110° C. for 2 hours, and then dried directly. The crude product was separated and purified by flash preparative chromatography (column: Phenomenex Gemini C18 250*50 mm*10 µm; mobile phase: [water (0.05% aqueous ammonia v/v)-ACN]; B %: 38%-48%, 8 min) to obtain compound WX055. $^1$H NMR (400 MHz, DMSO-d6) δ ppm 0.72 (br d, J=2.76 Hz, 2H) 0.81 (br d, J=8.03 Hz, 2H) 1.48 (br d, J=6.53 Hz, 6H) 1.87 (br d, J=4.77 Hz, 1H) 2.60 (s, 6H) 5.23-5.40 (m, 1H) 7.21 (s, 1H) 7.24 (s, 1H) 7.81 (s, 1H) 7.88 (s, 1H) 7.91-7.97 (m, 1H) 8.25 (br d, J=3.76 Hz, 2H) 8.67 (s, 1H) 8.95 (s, 1H).

Example 056: WX056

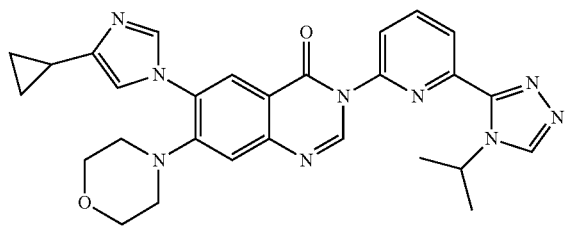 [SMILES: CC(C)n1cnnc1-c1cccc(-n2cnc3cc(N4CCOCC4)c(-n4cnc(C5CC5)c4)cc3c2=O)n1]

Synthetic Route:

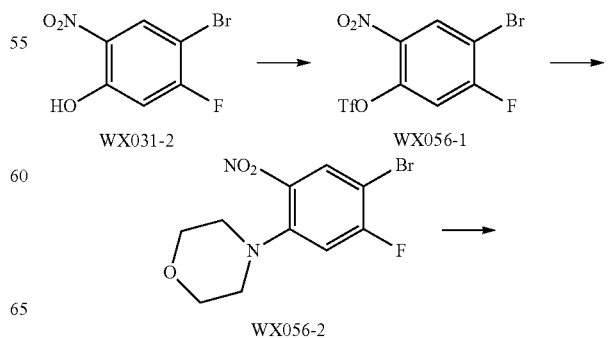

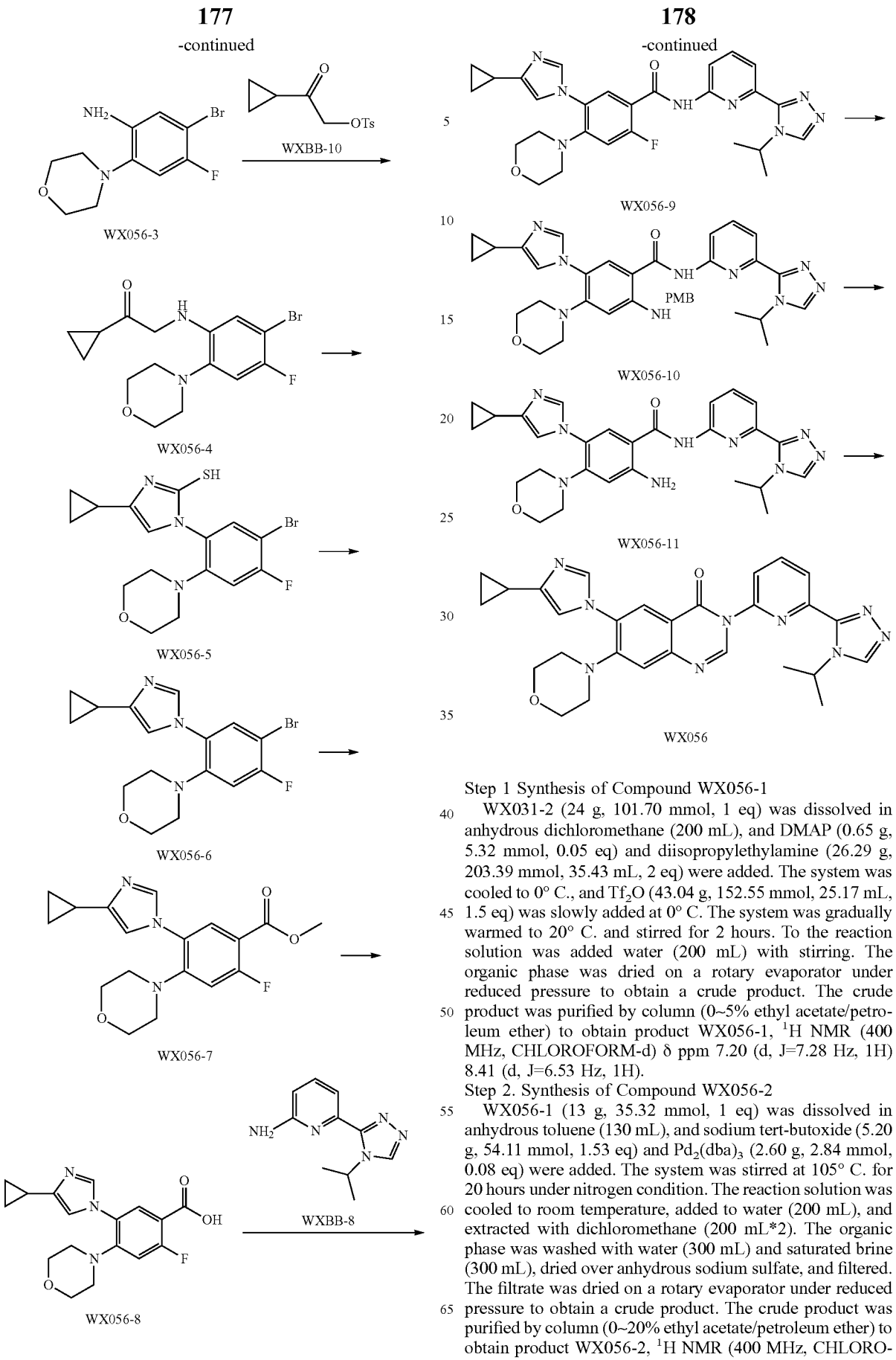

Step 1 Synthesis of Compound WX056-1

WX031-2 (24 g, 101.70 mmol, 1 eq) was dissolved in anhydrous dichloromethane (200 mL), and DMAP (0.65 g, 5.32 mmol, 0.05 eq) and diisopropylethylamine (26.29 g, 203.39 mmol, 35.43 mL, 2 eq) were added. The system was cooled to 0° C., and Tf$_2$O (43.04 g, 152.55 mmol, 25.17 mL, 1.5 eq) was slowly added at 0° C. The system was gradually warmed to 20° C. and stirred for 2 hours. To the reaction solution was added water (200 mL) with stirring. The organic phase was dried on a rotary evaporator under reduced pressure to obtain a crude product. The crude product was purified by column (0~5% ethyl acetate/petroleum ether) to obtain product WX056-1, $^1$H NMR (400 MHz, CHLOROFORM-d) δ ppm 7.20 (d, J=7.28 Hz, 1H) 8.41 (d, J=6.53 Hz, 1H).

Step 2. Synthesis of Compound WX056-2

WX056-1 (13 g, 35.32 mmol, 1 eq) was dissolved in anhydrous toluene (130 mL), and sodium tert-butoxide (5.20 g, 54.11 mmol, 1.53 eq) and Pd$_2$(dba)$_3$ (2.60 g, 2.84 mmol, 0.08 eq) were added. The system was stirred at 105° C. for 20 hours under nitrogen condition. The reaction solution was cooled to room temperature, added to water (200 mL), and extracted with dichloromethane (200 mL*2). The organic phase was washed with water (300 mL) and saturated brine (300 mL), dried over anhydrous sodium sulfate, and filtered. The filtrate was dried on a rotary evaporator under reduced pressure to obtain a crude product. The crude product was purified by column (0~20% ethyl acetate/petroleum ether) to obtain product WX056-2, $^1$H NMR (400 MHz, CHLORO- FORM-d) δ ppm 3.04-3.09 (m, 4H) 3.84-3.87 (m, 4H) 6.86 (d, J=10.04 Hz, 1H) 8.12 (d, J=7.03 Hz, 1H).

Step 3. Synthesis of Compound WX056-3

WX056-2 (8 g, 26.22 mmol, 1 eq) was dissolved in glacial acetic acid (80 mL), and iron powder (5.86 g, 104.88 mmol, 4 eq) was added slowly in portions with stirring. The system was stirred at 20° C. for 1 hour. The reaction solution was dried on a rotary evaporator under reduced pressure to obtain a crude product, added with water (200 mL) to dilute, added with saturated sodium bicarbonate solution (200 mL) to adjust the pH to 8~9, and extracted with dichloromethane (100 mL*2). The organic phase was washed with water (200 mL), dried over anhydrous sodium sulfate, and filtered. The filtrate was dried on a rotary evaporator under reduced pressure to obtain a product WX056-3.

Step 4. Synthesis of Compound WX056-4

WXBB-10 (6.98 g, 27.47 mmol, 3 eq) was dissolved in anhydrous toluene (30 mL), and WX056-3 (3 g, 9.16 mmol, 1 eq) (purity 83.959%) and diisopropylethylamine (2.49 g, 19.27 mmol, 3.36 mL, 2.1 eq) were added. The system was heated to 140° C. under microwave condition and stirred for 1 h. The reaction solution was cooled to room temperature, added with water (50 mL), and extracted with dichloromethane (50 mL*2). The organic phase was dried over anhydrous sodium sulfate and filtered. The filtrate was dried on a rotary evaporator under reduced pressure to obtain a crude product. The crude product was purified by column (0~12% ethyl acetate/petroleum ether) to obtain WX056-4.

Step 5. Synthesis of Compound WX056-5

WX056-4 (1.2 g, 2.71 mmol, 1 eq) (purity 80.641%) was dissolved in glacial acetic acid (20 mL), and potassium thiocyanate (0.36 g, 3.70 mmol, 360.00 μL, 1.37 eq) was added. The system was stirred at 110° C. for 3 hours. The reaction solution was cooled to room temperature, diluted with water (50 mL), and extracted with dichloromethane (100 mL*3). The organic phase was combined, added with a saturated sodium bicarbonate solution (200 mL), and stirred for 5 min. The pH of the organic phase was determined with a pH test paper to be 7-8. The organic phase was separated, washed with water (200 mL), dried over anhydrous magnesium sulfate and filtered. The filtrate was dried on a rotary evaporator under reduced pressure to obtain a product WX056-5.

Step 6. Synthesis of Compound WX056-6

WX056-5 (1.2 g, 2.62 mmol, 1 eq) (purity 87.114) was dissolved in a mixture of glacial acetic acid (12 mL) and water (2.5 mL), and hydrogen peroxide (0.9 g, 7.94 mmol, 762.71 μL, 30% purity, 3.02 eq) was added with stirring. The system was stirred at 45° C. for 0.5 hour. The reaction solution was cooled to room temperature, diluted with water (100 mL), and extracted with dichloromethane (50 mL*3). The organic phase was combined, added with a saturated sodium sulfite solution (50 mL), and stirred for 5 min. No blue color was detected with a starch potassium iodide test paper. Then a saturated $Na_2CO_3$ solution (200 mL) was added and stirred for 5 min. The pH of the organic phase was determined with a pH test paper to be 7~8. The organic phase was separated, washed with water (200 mL), dried over anhydrous magnesium sulfate and filtered. The filtrate was dried on a rotary evaporator under reduced pressure to obtain a product WX056-6.

Step 7. Synthesis of Compound WX056-7

WX056-6 (1 g, 1.78 mmol, 1 eq) (purity 65.303%) was dissolved in methanol (10 mL), and Pd(dppf)Cl$_2$ (0.04 g, 54.67 μmol, 0.15 eq) and triethylamine (400.00 mg, 3.95 mmol, 550.21 μL, 2.22 eq) were added. The system was stirred at 70° C. for 16 hours under CO (50 psi) condition. The reaction solution was dried on a rotary evaporator under reduced pressure to obtain a crude product which was purified by column (0~40% ethyl acetate/petroleum ether) to obtain WX056-7.

Step 8. Synthesis of Compound WX056-8

WX056-7 (0.6 g, 1.55 mmol, 1 eq) (purity 89.457%) was dissolved in anhydrous tetrahydrofuran (5 mL), and a solution of lithium hydroxide (0.112 g, 4.68 mmol, 3.01 eq) in water (5 mL) was added. The system was stirred at 20° C. for 1 hour. The reaction solution was dried on a rotary evaporator under reduced pressure to obtain a crude product. To the crude product was added a mixture of dichloromethane/methanol=10/1 (15 mL), stirred for 15 min, allowed to stand and filtered. The filtrate was dried on a rotary evaporator under reduced pressure to obtain a product WX056-8. $^1$H NMR (400 MHz, DMSO-$d_6$) δ ppm 0.66 (br d, J=3.01 Hz, 2H) 0.72-0.84 (m, 2H) 1.77-1.91 (m, 1H) 2.58 (br s, 4H) 3.55 (br s, 4H) 6.74 (d, J=11.80 Hz, 1H) 7.16 (s, 1H) 7.50 (d, J=7.78 Hz, 1H) 7.72 (s, 1H).

Step 9. Synthesis of Compound WX056-9

Compound WX056-8 (350 mg, 1.06 mmol, 1 eq) and compound WXBB-8 (214 mg, 1.05 mmol, 9.97e-1 eq) were dissolved in pyridine (4 mL), and phosphorus oxychloride (336.00 mg, 2.19 mmol, 203.64 μL, 2.07 eq) was added. The mixture was stirred at 20° C. for 6 hours, and then added with water (20 mL) and extracted with dichloromethane (20 mL*3). The organic phases were combined, washed with saturated sodium chloride (50 mL), dried over anhydrous sodium sulfate, and filtered. The filtrate was dried on a rotary evaporator under reduced pressure. The crude product was purified by prep-TLC (methanol/dichloromethane=1/10) to obtain compound WX056-9. $^1$H NMR (400 MHz, CHLOROFORM-d) δ ppm 0.72-1.02 (m, 3H) 1.16-1.38 (m, 1H) 1.41-1.80 (m, 10H) 1.92 (br s, 1H) 2.79 (br s, 2H) 3.72 (br s, 2H) 5.50 (br d, J=6.84 Hz, 1H) 6.82 (br d, J=14.33 Hz, 1H) 6.89-7.09 (m, 1H) 7.27 (s, 1H) 7.71 (s, 1H) 7.81-7.97 (m, 1H) 7.97-8.12 (m, 1H) 8.24-8.49 (m, 1H) 9.04 (br d, J=16.54 Hz, 1H).

Step 10: Synthesis of Compound WX056-10

Compound WX056-9 (120 mg, 220.33 μmol, 1 eq) (purity 94.848%) was dissolved in acetonitrile (1 mL), and p-methoxybenzylamine (302 mg, 2.20 mmol, 284.91 μL, 9.99 eq) and potassium carbonate (61 mg, 441.37 μmol, 2 eq) were added. The mixture was stirred at 110° C. for 40 hours. The reaction solution was added with water (20 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure. The crude product was purified by prep-TLC (methanol/dichloromethane=1/10) to obtain WX056-10 (220 mg, crude). MS: m/z=317.8 [M+1]/2.

Step 11: Synthesis of Compound WX056-11

Compound WX056-10 (220 mg, 347.14 μmol, 1 eq) (crude) was dissolved in TFA (2 mL). The mixture was stirred at 20° C. for 2 hours. The reaction solution was adjusted to pH=8 by adding slowly saturated sodium carbonate (20 mL), and extracted with dichloromethane (20 mL*3). The organic phases were combined, washed with saturated sodium chloride (20 mL), dried over anhydrous sodium sulfate, and filtered. The filtrate was dried on a rotary evaporator under reduced pressure. Compound WX056-11 was obtained, MS: m/z=257.7 [M+1]/2.

Step 12. Synthesis of Compound WX056

Compound WX056-11 (150 mg, 210.23 μmol, 1 eq) (purity 71.98%) was dissolved in trimethyl orthoformate (2 mL). The mixture was stirred at 110° C. for 2 hours. The reaction was dried directly. The crude product was purified by prep-TLC (methanol/dichloromethane=1/10). The crude product was separated and purified by flash preparative chromatography (column: Phenomenex Gemini C18 250*50 mm*10 μm; mobile phase: [water (0.05% aqueous ammonia v/v)-ACN]; B %: 25%-55%, 8 mM) to obtain compound WX056. ¹H NMR (400 MHz, DMSO-d6) δ ppm 0.71 (br d, J=2.76 Hz, 2H) 0.79-0.86 (m, 2H) 1.47 (s, 3H) 1.49 (s, 3H) 1.84-1.95 (m, 1H) 2.77 (br s, 4H) 3.64 (br s, 4H) 5.18-5.42 (m, 1H) 7.33 (s, 1H) 7.37 (s, 1H) 7.93-7.98 (m, 3H) 8.26 (d, J=3.76 Hz, 2H) 8.71 (s, 1H) 8.95 (s, 1H).

Example 057: WX057

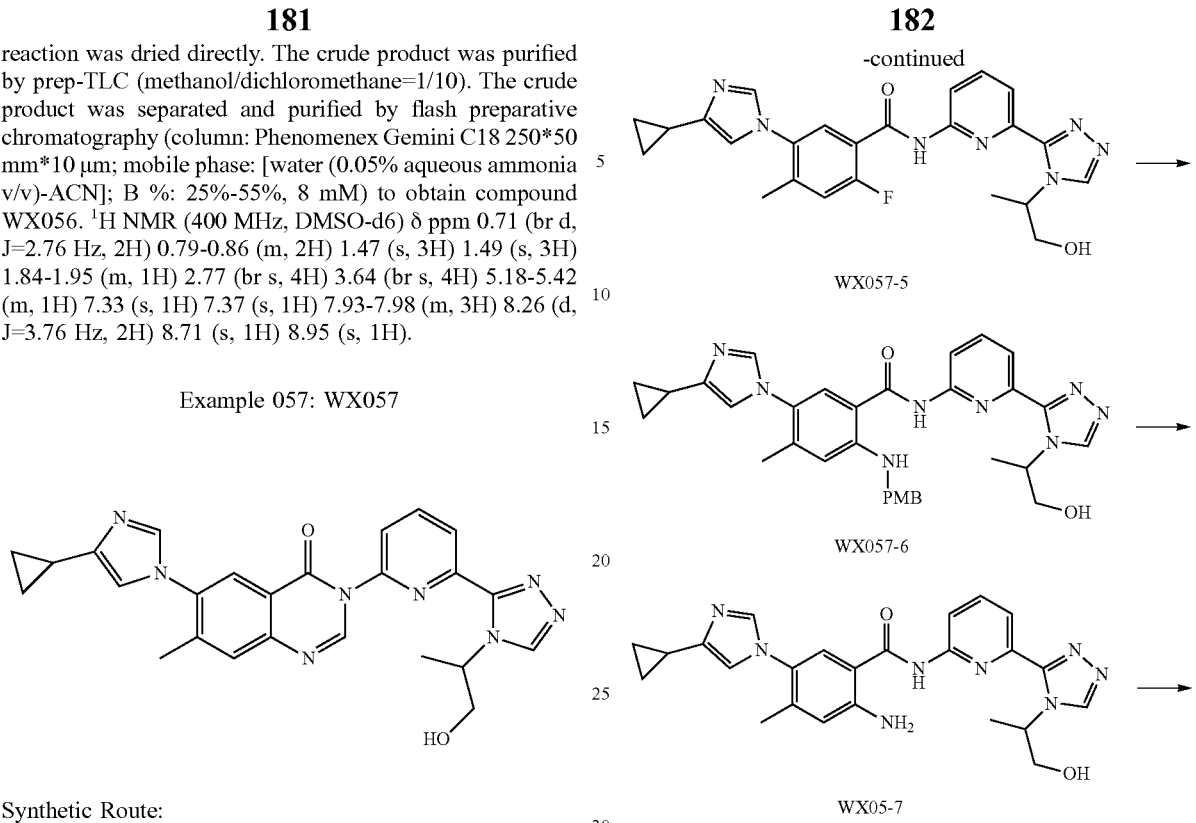

Synthetic Route:

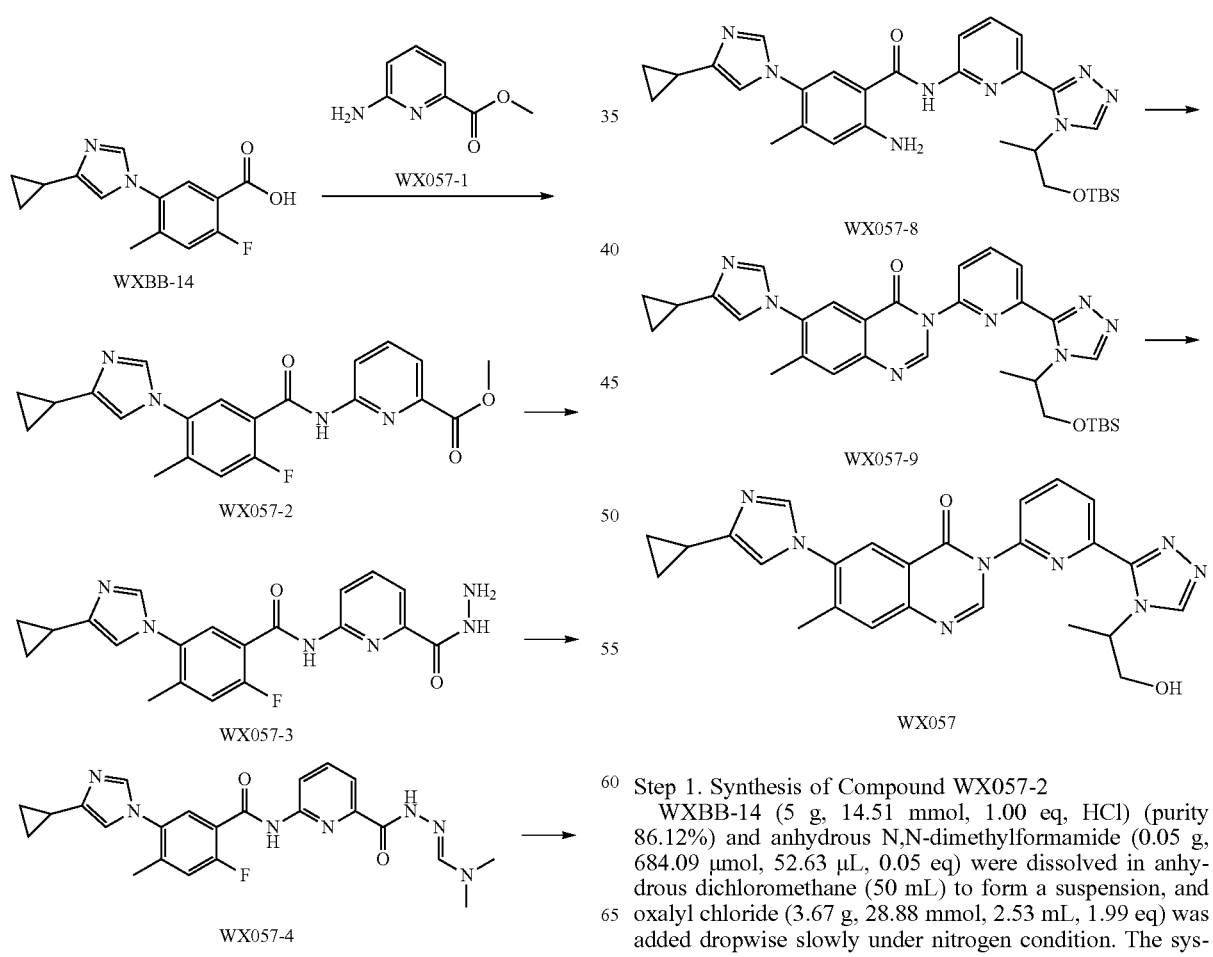

Step 1. Synthesis of Compound WX057-2

WXBB-14 (5 g, 14.51 mmol, 1.00 eq, HCl) (purity 86.12%) and anhydrous N,N-dimethylformamide (0.05 g, 684.09 μmol, 52.63 μL, 0.05 eq) were dissolved in anhydrous dichloromethane (50 mL) to form a suspension, and oxalyl chloride (3.67 g, 28.88 mmol, 2.53 mL, 1.99 eq) was added dropwise slowly under nitrogen condition. The system was stirred at 25° C. for 0.5 hour. The reaction solution was then evaporated on a rotary evaporator under reduced pressure to become thick, added with anhydrous dichloromethane (50 mL), evaporated on a rotary evaporator under reduced pressure to become thick again. This process was repeated three times. Afterwards, Anhydrous dichloromethane (50 mL) was added, and then diisopropylethylamine (3.75 g, 29.02 mmol, 5.07 mL, 2 eq), WX057-1 (2.21 g, 14.51 mmol, 1 eq) were added successively. The system was stirred at 25° C. for 0.5 hour. The reaction solution was added with water (100 mL) with stirring, and extracted with dichloromethane (100 mL*2). The organic phase was washed with saturated brine (100 mL), dried over anhydrous sodium sulfate, and filtered. The filtrate was dried on a rotary evaporator under reduced pressure to obtain a crude product which was then added with acetonitrile (8 mL), cooled to 0° C. and stirred for 10 min. A large amount of solid precipitated out and was filtered, and the filter cake was dried to give product WX057-2. $^1$H NMR (400 MHz, CHLOROFORM-d) δ ppm 0.79-0.87 (m, 2H) 0.87-0.94 (m, 2H) 1.89-1.93 (m, 1H) 2.28 (s, 3H) 4.01 (s, 3H) 6.79 (d, J=1.25 Hz, 1H) 7.20 (d, J=11.80 Hz, 1H) 7.46 (d, J=1.25 Hz, 1H) 7.91-7.96 (m, 2H) 7.98 (d, J=7.28 Hz, 1H) 8.48-8.63 (m, 1H) 9.14 (br d, J=12.05 Hz, 1H).

Step 2. Synthesis of Compound WX057-3

WX057-2 (4.5 g, 11.41 mmol, 1 eq) was dissolved in anhydrous methanol (40 mL), and hydrazine hydrate (1.34 g, 22.82 mmol, 1.30 mL, 85% purity, 2 eq) was added. The system was stirred at 80° C. for 2 hours. The reaction solution was cooled to room temperature and filtered. The filter cake was washed with ethyl acetate (20 mL) and then dried to give WX057-3. $^1$H NMR (400 MHz, DMSO-d6) δ ppm 0.64-0.73 (m, 2H) 0.75-0.84 (m, 2H) 1.79-1.88 (m, 1H) 2.24 (s, 3H) 4.59 (br s, 2H) 7.19 (d, J=1.00 Hz, 1H) 7.48 (d, J=11.29 Hz, 1H) 7.63-7.77 (m, 3H) 8.03 (t, J=7.91 Hz, 1H) 8.28 (br d, J=7.78 Hz, 1H) 9.35 (br s, 1H).

Step 3. Synthesis of Compound WX057-4

WX057-3 (3.5 g, 8.34 mmol, 1 eq) (purity 93.96%) was dissolved in dimethylformamide dimethyl acetal (35 mL). The system was stirred at 110° C. for 3 hours. The reaction solution was dried on a rotary evaporator under reduced pressure to obtain a crude product. The crude product was added with ethyl acetate (20 mL), stirred for 10 min, allowed to stand and filtered. The filter cake was dried to give WX057-4. $^1$H NMR (400 MHz, CHLOROFORM-d) δ ppm 0.78-0.86 (m, 2H) 0.87-0.94 (m, 2H) 1.86-1.97 (m, 1H) 2.29 (s, 3H) 2.93-3.04 (m, 6H) 6.80 (d, J=1.25 Hz, 1H) 7.21 (d, J=12.30 Hz, 1H) 7.45 (d, J=1.25 Hz, 1H) 7.88-7.96 (m, 1H) 7.97-8.02 (m, 1H) 8.05 (d, J=7.28 Hz, 1H) 8.13 (s, 1H) 8.47 (d, J=7.53 Hz, 1H) 9.04 (br d, J=14.81 Hz, 1H) 9.76 (s, 1H).

Step 4. Synthesis of Compound WX057-5

WX057-4 (2.5 g, 5.56 mmol, 1 eq) was dissolved in acetonitrile (20 mL), and glacial acetic acid (5 mL) and 2-aminopropanol (2.00 g, 26.63 mmol, 2.09 mL, 4.79 eq) were added. The system was stirred at 80° C. for 16 hours. The reaction solution was cooled to room temperature, added with water (50 mL), added with saturated sodium bicarbonate solution (150 mL) to adjust the pH to 8-9, and extracted with dichloromethane (100 mL*2). The organic phase was washed with water (100 mL), dried over anhydrous sodium sulfate, and filtered. The filtrate was dried on a rotary evaporator under reduced pressure to obtain a crude product. The crude product was purified by column (0-15 methanol/dichloromethane) to obtain product WX057-5. $^1$H NMR (400 MHz, CHLOROFORM-d) δ ppm 0.81-0.85 (m, 2H) 0.88-0.92 (m, 2H) 1.61 (d, J=7.03 Hz, 3H) 1.88-1.93 (m, 1H) 2.29 (s, 3H) 3.91 (dd, J=11.67, 5.90 Hz, 1H) 4.11 (dd, J=11.67, 3.64 Hz, 1H) 5.36-5.49 (m, 1H) 6.80 (d, J=1.00 Hz, 1H) 7.20 (d, J=12.30 Hz, 1H) 7.43 (d, J=1.25 Hz, 1H) 7.86-7.93 (m, 2H) 8.05 (d, J=7.28 Hz, 1H) 8.32-8.38 (m, 2H) 9.11 (d, J=15.31 Hz, 1H).

Step 5. Synthesis of Compound WX057-6

WX057-5 (0.4 g, 774.97 μmol, 1 eq) (89.41%) was dissolved in acetonitrile (1 mL), and p-methoxybenzylamine (2.13 g, 15.50 mmol, 2.01 mL, 20 eq) and potassium carbonate (0.22 g, 1.59 mmol, 2.05 eq) were added. The system was stirred at 100° C. for 16 hours. The reaction solution was cooled to room temperature, combined, added to water (50 mL), and extracted with dichloromethane (30 mL*2). The organic phase was dried on a rotary evaporator under reduced pressure to obtain a crude product. The crude product was separated and purified with prep-TLC (dichloromethane/methanol=10/1) to obtain product WX057-6.

Step 6. Synthesis of Compound WX057-7

WX057-6 (0.2 g, 324.06 μmol, 1 eq) (purity 93.76%) was dissolved in trifluoroacetic acid (2 mL). The system was stirred at 20° C. for 1 hour. The reaction solution was added with saturated aqueous sodium bicarbonate (30 mL) with stirring, and extracted with dichloromethane (30 mL*2). The organic phase was washed with water (30 mL), dried over anhydrous sodium sulfate, and filtered. The filtrate was dried on a rotary evaporator to obtain WX057-7.

Step 7. Synthesis of Compound WX057-8

WX057-7 (0.15 g, 327.14 μmol, 1 eq) was dissolved in anhydrous dichloromethane (2 mL), and imidazole (0.07 g, 1.03 mmol, 3.14 eq) was added. Then TBSCl (0.1 g, 663.48 μmol, 81.30 μL, 2.03 eq) was added with stirring. The system was stirred at 25° C. for 10 min. The reaction solution was added with saturated aqueous sodium bicarbonate (20 mL), and extracted with dichloromethane (20 mL*2). The organic phase was dried over anhydrous magnesium sulfate and filtered. The filtrate was dried on a rotary evaporator under reduced pressure to obtain a crude product to obtain product WX057-8.

Step 8. Synthesis of Compound WX057-9

WX057-8 (228.62 mg, 349.18 μmol, 1 eq) (purity 87.48%) was dissolved in trimethyl orthoformate (2 mL). The system was stirred at 110° C. for 20 hours, and then heated to 110° C. by microwave and stirred for 1 hour. The reaction solution was dried on a rotary evaporator under reduced pressure to obtain a crude product. The crude product was separated and purified with prep-TLC (dichloromethane/methanol=10/1) plate to obtain product WX057-9.

Step 9. Synthesis of Compound WX057

WX057-9 (0.02 g, 34.32 μmol, 1 eq) was dissolved in methanol (1 mL), and hydrochloric acid (0.01 g, 98.74 μmol, 9.80 μL, 36% purity, 2.88 eq) was added. The system was stirred at 25° C. for 1 hour. The reaction solution was dried on a rotary evaporator under reduced pressure to obtain a crude product. The crude product was separated and purified by prep-HPLC (column: YMC-Actus Triart C18 100*30 mm*5 μm; mobile phase: [water (0.05% HCl)-ACN]; B %: 0%-55%, 8 min) to obtain product WX057. $^1$H NMR (400 MHz, METHANOL-d4) δ ppm 0.91-0.99 (m, 2H) 1.13-1.21 (m, 2H) 1.67 (d, J=7.03 Hz, 3H) 2.05-2.14 (m, 1H) 2.45 (s, 3H) 3.85 (dd, J=11.80, 5.27 Hz, 1H) 3.92-4.04 (m, 1H) 5.71 (br s, 1H) 7.67 (s, 1H) 7.90 (s, 1H) 8.15 (dd, J=6.65, 1.88 Hz, 1H) 8.32-8.40 (m, 2H) 8.43 (s, 1H) 8.79 (s, 1H) 9.21 (s, 1H) 9.97 (s, 1H).

Example 058: WX058

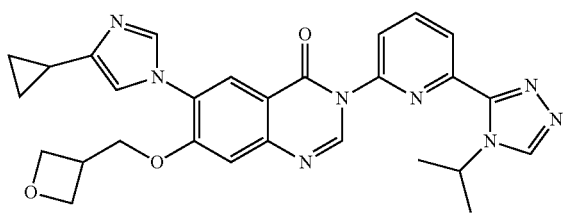 [SMILES: CC(C)n1cnnc1-c1cccc(-n2cnc3cc(OCC4COC4)c(-n4cnc(C5CC5)c4)cc3c2=O)n1]

Synthetic Route:

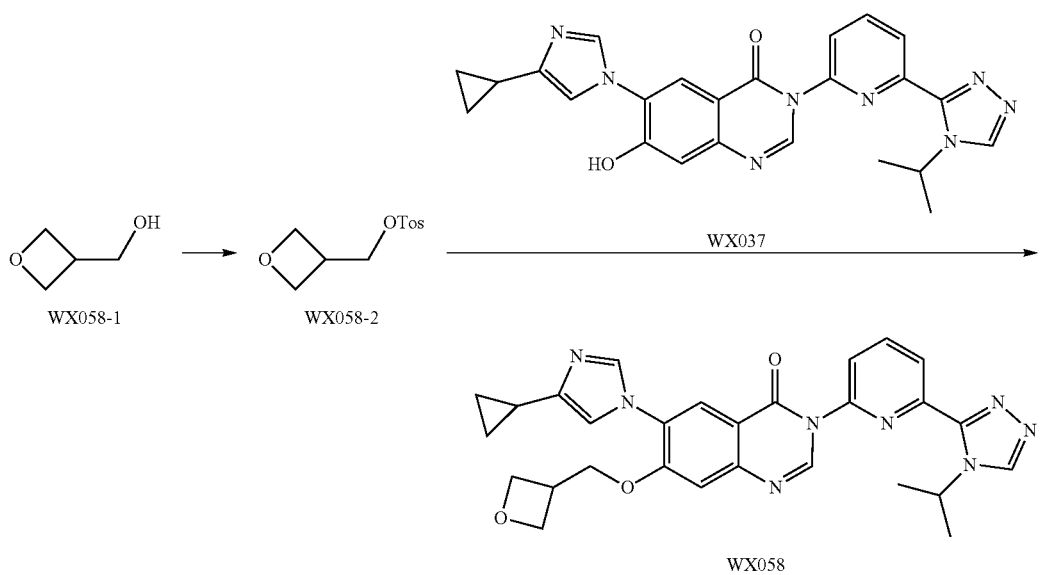

Step 1: Synthesis of Compound WX058-2

Compound WX058-1 (200 mg, 2.27 mmol, 1 eq) and dichloromethane (5 mL) were added into a 40 mL pre-dried reaction bottle, and triethylamine (344.56 mg, 3.41 mmol, 473.94 μL, 1.5 eq), dimethylaminopyridine (27.73 mg, 227.00 μmol, 0.1 eq) and p-toluenesulfonyl chloride (519.34 mg, 2.72 mmol, 1.2 eq) were added. The reaction solution was stirred at 25° C. for 16 hours. The reaction solution was added with saturated aqueous ammonium chloride solution (20 mL), and extracted with dichloromethane (20 mL×3). The organic phases were combined, dried over anhydrous sodium sulfate, and concentrated under reduced pressure to obtain a crude product. The crude product was purified by a thin layer chromatography silica gel plate (petroleum ether: ethyl acetate=3:1) to obtain WX058-2. $^1$H NMR (400 MHz, CHLOROFORM-d) δ=7.78 (d, J=8.0 Hz, 2H), 7.34 (d, J=8.0 Hz, 2H), 4.70 (dd, J=7.6, 6.4 Hz, 2H), 4.30 (t, J=6.4 Hz, 2H), 4.23 (d, J=76.8 Hz, 2H), 3.29-3.22 (m, 1H), 2.43 (s, 3H).

Step 2: Synthesis of Compound WX058

Compound WX037 (100 mg, 220.03 μmol, 1 eq), potassium carbonate (60.82 mg, 440.06 μmol, 2 eq), N,N-dimethylformamide (4 mL) and compound WX058-2 (63.97 mg, 264.04 μmol, 3.12 μL, 1.2 eq) were added into a 40 mL pre-dried reaction bottle. The reaction solution was stirred at 80° C. for 16 hours. The reaction solution was filtered with a filter to give a clear N, N-dimethylformamide solution. The clear solution was separated and purified by flash chromatography {column: Agela Durashell C18 150*25 mm 5 μm; mobile phase: [water (10 mM NH$_4$HCO$_3$)-ACN]; B %: 20%-50%, 10.5 min} to give WX058. $^1$H NMR (400 MHz, CHLOROFORM-d) δ=8.59 (s, 1H), 8.47-8.43 (m, 1H), 8.42 (s, 1H), 8.28 (s, 1H), 8.11 (t, J=7.9 Hz, 1H), 7.99-7.94 (m, 1H), 7.74 (d, J=1.1 Hz, 1H), 7.36 (s, 1H), 7.03 (d, J=1.1 Hz, 1H), 5.50 (td, J=6.9, 13.6 Hz, 1H), 4.92 (dd, J=6.5, 7.6 Hz, 2H), 4.53 (t, J=6.1 Hz, 2H), 4.47 (d, J=7.1 Hz, 2H), 3.51 (td, J=6.8, 13.1 Hz, 2H), 1.97-1.88 (m, 1H), 1.58-1.58 (m, 3H), 1.57 (s, 3H), 0.94-0.88 (m, 2H), 0.86-0.80 (m, 2H).

Biological Activity Test

Example 1: Evaluation of In Vitro Enzyme Activity

Reagents:
Base Reaction Buffer: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO Compound Treatment:
The test compound was formulated into a 10 mM stock solution in DMSO, which was diluted into 10 concentrations in 3-fold degression, and placed in a 384-well plate (Cyclic Olefin Copolymer LDV Echo®).
Kinase Name: ASK1/MAP3K5 (Invitrogen, Carlsbad, Calif.)
Type: Recombinant Human Full Length Protein, GST-tagged
Final concentration of the enzyme: 20 nM
Substrate: Myelin basic protein, MBP (Active Motif, Carlsbad, Calif.)
Final concentration of the substrate: 20 μM
Experimental Operations:
1. The substrate was dissolved in a freshly prepared base reaction buffer.
2. A desired coenzyme was added to the above substrate solution.
3. The kinase was added to the substrate solution and mixed slowly.

4. The solution of the test compound in DMSO was added to the kinase reaction solution and incubated at room temperature for 20 minutes.

5. $^{33}$P-ATP (specific activity of 10 μCi/μl) was added to the reaction solution to initiate the reaction.

6. Incubated at room temperature for 2 hours.

7. A small portion of the reactants was placed onto a P-81 ion exchange filter paper.

8. The filter paper was washed three times with 0.75% phosphate buffer to wash off the unbound phosphate, and then the filter paper was dried.

9. The radioactivity remaining on the filter paper was determined.

10. Kinase activity data was expressed as the ratio of the kinase activity remaining in the test sample to the kinase activity in the vehicle (DMSO).

11. IC50 values and curve fits was obtained with Prism (GraphPad software). The experimental results were shown in Table 1:

TABLE 1

Results of in vitro screening test of the compounds of the present disclosure

| No. | Compound | IC50 value |
|---|---|---|
| 1 | Example 001 | A |
| 2 | Example 002 | A |
| 3 | Example 003 | A |
| 4 | Example 004 | A |
| 5 | Example 005 | A |
| 6 | Example 006 | A |
| 7 | Example 007 | A |
| 8 | Example 008 | A |
| 9 | Example 009 | A |
| 10 | Example 010 | B |
| 11 | Example 011 | A |
| 12 | Example 012 | C |
| 13 | Example 013 | A |
| 14 | Example 014 | B |
| 15 | Example 015 | C |
| 16 | Example 016 | B |
| 17 | Example 017 | B |
| 18 | Example 018 | A |
| 19 | Example 019 | A |
| 20 | Example 020 | C |
| 21 | Example 021 | A |
| 22 | Example 022 | A |
| 23 | Example 023 | A |
| 24 | Example 024 | A |
| 25 | Example 025 | A |
| 26 | Example 026 | A |
| 27 | Example 028 | B |
| 28 | Example 029 | C |
| 29 | Example 030 | A |
| 30 | Example 031 | A |
| 31 | Example 032 | A |
| 32 | Example 033 | A |
| 33 | Example 034 | A |
| 34 | Example 035 | A |
| 35 | Example 036 | A |
| 36 | Example 038 | A |
| 37 | Example 037 | A |
| 38 | Example 039 | A |
| 39 | Example 040 | A |
| 40 | Example 041 | A |
| 41 | Example 042 | C |
| 42 | Example 043 | C |
| 43 | Example 044 | A |
| 44 | Example 045 | A |
| 45 | Example 046 | A |
| 46 | Example 047 | A |
| 47 | Example 048 | B |
| 48 | Example 049 | B |
| 49 | Example 050 | A |
| 50 | Example 051 | A |
| 51 | Example 052 | A |
| 52 | Example 053 | A |
| 53 | Example 054 | A |
| 54 | Example 055 | A |
| 55 | Example 056 | A |
| 56 | Example 057 | A |
| 57 | Example 058 | A |

Note:
A ≤ 50 nM;
50 nM < B ≤ 1 μM;
C > 1 μM.

Conclusion: The compounds of the present disclosure had a significant inhibitory effect on ASK1.

Example 2: Studies on Pharmacokinetic Properties

Experimental Method:

C57BL/6 male mice were used as subject animals in the study. The concentration of the drug in the plasma of mice injected intravenously or administered orally with the test compound was quantified at different time points by using a LC/MS/MS method to evaluate the pharmacokinetic characteristics of the test drug in mice.

A clear solution of the test compound was injected into C57BL/6 mice (overnight-fasted, 7-10 weeks old) via the tail vein, and the test compound was intragastrically administered to C57BL/6 mice (overnight-fasted, 7-10 weeks old). Approximately 30 μL of blood was collected from each animal via the jugular vein or tail vein at 0.0833, 0.25, 0.5, 1, 2, 4, 6, 8 and 24 hours after administration, and placed in an anticoagulant tube supplemented with EDTA-K2. Centrifuged at 3000 g at 4° C. for 15 min, and the plasma was collected. The plasma concentration was determined by LC-MS/MS. The pharmacokinetic parameters were calculated by using the non-compartment model and linear logarithmic trapezoidal method using the pharmacokinetic software WinNonlin™ Version 6.3 (Pharsight, Mountain View, Calif.). The experimental results were shown in Table 2:

TABLE 2

Results of the pharmacokinetic test

| Compound | Exposure (nM · h) | Bioavailability |
|---|---|---|
| Example 001 | 69652 | 133% |
| Example 002 | 29277 | 92% |
| Example 003 | 66259 | 214% |
| Example 007 | 29007 | 123% |
| Example 008 | 103950 | 98.5% |
| Example 009 | 89099 | 115% |
| Example 011 | 31832 | 108% |
| Example 018 | 59568 | 111% |
| Example 033 | 20356 | 148% |

Conclusion: The compounds of the invention had high exposure and bioavailability in mice.

The invention claimed is:
1. A compound as shown in formula (II):

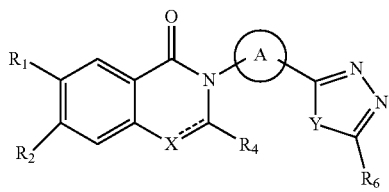

wherein

⫶ is selected from a single bond or a double bond;
X is selected from the group consisting of C(R$_3$), CH(R$_3$), N and N(R$_3$);
Y is selected from the group consisting of N(R$_5$) and 0;
ring A is selected from the group consisting of phenyl and 5- to 6-membered heteroaryl;
R$_1$ is selected from 5- to 10-membered heteroaryl optionally substituted with one, two or three R group(s);
R$_2$ is selected from the group consisting of H, F, Cl, Br, I, OH, and NH$_2$, or selected from the group consisting of C$_{1-6}$ alkyl, C$_{1-3}$ heteroalkyl, 5- to 6-membered heterocycloalkyl, phenyl and 5- to 6-membered heteroaryl, each optionally substituted with one, two or three R group(s);
R$_3$ is selected from the group consisting of H, F, Cl, Br, I, OH, and NH$_2$;
R$_4$ is selected from H, or selected from the group consisting of C$_{1-3}$ alkyl and C$_{1-3}$ alkoxy;
R$_5$ is selected from H, or selected from the group consisting of C$_{1-8}$ alkyl, C$_{3-7}$ cycloalkyl and 3- to 6-membered heterocycloalkyl, each optionally substituted with one, two or three R group(s);
R$_6$ is selected from H, or selected from C$_{1-6}$ alkyl;
or R$_5$ and R$_6$ are joined together to form a 5- to 6-membered ring;
R is selected from the group consisting of H, F, Cl, Br, I, OH, and NH$_2$, and NH$_2$—(C=O)—, or selected from the group consisting of C$_{1-3}$ alkyl, C$_{1-3}$ alkoxy, C$_{1-3}$ alkyl-NH—(C=O)—, C$_{1-3}$alkyl-S(=O)$_2$—, C$_{3-6}$cycloalkyl, 3- to 6-membered heterocycloalkyl and phenyl;
the "hetero" in the 5- to 10-membered heteroaryl, C$_{1-3}$ heteroalkyl, 5- to 6-membered heterocycloalkyl, 5- to 6-membered heteroaryl, and 3- to 6-membered heterocycloalkyl is respectively and independently selected from the group consisting of —NH—, N, —O—, —S—, —S(=O)$_2$— and —NH—C(=O)—;
in any of the above cases, the number of heteroatoms or heteroatomic groups is respectively and independently selected from 1, 2 or 3,
a pharmaceutically acceptable salt and a tautomer thereof.

2. The compound and a pharmaceutically acceptable salt thereof according to claim 1, wherein R is selected from the group consisting of H, F, Cl, Br, I, OH, NH$_2$, Me, Et,

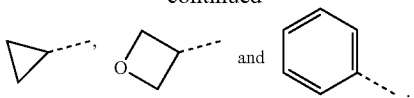

3. The compound and a pharmaceutically acceptable salt thereof according to claim 1, wherein R$_1$ is selected from the group consisting of imidazolyl, 4,5,6,7-tetrahydro-1H-benzo[d]imidazolyl and pyridyl, each optionally substituted with one, two or three R group(s).

4. The compound and a pharmaceutically acceptable salt thereof according to claim 3, wherein R$_1$ is selected from the group consisting of

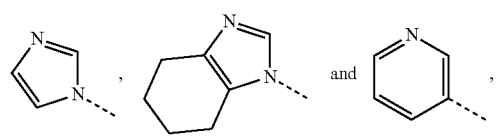

each optionally substituted with one, two or three R group(s).

5. The compound and a pharmaceutically acceptable salt thereof according to claim 4, wherein R$_1$ is selected from the group consisting of

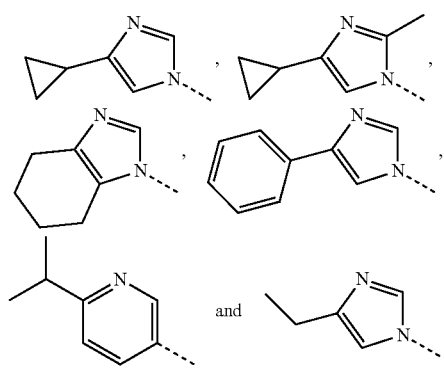

6. The compound and a pharmaceutically acceptable salt thereof according to claim 1, wherein R$_2$ is selected from the group consisting of H, F, Cl, Br, I, OH, and NH$_2$, or selected from the group consisting of C$_{1-3}$ alkyl, C$_{1-3}$ alkylamino, C$_{1-3}$ alkoxy, morpholino, phenyl, pyridyl and thienyl, each optionally substituted with one, two or three R group(s).

7. The compound and a pharmaceutically acceptable salt thereof according to claim 6, wherein R$_2$ is selected from the group consisting of H, F, Cl, Br, I, OH, and NH$_2$, or selected from the group consisting of Me, Et,

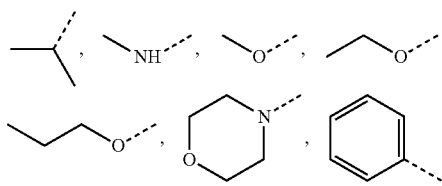

-continued

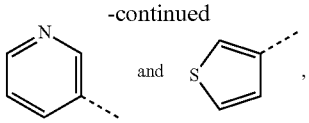

each optionally substituted with one, two or three R group(s).

8. The compound and a pharmaceutically acceptable salt thereof according to claim 7, wherein $R_2$ is selected from the group consisting of H, F, Cl, Br, I, OH, $NH_2$, Me, Et,

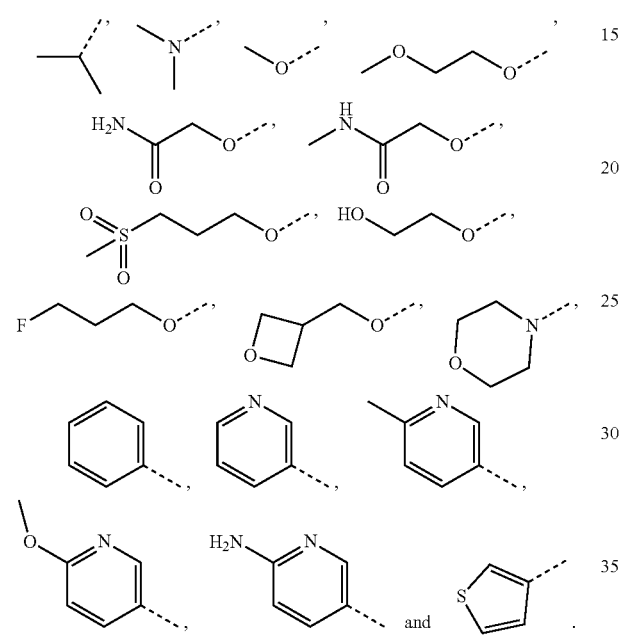

9. The compound and a pharmaceutically acceptable salt thereof according to claim 1, wherein $R_4$ is selected from the group consisting of H, Me, Et and

10. The compound and a pharmaceutically acceptable salt thereof according to claim 1, wherein $R_5$ is selected from H, or selected from the group consisting of $C_{1-6}$ alkyl, $C_{3-6}$ cycloalkyl and 5- to 6-membered heterocycloalkyl, each optionally substituted with one, two or three R group(s).

11. The compound and a pharmaceutically acceptable salt thereof according to claim 10, wherein $R_5$ is selected from H, or selected from the group consisting of Me, Et,

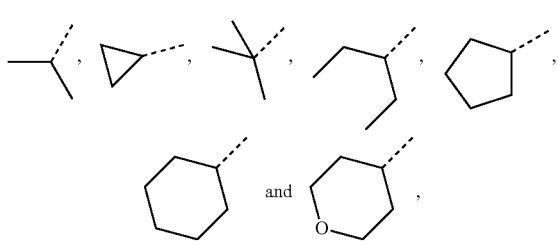

each optionally substituted with one, two or three R group(s).

12. The compound and a pharmaceutically acceptable salt thereof according to claim 11, wherein $R_5$ is selected from the group consisting of H, Me, Et,

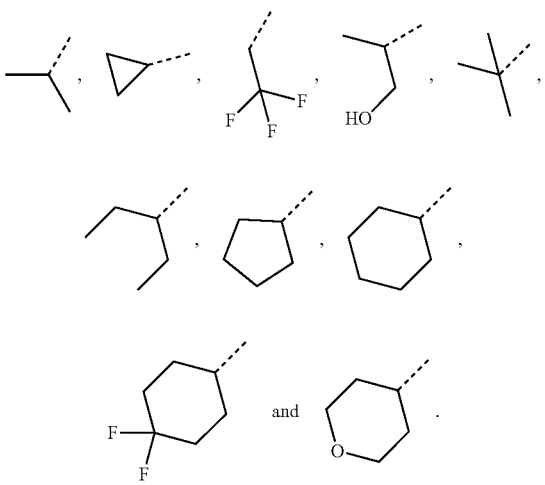

13. The compound and a pharmaceutically acceptable salt thereof according to claim 1, wherein $R_6$ is selected from H, or selected from $C_{1-3}$ alkyl.

14. The compound and a pharmaceutically acceptable salt thereof according to claim 13, wherein $R_6$ is selected from the group consisting of H, Me and Et.

15. The compound and a pharmaceutically acceptable salt thereof according to claim 1, wherein ring A is selected from the group consisting of phenyl, pyridyl, thienyl and thiazolyl.

16. The compound and a pharmaceutically acceptable salt thereof according to claim 15, wherein ring A is selected from the group consisting of

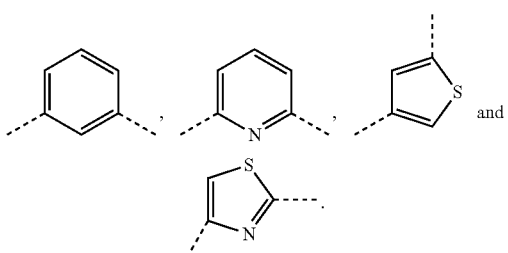

17. The compound and a pharmaceutically acceptable salt thereof according to claim 1, wherein the structural unit

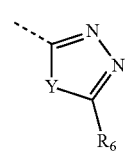

is selected from the group consisting of

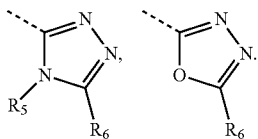

18. The compound and a pharmaceutically acceptable salt thereof according to claim 1, wherein when $R_5$ and $R_6$ are joined together to form a 5- to 6-membered ring, the structural unit

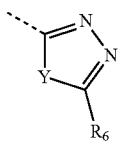

is selected from the group consisting of

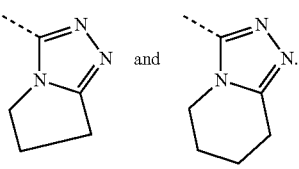

19. The compound and a pharmaceutically acceptable salt thereof according to claim 17, wherein the structural unit is

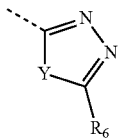

selected from the group consisting of

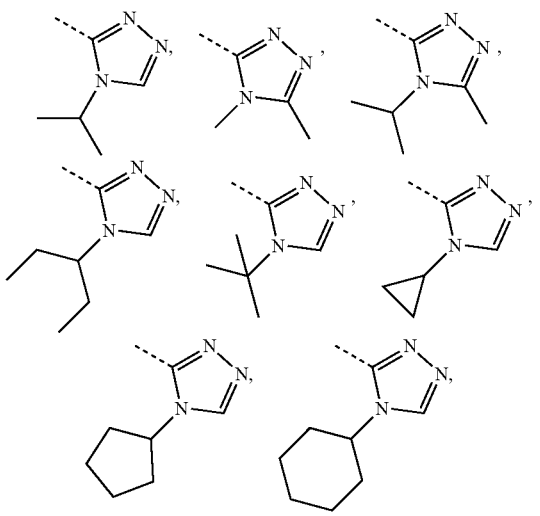

-continued

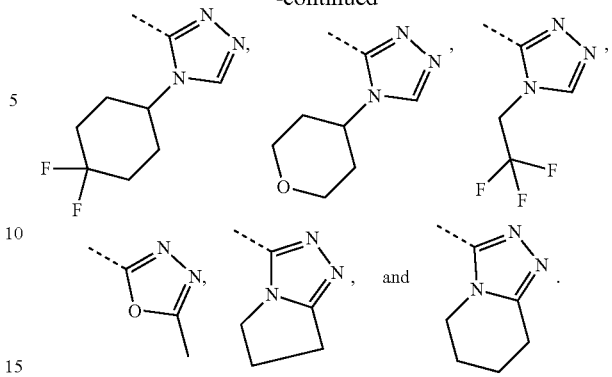

20. The compound and a pharmaceutically acceptable salt thereof according to claim 1, wherein the structural unit

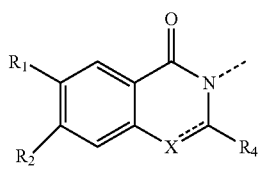

is selected from the group consisting of

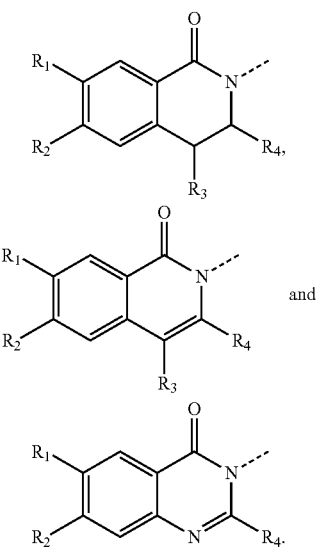

21. The compound and a pharmaceutically acceptable salt thereof according to claim 1, wherein the compound is selected from the group consisting of (2)

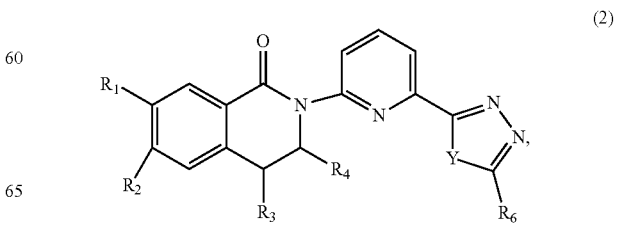

(3)
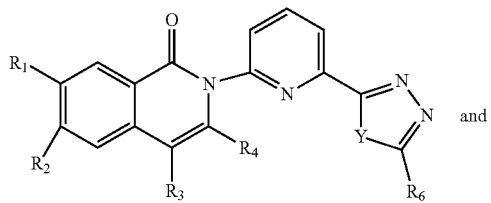
and (4)
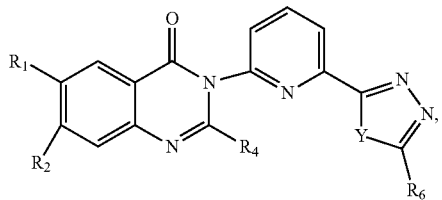

wherein Y, $R_1$, $R_2$, $R_3$, $R_4$, and $R_6$ are as defined.

22. The compound and a pharmaceutically acceptable salt thereof according to claim 21, wherein the compound is selected from the group consisting of (5)
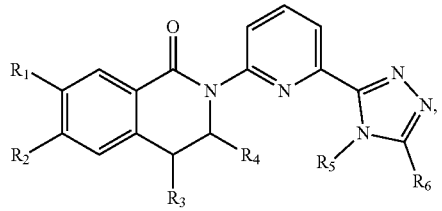

(6)
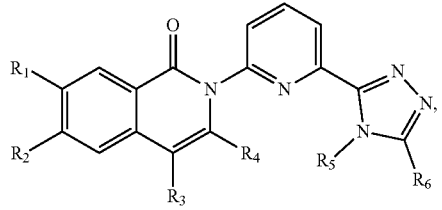

(7)
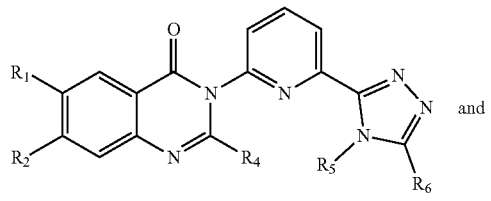
and (8)
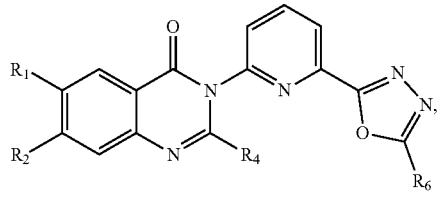

wherein $R_1$, $R_2$, $R_3$, $R_4$, $R_5$, and $R_6$ are as defined.

23. The compound and a pharmaceutically acceptable salt thereof according to claim 22, wherein the compound is selected from the group consisting of (9)
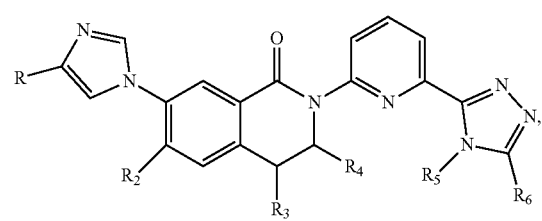

(10)
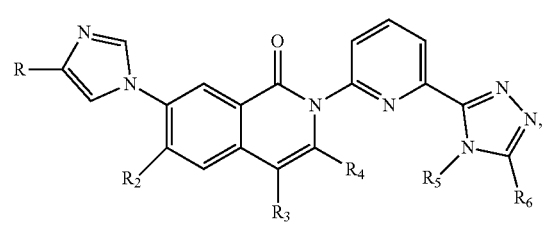

(11)
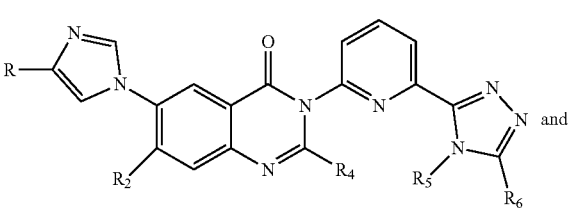
and

(12)
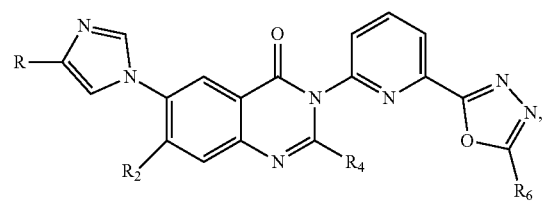

wherein $R_1$, $R_2$, $R_3$, $R_4$, $R_5$, and $R_6$ are as defined.

24. Compounds of the following formula:

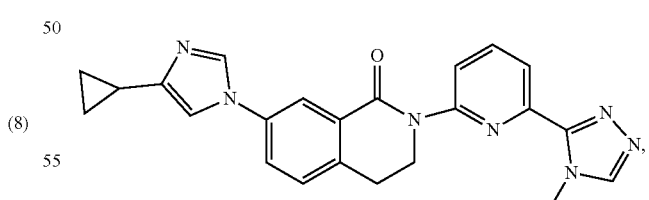

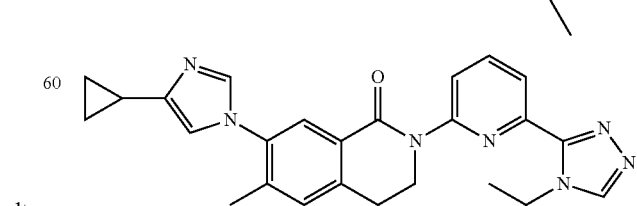

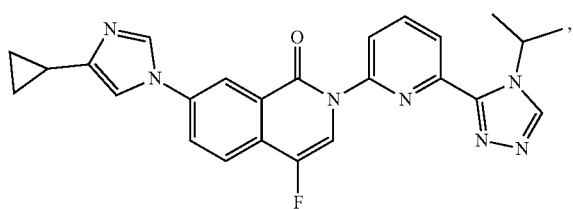
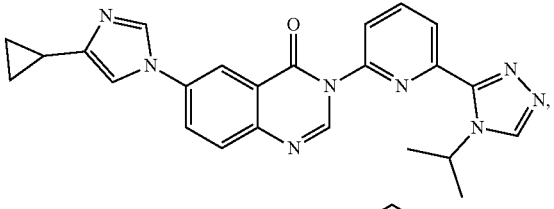
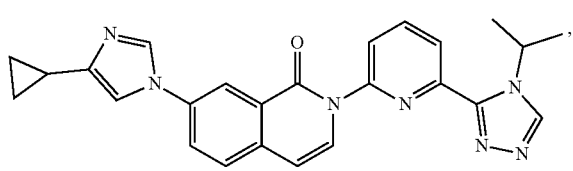
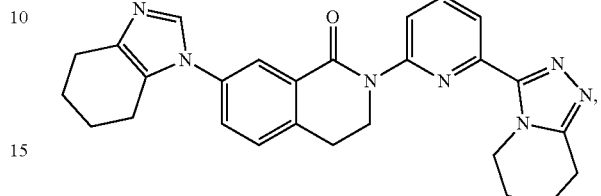
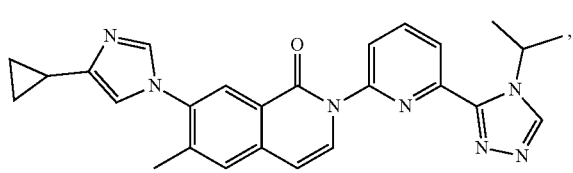
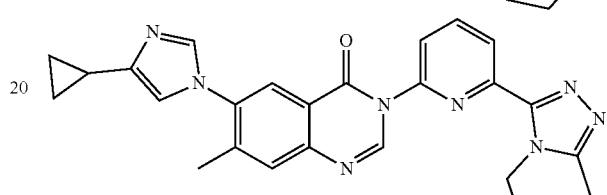
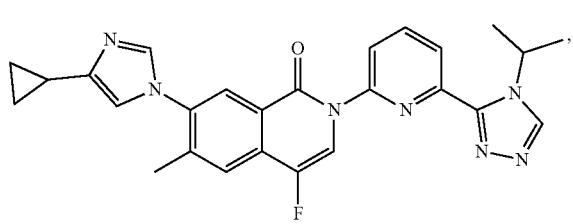
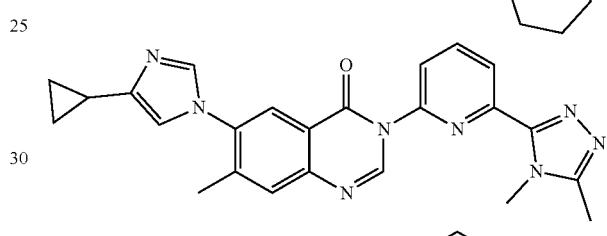
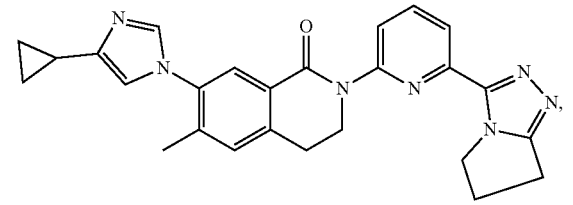
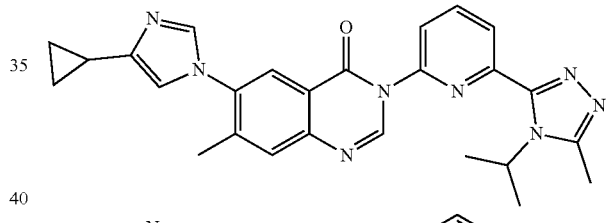
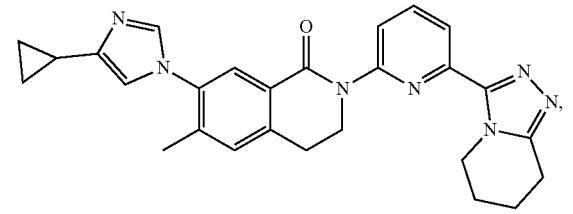
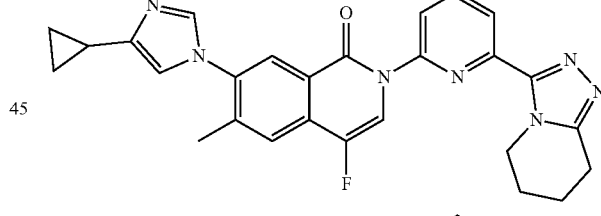
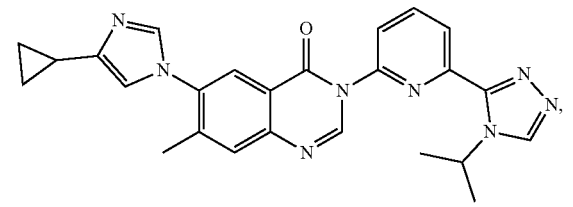
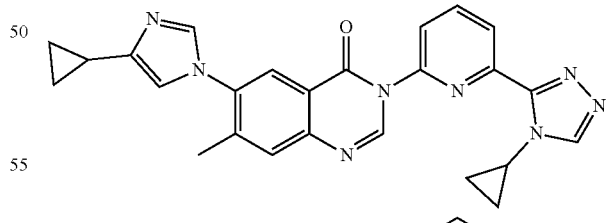
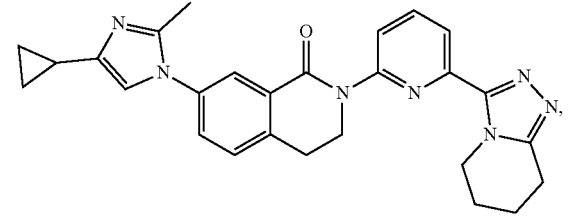
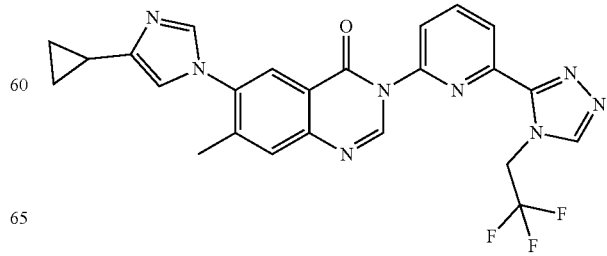

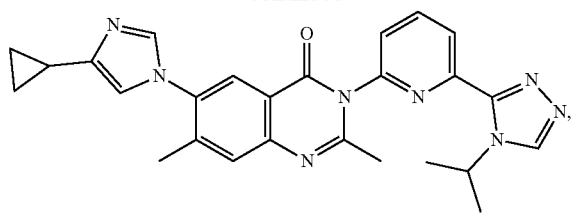
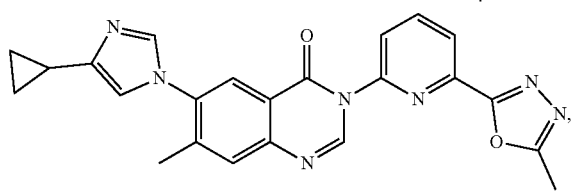
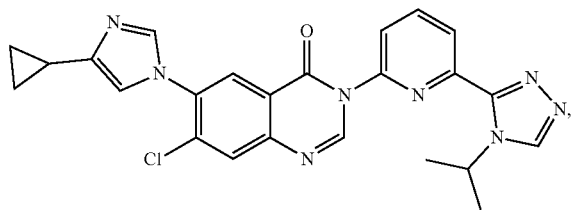
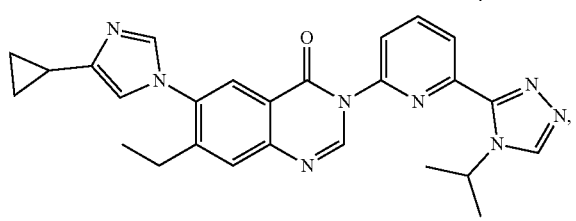
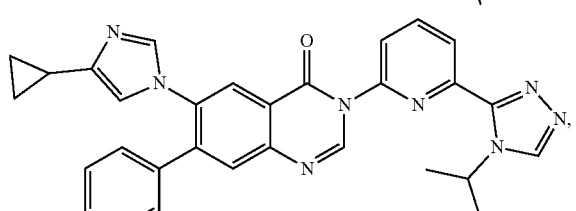
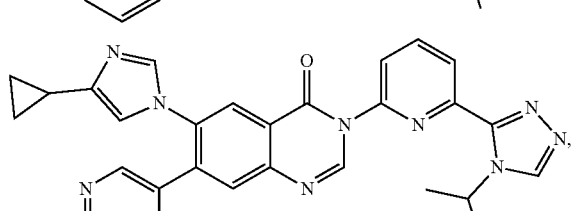
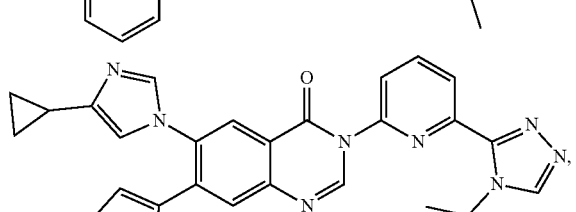
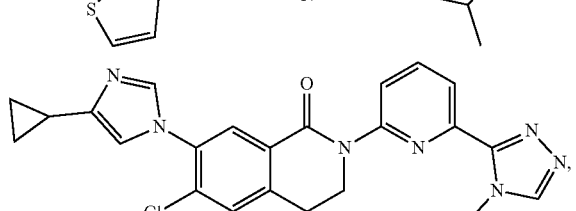
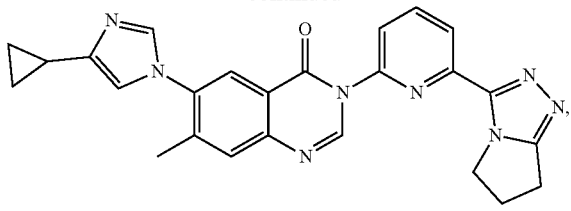
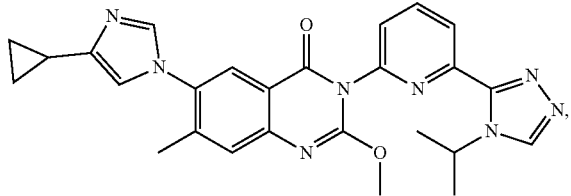
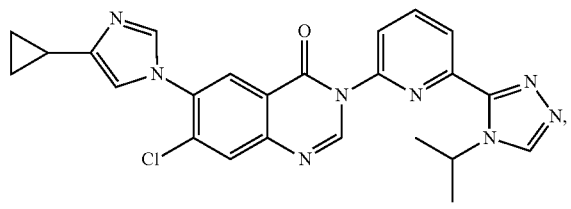
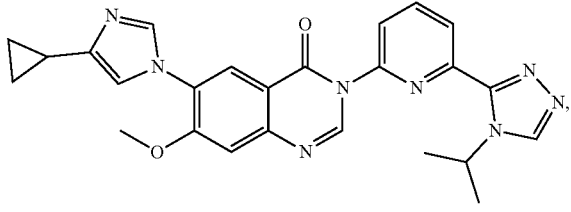
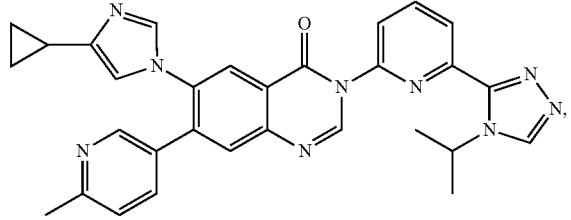
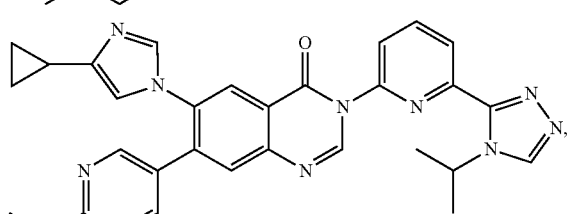
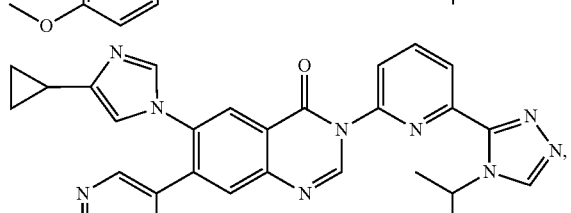
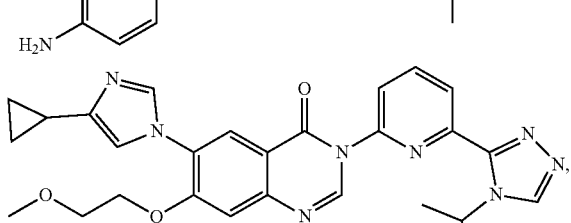

201
-continued
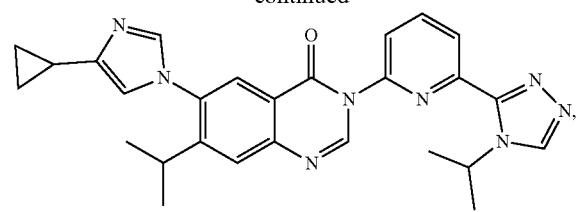
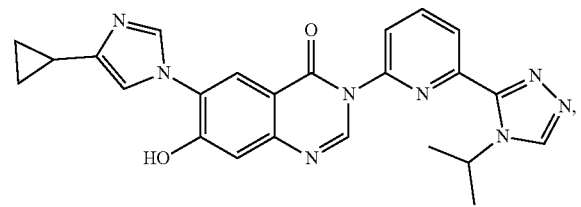
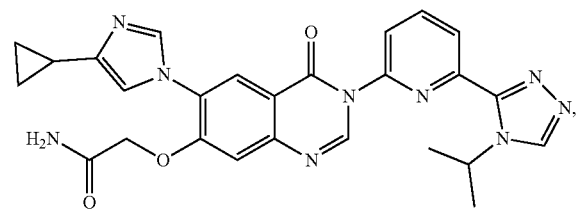
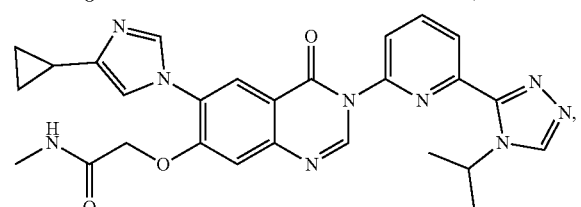
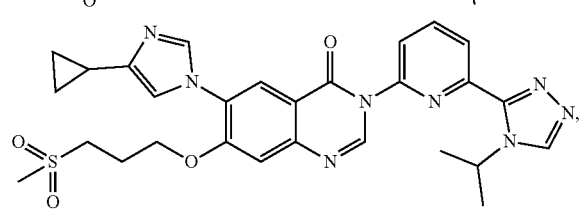
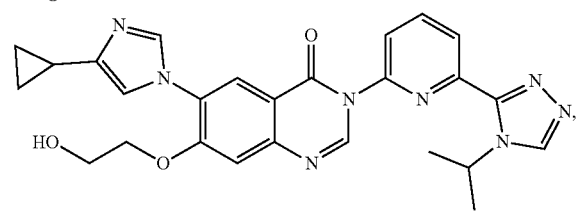
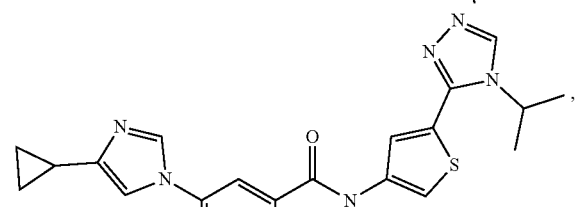
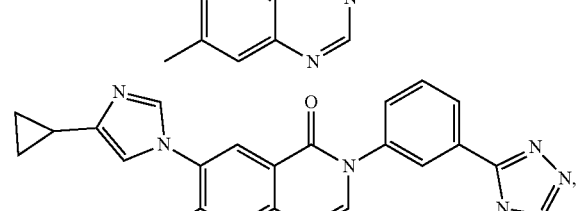
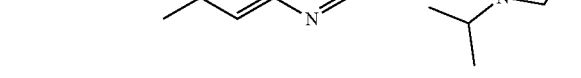
202
-continued
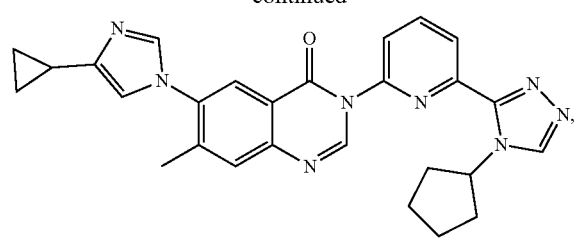
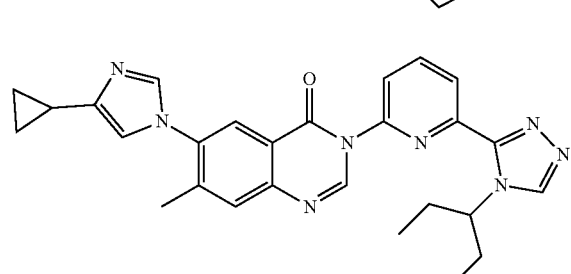
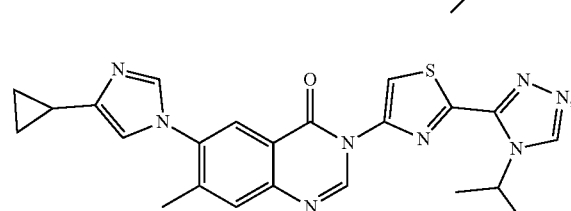
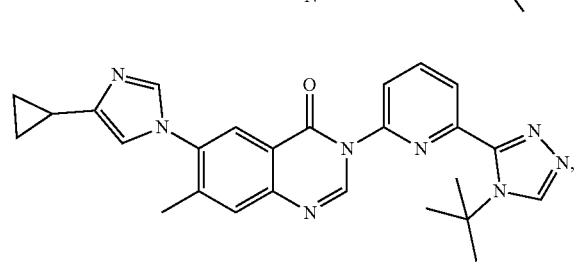
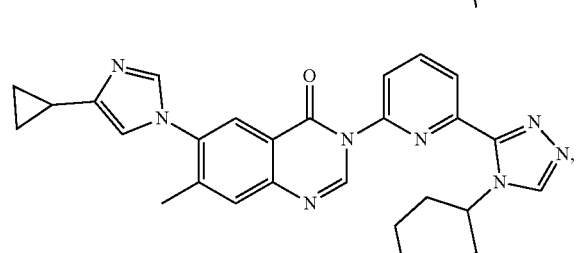
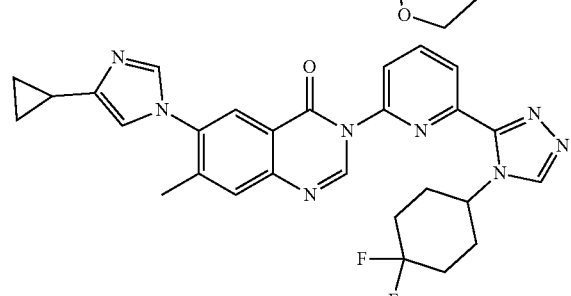
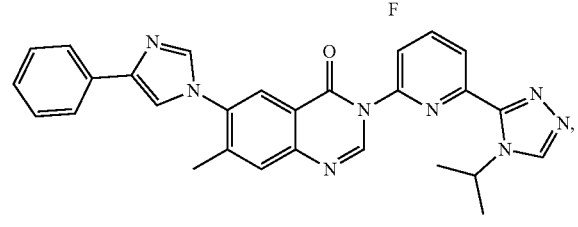

-continued

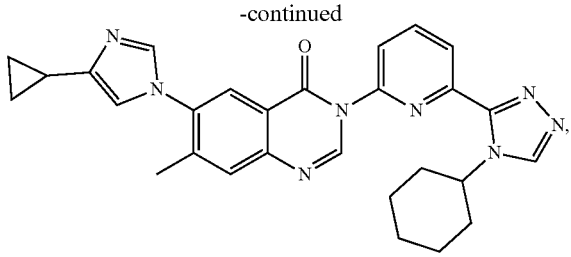

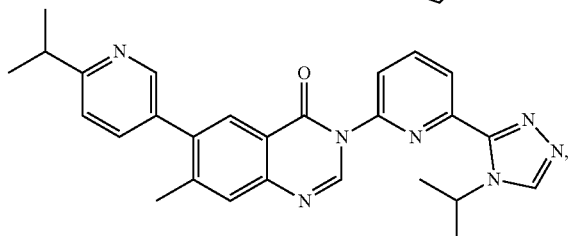

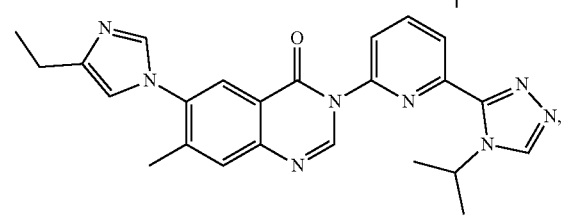

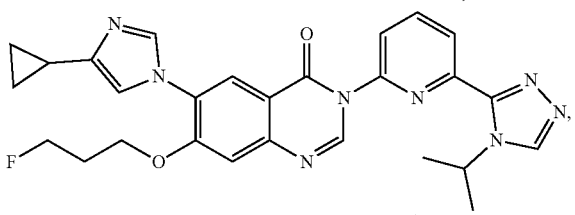

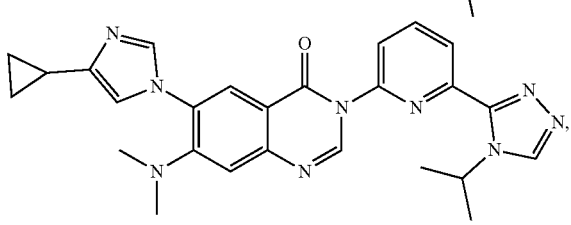

-continued

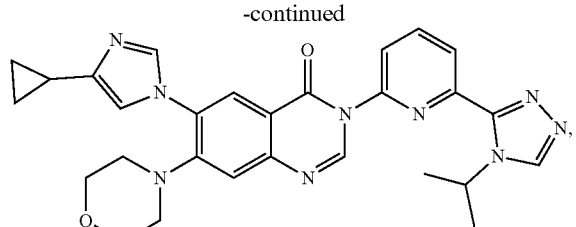

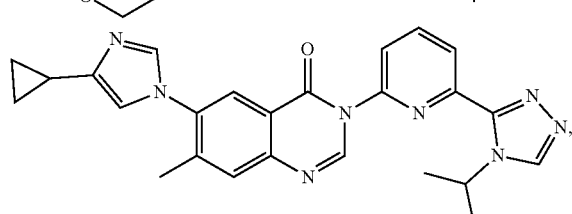

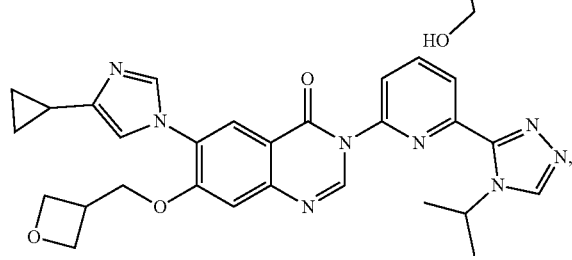

and pharmaceutically acceptable salts thereof.

25. A pharmaceutical composition comprising a therapeutically effective amount of the compound or a pharmaceutically acceptable salt thereof according to claim 1, as an active ingredient, and a pharmaceutically acceptable carrier.

26. A method for treating an ASK1-related disorder comprising the administration of the compound or a pharmaceutically acceptable salt thereof according to claim 1 to a patient in need thereof.

27. A method for treating an ASK1-related disorder comprising the administration of the composition according to claim 25 to a patient in need.

* * * * *